US012723101B2

(12) United States Patent
Urech et al.

(10) Patent No.: US 12,723,101 B2
(45) Date of Patent: Sep. 1, 2026

(54) ANTIBODY SPECIFICALLY BINDING TO HUMAN SERUM ALBUMIN

(71) Applicant: Numab Therapeutics AG, Wädenswil (CH)

(72) Inventors: David Urech, Jona (CH); Christian Hess, Zurich (CH); Alexandre Simonin, Rosenau (FR); Stefan Warmuth, Au (CH)

(73) Assignee: Numab Therapeutics AG, Horgen (CH)

( * ) Notice: Subject to any disclaimer, the term of this patent is extended or adjusted under 35 U.S.C. 154(b) by 992 days.

(21) Appl. No.: 17/771,836

(22) PCT Filed: Nov. 4, 2020

(86) PCT No.: PCT/EP2020/080941
§ 371 (c)(1),
(2) Date: Apr. 26, 2022

(87) PCT Pub. No.: WO2021/089609
PCT Pub. Date: May 14, 2021

(65) Prior Publication Data

US 2022/0411536 A1 Dec. 29, 2022

(30) Foreign Application Priority Data

Nov. 4, 2019 (EP) .................................... 19206959

(51) Int. Cl.
*C07K 16/32* (2006.01)
*C07K 16/18* (2006.01)
*C07K 16/28* (2006.01)

(52) U.S. Cl.
CPC .............. *C07K 16/32* (2013.01); *C07K 16/18* (2013.01); *C07K 16/2809* (2013.01); *C07K 16/2827* (2013.01); *C07K 16/2878* (2013.01); *C07K 2317/31* (2013.01); *C07K 2317/622* (2013.01); *C07K 2317/73* (2013.01); *C07K 2317/75* (2013.01); *C07K 2317/76* (2013.01); *C07K 2317/92* (2013.01); *C07K 2317/94* (2013.01)

(58) Field of Classification Search
CPC .... C07K 16/32; C07K 16/18; C07K 16/2809; C07K 16/2827; C07K 16/2878; C07K 2317/31; C07K 2317/622; C07K 2317/73; C07K 2317/75; C07K 2317/76; C07K 2317/92; C07K 2317/94; C07K 2317/62; C07K 2317/624; C07K 16/2866; C07K 2317/569; A61K 2039/505; A61P 35/00
See application file for complete search history.

(56) References Cited

U.S. PATENT DOCUMENTS

| | | | | |
|---|---|---|---|---|
| 2023/0203162 | A1 * | 6/2023 | Lichtlen | A61P 35/00 530/387.3 |
| 2024/0084039 | A1 * | 3/2024 | Johansson | C07K 16/2878 |
| 2024/0392003 | A1 * | 11/2024 | Chatterjee | A61P 35/00 |

FOREIGN PATENT DOCUMENTS

| | | | | |
|---|---|---|---|---|
| EP | 3 470 426 | A1 | 4/2019 | |
| WO | 2017/220988 | A1 | 12/2017 | |
| WO | 2017/220988 | A9 | 2/2018 | |
| WO | 2018/224441 | A1 | 12/2018 | |
| WO | WO-2018224439 | A1 * | 12/2018 | C07K 16/18 |
| WO | 2019/072868 | A1 | 4/2019 | |
| WO | 2019166650 | A1 | 9/2019 | |

OTHER PUBLICATIONS

U.S. Appl. No. 18/863,208, Warmuth, Stefan.*
Brown M, et al. Tolerance of single, but not multiple, amino acid replacements in antibody VH CDR 2: a means of minimizing B cell wastage from somatic hypermutation? J Immunol. May 1, 1996;156(9):3285-91. PMID: 8617951. (Year: 1996).*
Vajdos FF, et al. Comprehensive functional maps of the antigen-binding site of an anti-ErbB2 antibody obtained with shotgun scanning mutagenesis. J Mol Biol. Jul. 5, 2002;320(2):415-28. doi: 10.1016/S0022-2836(02)00264-4. PMID: 12079396. (Year: 2002).*
Gunde T, et al. A novel, monovalent tri-specific antibody-based molecule. Cancer Res (2019) 79 (13_Supplement): 1532. https://doi.org/10.1158/1538-7445.AM2019-1532 (Year: 2019).*
Law CL, et al. Preclinical and Nonclinical Characterization of HPN217. Blood. vol. 132, Supplement 1, Nov. 29, 2018, p. 3225 (Year: 2018).*
Tiller KE, et al. Facile Affinity Maturation of Antibody Variable Domains Using Natural Diversity Mutagenesis. Front Immunol. Sep. 4, 2017;8:986. doi: 10.3389/fimmu.2017.00986. PMID: 28928732; PMCID: PMC5591402. (Year: 2017).*

* cited by examiner

*Primary Examiner* — Maher M Haddad
*Assistant Examiner* — Alec Jon Peters
(74) *Attorney, Agent, or Firm* — Prismatic Law Group, PLLC; Ronald J. Kamis

(57) ABSTRACT

The present invention relates to a multispecific antibody comprising at least one domain specifically binding to a tumor-associated immune checkpoint antigen with low affinity, and at least one domain specifically binding to a tumor-associated antigen (TAA), and pharmaceutical compositions and methods of use thereof. The present invention further relates to a nucleic acid encoding said multispecific antibody, a vector comprising said nucleic acid, a host cell comprising said nucleic acid or said vector, and method of producing said multispecific antibody.

15 Claims, 16 Drawing Sheets

Specification includes a Sequence Listing.

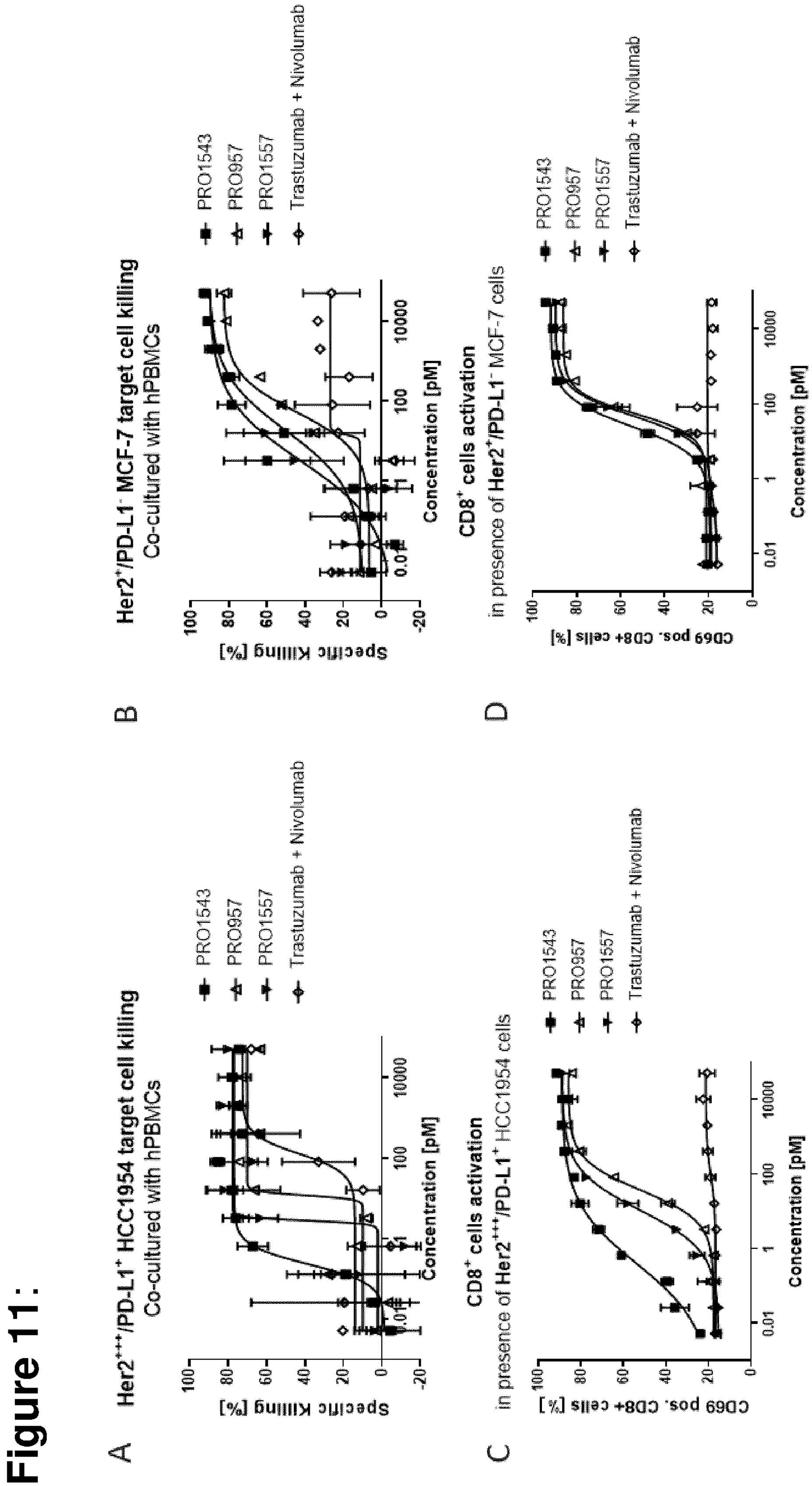
Figure 11:
A
Her2+++/PD-L1+ HCC1954 target cell killing
Co-cultured with hPBMCs
Specific Killing [%]
Concentration [pM]
PRO1543
PRO957
PRO1557
Trastuzumab + Nivolumab
B
Her2+/PD-L1- MCF-7 target cell killing
Co-cultured with hPBMCs
Specific Killing [%]
Concentration [pM]
PRO1543
PRO957
PRO1557
Trastuzumab + Nivolumab
C
CD8+ cells activation
in presence of Her2+++/PD-L1+ HCC1954 cells
CD69 pos. CD8+ cells [%]
Concentration [pM]
PRO1543
PRO957
PRO1557
Trastuzumab + Nivolumab
D
CD8+ cells activation
in presence of Her2+/PD-L1- MCF-7 cells
CD69 pos. CD8+ cells [%]
Concentration [pM]
PRO1543
PRO957
PRO1557
Trastuzumab + Nivolumab

MATCH4

Figure 17:
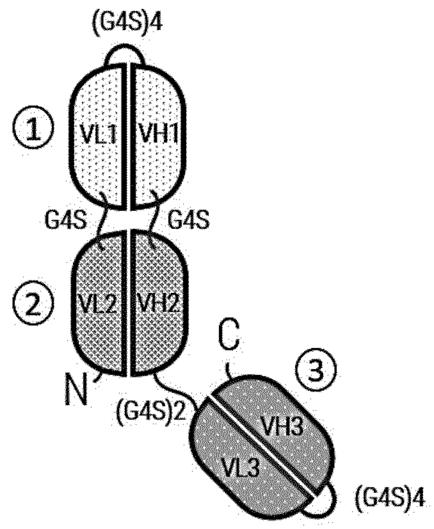
scDb-scFv
 Peptide linker
N N-terminus
C C-terminus
VLx/VHx Variable light (VL) and heavy (VH) domain #

ANTIBODY SPECIFICALLY BINDING TO HUMAN SERUM ALBUMIN

CROSS-REFERENCE TO RELATED APPLICATIONS

This application is a 371 National Phase of International Patent Application PCT/EP2020/080941 filed on Nov. 4, 2020, which claims priority to EP 19206959.9 filed on Nov. 4, 2019, the content of each of which applications is incorporated herein by reference.

INCORPORATION OF SEQUENCE LISTING

This application contains a sequence listing submitted electronically via EFS-web, which serves as both the paper copy and the computer readable form (CRF) and consists of a file entitled "WRN20NP_seqlist.txt", which was created on Apr. 25, 2022, which is 324,667 bytes in size, and which is herein incorporated by reference in its entirety.

FIELD OF THE INVENTION

The present invention relates to a multispecific antibody comprising at least one domain specifically binding to a tumor-associated immune checkpoint antigen with low affinity, at least one domain specifically binding to a tumor-associated antigen (TAA), and optionally at least one domain specifically binding to an immune cell antigen. Additionally, the present invention relates to specific domains for use in said multispecific antibody, and pharmaceutical compositions and methods of use thereof. The present invention further relates to a nucleic acid encoding said multispecific antibody or specific domains thereof, a vector comprising said nucleic acid, a host cell comprising said nucleic acid or said vector, and a method of producing said multispecific antibody or specific domains thereof.

BACKGROUND OF THE INVENTION

Cancer continues to pose a major unmet medical need, despite the considerable progress made in its treatment. Some of the most substantial progress made in cancer treatment in recent years has come with the advent of immunotherapies of various molecular classes, including, but not limited to: monoclonal antibodies (mAbs), bispecific antibodies (bsAbs), recombinant proteins, and chimeric antigen receptor-T cell (CAR-T cell) therapies. Such therapies induce anti-tumor immunity by: a) actively directing immune-effector cells to tumor-resident cells and/or b) stimulating immune-effector cells and/or c) relieving tumor-mediated immune-suppression. These immunotherapies commonly exploit the overexpression—as compared to extratumoral loci—of specific antigens by tumor-resident cells (e.g., malignant cells, cells of the tumor vasculature, stromal cells, immune cells, etc.) to target their pharmacological activity to tumors. Among these antigens, tumor-associated antigens (TAAs) comprise cell-surface proteins selectively overexpressed by malignant cells. By binding to TAAs with high affinity, immunotherapies can, to a degree, restrict their immunomodulatory activity to immunological synapses between tumor cells and immune effector cells.

A common class of TAA-binding immunotherapies are mAbs that elicit anti-tumor immunity by opsonizing tumor-cells and triggering antibody-dependent cell-mediated cytotoxicity (ADCC) by Fcγ receptor (FcγR)-expressing cells, primarily natural killer (NK) cells. Other TAA-binding immunotherapies leverage cytotoxic T lymphocytes (CTLs) to induce targeted depletion of malignant cells, such as CAR-T cells as well as bsAbs that simultaneously engage the T cell antigen, CD3 (TAA/CD3 bsAbs). While the therapeutic utility of TAA-(re)directed CTLs has been clinically validated, such utility can be limited in instances when tumor-mediated immune-suppression impairs the activation/stimulation of CTLs. Even in tumors where tumor-infiltrating lymphocytes (TILs) are abundant (i.e., "inflamed" or "hot" tumors), tumor immune-evasion can be induced by a variety of means, such as through the expression of immune-checkpoint ligands/receptors (e.g., PD-1, PD-L1, CTLA-4) as well as the recruitment of regulatory T cells (Tregs) and myeloid-derived suppressor cells (MDSCs).

Immune checkpoints are regulators of the immune system and are involved in processes such as self-tolerance or immune suppression in cancer.

PD-L1 (CD274, B7-H1) is a 40 kDa type I transmembrane protein. PD-L1 is a surface glycoprotein ligand for PD-1, a key immune checkpoint receptor expressed by activated T and B cells and mediates immunosuppression. PD-L1 is implicated in the suppression of immune system responses during chronic infections, pregnancy, tissue allografts, autoimmune diseases, and cancer. PD-L1 is found on both antigen-presenting cells and human cancer cells, such as squamous cell carcinoma of the head and neck, melanoma, and brain tumor, thyroid, thymus, esophagus, lung, breast, gastrointestinal tract, colorectum, liver, pancreas, kidney, adrenal cortex, bladder, urothelium, ovary, and skin (Katsuya Y, et al., Lung Cancer. 88(2):154-159 (2015); Nakanishi J, et al., Cancer Immunol Immunother. 56(8): 1173-1182 (2007); Nomi T, et al., Clin Cancer Res. 13(7): 2151-2157 (2007); Fay A P, et al., J Immunother Cancer. 3:3 (2015); Strome S E, et al., Cancer Res. 63(19):6501-6505 (2003); Jacobs J F, et al. Neuro Oncol. 11(4):394-402 (2009); Wilmotte R, et al. Neuroreport. 16(10):1081-1085 (2005)). PD-L1 is rarely expressed on normal tissues but inducibly expressed on tumor site (Dong H, et al., Nat Med. 8(8):793-800 (2002); Wang et al., Onco Targets Ther. 9: 5023-5039 (2016)). PD-L1 downregulates T cell activation and cytokine secretion by binding to PD-1 (Freeman et al., 2000; Latchman et al, 2001). PD-1, activated by PD-L1, potentially provides an immune-tolerant environment for tumor development and growth. PD-L1 also negatively regulates T-cell function through interaction with another receptor, B7.1 (B7-1, CD80).

Inhibition of the PD-L1/PD-1 interaction allows for potent anti-tumor activity. A number of antibodies that disrupt the PD-1 signaling have entered clinical development. These antibodies belong to the following two main categories: those that target PD-1 (nivolumab, Bristol-Myers Squibb; pembrolizumab, Merck, Whitehouse Station, N.J.; pidilizumab, CureTech, Yavne, Israel) and those that target PD-L1 (MPDL3280A, Genentech, South San Francisco, CA; MED14736, Medimmune/AstraZeneca; BMS-936559, Bristol-Myers Squibb; MSB0010718C, EMD Serono, Rockland, MA) (for review see Postow M A et al., J Clin Oncol. Jun 10; 33(17):1974-82 (2015)). Targeting PD-L1 versus targeting PD-1 may result in different biologic effects. PD-1 antibodies prevent interaction of PD-1 with both its ligands, PD-L1 and PD-L2. PD-L1 antibodies do not prevent PD-1 from interacting with PDL2, although the effect of this interaction remains unknown. PD-L1 antibodies however prevent interaction of PD-L1 with not only PD-1, but also B7-1 (Butte M J, et al., Immunity 27:111-122, (2007)), which is believed to exert negative signals on T cells. Blocking PD-L1 has demonstrated promising early data, and currently, four clinical anti-PD-L1 mAbs are in the testing: atezolizumab and MED14736 (both are Fc null variants of human IgG1), MSB001078C (IgG1), and BMS-936559 (IgG4) (Chester C., et al., Cancer Immunol Immunother October; 65(10):1243-8 (2016)).

New and emerging treatments frequently combine TAA-targeting immunotherapies with one or more additional immunotherapies that target immune-checkpoint pathways in an effort to further relieve, or overcome, tumor-mediated immune-suppression. Monoclonal antibodies that block immune-suppressive antigens, such as CTLA-4 (e.g., ipilimumab), PD-1 (e.g., nivolumab, pembrolizumab) and PD-L1 (e.g., avelumab, atezolizumab), have elicited impressive response rates in patients exhibiting a variety of tumor histologies. Initial results of combined treatment with immune-checkpoint modulators and TAA-binding immunotherapies have been encouraging. As an example, the HER2-targeting mAb, trastuzumab (Herceptin®, Genentech), is currently being clinically evaluated (phase II) in combination with nivolumab (Opdivo®, Bristol-Myers Squibb) as well as in combination with both nivolumab and ipilimumab (Yervoy®, Bristol-Myers Squibb), National Clinical Trial (NCT) 03409848. Similarly, the CD19/CD3 bsAb, blinatumomab (Blincyto®, Amgen), is currently being clinically evaluated (phase I/II) in combination with pembrolizumab (Keytruda®, Merck) as well as in a phase I trial as part of a triple immunotherapy combination with both nivolumab and ipilimumab, NCT03512405 and NCT02879695, respectively.

Additionally, combinations of targeting immune checkpoints and T-cell co-stimulatory receptors have been evaluated. The combination of anti-PD-L1 and anti-CD137 antibodies increased overall survival and enhanced T-cell effector function in the ID-8 ovarian adenocarcinoma model (Duraiswamy J, et al., Cancer Res 73:6900-6912 (2013)). The combination of urelumab (anti-CD137) with nivolumab (anti-PD-1) in both solid tumors and B-cell non-Hodgkin's lymphoma is being tested in a phase I/II trial (NCT02253992), while PF-05082566 (anti-CD137) is being tested in a phase I trial with pembrolizumab (anti-PD-1) in patients with solid tumors (NCT02179918) (Chester C., et al., Cancer Immunol Immunother October; 65(10):1243-8 (2016)).

Recently, the effect of multivalent and multispecific fusion polypeptides that bind PD-L1 and CD137 has been evaluated in vitro on T-cell activation and proliferation. Using an autologous in vitro co-culture system implementing immature DC and donor matched T-cells, it has been demonstrated that INBRX-105, a multispecific and multivalent polypeptide having two PD-L1 binding domains, two CD137 binding domains and an Fc region, is superior in stimulating interferon-gamma production, when compared to the monospecific PD-L1 sd-Ab-Fc fusion protein, the CD137 sdAb-Fc fusion protein, the combination of the two, the anti-PD-L1 antibody atezolizumab, the anti-CD137 antibody utomilumab (PF-05082566), or the anti-PD-L1 antibody prembrolizumab, and combinations thereof, at inducing IFNγ or mediating CD8+ T-cell proliferation and activation (WO 2017/123650). Additionally, WO 2016/149201 discloses certain antibodies directed against PD-L1 and suggests creating bispecific antibody constructs further comprising a T-cell engaging antibody, with CD137 being contained in a non-exclusive list of more than 20 potential T-cell targets.

While immunotherapy combinations have demonstrated their potential to enhance anti-tumor responses through additive or synergistic activity, they are beset with two consistent limitations: 1) clinical development challenges due to the complexity of adjusting the doses of multiple component therapies across various patient cohorts, and 2) reliance on two or more separate manufacturing processes for component therapies, with the attendant implication of high cost of goods sold (COGS) and treatment-pricing. These limitations are even more severe when the number of immunotherapies included in combination regimens increases. Additionally, even for treatment regimens that include only a single immunotherapy, dose-limiting toxicities (DLTs) often preclude administration at maximally effective doses (MEDs) or lead to discontinuation of treatment, resulting in limited efficacy. Unfortunately, similar to their anti-tumor activity, the drug-related toxicities elicited by each component immunotherapy in combination regimens also tend to be additive or synergistic.

Thus, despite the promising opportunities offered by inhibiting the interaction between PD-1 and PD-L1, the applications described above have often resulted in toxicities caused by binding of anti-PD-L1 antibodies to PD-L1 expressed on non-target cells (for a review, see Wang et al., Cancer J. 24 (2018) 36-40).

The exact pathways by which such DLTs arise can vary, but the risk of immunotherapy-related toxicities can typically be minimized, or eliminated, by enhancing the tumor-localization of pharmacological activity. Extratumoral activity of immunotherapies results in the secretion of pro-inflammatory cytokines in healthy tissues, which can result in undesirable safety profiles. Leveraging T cell-engaging bsAbs that require binding to a TAA to elicit immunomodulatory activity is a promising strategy to restrict such cytokine release to cytolytic/immunological synapses between tumor-resident cells and T cells. However, conventional TAA/CD3 bsAbs are also commonly associated with toxicities, such as cytokine release syndrome (CRS), putatively due to excessive activity of anti-CD3 domains. Additionally, while TAA/CD3 bsAbs potently deplete TAA-overexpressing cells, they do so by recruiting and stimulating CTLs whether or not such cells express a T cell receptor (TCR) that recognizes a tumor-antigen(s) (i.e., tumor-reactive T cell). Therefore, rather than stimulating, or reactivating, the host's native anti-tumor immunity, TAA/CD3 bsAbs somewhat indiscriminately stimulate CTLs, potentially posing safety risks and leading to insufficient anti-cancer immune-memory formation.

In addition to CD3, T cell co-stimulatory receptors (e.g., 4-1BB, OX40, ICOS, GITR) are currently being clinically evaluated as targets for therapeutic stimulation of T cells in cancer. One putative advantage of anti-tumor T cell stimulation via such targets is that they are transiently expressed upon TCR signaling. As such, their expression tends to be selectively heightened in inflamed TMEs, particularly on tumor-reactive T cells, whose TCRs are receiving consistent stimulation by dint of abundant interactions with major histocompatibility complexes (MHCs) expressed by malignant cells and antigen-presenting cells (APCs). Therefore, targeting costimulatory receptors with, e.g., mAbs and bsAbs, should more selectively stimulate, and expand, pre-existing anti-tumor T cells than CD3-targeting approaches, potentially rendering such biologics safer and their effects more durable.

Among costimulatory receptors, 4-1 BB (CD137, TNF-receptor superfamily 9, TNFRSF9) has emerged as especially promising due to its expression profile and its role as a multipotent mediator of anti-tumor immunity (Bartkowiak and Curran 2015; Yonezawa et al. 2015). 4-1 BB is an inducible T cell costimulatory receptor. Its expression is activation-dependent and encompasses a broad subset of immune cells, including activated CD8+ T cells, CD4+ T cells, NK and NKT cells, Tregs, dendritic cells (DC) including follicular DC, stimulated mast cells, differentiating myeloid cells, monocytes, neutrophils, eosinophils (Wang et al, Immunol Rev. 229(1): 192-215 (2009)), and activated B cells (Zhang et al, J Immunol. 184(2):787-795 (2010)). In addition, 4-1 BB expression has also been demonstrated on tumor vasculature (Broil K et al., Am J Clin Pathol. 115(4): 543-549 (2001); Seaman et al, Cancer Cell 11(6):539-554 (2007)) and atherosclerotic endothelium (Olofsson et al, Circulation 117(10): 1292 1301 (2008)).

4-1 BB costimulates T cells to carry out effector functions such as eradication of established tumors, broadening primary CD8+ T cell responses, and enhancing the memory pool of antigen-specific CD8+ T cells. In vivo efficacy studies in mice have revealed that 4-1 BB-agonistic mAbs, administered as both a monotherapy and as a component of combination regimens, leads to anti-tumor protective T cell memory responses and tumor regression in multiple tumor models. Additionally, two 4-1 BB-agonistic mAbs are currently in the clinic: urelumab (Bristol-Myers Squibb), a fully humanized IgG4 mAb, and utomilumab (PF-05082566, Pfizer), a fully human IgG2 mAb (Chester C., et al., Cancer Immunol Immunother October; 65(10):1243-8 (2016)). Although utilization of 4-1BB-agonistic mAbs is a very promising treatment strategy, clinical data collected thus far suggest that an mAb-based approach to 4-1BB stimulation results in a trade-off between efficacy and safety. Namely, highly active 4-1 BB-agonistic mAbs elicit DLTs that attenuate treatment efficacy, whereas weakly active 4-1 BB-agonistic mAbs are well tolerated but do not seem to be highly efficacious, including at their predicted MED.

Highly active 4-1BB-agonistic mAbs lead to alterations in the immune system and organ function, increasing risks of toxicities. High doses of such mAbs in naïve and tumor-bearing mice have been reported to induce T cell-infiltration to the liver and elevations of aspartate aminotransferase and alanine aminotransferase, consistent with liver inflammation (Niu L, et al. J Immunol 178(7):4194-4213 (2007); Dubrot J, et al., Int J Cancer 128(1):105-118 (2011)). Initial clinical studies into the human therapeutic use of 4-1 BB-agonistic mAbs have also demonstrated elevations of liver enzymes and increased incidence of hepatitis (Sznol M., et al., J Clin Oncol 26(115S):3007 (2008); Ascierto P A, et al., Semin Oncol 37(5):508-516 (2010); Chester C., et al., Cancer Immunol Immunother October; 65(10):1243-8 (2016)). Potentially fatal hepatitis was observed in a Bristol-Myers Squibb (BMS) phase II anti-CD137 study for previously treated stage III/IV melanoma, National Clinical Trial (NCT) 00612664. This study and several others (NCT00803374, NCT00309023, NCT00461110, NCT00351325) were terminated due to adverse events (Chester C., et al., Cancer Immunol Immunother October; 65(10):1243-8 (2016)). Such adverse events are most probably due to systemic overstimulation of T cells.

Similar to TAA/CD3 bsAbs, TAA/4-1 BB bsAbs are designed to selectively agonize 4-1 BB in the context of immunological synapses between tumor-resident cells and immune-effector cells, thereby preventing the toxicities associated with extratumoral T cell stimulation. As an example, the 5T4/4-1 BB bsAb (APV-527) being co-developed by Aptevo Therapeutics and Alligator Biosciences (WO2017182672 A1) is designed to elicit targeted costimulation of T cells by anchoring to 5T4, a TAA expressed by a variety of solid tumors. APV-527 pre-clinical data suggest that conditionally stimulating 4-1 BB in the presence of 5T4 effectively tumor-localizes T cell costimulation, leads to considerable enhancement of T cell activation in the TME and inhibits tumor growth in 5T4+ tumor models. This same tumor-localizing strategy can conceivably leverage a variety of clinically validated TAAs, for which therapeutic targeting has been demonstrated to be both efficacious and safe.

HER2 has been established as a TAA that can be targeted effectively and safely to address HER2+ cancers. The most notable HER2-targeted therapies approved for use in patients with HER2+ tumors are the mAbs, trastuzumab (Herceptin®, Genentech) and pertuzumab (Perjeta®, Genentech). While trastuzumab and pertuzumab are similar insofar as they act, in part, by opsonizing HER2+ cells and triggering ADCC, the two antibodies are dissimilar in the means by which they prevent pro-proliferative HER2-signaling. In the case of trastuzumab, binding to its epitope prevents HER2 homodimerization and thereby inhibits HER2-signaling. However, in a subset of patients, compensatory HER3 overexpression, and the formation of HER2/HER3 heterodimers, leads to heightened signaling, rendering such patients refractory to treatment with trastuzumab. By contrast, pertuzumab binds to an epitope that prevents HER2/HER3 heterodimerization, likewise inhibiting pro-proliferative signaling. Due to this mechanism of action (MoA) complementarity, pertuzumab and trastuzumab are synergistic, and their combination has been approved for the treatment of HER2+ breast cancer.

While combined inhibition of HER2-signaling and ADCC-mediated depletion of HER2+ cells has been effective for many patients, many other patients exhibit a HER2+ tumor phenotype that very weakly responds to treatment with conventional antibodies. In some cases, this is because the particular HER2+ tumor does not rely on HER2-signaling for proliferation, rendering the primary MoA of trastuzumab/pertuzumab ineffective. This has engendered the hypothesis that a targeted cytotoxic approach that is more potent than ADCC could be of considerable benefit. Validation of this concept has somewhat emerged with the market approval of the ADC trastuzumab-emtansine (Kadcyla®, Genentech). In that same vein, multiple companies are currently developing HER2/CD3 bsAbs to stimulate redirected T cells to induce potent, targeted cytotoxicity. Additionally, in several patients exhibiting primary or secondary non-responsiveness to HER2-targeting mAbs, the HER2+ tumor phenotype includes heightened expression of ligands/receptors (e.g., PD-L1) that actively suppress anti-tumor immune-responses. Predictably, this has led to the combination of HER2-targeting mAbs with immune-checkpoint-modulating mAbs, which have achieved some success in clinical settings. TAAs that are almost exclusively expressed on cancer cells, such as oncofetal tumor antigens, are referred to as clean TAAs. TAA that are also expressed on normal, non-cancer cells—typically at lower level compared to cancer cells—are non-clean TAAs. Due to the very high potency of TAA/CD3 bsAbs approaches, non-clean TAAs are a challenge as they lead to the depletion of non-tumor cells also expressing the TAA. A well-known example of a non-clean TAA is HER2, which is not only expressed on tumor cells but—at a lower level—also in various other tissues. Therefore, novel therapies that improve the selectivity of TAA/CD3 bsAbs approaches for tumor tissues are needed.

There is precedent, as well, for the use of HER2 as a target to tumor-localize 4-1 BB stimulation by a bispecific molecule. *Pieris* Pharmaceuticals has initiated clinical trials to evaluate a HER2/4-1 BB bispecific fusion protein (PRS-343) (NCT03330561). PRS-343 comprises an IgG4 variant of trastuzumab fused to a bivalent 4-1 BB-binding anticalin. Preclinical and clinical evidence supporting: 1) the potential benefits of PD-(L)1 blockade and 4-1 BB stimulation, 2) the benefits of combining HER2-targeting immunotherapies with PD-(L)1-blocking immunotherapies, and 3) the synergy of trastuzumab and pertuzumab, suggests a potential benefit to combining such a HER2/4-1 BB bispecific molecule with as many as two additional immunotherapies in a single treatment. In fact, PRS-343 is also currently being clinically evaluated in combination with the PD-L1-blocking mAb, atezolizumab (Tecentriq®, Genentech) (NCT03650348).

As mentioned previously, an inevitable drawback of combination therapies, particularly as the number of component therapies increases, is that their clinical development can be burdensomely complex and therefore expensive. The requirement to develop multiple manufacturing processes adds further up the development cost and multiplies COGS. The inclusion of more than two specificities in a single molecule (e.g., tri- or tetra-specific antibodies) could theoretically address many of the foregoing limitations with respect to safety, efficacy and cost. Tri-/tetra-specific molecules that are TAA-targeted are theoretically capable of eliciting highly tumor-localized, and synergistic, anti-tumor modulation of multiple immune-checkpoint pathways, which could provide safer and more effective therapies for a variety of cancers. Additionally, such molecules would further limit the need for co-administration of additional immunotherapies to boost patient responses, supporting ease-of-development and minimizing treatment costs. However, implementation of tri-/tetra-specific antibodies for therapeutic use has been complicated due to issues with their molecular architecture, the properties of their component antigen-binding domains and/or poor biophysical properties. Therefore, there remains a clear need for novel tri-/tetra-specific antibodies that elicit tumor-localized, synergistic immunomodulation and that have biophysical properties rendering them suitable for pharmaceutical development.

In addition, despite the fact that numerous antibodies already exist that are specific for tumor-associated immune checkpoint antigens, TAAs and/or T cell co-stimulatory receptor, the complex and specific requirements of such tri- or tetraspecific antibodies require the development of novel antibody domains with tailor-made properties.

Thus, in spite of numerous treatment options for patients suffering from cancer, there remains a need for effective and safe therapeutic agents and a need for their preferential use in a more targeted manner. Immune-modulating biologics offer promising approaches in treatment of cancers due to their modes of actions, however global immunostimulation and lack of any restriction of this immunomodulation to pathologically relevant cells and sites causes numerous side effects and significant toxicities, which potentially may lead to increased morbidity and mortality of patients. It is therefore an object of the present invention to provide a medicament to improve treatment of a proliferative disease, particularly a cancer.

SUMMARY OF THE INVENTION

It is an object of the present invention to provide a medicament to improve treatment of a proliferative disease, particularly a cancer. The present invention addresses the need for precision therapeutics for immuno-oncology that target only the disease-related cells.

In one aspect, the present invention relates to a multispecific antibody comprising at least a first domain specifically binding to a tumor-associated immune checkpoint antigen with low affinity, and at least a second domain specifically binding to a tumor-associated antigen (TAA).

The present invention further relates to a multispecific antibody comprising at least a first domain specifically binding to a tumor-associated immune checkpoint antigen with low affinity, at least a second domain specifically binding to a tumor-associated antigen (TAA), and at least a third domain specifically binding to an immune cell antigen, in particular wherein said immune cell antigen is present on T cell or NK cell.

More specifically, the present invention relates to a multispecific antibody wherein said first domain specifically binding to PD-L1 comprises a VH sequence of SEQ ID NO: 11 and a VL sequence of SEQ ID NO: 16.

The present invention further relates to a combination comprising (i) the multispecific antibody of the present invention and (ii) a second compound selected from (iia) an antibody directed at a TAA, in particular an antibody directed at HER2, in particular wherein the antibody is trastuzumab, (iib) a modulator of an immune checkpoint antigen, in particular wherein said immune checkpoint antigen is not a tumor-associated immune checkpoint antigen, and/or in particular wherein said immune checkpoint antigen is present on T cell or NK cell, and (iic) a modulator of angiogenesis.

In another aspect, the present invention relates to a pharmaceutical composition comprising the multispecific antibody of the invention and a pharmaceutically acceptable carrier.

In a further aspect, the present invention provides the multispecific antibody of the invention or the pharmaceutical composition of the invention for use as a medicament.

In a further aspect, the present invention provides the multispecific antibody of the invention or the pharmaceutical composition of the invention for use in treatment of cancer in a subject in need thereof.

In one aspect, the present invention provides use of the multispecific antibody of the invention or the pharmaceutical composition of the invention for treating cancer in a subject in need thereof.

In one aspect, the present invention provides use of the multispecific antibody of the invention or the pharmaceutical composition of the invention in the manufacture of a medicament for treatment of a cancer, in a subject in need thereof.

In yet another aspect, the present invention provides a method of treating a cancer in a subject in need thereof comprising administering to the subject a therapeutically effective amount of the multispecific antibody of the invention or the pharmaceutical composition of the invention.

In a further aspect, the present invention provides a nucleic acid comprising a nucleotide sequence encoding the multispecific antibody of the invention. In a further aspect, the present invention provides a vector comprising said nucleic acid. In a further aspect, the present invention provides a host cell comprising said nucleic or said vector.

In yet another aspect, the present invention provides a method of producing the multispecific antibody of the invention or a binding domain thereof or a fragment thereof, the method comprising the step of culturing a host cell comprising a nucleic acid or a vector encoding the multispecific antibody of the invention or a binding domain thereof or a fragment thereof.

The aspects, advantageous features and preferred embodiments of the present invention summarized in the following items, respectively alone or in combination, further contribute to solving the object of the invention:

1. A multispecific antibody comprising
   (a) a first domain specifically binding to a tumor-associated immune checkpoint antigen wherein said first domain binds to said tumor-associated immune checkpoint antigen with a dissociation constant (KD) of more than 50 nM, particularly with a dissociation constant (KD) of between 50 nM and 1 μM, particularly more than 100 nM, particularly with a dissociation constant (KD) of between 100 nM and 900 nM, particularly more than 200 nM, particularly with a dissociation constant (KD) of between 200 nM and 800 nM, particularly more than 300 nM, particularly with a dissociation constant (KD) of between 300 nM and 700 nM, particularly more than 400 nM, particularly with a dissociation constant (KD) of between 400 nM and 600 nM, particularly more than 450 nM, particularly with a dissociation constant (KD) of between 450 nM and 550 nM, particularly more than 475 nM, particularly with a dissociation constant (KD) of between 475 nM and 525 nM, particularly with a dissociation constant (KD) of about 500 nM, in each case when measured by SPR in an scFv format (monovalent affinity), and
   (b) a second domain specifically binding to a tumor-associated antigen (TAA).
2. The multispecific antibody of item 1, wherein said second domain binds to said TAA with a dissociation constant (KD) of less than 50 nM, particularly less than 20 nM, particularly less than 10 nM, particularly less than 5 nM, particularly less than 2 nM, particularly less than 1 nM, particularly less than 0.5 nM, when measured by SPR in an scFv format (monovalent affinity).
3. The multispecific antibody of item 1 or item 2, wherein said tumor-associated immune checkpoint antigen and said TAA are both present on the same tumor cell.
4. The multispecific antibody of any one of the preceding items, wherein said tumor-associated immune checkpoint antigen is selected from the group consisting of PD-L1, PD-L2, CD80, CD86, CD276 (B7-H3), and VTCN1 (B7-H4).
5. The multispecific antibody of item 4, wherein said tumor-associated immune checkpoint antigen is PD-L1.
6. The multispecific antibody of any one of the preceding items, wherein said first domain is an inhibitor of said tumor-associated immune checkpoint antigen.
7. The multispecific antibody of any one of the preceding items, wherein said TAA is not PD-L1.
8. The multispecific antibody of any one of the preceding items, wherein said TAA is selected from the group consisting of EGFRvIII, 5T4, CD19, CD20, CD22, CD38, BCMA, IL4RA, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11Ra, IL-13RA2, ROR1, PSCA, MAD-CT-1, MAD-CT-2, VEGFR2, CLEC12A, LewisY, CD24, PDGFR-beta, SSEA-4, folate receptor alpha, ERBBs (e.g., ERBB2), Her2/neu (HER2), MUC1, MUC16, EGFR, NCAM, Ephrin B2, CAIX, LMP2, sLe, HMWMAA, o-acetyl-GD2, folate receptor beta, TEM1/CD248, CD33, CD123, CD133, CD135, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, GFRalpha4; GPC3, CDH3, B7H3; FGFR1, SSTR2, CECAM6, GA733, and gp120.
9. The multispecific antibody of item 8, wherein said TAA is selected from HER2 and mesothelin, in particular HER2.
10. The multispecific antibody of any one of the preceding items further comprising a third domain specifically binding to an immune cell antigen, in particular wherein said immune cell antigen is present on T cell or NK cell.
11. The multispecific antibody of item 10, wherein said third domain is specifically binding to an immune cell antigen, which is a stimulatory or co-stimulatory molecule of said immune cell.
12. The multispecific antibody of item 11, wherein said third domain is an agonist and said immune cell antigen is a stimulatory immune cell antigen.
13. The multispecific antibody of item 12, wherein said stimulatory immune cell antigen is selected from the group consisting of CD3 and CD16.
14. The multispecific antibody of item 13, wherein said stimulatory immune cell antigen is CD3, in particular CD38.
15. The multispecific antibody of item 11, wherein said third domain is an agonist and said immune cell antigen is a co-stimulatory immune cell antigen.
16. The multispecific antibody of item 15, wherein said co-stimulatory immune cell antigen is selected from the group consisting of CD137, CD28, ICOS, HVEM, CD27, OX40, DR3, GITR, CD30, SLAM, CD2, 2B4, TIM1, TIM2, and CD226.
17. The multispecific antibody of item 16, wherein said stimulatory immune cell antigen is CD137.
18. The multispecific antibody of item 17, wherein said third domain specifically binds to CD137 at an epitope comprised in the distal part of the extracellular domain of CD137, particularly within the cysteine-rich domains CRD1 and/or CRD2, more particularly within amino acid residues 24-86 of SEQ ID NO: 153, provided that amino acid residue Asn42 of CD137 is not a critical residue for binding.
19. The multispecific antibody of item 11, wherein said third domain is an inhibitor and said immune checkpoint antigen is an inhibitory immune cell antigen.
20. The multispecific antibody of item 19, wherein said inhibitory immune cell antigen is selected from the group consisting of cytotoxic T-lymphocyte-associated protein 4 (CTLA4), PD-1, lymphocyte-activation gene 3, and T-cell immunoglobulin mucin-3, BTLA, TIM3, TIGIT, CD160, LAG3, LAIR1, B7-1, and B7-H1.
21. The multispecific antibody of any one of the preceding items further comprising a domain specifically binding to human serum albumin (HSA).
22. The multispecific antibody of any one of the preceding items, wherein said domains are capable of binding to their respective antigens simultaneously.
23. The multispecific antibody of any one of the preceding items, wherein said domains are independently selected from the group consisting of a Fab, an Fv, an scFv, dsFv, an scAb, STAB, a single domain antibody (sdAb or dAb), a single domain heavy chain antibody, a single domain light chain antibody, a VHH, and a single domain antibody based on the VNAR structure from shark.

24. The multispecific antibody of any one of the preceding items, wherein said multispecific antibody is in a format selected from the group consisting of a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH3-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs); scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH and DuoBodies.

25. The multispecific antibody of any one of the preceding items, wherein said antibody does not comprise an immunoglobulin Fc region polypeptide, and, optionally, does not comprise CH1 and/or CL regions.

26. The multispecific antibody of any one of the preceding items, wherein said antibody comprises CH1 and/or CL regions, and optionally comprises an immunoglobulin Fc region polypeptide.

27. The multispecific antibody of any one of the preceding items, wherein said antibody is monovalent for each specificity.

28. The multispecific antibody of any one of the preceding items, wherein said antibody is a scDb-scFv, tribody, DVD-tribody, MATCH, in particular wherein said multispecific antibody is in a MATCH or tribody format, more particularly wherein said multispecific antibody is in a MATCH format, more particularly wherein said multispecific antibody is a MATCH3 or a MATCH4.

29. The multispecific antibody of any one of items 5 to 28, wherein:

a. said first domain binds to human PD-L1 with a dissociation constant (KD) of 100 nM to 1000 nM, e.g., of 100 nM to 900 nM, of 150 nM to 850 nM, of 200 nM to 800 nM, of 250 nM to 750 nM, of 300 nM to 700 nM, preferably of 350 nM to 650 nM, more preferably of 400 nM to 600 nM, in particular as measured by SPR;

b. said first domain, when in scFv format, does not bind to cells expressing PD-L1, in particular as determined by flow cytometry, in particular wherein said scFv is at a concentration of less than 100 μg/ml;

c. said first domain, when in scFv format, (i) does not neutralize PD-L1 binding to PD-1, in particular as determined by NFAT reporter gene assay, or (ii) neutralizes PD-L1 binding to PD-1 with a potency relative to that of avelumab (relative potency), as determined by NFAT reporter gene assay, of less than 0.001, preferably less than 0.0005, and wherein said relative potency is the ratio of the $IC_{50}$ value in ng/ml of avelumab as measured in the NFAT reporter gene assay to the $IC_{50}$ value in ng/ml of said scFv as measured in the NFAT reporter gene assay;

30. The multispecific antibody of any one of items 5 to 29, wherein said multispecific antibody (i) in the presence of TAA−/PD-L1+ cells, has the ability to block interaction between PD-L1 and PD-1 with a potency relative to that of avelumab (relative potency), as determined by flow cytometry assay, of less than 0.001, preferably less than 0.0005, and wherein said relative potency is the ratio of the IC50 value in ng/ml of avelumab as measured in the flow cytometry assay to the IC50 value in ng/ml of said multispecific antibody as measured in flow cytometry assay; and (ii) in the presence of TAA+/PD-L1+ cells, has the ability to block interaction between PD-L1 and PD-1 with a potency relative to that of avelumab (relative potency), as determined by flow cytometry assay, of more than 0.01, preferably more than 0.05, more preferably more than 0.1, and wherein said relative potency is the ratio of the IC50 value in ng/ml of avelumab as measured in the flow cytometry assay to the IC50 value in ng/ml of said multispecific antibody as measured in flow cytometry assay.

31. The multispecific antibody of any one of items 5 to 30, wherein:

a. said first domain, when in scFv format, has a melting temperature (Tm), determined by differential scanning fluorimetry, of at least 65° C., preferably at least 70° C., in particular wherein said scFv is formulated in 50 mM phosphate-citrate buffer at pH 6.4, 150 mM NaCl;

b. said first domain, when in scFv format, has a loss in monomer content, after four consecutive freeze-thaw cycles, of less than 3%, preferably less than 1%, when said scFv is at a starting concentration of 10 mg/ml, in particular wherein said scFv is formulated in 50 mM phosphate citrate buffer with 150 mM NaCl at pH 6.4; and c. said first domain, when in scFv format, has a loss in monomer content, after storage for at least two weeks, particularly for at least four weeks, at 4° C., of less than 10%, e.g., less than 9%, less than 8%, less than 7%, less than 6%, preferably less than 5%, when said scFv is at a starting concentration of 10 mg/ml, and in particular wherein said scFv is formulated in 50 mM phosphate citrate buffer with 150 mM NaCl at pH 6.4.

32. The multispecific antibody of any one of the preceding items wherein each domain comprises a heavy chain variable region (VH) and a light chain variable region (VL), wherein:

a. said VH comprises, in sequence, the three complementary determining regions HCDR1, HCDR2 and HCDR3, and b. said VL comprises, in sequence, the three complementary determining regions LCDR1, LCDR2 and LCDR3.

33. The multispecific antibody of any one of the preceding items, wherein said first domain specifically binding to said tumor-associated immune checkpoint antigen, and/or said second domains specifically binding to said TAA, and, optionally, said third domain specifically binding to an immune cell antigen, and, optionally, a further domain specifically binding to human serum albumin (HSA) comprise(s) a light chain variable region (VL) and wherein said VL comprises $V_K$ frameworks FR1, FR2 and FR3, particularly $V_K1$ or $V_K3$ FR1 to FR3, preferably $V_K1$ FR1 to FR3, and a framework FR4, which is selected from a $V_K$ FR4, particularly $V_K$1 FR4, $V_K$3 FR4, and Vλ FR4, particularly Vλ FR4 comprising the amino acid sequence having at least 80, particularly at least 90 percent identity to an amino acid sequence selected from any of SEQ ID NO: 145 to SEQ ID NO: 152, preferably Vλ FR4 as set forth in any of SEQ ID NO: 145 to SEQ ID NO: 152, preferably Vλ FR4 as set forth in SEQ ID NO: 145, 146 or 152, more preferably Vλ FR4 as set forth in SEQ ID NO: 146 or 152.

34. The multispecific antibody of any one of the preceding items, wherein said first domain comprises HCDR1, HCDR2, and HCDR3 sequences of SEQ ID NOs: 1, 2, and 3, respectively, and LCDR1, LCDR2, and LCDR3 sequences of SEQ ID NOs: 5, 6, and 7, wherein one or more of said CDR sequences optionally comprises one or two mutations, particularly mutations to an alanine residue, more particularly wherein: (i) said LCDR3 comprises Q108A (according to AHo numbering), (ii) said LCDR3 comprises G109A (according to AHo numbering), or (iii) said LCDR3 comprises Q108A and G109A (according to AHo numbering), and/or (iv) said HCDR3 comprises Y112A (according to AHo numbering).

35. The multispecific antibody of item 34, wherein said first domain comprises HCDR1, HCDR2, and HCDR3 sequences of SEQ ID NOs: 1, 2, and 3, respectively, and LCDR1, LCDR2, and LCDR3 sequences of SEQ ID NOs: 5, 6, and 9.

36. The multispecific antibody of item 34, wherein said first domain comprises HCDR1, HCDR2, and HCDR3 sequences of SEQ ID NOs: 1, 2, and 3, respectively, and LCDR1, LCDR2, and LCDR3 sequences of SEQ ID NOs: 5, 6, and 10.

37. The multispecific antibody of item 35 or item 36, wherein said first domain comprises a heavy chain variable region (VH) and wherein said VH is VH3 or VH4, preferably VH4.

38. The multispecific antibody of item 35, wherein said antibody comprises a VH comprising an amino acid sequence that is at least 90 percent, in particular at least 95 percent identical to the amino acid sequence SEQ ID NO: 11; and a VL comprising an amino acid sequence that is at least 90 percent, in particular at least 95 percent identical to the amino acid sequence SEQ ID NO: 15.

39. The multispecific antibody of item 38 comprising a VH sequence of SEQ ID NO: 11 and a VL sequence of SEQ ID NO: 15.

40. The multispecific antibody of item 36, wherein said antibody comprises a VH comprising an amino acid sequence that is at least 90 percent, in particular at least 95 percent identical to the amino acid sequence SEQ ID NO: 11; and a VL comprising an amino acid sequence that is at least 90 percent, in particular at least 95 percent identical to the amino acid sequence SEQ ID NO: 16.

41. The multispecific antibody of item 40, comprising a VH sequence of SEQ ID NO: 11 and a VL sequence of SEQ ID NO: 16.

42. The multispecific antibody of any one of the preceding items, wherein said second domain comprises (i) HCDR1, HCDR2, and HCDR3 sequences of SEQ ID NOs: 17, 18 and 19, respectively, and LCDR1, LCDR2, and LCDR3 sequences of SEQ ID NOs: 20, 21 and 22, or, in particular, (ii) HCDR1, HCDR2, and HCDR3 sequences of SEQ ID NOs: 27, 28 and 29, respectively, and LCDR1, LCDR2, and LCDR3 sequences of SEQ ID NOs: 30, 31 and 32, wherein one or more of said CDR sequences optionally comprises one or two mutations, particularly mutations to an alanine residue.

43. The multispecific antibody of item 42, wherein said second domain comprises a VH comprising an amino acid sequence that is (i) at least 90 percent, particularly at least 95 percent identical to the amino acid sequence SEQ ID NO: 23; and a VL comprising an amino acid sequence that is at least 90 percent, particularly at least 95 percent identical to the amino acid sequence SEQ ID NO: 25, in particular wherein said VH comprises Cys at the position 51, and said VL comprises Cys at the position 141 (AHo numbering), or, in particular, (ii) at least 90 percent, particularly at least 95 percent identical to the amino acid sequence SEQ ID NO: 33; and a VL comprising an amino acid sequence that is at least 90 percent, particularly at least 95 percent identical to the amino acid sequence SEQ ID NO: 35, in particular wherein said VH comprises Cys at the position 51, and said VL comprises Cys at the position 141 (AHo numbering).

44. The multispecific antibody of item 43 comprising (i) a VH sequence of SEQ ID NO: 24 and a VL sequence of SEQ ID NO: 26, or (ii) a VH sequence of SEQ ID NO: 34 and a VL sequence of SEQ ID NO: 36, particularly a VH sequence of SEQ ID NO: 34 and a VL sequence of SEQ ID NO: 36.

45. The multispecific antibody of any one of items 10 to 44, wherein said third domain (i) is directed at CD3, in particular wherein said third domain comprises HCDR1, HCDR2, and HCDR3 sequences of SEQ ID NOs: 37, 38 and 39, respectively, and LCDR1, LCDR2, and LCDR3 sequences of SEQ ID NOs: 40, 41 and 42, or (ii) is directed at CD137, in particular wherein said third domain comprises HCDR1, HCDR2, and HCDR3 sequences of SEQ ID NOs: 71, 72 and 73, respectively, and LCDR1, LCDR2, and LCDR3 sequences of SEQ ID NOs: 74, 75 and 76, wherein one or more of said CDR sequences optionally comprises one or two mutations, particularly mutations to an alanine residue.

46. The multispecific antibody of item 45, wherein said third domain (i) is directed at CD3 and comprises a VH comprising an amino acid sequence that is at least 90 percent, in particular at least 95 percent identical to the amino acid sequence SEQ ID NO: 43; and a VL comprising an amino acid sequence that is at least 90 percent, in particular at least 95 percent identical to the amino acid sequence SEQ ID NO: 44, or (ii) is directed at CD137 and comprises a VH comprising an amino acid sequence that is at least 90 percent, in particular at least 95 percent identical to the amino acid sequence SEQ ID NO: 77; and a VL comprising an amino acid sequence that is at least 90 percent, in particular at least 95 percent identical to the amino acid sequence SEQ ID NO: 78.

47. The multispecific antibody of item 46 (i) is directed at CD3 and comprises a VH sequence of SEQ ID NO: 43 and a VL sequence of SEQ ID NO: 44, or (ii) is directed at CD137 and comprises a VH sequence of SEQ ID NO: 77 and a VL sequence of SEQ ID NO: 78.

48. The multispecific antibody of any one of items 21 to 28, wherein said domain specifically binding to HSA comprises (i) HCDR1, HCDR2, and HCDR3 sequences of SEQ ID NOs: 45, 46 and 47, respectively, and LCDR1, LCDR2, and LCDR3 sequences of SEQ ID NOs: 48, 49 and 50, (ii) HCDR1, HCDR2, and HCDR3 sequences of SEQ ID NOs: 53, 54 and 55, respectively, and LCDR1, LCDR2, and LCDR3 sequences of SEQ ID NOs: 56, 57 and 58, or (iii) HCDR1, HCDR2, and HCDR3 sequences of SEQ ID NOs: 61, 62 and 63, respectively, and LCDR1, LCDR2, and LCDR3 sequences of SEQ ID NOs: 64, 65 and 66, wherein one or more of said CDR sequences optionally comprises one or two mutations, particularly mutations to an alanine residue.

49. The multispecific antibody of item 48, wherein said domain specifically binding to HSA comprises (i) a VH comprising an amino acid sequence that is at least 90 percent, in particular at least 95 percent identical to the amino acid sequence SEQ ID NO: 51; and a VL comprising an amino acid sequence that is at least 90 percent, in particular at least 95 percent identical to the amino acid sequence SEQ ID NO: 52; (i) a VH comprising an amino acid sequence that is at least 90 percent, in particular at least 95 percent identical to the amino acid sequence SEQ ID NO: 59; and a VL comprising an amino acid sequence that is at least 90 percent, in particular at least 95 percent identical to the amino acid sequence SEQ ID NO: 60; (i) a VH comprising an amino acid sequence that is at least 90 percent, in particular at least 95 percent identical to the amino acid sequence SEQ ID NO: 67; and a VL comprising an amino acid sequence that is at least 90 percent, in particular at least 95 percent identical to the amino acid sequence SEQ ID NO: 69; or (i) a VH comprising an amino acid sequence that is at least 90 percent, in particular at least 95 percent identical to the amino acid sequence SEQ ID NO: 68; and a VL comprising an amino acid sequence that is at least 90 percent, in particular at least 95 percent identical to the amino acid sequence SEQ ID NO: 70.

50. The multispecific antibody of item 49 comprising (i) a VH sequence of SEQ ID NO: 51 and a VL sequence of SEQ ID NO: 52; (ii) a VH sequence of SEQ ID NO: 59 and a VL sequence of SEQ ID NO: 60; (iii) a VH sequence of SEQ ID NO: 67 and a VL sequence of SEQ ID NO: 69; or (iv) a VH sequence of SEQ ID NO: 68 and a VL sequence of SEQ ID NO: 70.

51. The multispecific antibody of any of the preceding items, wherein the antibody comprises a combination of two chains, each having an amino acid sequence having at least 80% identity, particularly at least 90% identity, more particularly at least 95% identity, including 100% identity (i) to the sequences of a combination of chains selected from SEQ ID NOs: 79 and 80; SEQ ID NOs: 81 and 82, SEQ ID NOs: 83 and 84, SEQ ID NOs: 85 and 86, SEQ ID NOs: 87 and 88, SEQ ID NOs: 89 and 90, SEQ ID NOs: 91 and 92, SEQ ID NOs: 93 and 94, SEQ ID NOs: 95 and 96, SEQ ID NOs: 97 and 98, SEQ ID NOs: 99 and 100, SEQ ID NOs: 101 and 102, SEQ ID NOs: 103 and 104, SEQ ID NOs: 105 and 106, SEQ ID NOs: 107 and 108, SEQ ID NOs: 109 and 110, SEQ ID NOs: 111 and 112, SEQ ID NOs: 113 and 114, SEQ ID NOs: 123 and 124, SEQ ID NOs: 125 and 126, SEQ ID NOs: 127 and 128, SEQ ID NOs: 129 and 130, SEQ ID NOs: 131 and 132, SEQ ID NOs: 133 and 134, and SEQ ID NOs: 135 and 136, or to the combination of sequences comprised in one of the sequences selected from SEQ ID NOs: 115 to 136, in particular the combination of chains of SEQ ID NOs: 123 and 124, or of SEQ ID NOs: 127 and 128, and wherein the antibody comprises (i) a first domain specifically binding PD-L1 comprising HCDR1, HCDR2, and HCDR3 sequences of SEQ ID NOs: 1, 2, and 3, respectively, or of SEQ ID NOs: 1, 2, and 4, respectively, and LCDR1, LCDR2, and LCDR3 sequences of SEQ ID NOs: 5, 6, and 7, respectively, SEQ ID NOs: 5, 6, and 8, respectively, SEQ ID NOs: 5, 6, and 9, respectively, or, in particular SEQ ID NOs: 5, 6, and 10, respectively, and (ii) a second domain specifically binding HER2 comprising (i) HCDR1, HCDR2, and HCDR3 sequences of SEQ ID NOs: 17, 18 and 19, respectively, and LCDR1, LCDR2, and LCDR3 sequences of SEQ ID NOs: 20, 21 and 22, respectively, or, in particular, (ii) HCDR1, HCDR2, and HCDR3 sequences of SEQ ID NOs: 27, 28 and 29, respectively, and LCDR1, LCDR2, and LCDR3 sequences of SEQ ID NOs: 30, 31 and 32, respectively (iii) optionally, a third domain specifically binding (i) CD3 comprising HCDR1, HCDR2, and HCDR3 sequences of SEQ ID NOs: 37, 38 and 39, respectively, and LCDR1, LCDR2, and LCDR3 sequences of SEQ ID NOs: 40, 41 and 42, respectively, or (ii) CD137 comprising HCDR1, HCDR2, and HCDR3 sequences of SEQ ID NOs: 71, 72 and 73, respectively, and LCDR1, LCDR2, and LCDR3 sequences of SEQ ID NOs: 74, 75 and 76, respectively, (iv) optionally, a further domain specifically binding HSA comprising (i) HCDR1, HCDR2, and HCDR3 sequences of SEQ ID NOs: 45, 46 and 47, respectively, and LCDR1, LCDR2, and LCDR3 sequences of SEQ ID NOs: 48, 49 and 50, respectively, (ii) HCDR1, HCDR2, and HCDR3 sequences of SEQ ID NOs: 53, 54 and 55, respectively, and LCDR1, LCDR2, and LCDR3 sequences of SEQ ID NOs: 56, 57 and 58, respectively; or (iii) HCDR1, HCDR2, and HCDR3 sequences of SEQ ID NOs: 61, 62 and 63, respectively, and LCDR1, LCDR2, and LCDR3 sequences of SEQ ID NOs: 64, 65 and 66, respectively.

52. A combination comprising (i) the multispecific antibody of any one of items 1 to 51 and (ii) a second compound selected from (iia) an antibody directed at a TAA, in particular an antibody directed at HER2, in particular wherein the antibody is trastuzumab, (iib) a modulator of an immune checkpoint antigen, in particular wherein said immune checkpoint antigen is not a tumor-associated immune checkpoint antigen, and/or in particular wherein said immune checkpoint antigen is present on T cell or NK cell, and (iic) a modulator of angiogenesis.

53. The combination of item 52, wherein said modulator is an antibody.

54. The combination of item 52 or 53, wherein said modulator is an agonist and said immune checkpoint antigen is an immune cell antigen.

55. The combination of item 54, wherein said immune cell antigen is selected from the group consisting of CD28, ICOS, HVEM, CD27, OX40, DR3, GITR, CD30, SLAM, CD2, 2B4, TIM1, TIM2, CD226, CTLA4, PD-1, lymphocyte-activation gene 3, and T-cell immunoglobulin mucin-3, BTLA, TIM3, TIGIT, CD160, LAG3, LAIR1, B7-1, and B7-H1.

56. The combination of item 55, wherein said stimulatory immune cell antigen is CD3 or CD137, in particular CD3.

57. The combination of item 52 or 53, wherein said modulator is an inhibitor and said immune cell antigen is an inhibitory immune checkpoint antigen.

58. The combination of item 57, wherein said inhibitory immune cell antigen is selected from the group consisting of cytotoxic T-lymphocyte-associated protein 4 (CTLA4), PD-1, lymphocyte-activation gene 3, and T-cell immunoglobulin mucin-3, preferably wherein said inhibitory immune checkpoint antigen is cytotoxic T-lymphocyte-associated protein 4 (CTLA4), more preferably wherein said modulator is ipilimumab.
59. A combination comprising (i) the multispecific antibody of any one of items 1 to 51 and (ii) an antibody directed against a TAA.
60. The combination of item 59, wherein said TAA is selected from HER2 and mesothelin, particularly HER2, particularly wherein said antibody is trastuzumab.
61. A pharmaceutical composition comprising the multispecific antibody of any one of items 1 to 51, or the combination of any one of items 52 to 60, and a pharmaceutically acceptable carrier.
62. A PD-L1-binding domain as defined in any one of items 29, 30, and 34 to 41.
63. A HER2-binding domain as defined in any one of items 42 to 44.
64. A CD3-binding domain as defined in any one of items 45(i) to 47(i).
65. A CD137-binding domain as defined in any one of items 45(ii) to 47(ii).
66. An HSA-binding domain as defined in any one of items 48 to 50.
67. The multispecific antibody of any one of items 1 to 51, the combination of any one of items 52 to 60, or a binding domain of any one of items 62 to 66 for use as a medicament.
68. The multispecific antibody of any one of items 1 to 51, the combination of any one of items 52 to 60, the pharmaceutical composition of item 61, or a binding domain of any one of items 62 to 66 for use in treatment of a cancer in a subject in need thereof.
69. Use of the multispecific antibody of any one of items 1 to 51, the combination of any one of items 52 to 60, the pharmaceutical composition of item 61, or a binding domain of any one of items 62 to 66 for treating a cancer in a subject in need thereof.
70. Use of the multispecific antibody of any one of items 1 to 51, the combination of any one of items 52 to 60, the pharmaceutical composition of item 61, or a binding domain of any one of items 62 to 66 in the manufacture of a medicament for treatment of a cancer, in a subject in need thereof.
71. A method of treating a cancer in a subject in need thereof comprising administering to the subject a therapeutically effective amount of the multispecific antibody of any one of items 1 to 51, 67 and 68, the combination of any one of items 52 to 60, the pharmaceutical composition of item 61, or a binding domain of any one of items 62 to 66, or the use of items 69 or 70, wherein said cancer is a cancer positive for said TAA and said tumor-associated immune checkpoint antigen, in particular wherein said cancer is TAA*/PDL*, more particularly wherein said cancer is $HER2^{+}/PD\text{-}L1^{+}$.
72. The multispecific antibody of item 68, the use of items 69 or 70, or the method of item 71, wherein said cancer is a cancer positive HER2 and PD-L1, and wherein said cancer is refractory to a standard of care therapy, in particular to trastuzumab.
73. A nucleic acid encoding the multispecific antibody of any one of items 1 to 51 or a binding domain of any one of items 62 to 66.
74. A vector comprising the nucleic acid of item 73.
75. A host cell comprising the nucleic acid of item 73 or the vector of item 74.
76. A method of producing the multispecific antibody of any one of items 1 to 51, a binding domain of any one of items 62 to 66, the method comprising the step of culturing a host cell comprising a nucleic acid or a vector encoding the multispecific antibody of any one of items 1 to 51, a binding domain of any one of items 62 to 66.
77. A kit comprising the multispecific antibody of any one of items 1 to 51, the combination of any one of items 52 to 60, the pharmaceutical composition of item 61, or a binding domain of any one of items 62 to 66.
78. The multispecific antibody of any of items 1 to 50, wherein the antibody comprises a combination of two chains a combination of chains selected from SEQ ID NOs: 79 and 80; SEQ ID NOs: 81 and 82, SEQ ID NOs: 83 and 84, SEQ ID NOs: 85 and 86, SEQ ID NOs: 87 and 88, SEQ ID NOs: 89 and 90, SEQ ID NOs: 91 and 92, SEQ ID NOs: 93 and 94, SEQ ID NOs: 95 and 96, SEQ ID NOs: 97 and 98, SEQ ID NOs: 99 and 100, SEQ ID NOs: 101 and 102, SEQ ID NOs: 103 and 104, SEQ ID NOs: 105 and 106, SEQ ID NOs: 107 and 108, SEQ ID NOs:109 and 110, SEQ ID NOs: 111 and 112, SEQ ID NOs: 113 and 114, SEQ ID NOs: 123 and 124, SEQ ID NOs: 125 and 126, SEQ ID NOs: 127 and 128, SEQ ID NOs: 129 and 130, SEQ ID NOs: 131 and 132, SEQ ID NOs: 133 and 134, and SEQ ID NOs: 135 and 136, or to the combination of sequences comprised in one of the sequences selected from SEQ ID NOs: 115 to 136, in particular the combination of chains of SEQ ID NOs: 123 and 124 or of SEQ ID NOs: 127 and 128.

Figure 5:
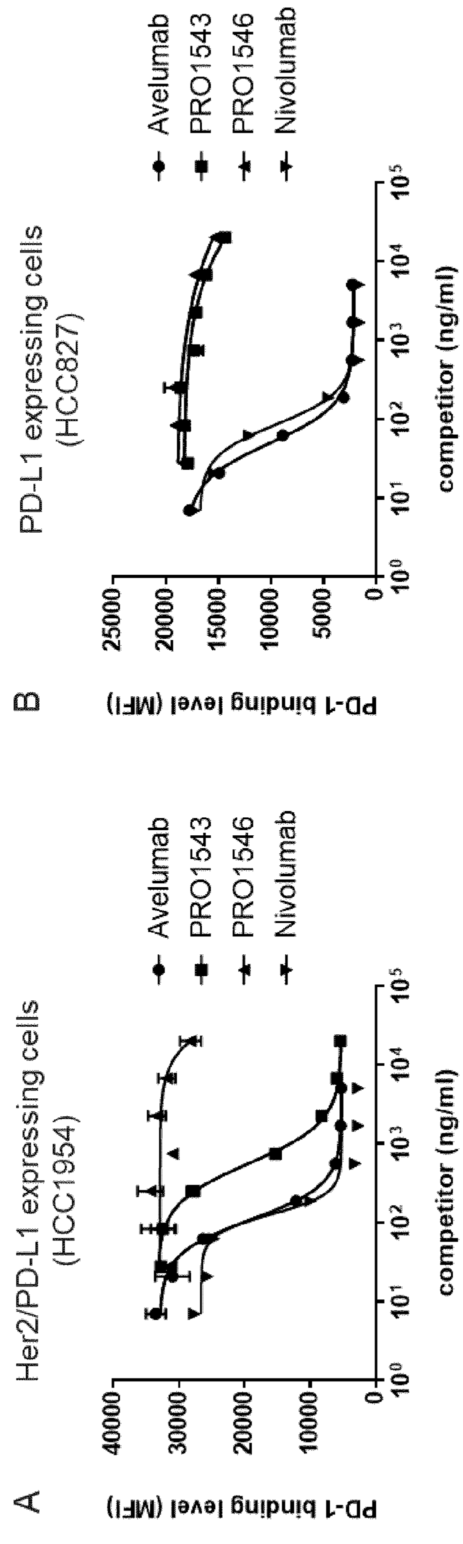

FIG. 5 Blockade of PD-1/PD-L1 interaction on Her2 expressing cells in presence of human serum albumin. A) Inhibition of PD-1 binding to cells expressing PD-L1 and Her2 (HCC1954) in presence of increasing concentrations of avelumab, nivolumab, PRO1543 (Her2×CD3×HSA×PD-L1 low affinity) and PRO1546 (HER2×CD3×HSA×IL23R). B) Inhibition of PD-1 binding to cells expressing PD-L1 without significant expression of Her2 (HCC827). PRO1543 inhibits PD-1 binding to PD-L1 exclusively on PD-L1/high Her2 expressing cells with an $IC_{50}$ value of 600 ng/ml. PRO1546 which does not contain an anti-PD-L1 domain did not affect PD-1 binding on both cell lines. Data were fitted using sigmoidal 4PL fit (GraphPad Prism).

Figure 6:
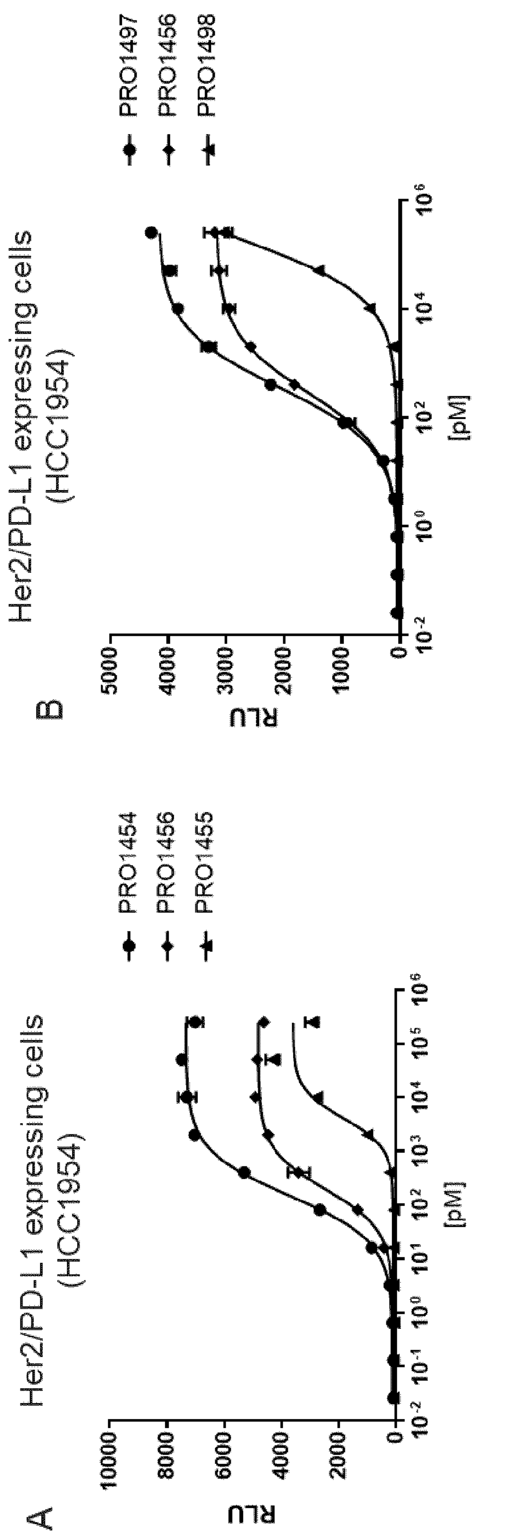

FIG. 6 CD3 activation and concomitant PD-L1 blockade by PRO1454 or PRO1497 assessed in the NFAT-Luciferase reporter gene assay in presence of human serum albumin. A) In the presence of PD-L1/Her2 expressing cells (HCC1954), PRO1454 and PRO1456 activated CD3 signaling in Jurkat cells with similar $EC_{50}$ but the maximal activation was higher for PRO1454, a molecule carrying the low affinity anti-PD-L1 domain, compared to PRO1456 containing an anti-IL23R dummy domain instead of the anti-PD-L1 domain. This suggests that PRO1454 simultaneously blocks PD-L1 and activates CD3 within the immunological synapse in presence of cells co-expressing Her2 and PD-L1. Weaker activation was observed with PRO1455, a molecule carrying no anti-Her2 domain but the low affinity anti-PD-L1 domain (33-03-G02 G109A). B) The Tribody molecule PRO1497 containing the anti-PD-L1 domain carrying two alanine mutations (Q108A and G109A) with at least 50-fold lower affinity than the domain incorporated in molecules tested in A and the corresponding controls were tested. For those molecules simultaneous blockade of PD-L1 and activation of CD3 was observed, since PRO1497, containing the low affinity anti-PD-L1 domain, induced a higher maximal activation than PRO1456 containing the anti-IL23R domain instead. In comparison to PRO1455, PRO1498 triggered a much weaker activation due to the much lower affinity of the incorporated anti-PD-L1 domain. Luminescence was read 5 h after addition of Jurkat reporter cells and data were fitted using sigmoidal 4PL fit (GraphPad Prism).

Figure 7:
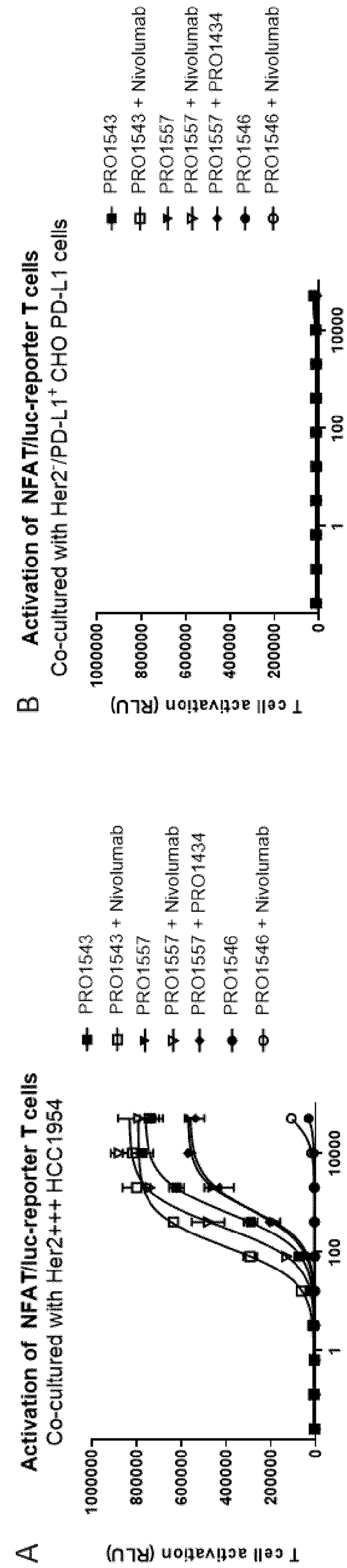

FIG. 7 CD3 activation and concomitant PD-L1 blockade by PRO1543 assessed in the NFAT-Luciferase reporter gene assay in presence of human serum albumin. A) In the presence of PD-1/Her2 expressing cells (HCC1954), PRO1543 and PRO1557 activated CD3 signaling in Jurkat cells with similar $EC_{50}$ but the maximal activation was higher for PRO1543, a molecule carrying the low affinity anti-PD-L1 domain, compared to PRO1557 containing an anti-IL23R dummy domain instead of the anti-PD-L1 domain. This suggests that PRO1543 simultaneously blocks PD-L1 and activates CD3 within the immunological synapse in presence of cells co-expressing Her2 and PD-L1. This observation was further supported by the addition of 1 μg/ml nivolumab to all molecules resulting in similar maximal activation in presence of PRO1557 and PRO1543 as for PRO1543 alone confirming complete PD-L1/PD-1 blockade by PRO1543. No activation was observed with PRO1546, molecule carrying no anti-Her2 domain but the low affinity anti-PD-L1 domain. B) No activation was observed for the molecules carrying an anti-PD-L1 domain (PRO1543 and PRO1546) independently of the presence of the anti-Her2 domain in presence of PD-L1 expressing CHO cells. No activation was seen with PRO1557 since this molecule does not contain an anti-PD-L1 domain. Luminescence was read 5 h after addition of Jurkat reporter cells and data were fitted using sigmoidal 4PL fit (GraphPad Prism).

Figure 8:
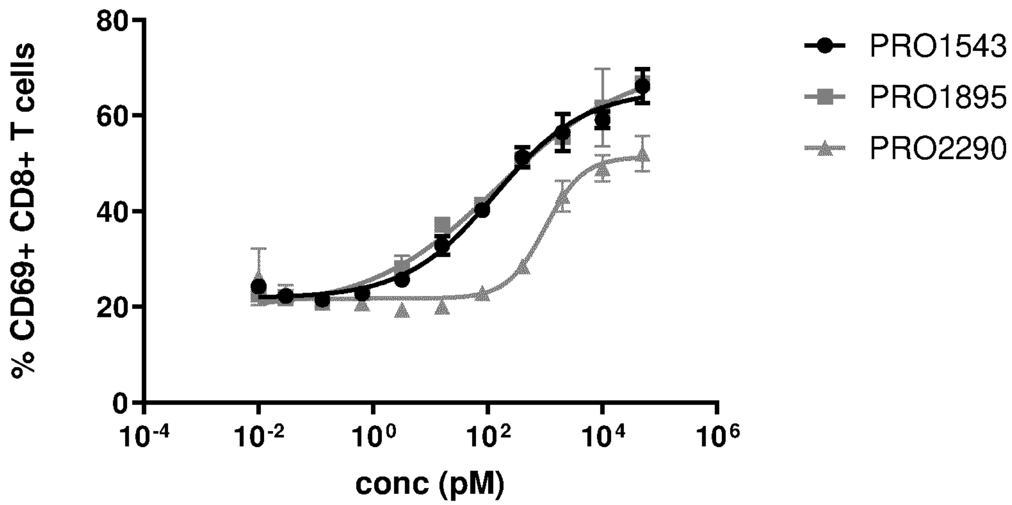

FIG. 8 Activation of CD8+ T cells, as measured by upregulation of CD69, in the presence of PRO1543, PRO1895 and control molecule PRO2290 following co-incubation with HCC827 tumor cells (HER2low, PD-L1+).

Figure 9:
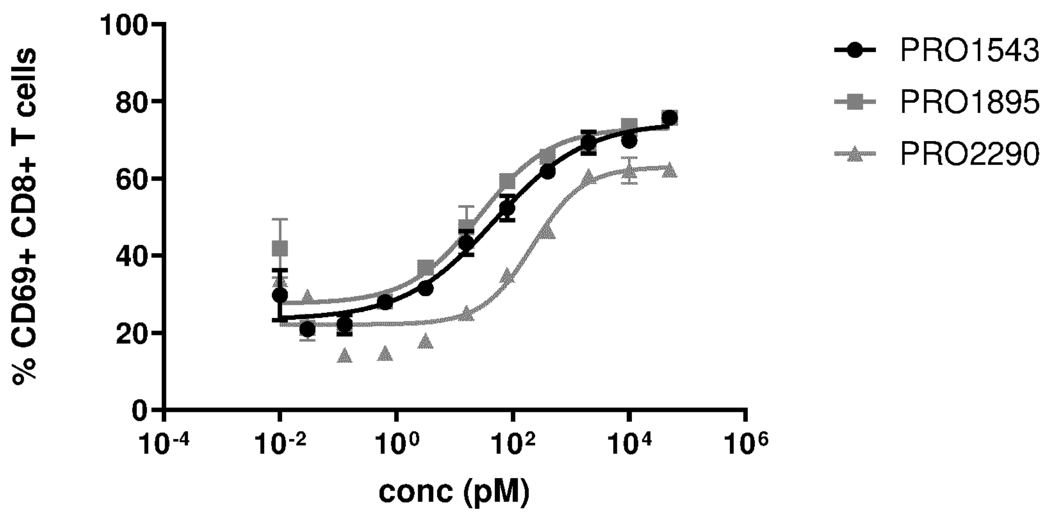

FIG. 9 Activation of CD8+ T cells, as measured by upregulation of CD69, in the presence of PRO1543, PRO1895 and control molecule PRO2290 following co-incubation with HCC1954 tumor cells (HER2high, PD-L1+).

Figure 10:
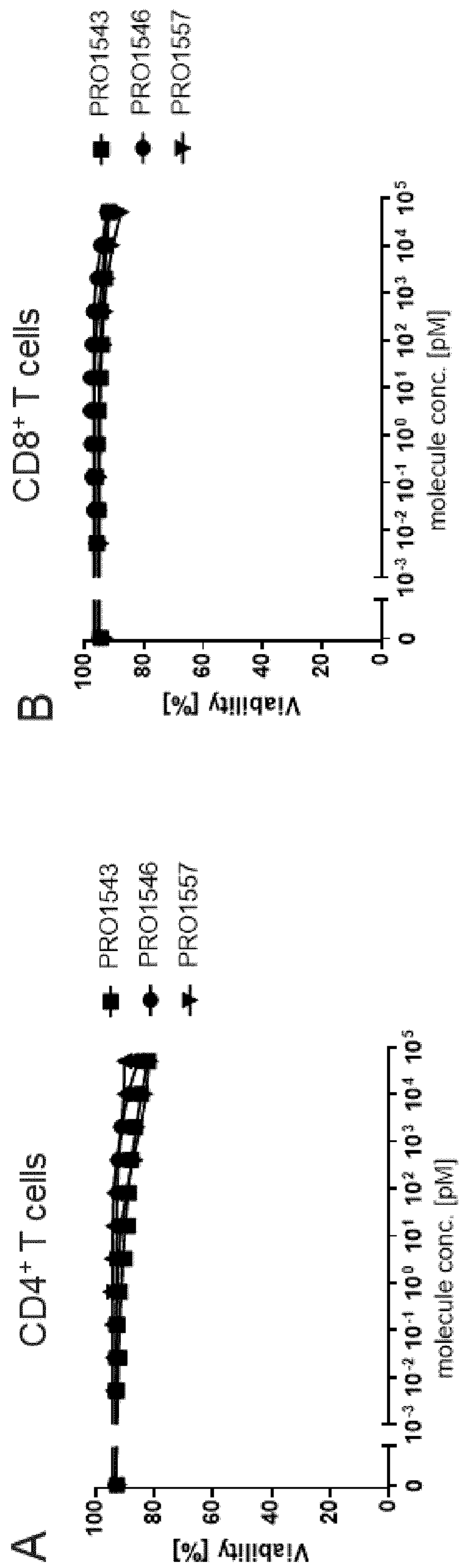

FIG. 10 Viability of CD4+ and CD8+ T cells. CD4+ T cells (A) and CD8+ T cell (B) viability was only reduced by 5 to 10% at the highest concentrations of molecules tested. CD4+ T cells and CD8+ T cells were stained by fluorescently labelled antibodies 40 h after the start of the cytotoxicity assessment of PBMCs in presence of PD-L1/high Her2 expressing cancer cells (HCC1954) and analyzed by flow cytometry. Similar data were obtained after 16 h.

FIG. 11 T cell mediated target cell killing and CD8+ cell activation in presence of A) $Her2^{+++}$/PD-L1 HCC1954 and B) $Her2^{+}$/PD-$L1^{-}$ MCF-7. In this assay, freshly isolated human PBMCs were co-cultured for 16 h with indicated target cells in presence of the different molecules tested. PRO1543 showed a 50 to 100-fold better potency than the Her2/CD3 scDb (PRO957) on $Her2^{+++}$/PD-$L1^{+}$ as compared to PD-L1 negative cells were only a slightly different potency is observed. As the $EC_{50}$ of PD-L1 blockade in these cells is considerably higher than the $EC_{50}$ of target cell lysis, it is highly likely that the improved activity of the molecule containing an anti-PD-L1 domains results from increased avidity. As a consequence, binding to Her2 and PD-L1 double positive cells is stronger than binding to PD-L1 negative cells expressing Her2. This avidity binding increases the therapeutic window as it selectively improves potency on tumor cells (Her2/PD-L1 double positive), but not on PD-L1 negative Her2 expressing normal cells.

Figure 12:
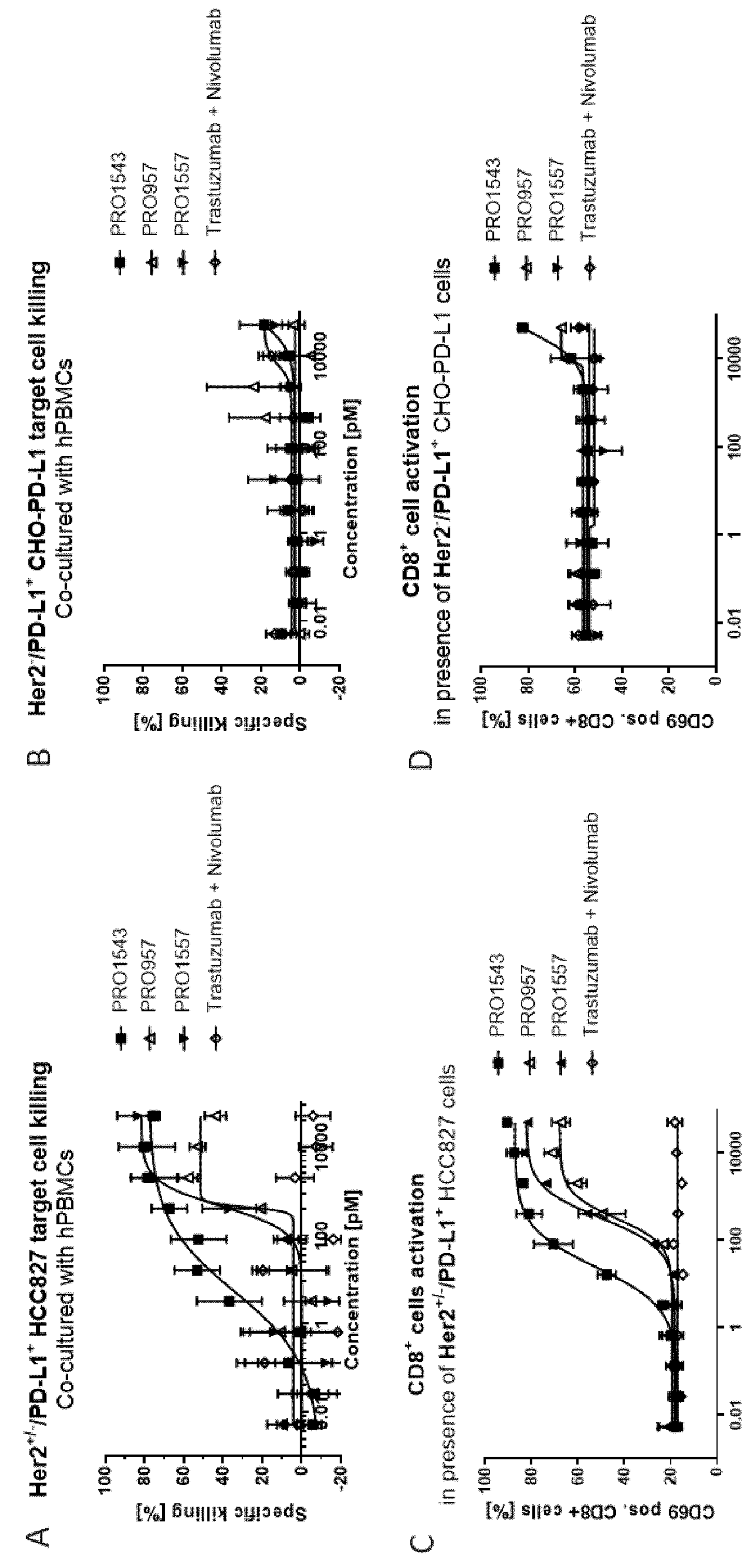

FIG. 12 T cell mediated target cell killing and CD8+ cell activation in presence of A) $Her2^{+/-}$/PD-L1 HCC827 and B) $Her2^{-}$/PD-L1 CHO PD-L1 cells. Freshly isolated human PBMCs were co-cultured for 16 h with indicated target cells in presence of the different molecules. PRO1543 showed a 20-fold better potency than the Her2/CD3 scDb on $Her2^{+/-}$/PD-L1. In presence of Her2 negative PD-L1 positive cells only a minor target cell killing and CD8+ cell activation was observed at high concentrations of the MATCH4 harboring the low affinity PD-L1 domain providing a very large therapeutic window.

Figure 13:
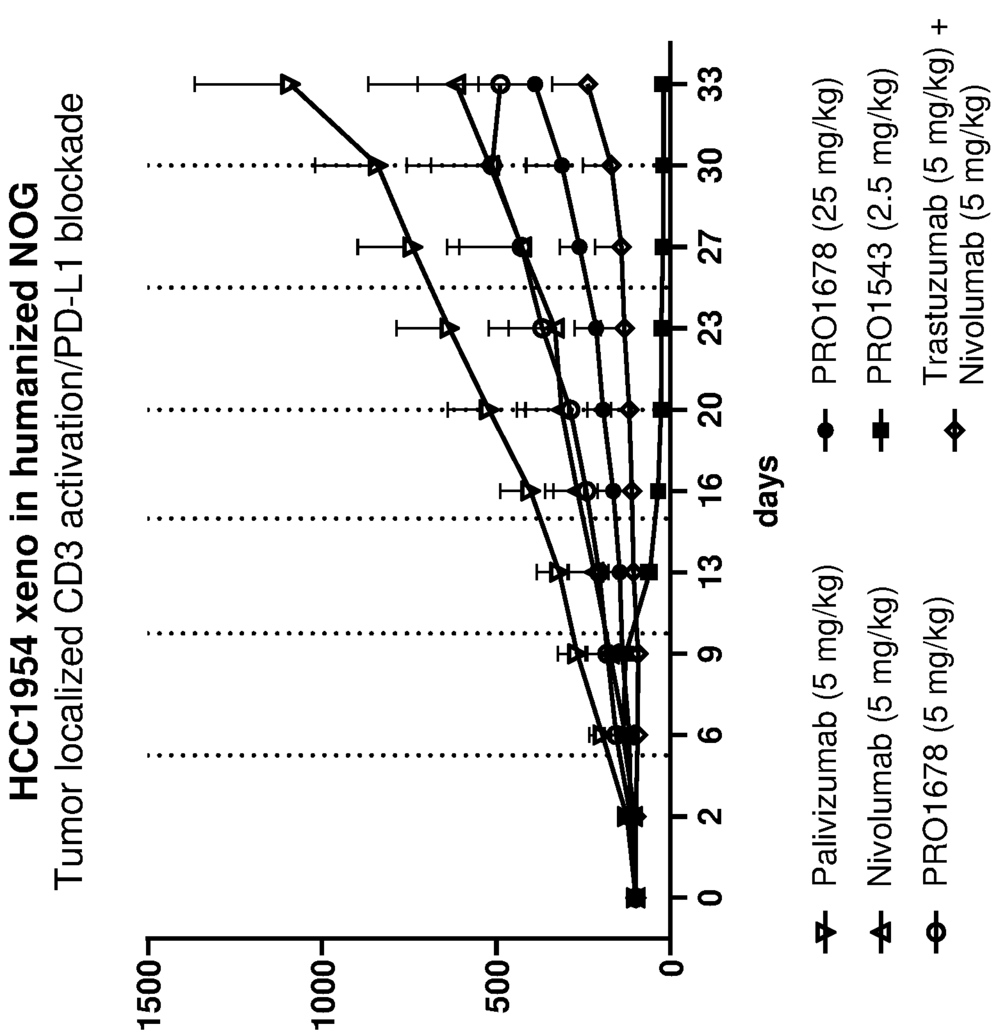

FIG. 13 Human PBMC-substituted NOG mice were engrafted with HCC1954 ductal breast carcinoma cells (n=8 each). Mice were treated on day 0, 5, 10, 15, 20, 25 and 30 (dotted vertical lines). Tumor growth and body weight were recorded twice weekly. PRO1678 scMATCH3 had similar antitumoral effect as nivolumab showing efficient tumor targeted PD-L1 blockade. PRO1543 MATCH4 therapy elicited greater antitumoral efficacy than nivolumab/trastuzumab combination.

Figure 14:
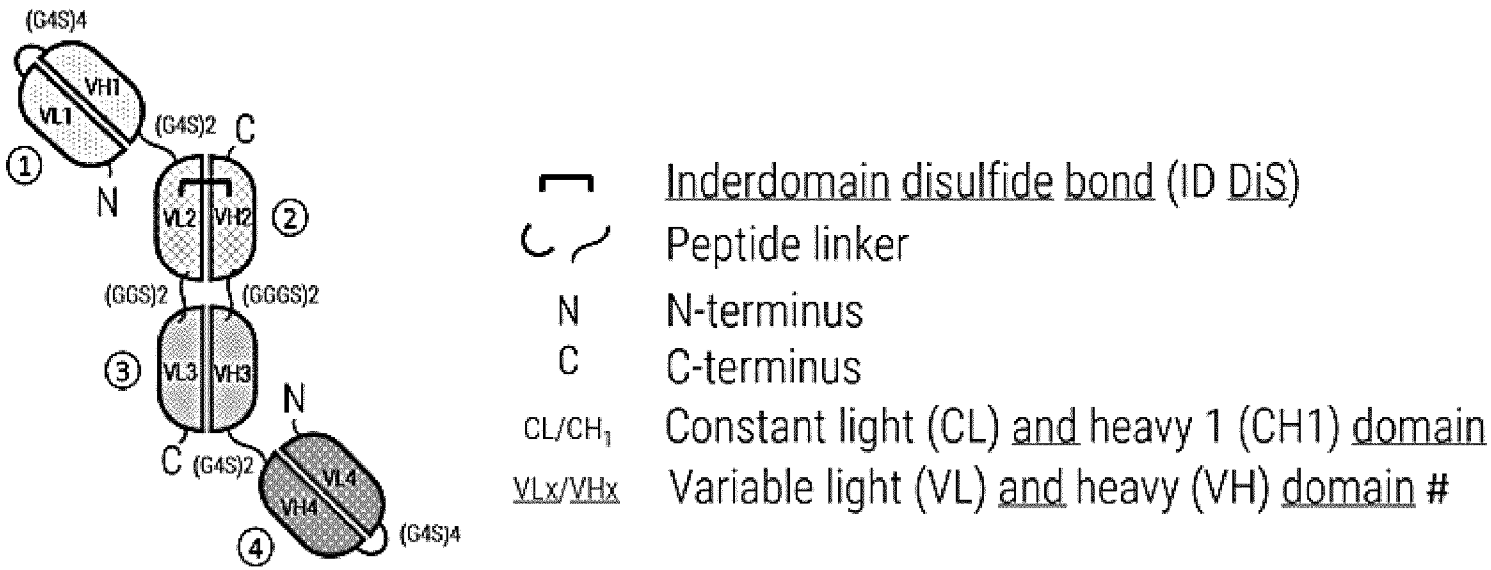

FIG. 14 Design of the multispecific molecules. Schematic representation and description of the three different multispecific formats tribody, DVD-tribody and MATCH-4. Table 25 describes the domain composition of the different molecules produced and their positioning within the molecules. The targets for the different domains are: trastuzumab: Her2; clone 14-11-D07: IL23R; clone 23-13-A01: human/mouse SA; clone 28-21-D09: CD3e; clone 33-02-G02 and mutants thereof: PD-L1. Gly-Ser linker sequences connecting individual domains are indicated in the Figure.

Figure 15:
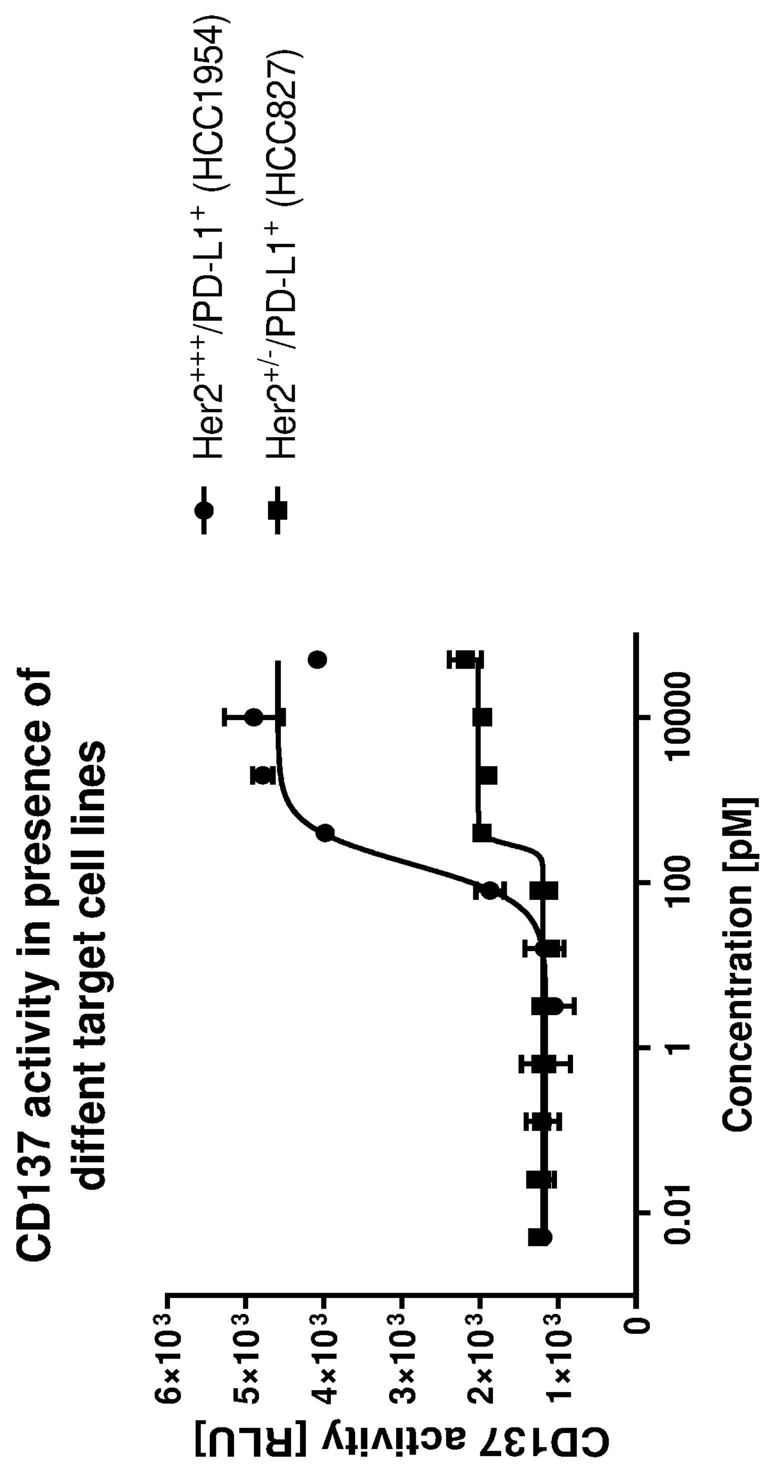

FIG. 15 Effect of PRO1993 on CD137 signal activity in NF-kB Jurkat reporter cells. After 24 h incubation of Jurkat cells with PRO1993 in presence of HCC1954 (high levels of expression for Her2 and PD-L1) and HCC827 (low levels of expression for Her2 but high levels for PD-L1), the activity of CD137 signaling was assessed by detection of luminescence. PRO1993 activated CD137 signaling in the presence of high Her2 expressing HCC1954 cells, whereas in presence of low levels of Her2 expressing HCC827 only a slight activation of CD137 signaling was observed. Data were fitted using sigmoidal 4PL fit (GraphPad Prism).

Figure 16:
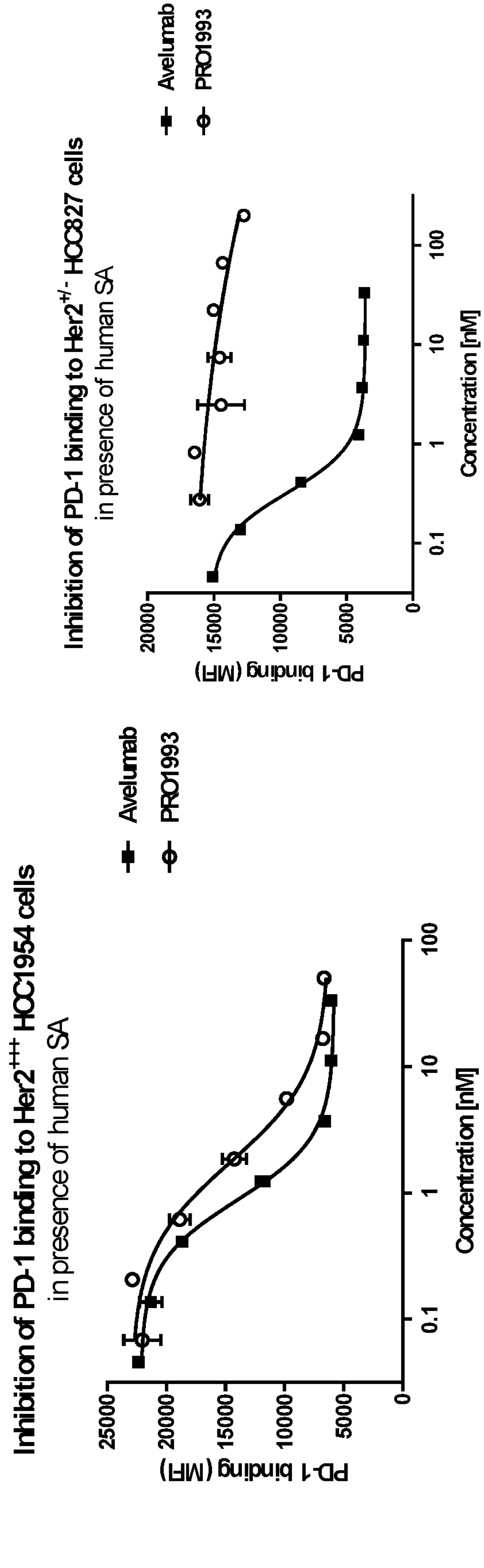

FIG. 16 Blockade of PD-1/PD-L1 interaction on Her2 expressing cells in presence of human serum albumin. A) PD-1 binding level to cells expressing PD-L1 and high Her2 levels (HCC1954) or (B) cells expressing PD-L1 and a lower level of Her2 (HCC827) in presence of increasing concentrations of avelumab and PRO1993 (Her2×CD137×HSA×PD-L1$_{low\ affinity}$). PRO1993 inhibits PD-1 binding to PD-L1 on PD-L1/high Her2 expressing cells with an IC50 value of 166.7 ng/ml whereas no inhibition of PD-1 binding was found on HCC827 cells. For comparison, avelumab inhibit this interaction with an IC50 of 127.7 ng/ml (HCC1954) and 46.03 ng/ml (HCC827). Data were fitted using sigmoidal 4PL fit (GraphPad Prism).

FIG. 17 Design of the scDb-scFv molecules. Schematic representation and description of the scDb-scFv molecules.

Figure 18:
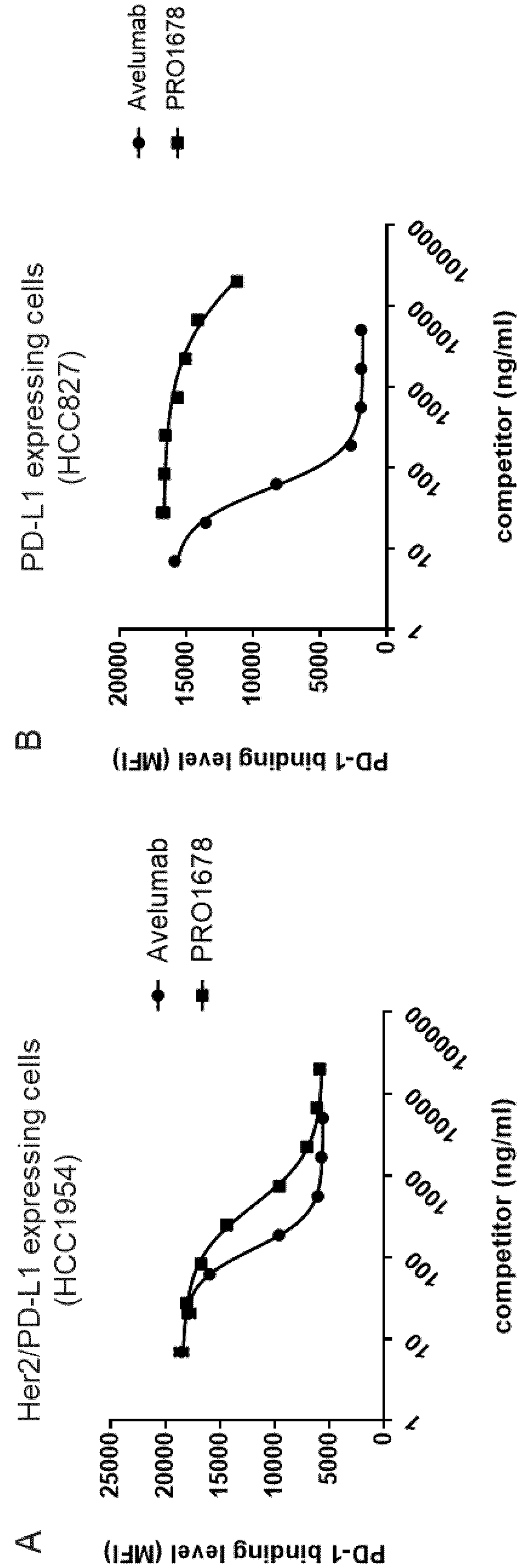

FIG. 18 Blockade of PD-1/PD-L1 interaction on Her2 expressing cells in presence of human serum albumin. A) PD-1 binding level to cells expressing PD-L1 and high Her2 levels (HCC1954) or (B) cells expressing PD-L1 and a lower level of Her2 (HCC827) in presence of increasing concentrations of avelumab and PRO1678 (Her2×HSA×PD-L1$_{low\ affinity}$). PRO1678 inhibits PD-1 binding to PD-L1 with a 100-fold better potency on PD-L1/high Her2 expressing cells than on PD-L1 expressing cells (HCC827) with an $IC_{50}$ value of 428.2 ng/ml. For comparison, avelumab inhibit this interaction with an $IC_{50}$ of 127.7 ng/ml (HCC1954) and 46.03 ng/ml (HCC827). Data were fitted using sigmoidal 4PL fit (GraphPad Prism).

Figure 19:
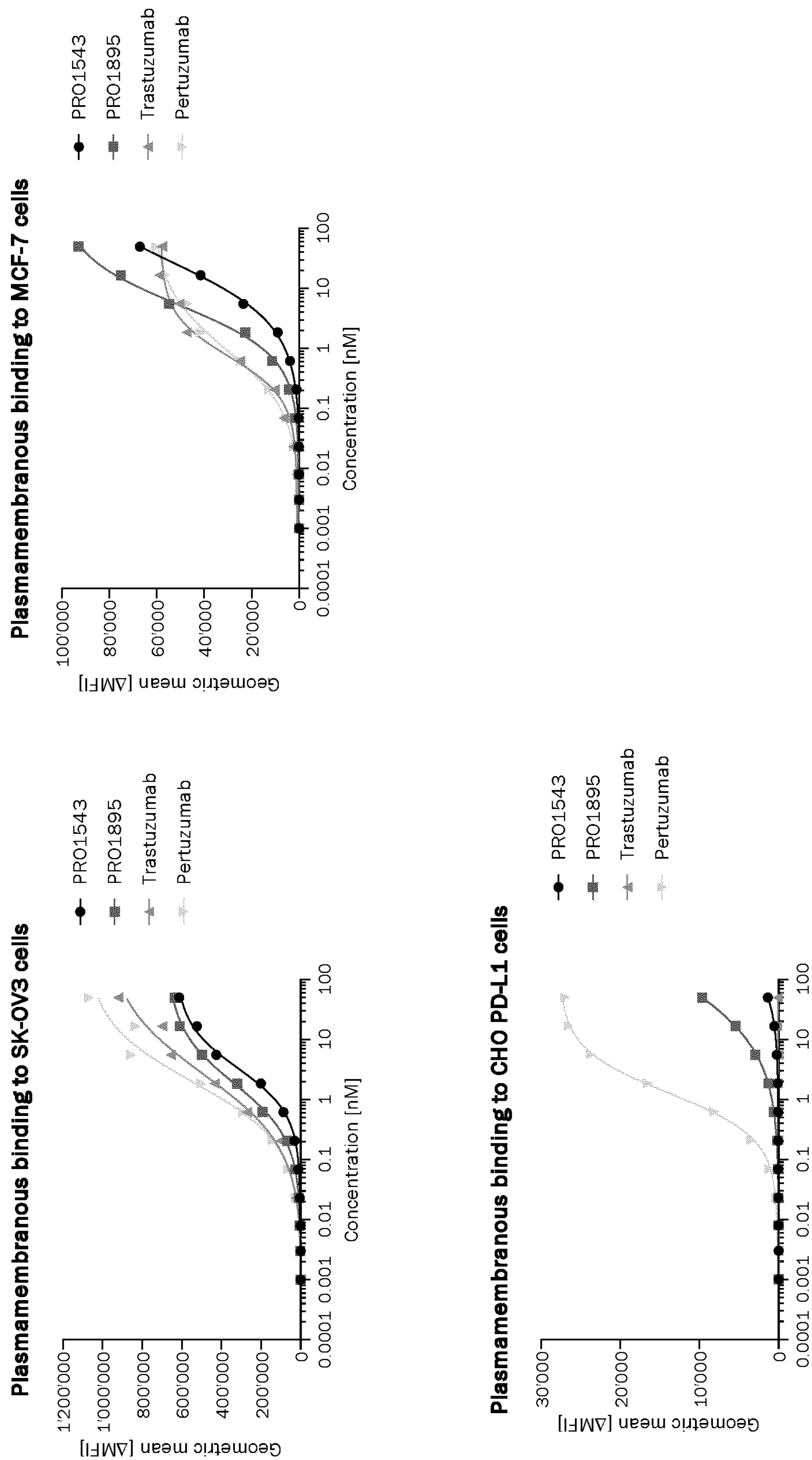

FIG. 19 Plasmamembranous binding of MATCH4 molecules PRO1543 and PRO1895 to SK-OV3, MCF-7 and CHO PD-L1 cells. Concentration-response curves of MATCH4 molecules PRO1543 and PRO1895 and clinical stage anti-HER2 antibodies trastuzumab and pertuzumab to SK-OV3 (upper left), MCF-7 (upper right) and CHO PD-L1 (lower right). MATCH4 molecules bound to SK-OV3 cells expressing high levels of HER2 with an apparent binding affinity comparable to the clinical stage antibodies trastuzumab and pertuzumab. On the other hand, apparent binding affinity of MATCH4 molecules is inferior to trastuzumab and pertuzumab when binding to MCF-7 cells was assessed.

Figure 20:
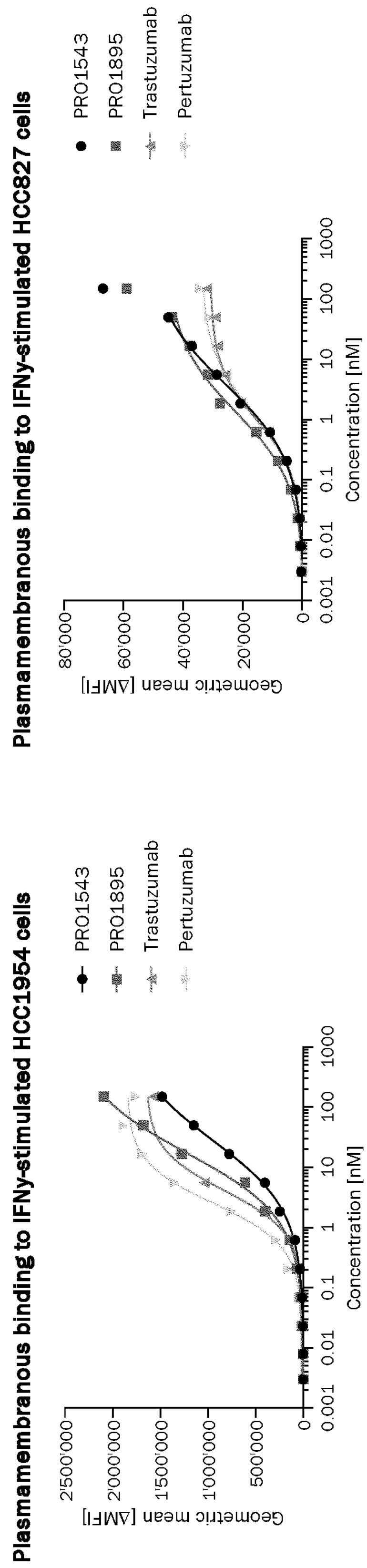

FIG. 20 Plasmamembranous binding of MATCH4 molecules PRO1543 and PRO1895 to IFNy-stimulated HCC1954 and HCC827 cells. Concentration-response curves of MATCH4 molecules PRO1543 and PRO1895 and clinical stage anti-HER2 antibodies trastuzumab and pertuzumab to HCC1954 (left) and HCC827 (right). Cells were stimulated for 24 h with 10 ng/ml of IFNy prior testing in flow cytometry. The apparent binding affinity of MATCH4 molecules is inferior to trastuzumab and pertuzumab when binding to HCC1954 cells that express high levels of HER2 and PD-L1 was assessed. On the other hand, MATCH4 molecules bound to HCC827 cells expressing low levels of HER2 and high levels of PD-L1 with an apparent binding affinity similar to the clinical stage antibodies trastuzumab and pertuzumab (right). Note that in the graph illustrated on the right the highest concentration of PRO1543 and PRO1895 were not used for fitting of the curve.

Figure 21:
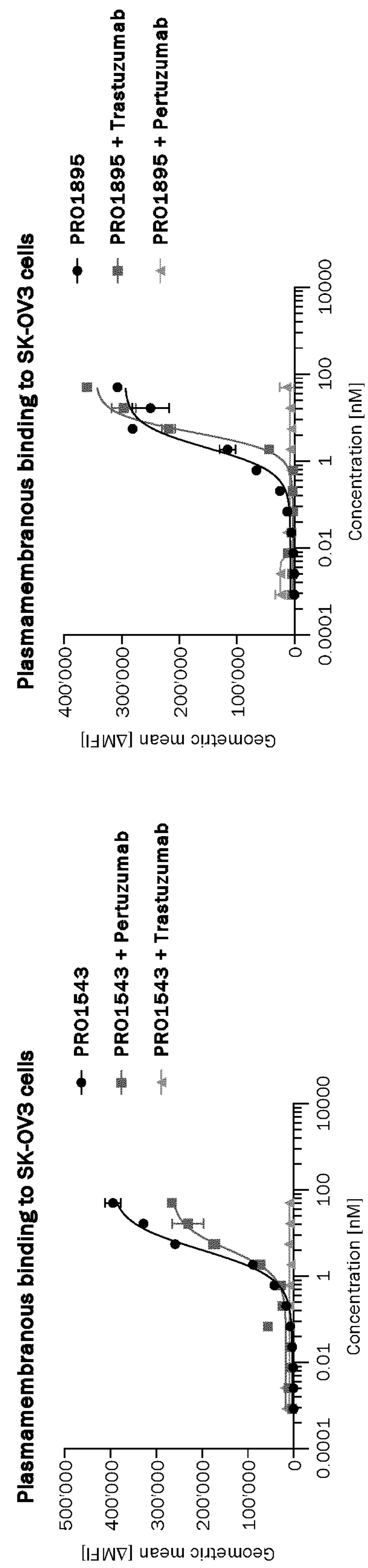

FIG. 21 Plasmamembranous binding of MATCH4 molecules PRO1543 and PRO1895 to SK-OV3 cells in presence of trastuzumab and pertuzumab. Concentration-response curves of MATCH4 molecules PRO1543 (left) and PRO1895 (right) with or without the addition of trastuzumab or pertuzumab are shown. Cells were incubated for 1 h with 50 nM of trastuzumab or pertuzumab prior the addition of MATCH4 molecules. Plasmamembranous binding of PRO1543 and PRO1895 was then assessed in flow cytometry. PRO1543 showed binding to HER2-expressing SK-OV3 cells when applied alone and when tested in presence of pertuzumab. PRO1895, on the other hand, demonstrated binding to the cells in presence of trastuzumab and when tested alone. No binding was found when PRO1543 and PRO1895 were tested in presence of trastuzumab or pertuzumab, respectively.

DETAILED DESCRIPTION OF THE INVENTION

Even though utilization of therapeutic antibodies inhibiting interaction of a tumor-associated immune checkpoint antigen, such as PD-L1, which its cognate ligand, such as PD-1, is a very promising treatment strategy, it is coupled to such difficulties as high toxicities and adverse events. There is thus a need in the medical field for novel approaches of inhibiting the interaction of a tumor-associated immune checkpoint antigen which its cognate ligand, which have lower rate of dose-limiting toxicities and adverse events than the currently available approaches.

The present invention provides a multispecific antibody comprising: at least a first domain specifically binding to a tumor-associated immune checkpoint antigen with low affinity, and at least a second domain specifically binding to a tumor-associated antigen (TAA)). The multispecific antibody of the present disclosure are capable of binding to a target cell displaying said TAA by virtue of said first domain specifically binding to said TAA, and of simultaneous binding of said low affinity binding domain, due to avidity effects, to said tumor-associated immune checkpoint antigen present on the same target cell, so that interaction of said tumor-associated immune checkpoint antigen is inhibited. Due to the low affinity of said first domain, specific binding to non-target cells displaying only said tumor-associated immune checkpoint antigen, but not said TAA, is not occurring to any relevant extent. Thus, the multispecific antibody of the present invention due to its ability to mediate, e.g. agonize, potent signaling of said tumor-associated immune checkpoint antigen on said target cells without interacting with non-target cells, so that the treatment with the multispecific antibody of the present invention does not lead to depletion of cells not expressing the TAA.

In addition, it has been surprisingly found that, the multispecific antibody of the present disclosure comprising (a) at least said first domain, (b) at least said second domain, and (c) at least a third domain specifically binding to an immune cell antigen demonstrated further beneficial properties as shown in the Examples and accompanying figures. Furthermore, the optional addition of a half-life-extending anti-HSA domain not only enables convenient dosing, but also should promote delivery of the molecule to tumor microenvironments.

The multispecific antibodies of the present invention thus provide distinct therapeutic advantages over conventional compositions and therapies.

Unless defined otherwise, all technical and scientific terms used herein have the same meaning as commonly understood by those of ordinary skill in the art to which this invention pertains.

The terms "comprising" and "including" are used herein in their open-ended and non-limiting sense unless otherwise noted. With respect to such latter embodiments, the term "comprising" thus includes the narrower term "consisting of".

The terms "a" and "an" and "the" and similar references in the context of describing the invention (especially in the context of the following claims) are to be construed to cover both the singular and the plural, unless otherwise indicated herein or clearly contradicted by context. For example, the term "a cell" includes a plurality of cells, including mixtures thereof. Where the plural form is used for compounds, salts, and the like, this is taken to mean also a single compound, salt, or the like.

In one aspect, the present invention relates to a multispecific antibody comprising at least a first domain specifically binding to a tumor-associated immune checkpoint antigen with low affinity, and at least a second domain specifically binding to a tumor-associated antigen (TAA).

The term "antibody" and the like, as used herein, includes whole antibodies or single chains thereof; and any antigen-binding fragment (i.e., "antigen-binding portion") or single chains thereof; and molecules comprising antibody CDRs, VH regions or VL regions (including without limitation multispecific antibodies). A naturally occurring "whole antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (Clq) of the classical complement system.

The terms "binding domain", "antigen-binding fragment thereof", "antigen binding portion" of an antibody, and the like, as used herein, refer to one or more fragments of an intact antibody that retain the ability to specifically bind to a given antigen (e.g., CD137, PD-L1, HSA). Antigen binding functions of an antibody can be performed by fragments of an intact antibody. In some embodiments, a binding domain of a multispecific antibody of the present invention is selected from the group consisting of a Fab fragment, a monovalent fragment consisting of the VL, VH, CL and CH1 domains; a F (ab)2 fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341: 544-546), which consists of a VH domain; an isolated complementarity determining region (CDR), dsFv, a scAb, STAB, a single domain antibody (sdAb or dAb), a single domain heavy chain antibody, and a single domain light chain antibody, a VHH, a VNAR, single domain antibodies based on the VNAR structure from shark, and binding domains based on alternative scaffolds including but limited to ankyrin-based domains, fynomers, avimers, anticalins, fibronectins, and binding sites being built into constant regions of antibodies (e.g. f-star technology (F-star's Modular Antibody Technology™)). Suitably, a binding domain of the present invention is a single-chain Fv fragment (scFv) or single antibody variable domains. In a preferred embodiment, a binding domain of the present invention is a single-chain Fv fragment (scFv).

The term "Complementarity Determining Regions" ("CDRs") are amino acid sequences with boundaries determined using any of a number of well-known schemes, including those described by Kabat et al. (1991), "Sequences of Proteins of Immunological Interest," 5th Ed. Public Health Service, National Institutes of Health, Bethesda, MD ("Kabat" numbering scheme), Al-Lazikani et al., (1997) JMB 273, 927-948 ("Chothia" numbering scheme), ImMunoGenTics (IMGT) numbering (Lefranc, M.-P., The Immunologist, 7, 132-136 (1999); Lefranc, M.-P. et al., Dev. Comp. Immunol., 27, 55-77 (2003) ("IMGT" numbering scheme) and numbering scheme described in Honegger & Pluckthun, J. Mol. Biol. 309 (2001) 657-670 ("AHo" numbering). For example, for classic formats, under Kabat, the CDR amino acid residues in the heavy chain variable domain (VH) are numbered 31-35 (HCDR1), 50-65 (HCDR2), and 95-102 (HCDR3); and the CDR amino acid residues in the light chain variable domain (VL) are numbered 24-34 (LCDR1), 50-56 (LCDR2), and 89-97 (LCDR3). Under Chothia the CDR amino acids in the VH are numbered 26-32 (HCDR1), 52-56 (HCDR2), and 95-102 (HCDR3); and the amino acid residues in VL are numbered 24-34 (LCDR1), 50-56 (LCDR2), and 89-97 (LCDR3). By combining the CDR definitions of both Kabat and Chothia, the CDRs consist of amino acid residues 26-35 (HCDR1), 50-65 (HCDR2), and 95-102 (HCDR3) in human VH and amino acid residues 24-34 (LCDR1), 50-56 (LCDR2), and 89-97 (LCDR3) in human VL. Under IMGT the CDR amino acid residues in the VH are numbered approximately 26-35 (HCDR1), 51-57 (HCDR2) and 93-102 (HCDR3), and the CDR amino acid residues in the VL are numbered approximately 27-32 (LCDR1), 50-52 (LCDR2), and 89-97 (LCDR3) (numbering according to "Kabat"). Under IMGT, the CDRs of an antibody can be determined using the program IMGT/DomainGap Align.

In the context of the present invention, the numbering system suggested by Honegger & Pluckthun ("AHo) is used (Honegger & Pluckthun, J. Mol. Biol. 309 (2001) 657-670), unless specifically mentioned otherwise. Furthermore, the following residues are defined as CDRs according to AHo numbering scheme: LCDR1 (also referred to as CDR-L1): L24-L42; LCDR2 (also referred to as CDR-L2): L58-L72;

LCDR3 (also referred to as CDR-L3): L107-L138; HCDR1 (also referred to as CDR-H1): H27-H42; HCDR2 (also referred to as CDR-H2): H57-H76; HCDR3 (also referred to as CDR-H3): H108-H138. For the sake of clarity, the numbering system according to Honegger & Pluckthun takes the length diversity into account that is found in naturally occurring antibodies, both in the different VH and VL subfamilies and, in particular, in the CDRs, and provides for gaps in the sequences. Thus, in a given antibody variable domain usually not all positions 1 to 149 will be occupied by an amino acid residue.

The term "binding specificity" as used herein refers to the ability of an individual antibody to react with one antigenic determinant and not with a different antigenic determinant. As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In its most general form (and when no defined reference is mentioned), "specific binding" is referring to the ability of the antibody to discriminate between the target of interest and an unrelated molecule, as determined, for example, in accordance with a specificity assay methods known in the art. Such methods comprise, but are not limited to Western blots, ELISA, RIA, ECL, IRMA, SPR (Surface plasmon resonance) tests and peptide scans. For example, a standard ELISA assay can be carried out. The scoring may be carried out by standard colour development (e.g. secondary antibody with horseradish peroxide and tetramethyl benzidine with hydrogen peroxide). The reaction in certain wells is scored by the optical density, for example, at 450 nm. Typical background (=negative reaction) may be about 0.1 OD; typical positive reaction may be about 1 OD. This means the ratio between a positive and a negative score can be 10-fold or higher. In a further example, an SPR assay can be carried out, wherein at least 10-fold, preferably at least 100-fold difference between a background and signal indicates on specific binding. Typically, determination of binding specificity is performed by using not a single reference molecule, but a set of about three to five unrelated molecules, such as milk powder, transferrin or the like.

Suitably, the antibody of the invention is an isolated antibody. The term "isolated antibody", as used herein, refers to an antibody that is substantially free of other antibodies having different antigenic specificities (e.g., an isolated antibody that specifically binds PD-L1 and HER2 is substantially free of antibodies that specifically bind antigens other than PD-L1 and HER2, e.g., an isolated antibody that specifically binds PD-L1, HER2 and human serum albumin is substantially free of antibodies that specifically bind antigens other than PD-L1, HER2 and human serum albumin). Moreover, an isolated antibody may be substantially free of other cellular material and/or chemicals.

Suitably, the antibody of the invention is a monoclonal antibody. The term "monoclonal antibody" or "monoclonal antibody composition" as used herein refers to antibodies that are substantially identical to amino acid sequence or are derived from the same genetic source. A monoclonal antibody composition displays a binding specificity and affinity for a particular epitope, or binding specificities and affinities for specific epitopes.

Antibodies of the invention include, but are not limited to, the chimeric, human and humanized.

The term "chimeric antibody" (or antigen-binding fragment thereof) is an antibody molecule (or antigen-binding fragment thereof) in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "human antibody" (or antigen-binding fragment thereof), as used herein, is intended to include antibodies (and antigen-binding fragments thereof) having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies and antigen-binding fragments thereof of the invention may include amino acid residues not encoded by human sequences (e.g., mutations introduced by random or site-specific mutagenesis in vitro or by somatic mutation in vivo). This definition of a human antibody specifically excludes a humanized antibody comprising non-human antigen-binding residues. Human antibodies can be produced using various techniques known in the art, including phage-display libraries (Hoogenboom and Winter, J. Mol. Biol, 227:381 (1991); Marks et al, J. Mol. Biol, 222:581 (1991)). Also available for the preparation of human monoclonal antibodies are methods described in Cole et al, Monoclonal Antibodies and Cancer Therapy, Alan R. Liss, p. 77 (1985); Boemer et al, J. Immunol, 147(I):86-95 (1991). See also van Dijk and van de Winkel, Curr. Opin. Pharmacol, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al, Proc. Natl. Acad. Sci. USA, 103:3557-3562 (2006) regarding human antibodies generated via a human B-cell hybridoma technology.

A "humanized" antibody (or antigen-binding fragment thereof), as used herein, is an antibody (or antigen-binding fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). Additional framework region modifications may be made within the human framework sequences as well as within the CDR sequences derived from the germline of another mammalian species. The humanized antibodies of the invention may include amino acid residues not encoded by human sequences (e.g., mutations introduced by random or site-specific mutagenesis in vitro or by somatic mutation in vivo, or a conservative substitution to promote stability or manufacturing). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239: 1534-1536, 1988; Padlan, Molec. Immun., 28:489-498, 1991; and Padlan, Molec. Immun., 31: 169-217, 1994. Other examples of human engineering technology include, but are not limited to, Xoma technology disclosed in U.S. Pat. No. 5,766,886.

The term "recombinant humanized antibody" as used herein, includes all human antibodies that are prepared, expressed, created or isolated by recombinant means, such as antibodies isolated from a host cell transformed to express the humanized antibody, e.g., from a transfectoma, and antibodies prepared, expressed, created or isolated by any other means that involve splicing of all or a portion of a human immunoglobulin gene, sequences to other DNA sequences.

Suitably, the antibody of the invention or antigen-binding fragment thereof is humanized. Suitably, the antibody of the invention or antigen-binding fragment thereof is humanized and comprises rabbit-derived CDRs.

The term "multispecific antibody" as used herein, refers to an antibody that binds to two or more different epitopes on at least two or more different targets (e.g., PD-L1 and HER2). The term "multispecific antibody" includes bispecific, trispecific, tetraspecific, pentaspecific and hexaspecific. The term "bispecific antibody" as used herein, refers to an antibody that binds to two different epitopes on at least two different targets (e.g., PD-L1 and HER2). The term "trispecific antibody" as used herein, refers to an antibody that binds to three different epitopes on at least three different targets (e.g., PD-L1, HER2 and HSA).

The term "epitope" means a protein determinant capable of specific binding to an antibody. Epitopes usually consist of chemically active surface groupings of molecules such as amino acids or sugar side chains and usually have specific three-dimensional structural characteristics, as well as specific charge characteristics. "Conformational" and "linear" epitopes are distinguished in that the binding to the former but not the latter is lost in the presence of denaturing solvents.

The term "conformational epitope" as used herein refers to amino acid residues of an antigen that come together on the surface when the polypeptide chain folds to form the native protein.

The term "linear epitope" refers to an epitope with all of the points of interaction between the protein and the interacting molecule (such as an antibody) occurring linearly along the primary amino acid sequence of the protein (continuous).

The term "distal epitope" refers to an epitope which is comprised in the region of the extracellular part of a cell-bound antigen that is distant from the cell surface.

The term "recognize" as used herein refers to an antibody antigen-binding fragment thereof that finds and interacts (e.g., binds) with its conformational epitope.

As used herein, the term "affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

"Binding affinity" generally refers to the strength of the sum total of non-covalent interactions between a single binding site of a molecule (e.g., of an antibody) and its binding partner (e.g., an antigen). Unless indicated otherwise, as used herein, "binding affinity", "bind to", "binds to" or "binding to" refers to intrinsic binding affinity that reflects a 1:1 interaction between members of a binding pair (e.g., an antibody fragment and antigen). The affinity of a molecule X for its partner Y can generally be represented by the dissociation constant (KD). Affinity can be measured by common methods known in the art, including those described herein.

Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative and exemplary embodiments for measuring binding affinity, i.e. binding strength are described in the following.

The term "Kassoc", "Ka" or "Kon", as used herein, is intended to refer to the association rate of a particular antibody-antigen interaction, whereas the term "Kdis", "Kd" or "Koff", as used herein, is intended to refer to the dissociation rate of a particular antibody-antigen interaction. In one embodiment, the term "KD", as used herein, is intended to refer to the dissociation constant, which is obtained from the ratio of Kd to Ka (i.e. Kd/Ka) and is expressed as a molar concentration (M). The "KD" or "KD value" or "KD" or "KD value" according to this invention is in one embodiment measured by using surface-plasmon resonance assays. Affinity to PD-L1 was determined by surface plasmon resonance (SPR) measurements as described in section [0185]. Binding affinities of multi-specific constructs towards recombinant human CD3E ECD, recombinant human IL-23R and recombinant human Her2 ECD were measured by SPR as described in section [0198]. Affinity of molecules to human serum albumin (HSA) and mouse serum albumin (MSA) was determined by SPR measurements as described in section [0199].

Suitably, the multispecific antibody of the present invention is monovalent, bivalent or multivalent for PD-L1 specificity. In one embodiment, the multispecific antibody of the present invention is bivalent for PD-L1 specificity. In a preferred embodiment, the multispecific antibody of the present invention is monovalent for PD-L1 specificity.

Suitable PD-L1-BDs for use in the multispecific antibody of the invention are binding domains provided in the present disclosure. The PD-L1-BDs of the invention include, but are not limited to, the humanized monoclonal antibodies whose sequences are listed in Table 1.

Suitably, the multispecific antibody of the present invention is monovalent, bivalent or multivalent for HER2 specificity. In one embodiment, the multispecific antibody of the present invention is bivalent for HER2 specificity. In a preferred embodiment, the multispecific antibody of the present invention is monovalent for HER2 specificity.

Suitable HER2-BDs for use in the multispecific antibody of the invention are binding domains provided in the present disclosure. The HER2-BDs of the invention include, but are not limited to, the humanized monoclonal antibodies whose sequences are listed in Table 2.

The term "multivalent antibody" refers to a single binding molecule with more than one valency, where "valency" is described as the number of antigen-binding moieties that binds to epitopes on identical target molecules. As such, the single binding molecule can bind to more than one binding site on a target molecule. Examples of multivalent antibodies include, but are not limited to bivalent antibodies, trivalent antibodies, tetravalent antibodies, pentavalent antibodies, and the like.

The term "monovalent antibody", as used herein, refers to an antibody that binds to a single epitope on a target molecule, such as PD-L1. Also, the term "binding domain" or "monovalent binding domain", as used herein, refers to a binding domain that binds to a single epitope on a target molecule such as PD-L1.

The term "bivalent antibody" as used herein, refers to an antibody that binds to two epitopes on at least two identical target molecules, such as PD-L1target molecules.

The inventors of the present invention have now surprisingly found that addition of the tri-specific molecule PRO1678 (anti-HSA×PDL1×HER2) resulted in a significantly reduced tumor growth in a HCC1954 xenograft NOG mouse model when compared to an equipotent dose (same activity as determined in vitro) of nivolumab. A five-time lower dose of PRO1678 led to the same reduction of tumor growth in this model (see FIG. 13). The inventors have furthermore surprisingly found that a tetra-specific molecule comprising a fourth, CD3-BD such as PRO1543 (anti-CD3×HSA×PDL1×HER2) resulted in a complete regression of the tumor in the HCC1954 xenograft NOG mouse model. This finding is insofar surprising as it cannot a priori be expected that all four binding domains remain functional without sterically or otherwise inhibiting each other in a complex multi-target, multi-cell in vivo situation. As the $EC_{50}$ of PD-L1 blockade in these cells is considerably higher than the $EC_{50}$ of target cell lysis, it is highly likely that the improved activity of the molecule containing an anti-PD-L1 domains results from increased avidity. As a consequence, binding to Her2 and PD-L1 double positive cells is stronger than binding to PD-L1 negative cells expressing Her2. This avidity binding increases the therapeutic window as it selectively improves potency on tumor cells (Her2/PD-L1 double positive), but not on PD-L1 negative Her2 expressing normal cells.

The term "tumor-associated immune checkpoint antigen" refers to a transmembrane protein expressed by the tumor that suppresses the activity of immune cells, particularly to an antigen taken from the group of: PD-L1, PD-L2, CD80, CD86, CD276 (B7-H3), and VTCN1 (B7-H4), more particularly PD-L1.

The term "low affinity" refers to a binding domain that binds to its cognate target with a dissociation constant (KD) of between 50 nM and 2000 nM, preferably between 100 nM and 1000 nM.

The term "tumor-associated antigen (TAA)" refers to an antigen that is expressed on the surface of a tumor cell. In particular embodiments, a TAA is an antigen that is preferentially expressed on a tumor cell when compared to non-tumor cells, particularly wherein expression of the TAA on a tumor cell is at least more than 5 fold, at least more than 10 fold, at least more than 20 fold, at least more than 50 fold, or at least more than 100 fold higher than on non-tumor cells from the same organism or patient. In particular, the TAA is taken from the group of: EGFRvIII, mesothelin, GD2, Tn antigen, sTn antigen, Tn-O-Glycopeptides, sTn-O-Glycopeptides, PSMA, CD97, TAG72, CD44v6, CEA, EPCAM, KIT, IL-13Ra2, leguman, GD3, CD171, IL-11 Ra, PSCA, MAD-CT-1, MAD-CT-2, VEGFR2, LewisY, CD24, PDGFR-beta, SSEA-4, folate receptor alpha, ERBBs (e.g., ERBB2), Her2/neu (HER2), MUC1, EGFR, NCAM, Ephrin B2, CAIX, LMP2, sLe, HMWMAA, o-acetyl-GD2, folate receptor beta, TEM1/CD248, TEM7R, FAP, Legumain, HPV E6 or E7, ML-IAP, CLDN6, TSHR, GPRC5D, ALK, Polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp 70-2, NA-17, NY-BR-1, UPK2, HAVCR1, ADRB3, PANX3, NY-ESO-1, GPR20, Ly6k, OR51E2, TARP, and GFRalpha4.

The term "immune cell antigen" refers to an antigen present in an immune cell, particularly an immune cell selected from a T cell, an NK cell, and myeloid cells. In particular, the term relates to a protein, which is a stimulatory or co-stimulatory molecule of said immune cell.

In the context of the present invention, the term "stimulatory molecule of said immune cells" relates to molecules such as CD3 and CD16.

In the context of the present invention, the term "co-stimulatory molecule of said immune cells" relates to molecules such as the molecules comprised in the group of molecules consisting of CD137, CD28, ICOS, HVEM, CD27, OX40, DR3, GITR, CD30, SLAM, CD2, 2B4, TIM1, TIM2, and CD226.

In particular embodiments, the multispecific antibody of the present invention furthermore comprises (i) a binding domain for CD3, or (ii) a binding domain for CD137.

Suitable CD3-BDs for use in the multispecific antibody of the invention are binding domains provided in the present disclosure. The CD3-BDs of the invention include, but are not limited to, the humanized monoclonal antibodies whose sequences are listed in Table 3.

Suitable CD137-BDs for use in the multispecific antibody of the invention are binding domains provided in the present disclosure. The CD137-BDs of the invention include, but are not limited to, the humanized monoclonal antibodies whose sequences are listed in Table 5.

Suitably, the multispecific antibody of the invention has two different specificities (PD-L1 and HER2). Suitably, the multispecific antibody of the invention is a bispecific antibody. The multispecific antibody of the present invention may comprise a further specificity (trispecific) or specificities (tetraspecific, pentaspecific or hexaspecific antibody). In one embodiment, the multispecific antibody is trispecific. In another embodiment, the multispecific antibody is tetraspecific In one embodiment, the multispecific antibody of the invention comprises an immunoglobulin Fc region polypeptide. The term "Fc region" herein is used to define a C-terminal region of an immunoglobulin heavy chain, including native-sequence Fc regions and variant Fc regions. Suitable native-sequence Fc regions include human IgG1, IgG2 (IgG2A, JgG2B), IgG3 and IgG4. "Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRI IB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain, (see M. Daeron, Annu. Rev. Immunol. 5:203-234 (1997). FcRs are reviewed in Ravetch and Kinet, Annu. Rev. Immunol. 9: 457-92 (1991); Capet et al, Immunomethods 4: 25-34 (1994); and de Haas et al, J. Lab. Clin. Med. 126: 330-41 (1995). Other FcRs, including those to be identified in the future, are encompassed by the term "FcR" herein. The term "Fc receptor" or "FcR" also includes the neonatal receptor, FcRn, which is responsible for the transfer of maternal IgGs to the fetus. Guyer et al., J. Immunol. 117: 587 (1976) and Kim et al., J. Immunol. 24: 249 (1994). Methods of measuring binding to FcRn are known (see, e.g., Ghetie and Ward, Immunol. Today 18: (12): 592-8 (1997); Ghetie et al., Nature Biotechnology 15 (7): 637-40 (1997); Hinton et al., J. Biol. Chem. TJI (8): 6213-6 (2004); WO 2004/92219 (Hinton et al). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., J. Biol. Chem. 9(2): 6591-6604 (2001).

In another embodiment, the antibody of the invention does not comprise an immunoglobulin Fc region polypeptide.

In order to increase the number of specificities/functionalities at the same or lower molecular weight, it is advantageous to use antibodies comprising antibody fragments, such as Fv, Fab, Fab' and F(ab')2 fragments and other antibody fragments. These smaller molecules retain the antigen binding activity of the whole antibody and can also exhibit improved tissue penetration and pharmacokinetic properties in comparison to the whole immunoglobulin molecules. Whilst such fragments appear to exhibit a number of advantages over whole immunoglobulins, they also suffer from an increased rate of clearance from serum since they lack the Fc domain that imparts a long half-life in vivo (Medasan et al., 1997, J. Immunol. 158:2211-2217). Molecules with lower molecular weights penetrate more efficiently into target tissues (e.g. solid cancers) and thus hold the promise for improved efficacy at the same or lower dose.

The inventors have surprisingly found that an addition of human serum albumin binding domain (HSA-BD) to the multispecific antibody of the invention does not interfere with the ability of the other binding domains to bind to their respective targets This finding is insofar surprising as it cannot a priori be expected that all four binding domains remain functional without sterically or otherwise inhibiting each other in a complex multi-target, multi-cell in vivo situation.

Suitably, the multispecific antibody of the present invention may comprise a further binding domain having specificity to human serum albumin. In one embodiment, the multispecific antibody comprises: (i) at least one PD-L1-BD; (ii) at least one HER2-BD; and (iii) at least one HSA-BD. Suitably, the multispecific antibody of the present invention comprises: (i) one PD-L1-BD; (ii) at least one HER2-BD, preferably one PD-L1-BD or two PD-L1-BDs, more preferably one PD-L1-BD; and (iii) at least one HSA-BD, preferably one HSA-BD.

The term "HSA" refers in particular to human serum albumin with UniProt ID number P02768. Human Serum Albumin (HSA) is 66.4 kDa abundant protein in human serum (50% of total protein) composing of 585 amino acids (Sugio, Protein Eng, Vol. 12, 1999, 439-446). Multifunctional HSA protein is associated with its structure that allowed to bind and transport a number of metabolizes such as fatty acids, metal ions, bilirubin and some drugs (Fanali, Molecular Aspects of Medicine, Vol. 33, 2012, 209-290). HSA concentration in serum is around 3.5-5 g/dL. Albumin binding antibodies and fragments thereof may be used for example, for extending the in vivo serum half-life of drugs or proteins conjugated thereto.

In some embodiments, the HSA-BD is derived from a monoclonal antibody or antibody fragment.

Suitable HSA-BDs for use in the multispecific antibody of the invention are binding domains provided in the present disclosure. The HSA-BDs of the invention include, but are not limited to, the humanized monoclonal antibodies whose sequences are listed in Table 4.

In particular, the HSA-BDs of the invention specifically bind to human serum albumin. The HSA-BDs of the invention comprise a VH CDR having an amino acid sequence of any one of the VH CDRs listed in Table 4. In particular, the invention provides HSA-BDs comprising (one, two, three, or more VH CDRs having an amino acid sequence of any of the VH CDRs listed in Table 4.

The invention also provides HSA-BDs comprising a VL CDR having an amino acid sequence of any one of the VL CDRs listed in Table 4. In particular, the invention provides HSA-BDs comprising one, two, three or more VL CDRs having an amino acid sequence of any of the VL CDRs listed in Table 4.

In a further embodiment, the invention provides an HSA-BD that specifically binds human serum albumin, wherein said binding domain comprises a VH domain and a VL domain.

Another suitable HSA-BD for use in the multispecific antibody of the invention comprises or is derived from an antibody selected from the group consisting of: (i) polypeptides that bind serum albumin (see, for example, Smith et al., 2001, Bioconjugate Chem. 12:750-756; EP0486525; U.S. Pat. No. 6,267,964; WO 2004/001064; WO 2002/076489; and WO 2001/45746); (ii) anti-serum albumin binding single variable domains described in Holt et al., Protein Engineering, Design & Selection, vol 21, 5, pp 283-288, WO 2004/003019, WO 2008/096158, WO 2005/118642, WO 2006/0591056 and WO 2011/006915; (iii) anti-serum albumin antibodies described in WO 2009/040562, WO 2010/035012 and WO 2011/086091.

In particular embodiments, the multispecific antibodies of the invention comprise an HSA binding domain having the CDR sequences as defined in SEQ ID NOs: 61 to 66 and VH/VL sequences as defined in SEQ ID NOs: 67 to 70.

These HSA-BDs exhibit particular advantageous properties, in particular a high stability and cross-reactivity to cynomolgus serum albumin (CSA) and mouse serum albumin (MSA), to further improve the already advantageous properties of the multispecific antibodies of the invention. More specifically, said HSA-BDs are characterized by one or more of the following parameters:

a. bind to human serum albumin (HSA) with a monovalent dissociation constant ($K_D$) of less than 20 nM, particularly with a $K_D$ of 0.01 to 20 nM, particularly of 0.05 to 10 nM, particularly of 0.1 to 5 nM at a pH value of about 5.5, as measured by surface plasmon resonance (SPR), particularly wherein said hSA-BD is in an scFv format;
b. bind to human serum albumin (HSA) with a monovalent dissociation constant ($K_D$) of less than 20 nM, particularly with a $K_D$ of 0.01 to 20 nM, particularly of 0.05 to 10 nM, particularly of 0.1 to 5 nM both at pH values of about 5.5 and at about 7.4, as measured by surface plasmon resonance (SPR), particularly wherein said HSA-BD is in an scFv format;
c. are cross-reactive with *Macaca fascicularis* (Cynomolgus) serum albumin (CSA), in particular bind to CSA with a monovalent less than 15 nM, particularly with a $K_D$ of 0.01 to 15 nM, particularly of 0.05 to 7 nM, particularly of 0.1 to 4 nM both at pH values of about 5.5 and at about 7.4, as measured by SPR, particularly wherein said HSA-BD is in an scFv format;

d. are cross reactive with *Mus musculus* (Mouse) serum albumin (MSA), in particular bind to MSA with a monovalent $K_D$ of less than 20 nM, particularly with a $K_D$ of 0.01 to 20 nM, particularly of 0.05 to 10 nM, particularly of 0.1 to 5 nM at a pH value of about 5.5, as measured by SPR, particularly wherein said HSA-BD is in an scFv format;

e. preserved ability of the antibody-bound HSA to bind to FcRn;

f. when being in scFv format, has a melting temperature (Tm), determined by differential scanning fluorimetry (DSF), of at least 72° C., preferably of at least 75° C., more preferably at least 78° C., in particular wherein said HSA-BD is formulated in 50 mM phosphate citrate buffer with 150 mM NaCl at pH 6.4;

g. when being in scFv format, has a loss in monomer content, after storage for at least two weeks, at 4° C., of less than 5%, e.g. less than 4%, less than 3%, less than 2%, preferably less than 1%, when said antigen-binding fragment is at a starting concentration of 50 mg/ml, and in particular wherein said HSA-BD is formulated in 50 mM phosphate citrate buffer with 150 mM NaCl at pH 6.4;

h. when being in scFv format, has a loss in monomer content, after storage for at least two weeks, at 40° C., of less than 11%, e.g. less than 8%, less than 5%, less than 2%, preferably less than 1%, when said antigen-binding fragment is at a starting concentration of 10 mg/ml, and in particular wherein said HSA-BD is formulated in 50 mM phosphate citrate buffer with 150 mM NaCl at pH 6.4; and/or i. when being in scFv format, has a loss in protein content, after storage for at least four weeks, at 40° C., of less than 5%, e.g. less than 4%, less than 3%, less than 2%, preferably less than 1%, when said antigen-binding fragment is at a starting concentration of 10 mg/mi, and in particular wherein said HSA-BD is formulated in 50 mM phosphate citrate buffer with 150 mM NaCl at pH 6.4.

Other variable domains of the invention include amino acids that have been mutated, yet have at least 60, 70, 80, 90, 91, 92, 93, 94, 95, 96, 97, 98 or 99 percent identity in the CDR regions with the CDR regions depicted in the sequences described in Tables 1 to 5. Other variable domains of the invention include mutant amino acid sequences wherein no more than 1, 2, 3, 4 or 5 amino acids have been mutated in the CDR regions when compared with the CDR regions depicted in the sequence described in Tables 1 to 5.

Suitably, the VH domains of the binding domains of the invention belong to a VH3 or VH4 family. In one embodiment, a binding domain of the invention comprises a VH domain belonging to the VH3 family. In the context of the present invention, the term "belonging to VHx family (or VLx family)" means that the framework sequences FR1 to FR2 show the highest degree of homology to said VHx family (or VLx, respectively). Examples of VH and VL families are given in Knappik et al., J. Mol. Biol. 296 (2000) 57-86, or in WO 2019/057787. A specific example of a VH domain belonging to VH3 family is represented by SEQ ID NO: 142, and a specific example of a VH domain belonging to VH4 family is represented by SEQ ID NO: 143. In particular, framework regions FR1 to FR4 taken from SEQ ID NO: 142 belong to VH3 family (Table 7, regions marked in non-bold). Suitably, a VH belonging to VH3 family, as used herein, is a VH comprising FR1 to FR4 having at least 85%, preferably at least 90%, more preferably at least 95% sequence identity to FR1 to FR4 of SEQ ID NO: 142. Alternative examples of VH3 sequences, and examples of VH4 sequences, may be found in Knappik et al., J. Mol. Biol. 296 (2000) 57-86 or in WO 2019/057787. Suitably, the HSA-BD of the invention comprises: $V_K$ frameworks FR1, FR2 and FR3, particularly $V_K1$ or $V_K3$ frameworks, preferably $V_K1$ frameworks FR1 to 3, and a framework FR4, which is selected from a $V_K$ FR4, particularly $V_K1$ FR4, $V_K3$ FR4, and a Vλ FR4. Suitable $V_K1$ frameworks FR1 to 3 are set forth in SEQ ID NO: 144 (Table 7, FR regions are marked in non-bold). Alternative examples of $V_K1$ sequences, and examples of $V_K2$, $V_K3$ or $V_K4$ sequences, may be found in Knappik et al., J. Mol. Biol. 296 (2000) 57-86. Suitable $V_K1$ frameworks FR1 to 3 comprise the amino acid sequences having at least 60, 70, 80, 90 percent identity to amino acid sequences corresponding to FR1 to 3 and taken from SEQ ID NO: 144 (Table 7, FR regions are marked in non-bold). Suitable Vλ FR4 are as set forth in SEQ ID NO: 145 to SEQ ID NO: 152. In one embodiment, the VL domains of the present invention comprises Vλ FR4 comprising the amino acid sequence having at least 60, 70, 80, 90 percent identity to an amino acid sequence selected from any of SEQ ID NO: 145 to SEQ ID NO: 152, preferably to SEQ ID NO: 146 or 152.

The binding domains of the invention comprises a VH domain listed in Tables 1 to 5. Suitably, a binding domain of the invention comprises a VH amino acid sequence listed in one of Tables 1 to 5, wherein no more than about 10 amino acids in a framework sequence (for example, a sequence which is not a CDR) have been mutated (wherein a mutation is, as various non-limiting examples, an addition, substitution or deletion). Suitably, a binding domain of the present invention comprises a VH amino acid sequence listed in one of Tables 1 to 5, wherein no more than about 20 amino acids in a framework sequence (for example, a sequence which is not a CDR) have been mutated (wherein a mutation is, as various non-limiting examples, an addition, substitution or deletion). Other binding domains of the invention include amino acids that have been mutated, yet have at least 60, 70, 80, 90, 91, 92, 93, 94, 95, 96, 97, 98 or 99 percent identity in the VH regions with the VH regions depicted in the corresponding sequences described in one of Tables 1 to 5.

In particular, a binding domain of the invention comprises a VL domain listed in one of Tables 1 to 5. Suitably, a binding domain of the invention comprises a VL amino acid sequence listed in one of Tables 1 to 5, wherein no more than about 10 amino acids in a framework sequence (for example, a sequence which is not a CDR) have been mutated (wherein a mutation is, as various non-limiting examples, an addition, substitution or deletion). Suitably, a binding domain of the invention comprises a VL amino acid sequence listed in one of Tables 1 to 5, wherein no more than about 20 amino acids in a framework sequence (for example, a sequence which is not a CDR) have been mutated (wherein a mutation is, as various non-limiting examples, an addition, substitution or deletion). Other binding domains of the invention include amino acids that have been mutated, yet have at least 60, 70, 80, 90, 91, 92, 93, 94, 95, 96, 97, 98 or 99 percent identity in the VL regions with a VL region depicted in the sequences described in Tables 1 to 5.

In the context of the present invention, the term "binding domain of the present invention" relates both to a binding domain a such, i.e. independent of a multispecific context, and, in particular, to a binding domain comprised in a multispecific construct, e.g. one of the binding domains comprised in a bispecific, trispecific or tetraspecific construct.

Suitably, a binding domain of the invention is selected from the group consisting of: a Fab, an Fv, an scFv, dsFv, a scAb, and STAB.

Suitably, a binding domain of the invention is an scFv antibody fragment.

The multispecific antibody of the invention may be in any suitable format.

Suitably, the binding domains of the multispecific antibody are operably linked. The binding domains of the multispecific antibody of the invention are capable of binding to their respective antigens or receptors simultaneously.

In one embodiment, the multispecific antibody of the invention comprises at least one PD-L1-BD, at least one HER2-BD, wherein: (i) said PD-L1-BD and said HER2-BD are both operably linked to each other. In one embodiment, the multispecific antibody of the invention comprises at least one PD-L1-BD, at least one HER2-BD, at least one HSA-BD, wherein: (i) said PD-L1-BD and said HER2-BD are both operably linked to said HSA-BD; or (ii) said PD-L1-BD and said HSA-BD are both operably linked to said HER2-BD; or (iii) said HER2-BD and said HSA-BD are both operably linked to said PD-L1-BD. In a preferred embodiment, the multispecific antibody of the invention comprises at least one PD-L1-BD, at least one HER2-BD, at least one HSA-BD, wherein said PD-L1-BD and said HSA-BD are both operably linked to said HER2-BD.

The term "operably linked", as used herein, indicates that two molecules (e.g., polypeptides, domains, binding domains) are attached so as to each retain functional activity. Two molecules can be "operably linked" whether they are attached directly or indirectly (e.g., via a linker, via a moiety, via a linker to a moiety). The term "linker" refers to a peptide or other moiety that is optionally located between binding domains or antibody fragments of the invention. A number of strategies may be used to covalently link molecules together. These include, but are not limited to, polypeptide linkages between N- and C-termini of proteins or protein domains, linkage via disulfide bonds, and linkage via chemical cross-linking reagents. In one aspect of this embodiment, the linker is a peptide bond, generated by recombinant techniques or peptide synthesis. Choosing a suitable linker for a specific case where two polypeptide chains are to be connected depends on various parameters, including but not limited to the nature of the two polypeptide chains (e.g., whether they naturally oligomerize), the distance between the N- and the C-termini to be connected if known, and/or the stability of the linker towards proteolysis and oxidation. Furthermore, the linker may contain amino acid residues that provide flexibility.

In the context of the present invention, the term "polypeptide linker" refers to a linker consisting of a chain of amino acid residues linked by peptide bonds that is connecting two domains, each being attached to one end of the linker. The polypeptide linker should have a length that is adequate to link two molecules in such a way that they assume the correct conformation relative to one another so that they retain the desired activity. In particular embodiments, the polypeptide linker has a continuous chain of between 2 and 30 amino acid residues (e.g., 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid residues). In addition, the amino acid residues selected for inclusion in the polypeptide linker should exhibit properties that do not interfere significantly with the activity of the polypeptide. Thus, the linker peptide on the whole should not exhibit a charge that would be inconsistent with the activity of the polypeptide, or interfere with internal folding, or form bonds or other interactions with amino acid residues in one or more of the monomers that would seriously impede the binding of receptor monomer domains. In particular embodiments, the polypeptide linker is non-structured polypeptide. Useful linkers include glycine-serine, or GS linkers. By "Gly-Ser" or "GS" linkers is meant a polymer of glycines and serines in series (including, for example, (Gly-Ser)n, (GSGGS)n (GGGGS)n and (GGGS)n, where n is an integer of at least one), glycine-alanine polymers, alanine-serine polymers, and other flexible linkers such as the tether for the shaker potassium channel, and a large variety of other flexible linkers, as will be appreciated by those in the art. Glycine-serine polymers are preferred since both of these amino acids are relatively unstructured, and therefore may be able to serve as a neutral tether between components. Secondly, serine is hydrophilic and therefore able to solubilize what could be a globular glycine chain. Third, similar chains have been shown to be effective in joining subunits of recombinant proteins such as single chain antibodies.

Suitably, the multispecific antibody is in a format selected from any suitable multispecific, e.g. bispecific, format known in the art, including, by way of non-limiting example, formats based on a single-chain diabody (scDb), a tandem scDb (Tandab), a linear dimeric scDb (LD-scDb), a circular dimeric scDb (CD-scDb), a bispecific T-cell engager (BiTE; tandem di-scFv), a tandem tri-scFv, a tribody (Fab-(scFv)2) or bibody (Fab-(scFv)1), Fab, Fab-Fv2, Morrison (IgG CH3-scFv fusion (Morrison L) or IgG CL-scFv fusion (Morrison H)), triabody, scDb-scFv, bispecific Fab2, di-miniantibody, tetrabody, scFv-Fc-scFv fusion, scFv-HSA-scFv fusion, di-diabody, DVD-Ig, COVD, IgG-scFab, scFab-dsscFv, Fv2-Fc, IgG-scFv fusions, such as bsAb (scFv linked to C-terminus of light chain), Bs1Ab (scFv linked to N-terminus of light chain), Bs2Ab (scFv linked to N-terminus of heavy chain), Bs3Ab (scFv linked to C-terminus of heavy chain), Ts1Ab (scFv linked to N-terminus of both heavy chain and light chain), Ts2Ab (dsscFv linked to C-terminus of heavy chain), Bispecific antibodies based on heterodimeric Fc domains, such as Knob-into-Hole antibodies (KiHs) (bispecific IgGs prepared by the KiH technology); an Fv, scFv, scDb, tandem-di-scFv, tandem tri-scFv, Fab-(scFv)2, Fab-(scFv)1, Fab, Fab-Fv2, COVD fused to the N- and/or the C-terminus of either chain of a heterodimeric Fc domain or any other heterodimerization domain, a MATCH (described in WO 2016/0202457; Egan T., et al., mAbs 9 (2017) 68-84) and DuoBodies (bispecific IgGs prepared by the Duobody technology) (MAbs. 2017 February/March; 9(2):182-212. doi: 10.1080/19420862.2016.1268307). Particularly suitable for use herein is a single-chain diabody (scDb) or scDb-scFv.

In one embodiment, the multispecific antibody of the invention is in a format selected from the list consisting of scDb (diabody), scDb-scFv, triabody, and tribody. Particularly suitable for use herein is a single-chain diabody (scDb), in particular a bispecific monomeric scDb. Also, particularly suitable for use herein is a scDb-scFv, in particular wherein said CD137-BD and said PD-L1-BD are in the form of a scDb and said HSA-BD is an scFv operably linked to said scDb.

The term "diabodies" refers to antibody fragments with two antigen-binding sites, which fragments comprise a VH connected to VL in the same polypeptide chain (VH-VL). By using a linker that is too short to allow pairing between the two domains on the same chain, the domains are forced to pair with the complementary domains of another chain to create two antigen-binding sites. Diabodies may be bivalent or bispecific. Diabodies are described more fully in, for example, EP404097, WO 93/01161, Hudson et al., Nat. Med. 9:129-134 (2003), and Hollinger et al., Proc. Natl. Acad. Sci. USA 90: 6444-6448 (1993). Triabodies and tetrabodies are also described in Hudson et al., Nat. Med. 9:129-134 (2003).

The bispecific scDb, in particular the bispecific monomeric scDb, particularly comprises two variable heavy chain domains (VH) or fragments thereof and two variable light chain domains (VL) or fragments thereof connected by linkers L1, L2 and L3 in the order VHA-L1-VLB-L2-VHB-L3-VLA, VHA-L1-VHB-L2-VLB-L3-VLA, VLA-L1-VLB-L2-VHB-L3-VHA, VLA-L1-VHB-L2-VLB-L3-VHA, VHB-L1-VLA-L2-VHA-L3-VLB, VHB-L1-VHA-L2-VLA-L3-VLB, VLB-L1-VLA-L2-VHA-L3-VHB or VLB-L1-VHA-L2-VLA-L3-VHB, wherein the VLA and VHA domains jointly form the antigen binding site for the first antigen, and VLB and VHB jointly form the antigen binding site for the second antigen.

The linker L1 particularly is a peptide of 2-10 amino acids, more particularly 3-7 amino acids, and most particularly 5 amino acids, and linker L3 particularly is a peptide of 1-10 amino acids, more particularly 2-7 amino acids, and most particularly 5 amino acids. In particular embodiments, the linker L1 and/or L3 comprises one or two units of four (4) glycine amino acid residues and one (1) serine amino acid residue (GGGGS)n, wherein n=1 or 2, preferably n=1.

The middle linker L2 particularly is a peptide of 10-40 amino acids, more particularly 15-30 amino acids, and most particularly 20-25 amino acids. In particular embodiments, said linker L2 comprises one or more units of four (4) glycine amino acid residues and one (1) serine amino acid residue (GGGGS)n, wherein n=1, 2, 3, 4, 5, 6, 7 or 8, preferably n=4.

In one embodiment, the multispecific antibody of the invention is a scDb-scFv. The term "scDb-scFv" refers to an antibody format, wherein a single-chain Fv (scFv) fragment is fused by a flexible Gly-Ser linker to a single-chain diabody (scDb). In one embodiment, said flexible Gly-Ser linker is a peptide of 2-40 amino acids, e.g., 2-35, 2-30, 2-25, 2-20, 2-15, 2-10 amino acids, particularly 10 amino acids. In particular embodiments, said linker comprises one or more units of four (4) glycine amino acid residues and one (1) serine amino acid residue (GGGGS)n, wherein n=1, 2, 3, 4, 5, 6, 7 or 8, preferably n=2.

In one embodiment of the present invention, the multispecific antibody of the invention is in a MATCH format described in WO 2016/0202457; Egan T., et al., mAbs 9 (2017) 68-84.

The multispecific antibody of the invention can be produced using any convenient antibody manufacturing method known in the art (see, e.g., Fischer, N. & Leger, O., Pathobiology 74 (2007) 3-14 with regard to the production of bispecific constructs; Hornig, N. & Fsrber-Schwarz, A., Methods Mol. Biol. 907 (2012)713-727, and WO 99/57150 with regard to bispecific diabodies and tandem scFvs). Specific examples of suitable methods for the preparation of the bispecific construct of the invention further include, inter alia, the Genmab (see Labrijn et al., Proc. Natl. Acad. Sci. USA 110 (2013) 5145-5150) and Merus (see de Kruif et al., Biotechnol. Bioeng. 106 (2010) 741-750) technologies. Methods for production of bispecific antibodies comprising a functional antibody Fc part are also known in the art (see, e.g., Zhu et al., Cancer Lett. 86 (1994) 127-134); and Suresh et al., Methods Enzymol. 121 (1986) 210-228).

These methods typically involve the generation of monoclonal antibodies, for example by means of fusing myeloma cells with the spleen cells from a mouse that has been immunized with the desired antigen using the hybridoma technology (see, e.g., Yokoyama et al., Curr. Protoc. Immunol. Chapter 2, Unit 2.5, 2006) or by means of recombinant antibody engineering (repertoire cloning or phage display/yeast display) (see, e.g., Chames & Baty, FEMS Microbiol. Letters 189 (2000) 1-8), and the combination of the antigen-binding domains or fragments or parts thereof of two or more different monoclonal antibodies to give a bispecific or multispecific construct using known molecular cloning techniques.

The multispecific molecules of the invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohaxane-I-carboxylate (sulfo-SMCC) (see e.g., Karpovsky et al., 1984 J. Exp. Med. 160: 1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, 111).

When the binding specificities are antibodies, they can be conjugated by sulfhydryl bonding of the C-terminus hinge regions of the two heavy chains. In a particular embodiment, the hinge region is modified to contain an odd number of sulfhydryl residues, for example one, prior to conjugation.

Alternatively, two or more binding specificities can be encoded in the same vector and expressed and assembled in the same host cell. This method is particularly useful where the bispecific molecule is a mAb X mAb, mAb X Fab, Fab X F (ab')2 or ligand X Fab fusion protein. A multispecific antibody of the invention can be a single chain molecule comprising one single chain antibody and a binding determinant, or a single chain multispecific antibody comprising two binding determinants. Multispecific antibody may comprise at least two single chain molecules. Methods for preparing multispecific antibodies and molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the multispecific antibodies to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In a further aspect, the invention provides a nucleic acid encoding the multispecific antibody of the invention or fragments thereof or binding domains thereof. Such nucleic acid sequences can be optimized for expression in mammalian cells.

The term "nucleic acid" is used herein interchangeably with the term "polynucleotide(s)" and refers to one or more deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphorates, 2-O-methyl ribonucleotides, peptide-nucleic acids (PNAs). Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260: 2605-2608, 1985; and Rossolini et al., Mol. Cell. Probes 8:91-98, 1994).

The invention provides substantially purified nucleic acid molecules which encode polypeptides comprising segments or domains of the multispecific antibody described above. When expressed from appropriate expression vectors, polypeptides encoded by these nucleic acid molecules are capable of exhibiting antigen binding capacity or capacities of the multispecific antibody of the present invention.

Also provided in the invention are polynucleotides which encode at least one CDR region and usually all three CDR regions of the binding domains of the multispecific antibody of the present invention set forth in Tables 1 to 4. Because of the degeneracy of the code, a variety of nucleic acid sequences will encode each of the immunoglobulin amino acid sequences.

The polynucleotide sequences can be produced by de novo solid-phase DNA synthesis or by PCR mutagenesis of an existing sequence (e.g., sequences as described in the Examples below) encoding the multispecific antibody of the invention or fragments thereof or binding domains thereof. Direct chemical synthesis of nucleic acids can be accomplished by methods known in the art, such as the phosphotriester method of Narang et al., 1979, Meth. Enzymol. 68:90; the phosphodiester method of Brown et al., Meth. Enzymol. 68: 109, 1979; the diethylphosphoramidite method of Beaucage et al., Tetra. Lett., 22: 1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the multispecific antibody of the invention or fragments thereof or binding domains thereof.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions. In this particular context, the term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

Various expression vectors can be employed to express the polynucleotides encoding the multispecific antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the CD137-binding polynucleotides and polypeptides in mammalian (e.g., human) cells include pThioHis A, B and C, pcDNA3.1/His, pEBVHis A, B and C, (Invitrogen, San Diego, Calif.), MPS V vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68: 143, 1992.

The choice of expression vector depends on the intended host cells in which the vector is to be expressed. Typically, the expression vectors contain a promoter and other regulatory sequences (e.g., enhancers) that are operably linked to the polynucleotides encoding a multispecific antibody chain or a fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of a multispecific antibody chain or a fragment. These elements typically include an ATG initiation codon and adjacent ribosome binding site or other sequences. In addition, the efficiency of expression may be enhanced by the inclusion of enhancers appropriate to the cell system in use (see, e.g., Scharf et al., Results Probl. Cell Differ. 20: 125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted the multispecific antibody of the invention or fragments thereof or binding domains thereof sequences. More often, the inserted the multispecific antibody of the invention or fragments thereof or binding domains thereof sequences are linked to signal sequences before inclusion in the vector. Vectors to be used to receive sequences encoding binding domains of the multispecific antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The host cells for harboring and expressing the multispecific antibody of the invention or fragments thereof or binding domains thereof can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express CD137-binding polypeptides of the invention. Insect cells in combination with baculovirus vectors can also be used.

In one embodiment, mammalian host cells are used to express and produce the multispecific antibody of the invention or fragments thereof or binding domains thereof. For example, they can be either a hybridoma cell line expressing endogenous immunoglobulin genes or a mammalian cell line harboring an exogenous expression vector. These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPS V promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation/nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express the multispecific antibody of the invention or fragments thereof or binding domains thereof can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type. The present invention thus provides a method of producing the antibody of the invention or antigen-binding fragment thereof, wherein said method comprises the step of culturing a host cell comprising a nucleic acid or a vector encoding the antibody of the invention or antigen-binding fragment thereof, whereby said antibody of the disclosure or a fragment thereof is expressed.

In one aspect, the present invention relates to a method of producing the multispecific antibody of the invention or a binding domain thereof or a fragment thereof, the method comprising the step of culturing a host cell expressing a nucleic acid encoding the multispecific antibody of the invention or a binding domain thereof or a fragment thereof.

In a further aspect, the present invention relates to a pharmaceutical composition comprising the multispecific antibody of the invention, and a pharmaceutically acceptable carrier. Pharmaceutically acceptable carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., the multispecific antibody of the invention, may be coated in a material to protect the compound from the action of acids and other natural conditions that may inactivate the compound.

Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the multispecific antibody of the invention is employed in the pharmaceutical compositions of the invention. The multispecific antibodies of the invention are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

The multispecific antibody of the invention is usually administered on multiple occasions. Intervals between single dosages can be weekly, monthly or yearly. Intervals can also be irregular as indicated by measuring blood levels of the multispecific antibody of the invention in the patient. Alternatively, the multispecific antibody of the invention can be administered as a sustained release formulation, in which case less frequent administration is required. Dosage and frequency vary depending on the half-life of the antibody in the patient. In general, humanized antibodies show longer half-life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In one aspect, the present invention relates to the multispecific antibody of the invention or the pharmaceutical composition of the invention for use as a medicament. In a suitable embodiment, the present invention provides the multispecific antibody or the pharmaceutical composition for use in treatment of a proliferative disease, in particular a cancer in a subject in need thereof.

In another aspect, the present invention provides the multispecific antibody or the pharmaceutical composition for use in a manufacture of a medicament for treatment of a proliferative disease, in particular a cancer.

In another aspect, the present invention relates to use of the multispecific antibody or the pharmaceutical composition for treating a proliferative disease, in particular a cancer in a subject in need thereof.

In a further aspect, the present invention relates to use of the multispecific antibody or the pharmaceutical composition in the manufacture of a medicament for treatment of a proliferative disease, in particular a cancer, in a subject in need thereof.

In another aspect, the present invention relates to a method of treating a subject comprising administering to the subject a therapeutically effective amount of the multispecific antibody of the present invention. In a suitable embodiment, the present invention relates to a method of treating a proliferative disease, in particular a cancer in a subject comprising administering to the subject a therapeutically effective amount of the multispecific antibody of the present invention.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The terms "treatment", "treating", "treat", "treated", and the like, as used herein, refer to obtaining a desired pharmacologic and/or physiologic effect. The effect may be therapeutic in terms of a partial or complete cure for a disease and/or adverse effect attributable to the disease or delaying the disease progression. "Treatment", as used herein, covers any treatment of a disease in a mammal, e.g., in a human, and includes: (a) inhibiting the disease, i.e., arresting its development; and (b) relieving the disease, i.e., causing regression of the disease.

The term "therapeutically effective amount" or "efficacious amount" refers to the amount of an agent that, when administered to a mammal or other subject for treating a disease, is sufficient to effect such treatment for the disease. The "therapeutically effective amount" will vary depending on the agent, the disease and its severity and the age, weight, etc., of the subject to be treated.

In one embodiment, the proliferative disease is a cancer. The term "cancer" refers to a disease characterized by the rapid and uncontrolled growth of aberrant cells. Cancer cells can spread locally or through the bloodstream and lymphatic system to other parts of the body. The terms "tumor" and "cancer" are used interchangeably herein, e.g., both terms encompass solid and liquid, e.g., diffuse or circulating, tumors. As used herein, the term "cancer" or "tumor" includes premalignant, as well as malignant cancers and tumors. The term "cancer" is used herein to mean a broad spectrum of tumors, including all solid and haematological malignancies. Examples of such tumors include, but are not limited to: a benign or especially malignant tumor, solid tumors, brain cancer, kidney cancer, liver cancer, adrenal gland cancer, bladder cancer, breast cancer, stomach cancer (e.g., gastric tumors), oesophageal cancer, ovarian cancer, cervical cancer, colon cancer, rectum cancer, prostate cancer, pancreatic cancer, lung cancer (e.g. non-small cell lung cancer and small cell lung cancer), vaginal cancer, thyroid cancer, melanoma (e.g., unresectable or metastatic melanoma), renal cell carcinoma, sarcoma, glioblastoma, multiple myeloma or gastrointestinal cancer, especially colon carcinoma or colorectal adenoma, a tumor of the neck and head, endometrial cancer, Cowden syndrome, Lhermitte-Duclos disease, Bannayan-Zonana syndrome, prostate hyperplasia, a neoplasia, especially of epithelial character, preferably mammary carcinoma or squamous cell carcinoma, chronic lymphocytic leukemia, chronic myelogenous leukemia (e.g., Philadelphia chromosome-positive chronic myelogenous leukemia), acute lymphoblastic leukemia (e.g., Philadelphia chromosome-positive acute lymphoblastic leukemia), non-Hodgkin's lymphoma, plasma cell myeloma, Hodgkin's lymphoma, a leukemia, and any combination thereof. In a preferred embodiment, the cancer is a lung cancer, preferably non-small cell lung cancer (NSCLC). In another embodiment, said cancer is a colorectal cancer.

The multispecific antibody of the present invention, or the composition of the present invention, inhibits the growth of solid tumors, but also liquid tumors. In a further embodiment, the proliferative disease is a solid tumor. The term "solid tumor" especially means a breast cancer, ovarian cancer, colon cancer, rectum cancer, prostate cancer, stomach cancer (especially gastric cancer), cervical cancer, lung cancer (e.g., non-small cell lung cancer and small cell lung cancer), and a tumor of the head and neck. Further, depending on the tumor type and the particular combination used, a decrease of the tumor volume can be obtained. The multispecific antibody of the present invention, or the composition of the present invention, is also suited to prevent the metastatic spread of tumors and the growth or development of micrometastases in a subject having a cancer.

In one embodiment, said cancer is PD-L1-positive, preferably wherein said cancer expresses high levels of PD-L1 in comparison to a healthy tissue, in particular wherein said cancer expresses PD-L1 (mRNA or protein) at least 2 times, at least 3 times, at least 4 times, at least 5 times, at least 6 times, at least 7 times, at least 8 times, at least 9 times, at least 10 times, at least 15 times, at least 20 times, at least 30 times, at least 40 times, at least 50 times, at least 60 times, at least 70 times, at least 80 times, at least 90 times, at least 100 times higher level in comparison to PD-L1 expression (mRNA or protein respectively) in a healthy tissue. In some embodiments, said cancer is malignant. In some embodiments, said cancer is benign. In some embodiments, said cancer is primary. In some embodiments, said cancer is secondary. In one embodiment, said cancer is lung cancer, preferably non-small cell lung cancer (NSCLC). In another embodiment, said cancer is colorectal cancer.

In one aspect, the present invention relates to a kit comprising the multispecific antibody of the invention or the pharmaceutical composition of the invention. The kit can include one or more other elements including: instructions for use; other reagents, e.g., a label, a therapeutic agent, or an agent useful for chelating, or otherwise coupling, an antibody to a label or therapeutic agent, or a radioprotective composition; devices or other materials for preparing the antibody molecule for administration; pharmaceutically acceptable carriers; and devices or other materials for administration to a subject. In a specific embodiment, the kit comprises the multispecific antibody of the invention in a pharmaceutically effective amount. In a further embodiment, the kit comprises a pharmaceutically effective amount of the multispecific antibody of the invention in lyophilized form and a diluent and, optionally, instructions for use. Said kit may further comprise a filter needle for reconstitution and a needle for injecting Sequence Listing (Mutations Designated According to AHo Numbering Scheme, CDRs Defined According to Numab CDR Definition)

TABLE 1

Examples of PDL1 binding domains of the present invention.

| SEQ ID NO: | Ab region | Sequence |
|---|---|---|
| 1 | HCDR1 | GFSFSSGYDMC |
| 2 | HCDR2 | CVVAGSVDITYYASWAKG |
| 3 | HCDR3 $_{33\text{-}03\text{-}002}$ | RKDAYSDAFNL |
| 4 | HCDR3 $_{33\text{-}03\text{-}G02,\ VH\text{-}Y112A}$ | RKDAASDAFNL |
| 5 | LCDR1 | QASQSINDYLA |
| 6 | LCDR2 | KASTLAS |
| 7 | LCDR3 $_{33\text{-}03\text{-}G02}$ | QQGYIITDIDNV |
| 8 | LCDR3 $_{33\text{-}03\text{-}G02,\ VL\text{-}Q108A}$ | QAGYIITDIDNV |
| 9 | LCDR3 $_{33\text{-}03\text{-}G02,\ VL\text{-}G109A}$ | QQAYIITDIDNV |
| 10 | LCDR3 $_{33\text{-}03\text{-}G02,\ VL\text{-}Q108A,\ VL\text{-}G109A}$ | QAAYIITDIDNV |
| 11 | VH $_{33\text{-}03\text{-}G02}$ (PRO830; PRO1075; PRO1076; PRO1434) | QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |

TABLE 1-continued

| Examples of PDL1 binding domains of the present invention. | | |
|---|---|---|
| SEQ ID NO: | Ab region | Sequence |
| 12 | $VH_{33\text{-}03\text{-}G02,\ VH\text{-}Y112A}$ (PRO1089; PRO1494) | QVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAASDAFNLWGQGTLVTVSS |
| 13 | $VL_{33\text{-}03\text{-}G02}$ (PRO830; PRO1089) | DIQMTQSPSSLSASVGDRVTITCQASQSINDYLAWYQQKPGKAPKLLIYKASTLASGVPSRFSGSGSGTDFTLTISSLQPEDFATYYCQQGYIITDIDNVFGTGTKVTVLG |
| 14 | $VL_{33\text{-}03\text{-}G02,\ VL\text{-}Q108A}$ (PRO1075; PRO1494) | DIQMTQSPSSLSASVGDRVTITCQASQSINDYLAWYQQKPGKAPKLLIYKASTLASGVPSRFSGSGSGTDFTLTISSLQPEDFATYYCQAGYIITDIDNVFGTGTKVTVLG |
| 15 | $VL_{33\text{-}03\text{-}G02,\ VL\text{-}G109A}$ (PRO1076) | DIQMTQSPSSLSASVGDRVTITCQASQSINDYLAWYQQKPGKAPKLLIYKASTLASGVPSRFSGSGSGTDFTLTISSLQPEDFATYYCQQAYIITDIDNVFGTGTKVTVLG |
| 16 | $VL_{33\text{-}03\text{-}G02,\ VL\text{-}Q108A,\ VL\text{-}G109A}$ (PRO1434) | DIQMTQSPSSLSASVGDRVTITCQASQSINDYLAWYQQKPGKAPKLLIYKASTLASGVPSRFSGSGSGTDFTLTISSLQPEDFATYYCQAAYIITDIDNVFGTGTKVTVLG |

TABLE 2

| Examples of HER2 binding domains of the present invention. | | |
|---|---|---|
| SEQ ID NO: | Description | Sequence |
| 17 | $HCDR1_{trastuzumab}$ | GFNIKDTYIH |
| 18 | $HCDR2_{trastuzumab}$ | RIYPTNGYTRYADSVKG |
| 19 | $HCDR3_{trastuzumab}$ | RWGGDGFYAMDY |
| 20 | $LCDR1_{trastuzumab}$ | RASQDVNTAVA |
| 21 | $LCDR2_{trastuzumab}$ | SASFLYS |

TABLE 2-continued

| Examples of HER2 binding domains of the present invention. | | |
|---|---|---|
| SEQ ID NO: | Description | Sequence |
| 22 | $LCDR3_{trastuzumab}$ | QQHYTTPPT |
| 23 | $VH_{trastuzumab}$ | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSS |
| 24 | $VH_{trastuzumab\ (G51C)}$ | EVQLVESGGGLVQPGGSLRLSCAASGFNIKDTYIHWVRQAPGKCLEWVARIYPTNGYTRYADSVKGRFTISADTSKNTAYLQMNSLRAEDTAVYYCSRWGGDGFYAMDYWGQGTLVTVSS |
| 25 | $VL_{trastuzumab\ (\lambda\text{-}capped)}$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGGGTKLTVLG |
| 26 | $VL_{trastuzumab\ (G141C)\ (\lambda\text{-}capped)}$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGCGTKLTVLG |
| 27 | $HCDR1_{pertuzumab}$ | GFTFTDYTMD |
| 28 | $HCDR2_{pertuzumab}$ | DVNPNSGGSIYNQRFKG |
| 29 | $HCDR3_{pertuzumab}$ | RNLGPSFYFDY |
| 30 | $LCDR1_{pertuzumab}$ | KASQDVSIGVA |
| 31 | $LCDR2_{pertuzumab}$ | SASYRYT |
| 32 | $LCDR3_{pertuzumab}$ | QQYYIYPYT |
| 33 | $VH_{pertuzumab}$ | EVQLVESGGGLVQPGGSLRLSCAASGFTFTDYTMDWVRQAPGKGLEWVADVNPNSGGSIYNQRFKGRFTLSVDRSKNTLYLQMNSLRAEDTAVYYCARNLGPSFYFDYWGQGTLVTVSS |
| 34 | $VH_{pertuzumab\ (G51C)}$ | EVQLVESGGGLVQPGGSLRLSCAASGFTFTDYTMDWVRQAPGKCLEWVADVN |

TABLE 2-continued

Examples of HER2 binding domains of the present invention.

| SEQ ID NO: | Description | Sequence |
|---|---|---|
| | | PNSGGSIYNQRFKGRFTLSVDRSKNTLYLQMNSLRAEDTAVYYCARNLGPSFYFDYWGQGTLVTVSS |
| 35 | VL$_{pertuzumab (\lambda\text{-}capped)}$ | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGTGTKVTVLG |
| 36 | VL$_{pertuzumab (G141C) (\lambda\text{-}capped)}$ | DIQMTQSPSSLSASVGDRVTITCKASQDVSIGVAWYQQKPGKAPKLLIYSASYRYTGVPSRFSGSGSGTDFTLTISSLQPEDFATYYCQQYYIYPYTFGCGTKVTVLG |

TABLE 3

Examples of CD3 binding domains of the present invention.

| SEQ ID NO: | Description | Sequence |
|---|---|---|
| 37 | HCDR1 | GFSLSSYDMS |
| 38 | HCDR2 | ASYASGPTYYASWAKG |
| 39 | HCDR3 | RGGWTGTSHSNI |
| 40 | LCDR1 | QSSQSVFSNNYLA |
| 41 | LCDR2 | SASTLAS |
| 42 | LCDR3 | LGSYACSSADCYV |
| 43 | VH$_{28\text{-}21\text{-}D09\ sc04}$ | EVQLVESGGGLVQPGGSLRLSCAASGFSLSSYDMSWVRQAPGKGLAWIGASYASGPTYYASWAKGRFTISRDNSKNTVYLQMNSLRAEDTATYFCARGGWTGTSHSNIWGQGTLVTVSS |
| 44 | VL$_{28\text{-}21\text{-}D09\ sc04}$ | DIQMTQSPSSLSASVGDRVTITCQSSQSVFSNNYLAWFQQKPGQSPKRLIYSASTLASGVPSRFSGSGSGTDFTLTISSLQPEDFATYYCLGSYACSSADCYVFGTGTKVTVLG |

TABLE 4

Examples of human serum albumin (HSA) binding domains of the present invention.

| SEQ ID NO: | Description | Sequence |
|---|---|---|
| | Anti-HSA domain 19-01-H04-sc03 | |
| 45 | HCDR1 | GFSLSSNAMG |
| 46 | HCDR2 | IISVGGFTYYASWAKG |
| 47 | HCDR3 | RDRHGGDSSGAFYL |
| 48 | LCDR1 | QSSESVYSNNQLS |
| 49 | LCDR2 | DASDLAS |
| 50 | LCDR3 | AGGFSSSSDTA |
| 51 | VH$_{19\text{-}01\text{-}H04\text{-}SC03}$ | EVQLVESGGGLVQPGGSLRLSCAASGFSLSSNAMGWVRQAPGKGLEYIGIISVGGFTYYASWAKGRFTISRDNSKNTVYLQMNSLRAEDTATYFCARDRHGGDSSGAFYLWGQGTLVTVSS |
| 52 | VL$_{19\text{-}01\text{-}H04\text{-}SC03}$ | DIQMTQSPSSLSASVGDRVTITCQSSESVYSNNQLSWYQQKPGQPPKLLIYDASDLASGVPSRFSGSGSGTDFTLTISSLQPEDFATYYCAGGFSSSSDTAFGGGTKLTVLG |
| | Anti-HSA domain 23-13-A01-sc02 | |
| 53 | HCDR1 | GFSFSSSYWIC |
| 54 | HCDR2 | CVFTGDGTTYYASWAKG |
| 55 | HCDR3 | RPVSVYYYGMDL |
| 56 | LCDR1 | QASQIISSRSA |
| 57 | LCDR2 | QASKLAS |
| 58 | LCDR3 | QCTYIDSNFGA |
| 59 | VH$_{23\text{-}13\text{-}A01\text{-}SC02}$ | EVQLVESGGGLVQPGGSLTRLSCAASGFSFSSSYWICWVRQAPGKGLEWVGCVFGDGTTYYASWAKGRFTISRDNSKNTVYLQMNSLRAEDTATYFCARPVSVYYYGMDLWGQGTLVTVSS |
| 60 | VL$_{23\text{-}13\text{-}A01\text{-}SC02}$ | DVVMTQSPSSLSASVGDRVTITCQASQIISSRSAWYQQKPGQPPKLLIYQASKLASGVPSRFSGSGSGTDFTLTISSLQPEDFATYYCQCTYIDSNFGAFGGGTKLTVLG |
| | Anti-HSA domain 19-04-A10-sc02 | |
| 61 | HCDR1 | GFSLSSYAMN |
| 62 | HCDR2 | HINAGDIAYYATWAKG |
| 63 | HCDR3 | RGAGGFSTGPFKL |
| 64 | LCDR1 | QASESINSRLA |
| 65 | LCDR2 | DASDLTS |
| 66 | LCDR3 | QGYGGSSTTT |

TABLE 4-continued

| Examples of human serum albumin (HSA) binding domains of the present invention. | | |
|---|---|---|
| SEQ ID NO: | Description | Sequence |
| 67 | VH $_{19-04-A10-SC02}$ (PRO2155) | EVQLVESGGGLVQPGGSLRLSCAASGFSLSSYAMNWVRQAPGKGLEWIGHINAGDIAYYATWAKGRFTISRDNSKNTVYLQMNSLRAEDTAVYFCARGAGGFSTGPFKLWGQGTLVTVSS |
| 68 | VH $_{19-04-A10-sc06(G51C)}$ (PRO2317) | EVQLVESGGGLVQPGGSLRLSCAASGFSLSSYAMNWVRQAPGKCLEWIGHINAGDIAYYATWAKGRFTISRDNSKNTVYLQMNSLRAEDTAVYFCARGAGGFSTGPFKLWGQGTLVTVSS |
| 69 | VL $_{19-04-A10-SC02}$ (PRO2155) | AFELTQSPSSLSASVGDRVTITCQASESINSRLAWYQQKPGQPPKLLIYDASDLTSGVPSRFSGSGSGTDFTLTISSLQPEDFATYYCQGYGGSSTTTFGGGTKLTVLG |
| 70 | VL $_{19-04-A10-sc06(G141C)}$ (PRO2317) | AFELTQSPSSLSASVGDRVTITCQASESINSRLAWYQQKPGQPPKLLIYDASDLTSGVPSRFSGSGSGTDFTLTISSLQPEDFATYYCQGYGGSSTTTFGCGTKLTVLG |

TABLE 5

| Examples of CD137 binding domains of the present invention. | | |
|---|---|---|
| SEQ ID NO: | Description | Sequence |
| Anti-CD137 domain 38-27-A11 sc07 | | |
| 71 | HCDR1 | GFSFSANYYPC |
| 72 | HCDR2 | CIYGGSSDITYDANWTKG |
| 73 | HCDR3 | RSAWYSGWGGDL |
| 74 | LCDR1 | QASQSISNRLA |
| 75 | LCDR2 | SASTLAS |
| 76 | LCDR3 | QSTYYGNDGNA |
| 77 | VH $_{38-27-A11\ sc07(G51C)}$ | EVQLVESGGGLVQPGGSLRLSCAASGFSFSANYYPCWVRQAPGKCLEWIGCIYGGSSDITYDANWTKGRFTISRDNSKNTVYLQMNSLRAEDTAVYYCARSAWYSGWGGDLWGQGTLVTVSS |
| 78 | VL $_{38-27-A11\ sc07(G141C)}$ | DIQMTQSPSSLSASVGDRVTITCQASQSISNRLAWYQQKPGKAPKLLIYSASTLASGVPSRFSGSGSGTDFTLTISSLQPEDFATYYCQSTYYGNDGNAFGCGTKVTVLG |

TABLE 6

| Examples of multispecific molecules of the present invention. | | |
|---|---|---|
| SEQ ID NO: | Description | Sequence |
| Constructs of Example 2: anti-HER2xPDL1($_{high\ KD}$)xCD3 (xHSA) PRO1454 (Tribody) | | |
| 79 | CHAIN_1$_{PRO1454}$ | DIQMTQSPSSLSASVGDRVTITCRASQDVNTAVAWYQQKPGKAPKLLIYSASFLYSGVPSRFSGSRSGTDFTLTISSLQPEDFATYYCQQHYTTPPTFGQGTKVEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSDIQMTQSPSSLSASVGDRVTITCQSSQSVFSNNYLAWFQQKPGQSPKRLIYSASTLASGVPSRFSGSGSGTDFTLTISSLQPEDFATYYCLGSYACSSADCYVFGTGTKVTVLGGGGGSGGGGSGGGGSGGGGSEVQLVESGGGLVQPGGSLRLSCAASGFSLSSYDMSWVRQAPGKGLAWIGASYASGPTYYASWAKGRFTISRDNSKNTVYLQMNSLRAEDTATYFCARGGWTGTSHSNIWGQGTLVTVSS |
| 80 | CHAIN_2$_{PRO14S4}$ | EVQLVESGGGLVQPGGSLRLSCAASGFNIKDTYIHWVRQAPGKGLEWVARIYPTNGYTRYADSVKGRFTISADTSKNTAYLQMNSLRAEDTAVYYCSRWGGDGFYAMDYWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKKVEPKSCGGGGSGGGGSDIQMTQSPSSLSASVGDRVTITCQASQSINDYLAWYQQKPGKAPKLLIYKASTLASGVPSRFSGSGSGTDFTLTISSLQPEDFATYYCQQAYIITDIDNVFGTGTKVTVLGGGGGSGGGGSGGGGSGGGGSQVQLQESGPGLVKPSETLSLTCKVSGFSFSSGYDMCWIRQPPGKGLEWIGCVVAGSVDITYYASWAKGRVTISVDSSKNQFSLKLSSVTAADTAVYYCARKDAYSDAFNLWGQGTLVTVSS |
| PRO1455 (Tribody) | | |
| 81 | CHAIN_1$_{PRO1455}$ | DIQMTQSPSSLSASVGDRVTITCQASENIYSFLAWYQQKPGKAPKLLIYSASKLAAGVPSRFSGSGSGTDFTLTISSLQPEDFATYYCQQTNRYSNPDIYNVFGTGTKVTVLGTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGECGGGGSGGGGSDIQMTQSPSSLSASVGDRVTITCQSSQSVFSNNYLAWFQQKPGQSPKRLIYSASTLASGVPSRFSGSGSGTDFTLTISSLQPEDFATYYCLGSYACSSADCYVFGTGTKVTVLGGG |

TABLE 6-continued

Examples of multispecific molecules of the present invention.

| SEQ ID NO: | Description | Sequence |
|---|---|---|
| | | GGSGGGGSGGGGSGGGGSEVQLVESGGGLVQPGGSLRLSCAASGFSLSSYDMSWV<br>RQAPGKGLAWIGASYASGPTYYASWAKGRFTISRDNSKNTVYLQMNSLRAEDTAT<br>YFCARGGWTGTSHSNIWGQGTLVTVSS |
| 82 | CHAIN_2P$_{RO1455}$ | EVQLVESGGGLVQPGGSLRLSCAASGIDFNSNYYMCWVRQAPGKGLEWIGCIYVGS<br>HVNTYYANWAKGRFTISRDNSKNTVYLQMNSLRAEDTAVYYCATSGSSVLYFKFW<br>GQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCG<br>GGGSGGGGSDIQMTQSPSSLSASVGDRVTITCQASQSINDYLAWYQQKPGKAPKLLI<br>YKASTLASGVPSRFSGSGSGTDFTLTISSLQPEDFATYYCQQAYIITDIDNVFGTGTKV<br>TVLGGGGGSGGGGSGGGGSGGGGSQVQLQESGPGLVKPSETLSLTCKVSGFSFSSG<br>YDMCWIRQPPGKGLEWIGCVVAGSVDITYYASWAKGRVTISVDSSKNQFSLKLSSV<br>TAADTAVYYCARKDAYSDAFNLWGQGTLVTVSS |
| | | PRO1456 (Tribody) |
| 83 | CHAIN_1$_{PRO1456}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGQGTKVEIKRTVAAPSVF<br>IFPPSDEQLKSGTASVVCLLNNFYPREAKVQWKVDNALQSGNSQESVTEQDSKDST<br>YSLSSTLTLSKADYEKHKVYACEVTHQGLSSPVTKSFNRGECGGGGSGGGGSDIQM<br>TQSPSSLSASVGDRVTITCQSSQSVFSNNYLAWFQQKPGQSPKRLIYSASTLASGVPS<br>RFSGSGSGTDFTLTISSLQPEDFATYYCLGSYACSSADCYVFGTGTKVTVLGGGGGS<br>GGGGSGGGGSGGGGSEVQLVESGGGLVQPGGSLRLSCAASGFSLSSYDMSWVRQA<br>PGKGLAWIGASYASGPTYYASWAKGRFTISRDNSKNTVYLQMNSLRAEDTATYFCA<br>RGGWTGTSHSNIWGQGTLVTVSS |
| 84 | CHAIN_2$_{PRO1456}$ | EVQLVESGGGLVQPGGSLRLSCAASGFNIKDTYIHWVRQAPGKGLEWVARIYPTNG<br>YTRYADSVKGRFTISADTSKNTAYLQMNSLRAEDTAVYYCSRWGGDGFYAMDYW<br>GQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCG<br>GGGSGGGGSDIQMTQSPSSLSASVGDRVTITCQASENIYSFLAWYQQKPGKAPKLLI<br>YSASKLAAGVPSRFSGSGSGTDFTLTISSLQPEDFATYYCQQTNRYSNPDIYNVFGTG<br>TKVTVLGGGGGSGGGGSGGGGSGGGGSEVQLVESGGGLVQPGGSLRLSCAASGIDF<br>NSNYYMCWVRQAPGKGLEWIGCIYVGSHVNTYYANWAKGRFTISRDNSKNTVYLQ<br>MNSLRAEDTAVYYCATSGSSVLYFKFWGQGTLVTVSS |
| | | PRO1497 (Tribody) |
| 85 | CHAIN_1$_{PRO1497}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGQGTKVEIKRTVAAPSVF<br>IFPPSDEQLKSGTASVVCLLNNFYPREAKVQWKVDNALQSGNSQESVTEQDSKDST<br>YSLSSTLTLSKADYEKHKVYACEVTHQGLSSPVTKSFNRGECGGGGSGGGGSDIQM<br>TQSPSSLSASVGDRVTITCQSSQSVFSNNYLAWFQQKPGQSPKRLIYSASTLASGVPS<br>RFSGSGSGTDFTLTISSLQPEDFATYYCLGSYACSSADCYVFGTGTKVTVLGGGGGS<br>GGGGSGGGGSGGGGSEVQLVESGGGLVQPGGSLRLSCAASGFSLSSYDMSWVRQA<br>PGKGLAWIGASYASGPTYYASWAKGRFTISRDNSKNTVYLQMNSLRAEDTATYFCA<br>RGGWTGTSHSNIWGQGTLVTVSS |
| 86 | CHAIN_2$_{PRO1497}$ | EVQLVESGGGLVQPGGSLRLSCAASGFNIKDTYIHWVRQAPGKGLEWVARIYPTNG<br>YTRYADSVKGRFTISADTSKNTAYLQMNSLRAEDTAVYYCSRWGGDGFYAMDYW<br>GQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCG<br>GGGSGGGGSDIQMTQSPSSLSASVGDRVTITCQASQSINDYLAWYQQKPGKAPKLLI<br>YKASTLASGVPSRFSGSGSGTDFTLTISSLQPEDFATYYCQAAYIITDIDNVFGTGTKV<br>TVLGGGGGSGGGGSGGGGSGGGGSQVQLQESGPGLVKPSETLSLTCKVSGFSFSSG<br>YDMCWIRQPPGKGLEWIGCVVAGSVDITYYASWAKGRVTISVDSSKNQFSLKLSSV<br>TAADTAVYYCARKDAYSDAFNLWGQGTLVTVSS |
| | | PRO1498 (Tribody) |
| 87 | CHAIN_1$_{PRO1498}$ | DIQMTQSPSSLSASVGDRVTITCQASENIYSFLAWYQQKPGKAPKLLIYSASKLAAGV<br>PSRFSGSGSGTDFTLTISSLQPEDFATYYCQQTNRYSNPDIYNVFGTGTKVTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGECGGGGSGGGGS<br>DIQMTQSPSSLSASVGDRVTITCQSSQSVFSNNYLAWFQQKPGQSPKRLIYSASTLAS<br>GVPSRFSGSGSGTDFTLTISSLQPEDFATYYCLGSYACSSADCYVFGTGTKVTVLGGG<br>GGSGGGGSGGGGSGGGGSEVQLVESGGGLVQPGGSLRLSCAASGFSLSSYDMSWV<br>RQAPGKGLAWIGASYASGPTYYASWAKGRFTISRDNSKNTVYLQMNSLRAEDTAT<br>YFCARGGWTGTSHSNIWGQGTLVTVSS |
| 88 | CHAIN_2$_{PRO1498}$ | EVQLVESGGGLVQPGGSLRLSCAASGIDFNSNYYMCWVRQAPGKGLEWIGCIYVGS<br>HVNTYYANWAKGRFTISRDNSKNTVYLQMNSLRAEDTAVYYCATSGSSVLYFKFW<br>GQGTLVTVSSASTKGPSVFPLAPSSKSTSGGTAALGCLVKDYFPEPVTVSWNSGALT<br>SGVHTFPAVLQSSGLYSLSSVVTVPSSSLGTQTYICNVNHKPSNTKVDKKVEPKSCG<br>GGGSGGGGSDIQMTQSPSSLSASVGDRVTITCQASQSINDYLAWYQQKPGKAPKLLI |

TABLE 6-continued

Examples of multispecific molecules of the present invention.

| SEQ ID NO: | Description | Sequence |
|---|---|---|
| | | YKASTLASGVPSRFSGSGSGTDFTLTISSLQPEDFATYYCQAAYIITDIDNVFGTGTKV<br>TVLGGGGGSGGGGSGGGGSGGGGSQVQLQESGPGLVKPSETLSLTCKVSGFSFSSG<br>YDMCWIRQPPGKGLEWIGCVVAGSVDITYYASWAKGRVTISVDSSKNQFSLKLSSV<br>TAADTAVYYCARKDAYSDAFNLWGQGTLVTVSS |
| | | PRO1543 (MATCH4) |
| 89 | CHAIN_1$_{PRO1543}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSGG<br>GGSGGGGSGGGGSEVQLVESGGGLVQPGGSLRLSCAASGFNIKDTYIHWVRQAPGK<br>CLEWVARIYPTNGYTRYADSVKGRFTISADTSKNTAYLQMNSLRAEDTAVYYCSR<br>WGGDGFYAMDYWGQGTLVTVSSGGGGSGGGGSDVVMTQSPSSLSASVGDRVTITC<br>QASQIISSRSAWYQQKPGQPPKLLIYQASKLASGVPSRFSGSGSGTDFTLTISSLQPED<br>FATYYCQCTYIDSNFGAFGCGTKLTVLGGGSGGSDIQMTQSPSSLSASVGDRVTITC<br>QSSQSVFSNNYLAWFQQKPGQSPKRLIYSASTLASGVPSRFSGSGSGTDFTLTISSLQP<br>EDFATYYCLGSYACSSADCYVFGTGTKVTVLG |
| 90 | CHAIN_2$_{PRO1543}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCWAGSVDITYYASWAKGRVTISVDSSKNQFSLKLSSVTAADTAVYYC<br>ARKDAYSDAFNLWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSFSSSYWICWVRQAPGKCLEWVGCVFTGDGTTYYA<br>SWAKGRFTISRDNSKNTVYLQMNSLRAEDTATYFCARPVSVYYYGMDLWGQGTLV<br>TVSS |
| | | PRO1544 (MATCH4) |
| 91 | CHAIN_1$_{PRO1544}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCWAGSVDITYYASWAKGRVTISVDSSKNQFSLKLSSVTAADTAVYYC<br>ARKDAYSDAFNLWGQGTLVTVSSGGGGSGGGGSDVVMTQSPSSLSASVGDRVTITC<br>QASQIISSRSAWYQQKPGQPPKLLIYQASKLASGVPSRFSGSGSGTDFTLTISSLQPED<br>FATYYCQCTYIDSNFGAFGCGTKLTVLGGGSGGSDIQMTQSPSSLSASVGDRVTITC<br>QSSQSVFSNNYLAWFQQKPGQSPKRLIYSASTLASGVPSRFSGSGSGTDFTLTISSLQP<br>EDFATYYCLGSYACSSADCYVFGTGTKVTVLG |
| 92 | CHAIN_2$_{PRO1544}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSGG<br>GGSGGGGSGGGGSEVQLVESGGGLVQPGGSLRLSCAASGFNIKDTYIHWVRQAPGK<br>CLEWVARIYPTNGYTRYADSVKGRFTISADTSKNTAYLQMNSLRAEDTAVYYCSR<br>WGGDGFYAMDYWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSFSSSYWICWVRQAPGKCLEWVGCVFTGDGTTYYA<br>SWAKGRFTISRDNSKNTVYLQMNSLRAEDTATYFCARPVSVYYYGMDLWGQGTLV<br>TVSS |
| | | PRO1545 (MATCH4) |
| 93 | CHAIN_1$_{PRO1545}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCVVAGSVDITYYASWAKGRVTISVDSSKNQFSLKLSSVTAADTAVYYC<br>ARKDAYSDAFNLWGQGTLVTVSSGGGGSGGGGSDVVMTQSPSSLSASVGDRVTITC<br>QASQIISSRSAWYQQKPGQPPKLLIYQASKLASGVPSRFSGSGSGTDFTLTISSLQPED<br>FATYYCQCTYIDSNFGAFGCGTKLTVLGGGSGGSDIQMTQSPSSLSASVGDRVTITC<br>QSSQSVFSNNYLAWFQQKPGQSPKRLIYSASTLASGVPSRFSGSGSGTDFTLTISSLQP<br>EDFATYYCLGSYACSSADCYVFGTGTKVTVLG |
| 94 | CHAIN_2$_{PRO1515}$ | DIQMTQSPSSLSASVGDRVTITCQASENIYSFLAWYQQKPGKAPKLLIYSASKLAAGV<br>PSRFSGSGSGTDFTLTISSLQPEDFATYYCQQTNRYSNPDIYNVFGTGTKVTVLGGGG<br>GSGGGGSGGGGSGGGGSEVQLVESGGGLVQPGGSLRLSCAASGIDFNSNYYMCWV<br>RQAPGKGLEWIGCIYVGSHVNTYYANWAKGRFTISRDNSKNTVYLQMNSLRAEDT<br>AVYYCATSGSSVLYFKFWGQGTLVTVSSGGGGSGGGGSEVQLVESGGGLVQPGGS<br>LRLSCAASGFSLSSYDMSWVRQAPGKGLAWIGASYASGPTYYASWAKGRFTISRDN<br>SKNTVYLQMNSLRAEDTATYFCARGGWTGTSHSNIWGQGTLVTVSSGGGSGGGSE<br>VQLVESGGGLVQPGGSLRLSCAASGFSFSSSYWICWVRQAPGKCLEWVGCVFTGDG<br>TTYYASWAKGRFTISRDNSKNTVYLQMNSLRAEDTATYFCARPVSVYYYGMDLWG<br>QGTLVTVSS |

TABLE 6-continued

Examples of multispecific molecules of the present invention.

| SEQ ID NO: | Description | Sequence |
|---|---|---|
| | | PRO1546 (MATCH4) |
| 95 | CHA1N_1$_{PRO1546}$ | DIQMTQSPSSLSASVGDRVTITCQASENIYSFLAWYQQKPGKAPKLLIYSASKLAAGV<br>PSRFSGSGSGTDFTLTISSLQPEDFATYYCQQTNRYSNPDIYNVFGTGTKVTVLGGGG<br>GSGGGGSGGGGSGGGGSEVQLVESGGGLVQPGGSLRLSCAASGIDFNSNYYMCWV<br>RQAPGKGLEWIGCIYVGSHVNTYYANWAKGRFTISRDNSKNTVYLQMNSLRAEDT<br>AVYYCATSGSSVLYFKFWGQGTLVTVSSGGGGSGGGGSDVVMTQSPSSLSASVGDR<br>VTITCQASQIISSRSAWYQQKPGQPPKLLIYQASKLASGVPSRFSGSGSGTDFTLTISSL<br>QPEDFATYYCQCTYIDSNFGAFGCGTKLTVLGGGSGGSDIQMTQSPSSLSASVGDRV<br>TITCQSSQSVFSNNYLAWFQQKPGQSPKRLIYSASTLASGVPSRFSGSGSGTDFTLTIS<br>SLQPEDFATYYCLGSYACSSADCYVFGTGTKVTVLG |
| 96 | CHAIN_2$_{PRO1546}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCVVAGSVDITYYASWAKGRVTISVDSSKNQFSLKLSSVTAADTAVYYC<br>ARKDAYSDAFNLWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSFSSSYWICWVRQAPGKCLEWVGCVFTGDGTTYYA<br>SWAKGRFTISRDNSKNTVYLQMNSLRAEDTATYFCARPVSVYYYGMDLWGQGTLV<br>TVSS |
| | | PRO1547 (DVD-Tribody) |
| 97 | CHAIN_1P$_{RO1547}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGQGTKVEIKRTVAAPSVF<br>IFPPDVVMTQSPSSLSASVGDRVTITCQASQIISSRSAWYQQKPGQPPKLLIYQASKLA<br>SGVPSRFSGSGSGTDFTLTISSLQPEDFATYYCQCTYIDSNFGAFGCGTKLTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGECGGGGSGGGGS<br>DIQMTQSPSSLSASVGDRVTITCQSSQSVFSNNYLAWFQQKPGQSPKRLIYSASTLAS<br>GVPSRFSGSGSGTDFTLTISSLQPEDFATYYCLGSYACSSADCYVFGTGTKVTVLGGG<br>GGSGGGGSGGGGSGGGGSEVQLVESGGGLVQPGGSLRLSCAASGFSLSSYDMSWV<br>RQAPGKGLAWIGASYASGPTYYASWAKGRFTISRDNSKNTVYLQMNSLRAEDTAT<br>YFCARGGWTGTSHSNIWGQGTLVTVSS |
| 98 | CHAIN_2$_{PRO1547}$ | EVQLVESGGGLVQPGGSLRLSCAASGFNIKDTYIHWVRQAPGKGLEWVARIYPTNG<br>YTRYADSVKGRFTISADTSKNTAYLQMNSLRAEDTAVYYCSRWGGDGFYAMDYW<br>GQGTLVTVSSASTKGPSVFPLAPEVQLVESGGGLVQPGGSLRLSCAASGFSFSSSYWI<br>CWVRQAPGKCLEWVGCVFTGDGTTYYASWAKGRFTISRDNSKNTVYLQMNSLRA<br>EDTATYFCARPVSVYYYGMDLWGQGTLVTVSSASTKGPSVFPLAPSSKSTSGGTAA<br>LGCLVKDYFPEPVTVSWNSGALTSGVHTFPAVLQSSGLYSLSSVVTVPSSSLGTQTYI<br>CNVNHKPSNTKVDKKVEPKSCGGGGSGGGGSIQMTQSPSSLSASVGDRVTITCQAS<br>QSINDYLAWYQQKPGKAPKLLIYKASTLASGVPSRFSGSGSGTDFTLTISSLQPEDFA<br>TYYCQAAYIITDIDNVFGTGTKVTVLGGGGGSGGGGSGGGGSGGGGSQVQLQESGP<br>GLVKPSETLSLTCKVSGFSFSSGYDMCWIRQPPGKGLEWIGCVVAGSVDITYYASWA<br>KGRVTISVDSSKNQFSLKLSSVTAADTAVYYCARKDAYSDAFNLWGQGTLVTVSS |
| | | PRO1548 (DVD-Tribody) |
| 99 | CHAIN_1$_{PRO1548}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGQGTKVEIKRTVAAPSVF<br>IFPPDVVMTQSPSSLSASVGDRVTITCQASQIISSRSAWYQQKPGQPPKLLIYQASKLA<br>SGVPSRFSGSGSGTDFTLTISSLQPEDFATYYCQCTYIDSNFGAFGCGTKLTVLGTVA<br>APSVFIFPPSDEQLKSGTASVVCLLNNFYPREAKVQWKVDNALQSGNSQESVTEQDS<br>KDSTYSLSSTLTLSKADYEKHKVYACEVTHQGLSSPVTKSFNRGECGGGGSGGGGS<br>DIQMTQSPSSLSASVGDRVTITCQSSQSVFSNNYLAWFQQKPGQSPKRLIYSASTLAS<br>GVPSRFSGSGSGTDFTLTISSLQPEDFATYYCLGSYACSSADCYVFGTGTKVTVLGGG<br>GGSGGGGSGGGGSGGGGSEVQLVESGGGLVQPGGSLRLSCAASGFSLSSYDMSWV<br>RQAPGKGLAWIGASYASGPTYYASWAKGRFTISRDNSKNTVYLQMNSLRAEDTAT<br>YFCARGGWTGTSHSNIWGQGTLVTVSS |
| 100 | CHAIN_2$_{PRO1548}$ | EVQLVESGGGLVQPGGSLRLSCAASGFNIKDTYIHWVRQAPGKGLEWVARIYPTNG<br>YTRYADSVKGRFTISADTSKNTAYLQMNSLRAEDTAVYYCSRWGGDGFYAMDYW<br>GQGTLVTVSSASTKGPSVFPLAPEVQLVESGGGLVQPGGSLRLSCAASGFSFSSSYWI<br>CWVRQAPGKCLEWVGCVFTGDGTTYYASWAKGRFTISRDNSKNTVYLQMNSLRA<br>EDTATYFCARPVSVYYYGMDLWGQGTLVTVSSASTKGPSVFPLAPSSKSTSGGTAA<br>LGCLVKDYFPEPVTVSWNSGALTSGVHTFPAVLQSSGLYSLSSVVTVPSSSLGTQTYI<br>CNVNHKPSNTKVDKKVEPKSCGGGGSGGGGSIQMTQSPSSLSASVGDRVTITCQASE |

TABLE 6-continued

Examples of multispecific molecules of the present invention.

| SEQ ID NO: | Description | Sequence |
|---|---|---|
| | | NIYSFLAWYQQKPGKAPKLLIYSASKLAAGVPSRFSGSGSGTDFTLTISSLQPEDFAT<br>YYCQQTNRYSNPDIYNVFGTGTKVTVLGGGGGSGGGGSGGGGSGGGGSEVQLVES<br>GGGLVQPGGSLRLSCAASGIDFNSNYYMCWVRQAPGKGLEWIGCIYVGSHVNTYY<br>ANWAKGRFTISRDNSKNTVYLQMNSLRAEDTAVYYCATSGSSVLYFKFWGQGTLV<br>TVSS |
| | | PRO1557 (MATCH4) |
| 101 | CHAIN_1$_{PRO1557}$ | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSGG<br>GGSGGGGSGGGGSEVQLVESGGGLVQPGGSLRLSCAASGFNIKDTYIHWVRQAPGK<br>CLEWVARIYPTNGYTRYADSVKGRFTISADTSKNTAYLQMNSLRAEDTAVYYCSR<br>WGGDGFYAMDYWGQGTLVTVSSGGGGSGGGGSDVVMTQSPSSLSASVGDRVTITC<br>QASQIISSRSAWYQQKPGQPPKLLIYQASKLASGVPSRFSGSGSGTDFTLTISSLQPED<br>FATYYCQCTYIDSNFGAFGCGTKLTVLGGGSGGSDIQMTQSPSSLSASVGDRVTITC<br>QSSQSVFSNNYLAWFQQKPGQSPKRLIYSASTLASGVPSRFSGSGSGTDFTLTISSLQP<br>EDFATYYCLGSYACSSADCYVFGTGTKVTVLG |
| 102 | CHAIN_2$_{PRO1557}$ | DIQMTQSPSSLSASVGDRVTITCQASENIYSFLAWYQQKPGKAPKLLIYSASKLAAGV<br>PSRFSGSGSGTDFTLTISSLQPEDFATYYCQQTNRYSNPDIYNVFGTGTKVTVLGGGG<br>GSGGGGSGGGGSGGGGSEVQLVESGGGLVQPGGSLRLSCAASGIDFNSNYYMCWV<br>RQAPGKGLEWIGCIYVGSHVNTYYANWAKGRFTISRDNSKNTVYLQMNSLRAEDT<br>AVYYCATSGSSVLYFKFWGQGTLVTVSSGGGGSGGGGSEVQLVESGGGLVQPGGS<br>LRLSCAASGFSLSSYDMSWVRQAPGKGLAWIGASYASGPTYYASWAKGRFTISRDN<br>SKNTVYLQMNSLRAEDTATYFCARGGWTGTSHSNIWGQGTLVTVSSGGGSGGGSE<br>VQLVESGGGLVQPGGSLRLSCAASGFSFSSSYWICWVRQAPGKCLEWVGCVFTGDG<br>TTYYASWAKGRFTISRDNSKNTVYLQMNSLRAEDTATYFCARPVSVYYYGMDLWG<br>QGTLVTVSS |
| | | PRO1558 (MATCH4) |
| 103 | CHAIN_1$_{PRO1558}$ | DIQMTQSPSSLSASVGDRVTITCQASENIYSFLAWYQQKPGKAPKLLIYSASKLAAGVPS<br>RFSGSGSGTDFTLTISSLQPEDFATYYCQQTNRYSNPDIYNVFGTGTKVTVLGGGGGSG<br>GGGSGGGGSGGGGSEVQLVESGGGLVQPGGSLRLSCAASGIDFNSNYYMCWVRQAPG<br>KGLEWIGCIYVGSHVNTYYANWAKGRFTISRDNSKNTVYLQMNSLRAEDTAVYYCAT<br>SGSSVLYFKFWGQGTLVTVSSGGGGSGGGGSDVVMTQSPSSLSASVGDRVTITCQASQI<br>ISSRSAWYQQKPGQPPKLLIYQASKLASGVPSRFSGSGSGTDFTLTISSLQPEDFATYYCQ<br>CTYIDSNFGAFGCGTKLTVLGGGSGGSDIQMTQSPSSLSASVGDRVTITCQSSQSVFSNN<br>YLAWFQQKPGQSPKRLIYSASTLASGVPSRFSGSGSGTDFTLTISSLQPEDFATYYCLGS<br>YACSSADCYVFGTGTKVTVLG |
| 104 | CHAIN_2$_{PRO1558}$ | DIQMTQSPSSLSASVGDRVTITCRASQDVNTAVAWYQQKPGKAPKLLIYSASFLYSGVP<br>SRFSGSRSGTDFTLTISSLQPEDFATYYCQQHYTTPPTFGCGTKLTVLGGGGGSGGGGSG<br>GGGSGGGGSEVQLVESGGGLVQPGGSLRLSCAASGFNIKDTYIHWVRQAPGKCLEWV<br>ARIYPTNGYTRYADSVKGRFTISADTSKNTAYLQMNSLRAEDTAVYYCSRWGGDGFY<br>AMDYWGQGTLVTVSSGGGGSGGGGSEVQLVESGGGLVQPGGSLRLSCAASGFSLSSY<br>DMSWVRQAPGKGLAWIGASYASGPTYYASWAKGRFTISRDNSKNTVYLQMNSLRAED<br>TATYFCARGGWTGTSHSNIWGQGTLVTVSSGGGSGGGSEVQLVESGGGLVQPGGSLRL<br>SCAASGFSFSSSYWICWVRQAPGKCLEWVGCVFTGDGTTYYASWAKGRFTISRDNSKN<br>TVYLQMNSLRAEDTATYFCARPVSVYYYGMDLWGQGTLVTVSS |
| | | Constructs of Example 3: anti-HER2xPDL1($_{high\ KD}$)xCD137xHSA<br>PR01778 (MATCH4) |
| 105 | CHAIN_1$_{PRO1778}$ | DIQMTQSPSSLSASVGDRVTITCRASQDVNTAVAWYQQKPGKAPKLLIYSASFLYSGVPS<br>RFSGSRSGTDFTLTISSLQPEDFATYYCQQHYTTPPTFGCGTKLTVLGGGGGSGGGGSGG<br>GGSGGGGSEVQLVESGGGLVQPGGSLRLSCAASGFNIKDTYIHWVRQAPGKCLEWVARI<br>YPTNGYTRYADSVKGRFTISADTSKNTAYLQMNSLRAEDTAVYYCSRWGGDGFYAMD<br>YWGQGTLVTVSSGGGGSGGGGSDIQMTQSPSSLSASVGDRVTITCQASQSISNRLAWYQ<br>QKPGKAPKLLIYSASTLASGVPSRFSGSGSGTDFTLTISSLQPEDFATYYCQSTYYGNDGN<br>AFGCGTKVTVLGGGSGGSDIQMTQSPSSLSASVGDRVTITCQASQSINDYLAWYQQKPG<br>KAPKLLIYKASTLASGVPSRFSGSGSGTDFTLTISSLQPEDFATYYCQAAYIITDIDNVFGT<br>GTKVTVLG |
| 106 | CHAIN_2$_{PRO1778}$ | DVVMTQSPSSLSASVGDRVTITCQASQIISSRSAWYQQKPGQPPKLLIYQASKLASGVPSR<br>FSGSGSGTDFTLTISSLQPEDFATYYCQCTYIDSNFGAFGGGTKLTVLGGGGGSGGGGSG<br>GGGSGGGGSEVQLVESGGGLVQPGGSLRLSCAASGFSFSSSYWICWVRQAPGKGLEWV<br>GCVFTGDGTTYYASWAKGRFTISRDNSKNTVYLQMNSLRAEDTATYFCARPVSVYYYG<br>MDLWGQGTLVTVSSGGGGSGGGGSQVQLQESGPGLVKPSETLSLTCKVSGFSFSSGYDM<br>CWIRQPPGKGLEWIGCVVAGSVDITYYASWAKGRVTISVDSSKNQFSLKLSSVTAADTA<br>VYYCARKDAYSDAFNLWGQGTLVTVSSGGGSGGGSEVQLVESGGGLVQPGGSLRLSCA<br>ASGFSFSANYYPCWVRQAPGKCLEWIGCIYGGSSDITYDANWTKGRFTISRDNSKNTVYL<br>QMNSLRAEDTAVYYCARSAWYSGWGGDLWGQGTLVTVSS |

TABLE 6-continued

Examples of multispecific molecules of the present invention.

| SEQ ID NO: | Description | Sequence |
|---|---|---|
| | | PRO1780 (MATCH4) |
| 107 | CHAIN_1$_{PRO1780}$ | DIQMTQSPSSLSASVGDRVTITCRASQDVNTAVAWYQQKPGKAPKLLIYSASFLYSGVPS<br>RFSGSRSGTDFTLTISSLQPEDFATYYCQQHYTTPPTFGCGTKLTVLGGGGGSGGGGSGG<br>GGSGGGGSEVQLVESGGGLVQPGGSLRLSCAASGFNIKDTYIHWVRQAPGKCLEWVARI<br>YPTNGYTRYADSVKGRFTISADTSKNTAYLQMNSLRAEDTAVYYCSRWGGDGFYAMD<br>YWGQGTLVTVSSGGGGSGGGGSDVVMTQSPSSLSASVGDRVTITCQASQIISSRSAWYQ<br>QKPGQPPKLLIYQASKLASGVPSRFSGSGSGTDFTLTISSLQPEDFATYYCQCTYIDSNFGA<br>FGCGTKLTVLGGGSGGSDIQMTQSPSSLSASVGDRVTITCQASQSINDYLAWYQQKPGK<br>APKLLIYKASTLASGVPSRFSGSGSGTDFTLTISSLQPEDFATYYCQAAYIITDIDNVFGTG<br>TKVTVLG |
| 108 | CHAIN_2$_{PRO1780}$ | DIQMTQSPSSLSASVGDRVTITCQASQSISNRLAWYQQKPGKAPKLLIYSASTLASGVPSR<br>FSGSGSGTDFTLTISSLQPEDFATYYCQSTYYGNDGNAFGCGTKVTVLGGGGGSGGGGS<br>GGGGSGGGGSEVQLVESGGGLVQPGGSLRLSCAASGFSFSANYYPCWVRQAPGKCLEWI<br>GCIYGGSSDITYDANWTKGRFTISRDNSKNTVYLQMNSLRAEDTAVYYCARSAWYSGW<br>GGDLWGQGTLVTVSSGGGGSGGGGSQVQLQESGPGLVKPSETLSLTCKVSGFSFSSGYD<br>MCWIRQPPGKGLEWIGCVVAGSVDITYYASWAKGRVTISVDSSKNQFSLKLSSVTAADT<br>AVYYCARKDAYSDAFNLWGQGTLVTVSSGGGSGGGSEVQLVESGGGLVQPGGSLRLSC<br>AASGFSFSSSYWICWVRQAPGKCLEWVGCVFTGDGTTYYASWAKGRFTISRDNSKNTV<br>YLQMNSLRAEDTATYFCARPVSVYYYGMDLWGQGTLVTVSS |
| | | PR01992 (MATCH4) |
| 109 | CHAIN_1$_{PRO1992}$ | DVVMTQSPSSLSASVGDRVTITCQASQIISSRSAWYQQKPGQPPKLLIYQASKLASGVPSR<br>FSGSGSGTDFTLTISSLQPEDFATYYCQCTYIDSNFGAFGTGTKLTVLGGGGGSGGGGSG<br>GGGSGGGGSEVQLVESGGGLVQPGGSLRLSCAASGFSFSSSYWICWVRQAPGKGLEWV<br>GCVFTGDGTTYYASWAKGRFTISRDNSKNTVYLQMNSLRAEDTATYFCARPVSVYYYG<br>MDLWGQGTLVTVSSGGGGSGGGGSDIQMTQSPSSLSASVGDRVTITCKASQDVSIGVAW<br>YQQKPGKAPKLLIYSASYRYTGVPSRFSGSGSGTDFTLTISSLQPEDFATYYCQQYYIYPY<br>TFGCGTKVTVLGGGSGGSDIQMTQSPSSLSASVGDRVTITCQASQSINDYLAWYQQKPG<br>KAPKLLIYKASTLASGVPSRFSGSGSGTDFTLTISSLQPEDFATYYCQAAYIITDIDNVFGT<br>GTKVTVLG |
| 110 | CHAIN_2$_{PRO1992}$ | DIQMTQSPSSLSASVGDRVTITCQASQSISNRLAWYQQKPGKAPKLLIYSASTLASGVPSR<br>FSGSGSGTDFTLTISSLQPEDFATYYCQSTYYGNDGNAFGCGTKVTVLGGGGGSGGGGS<br>GGGGSGGGGSEVQLVESGGGLVQPGGSLRLSCAASGFSFSANYYPCWVRQAPGKCLEWI<br>GCIYGGSSDITYDANWTKGRFTISRDNSKNTVYLQMNSLRAEDTAVYYCARSAWYSGW<br>GGDLWGQGTLVTVSSGGGGSGGGGSQVQLQESGPGLVKPSETLSLTCKVSGFSFSSGYD<br>MCWIRQPPGKGLEWIGCVVAGSVDITYYASWAKGRVTISVDSSKNQFSLKLSSVTAADT<br>AVYYCARKDAYSDAFNLWGQGTLVTVSSGGGSGGGSEVQLVESGGGLVQPGGSLRLSC<br>AASGFTFTDYTMDWVRQAPGKCLEWVADVNPNSGGSIYNQRFKGRFTLSVDRSKNTLY<br>LQMNSLRAEDTAVYYCARNLGPSFYFDYWGQGTLVTVSS |
| | | PR01993 (MATCH4) andPR01993 variant (MATCH4) |
| 111 | CHAIN_1$_{PRO1993}$ | DIQMTQSPSSLSASVGDRVTITCKASQDVSIGVAWYQQKPGKAPKLLIYSASYRYTG<br>VPSRFSGSGSGTDFTLTISSLQPEDFATYYCQQYYIYPYTFGCGTKVTVLGGGGGSGG<br>GGSGGGGSGGGGSEVQLVESGGGLVQPGGSLRLSCAASGFTFTDYTMDWVRQAPG<br>KCLEWVADVNPNSGGSIYNQRFKGRFTLSVDRSKNTLYLQMNSLRAEDTAVYYCA<br>RNLGPSFYFDYWGQGTLVTVSSGGGGSGGGGSDVVMTQSPSSLSASVGDRVTITCQ<br>ASQIISSRSAWYQQKPGQPPKLLIYQASKLASGVPSRFSGSGSGTDFTLTISSLQPEDF<br>ATYYCQCTYIDSNFGAFGTGTKLTVLGGGSGGSDIQMTQSPSSLSASVGDRVTITCQ<br>ASQSISNRLAWYQQKPGKAPKLLIYSASTLASGVPSRFSGSGSGTDFTLTISSLQPEDF<br>ATYYCQSTYYGNDGNAFGCGTKVTVLG |
| 112 | CHAIN_2$_{PRO1993}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCVVAGSVDITYYASWAKGRVTISVDSSKNQFSLKLSSVTAADTAVYYC<br>ARKDAYSDAFNLWGQGTLVTVSSGGGGSGGGGSEVQLVESGGGLVQPGGSLRLSC<br>AASGFSFSANYYPCWVRQAPGKCLEWIGCIYGGSSDITYDANWTKGRFTISRDNSKN<br>TVYLQMNSLRAEDTAVYYCARSAWYSGWGGDLWGQGTLVTVSSGGGSGGGSEVQ<br>LVESGGGLVQPGGSLRLSCAASGFSFSSSYWICWVRQAPGKGLEWVGCVFTGDGTT<br>YYASWAKGRFTISRDNSKNTVYLQMNSLRAEDTATYFCARPVSVYYYGMDLWGQ<br>GTLVTVSS |
| 113 | CHAIN_1$_{PRO1993}$ variant | DIQMTQSPSSLSASVGDRVTITCKASQDVSIGVAWYQQKPGKAPKLLIYSASYRYTGV<br>PSRFSGSGSGTDFTLTISSLQPEDFATYYCQQYYIYPYTFGCGTKVTVLGGGGGSGGGG<br>SGGGGSGGGGSEVQLVESGGGLVQPGGSLRLSCAASGFTFTDYTMDWVRQAPGKCL<br>EWVADVNPNSGGSIYNQRFKGRFTLSVDRSKNTLYLQMNSLRAEDTAVYYCARNLG<br>PSFYFDYWGQGTLVTVSSGGGGSGGGGSDIQMTQSPSSLSASVGDRVTITCQSSESVY<br>SNNQLSWYQQKPGQPPKLLIYDASDLASGVPSRFSGSGSGTDFTLTISSLQPEDFATYY<br>CAGGFSSSSDTAFGGGTKLTVLGGGSGGSDIQMTQSPSSLSASVGDRVTITCQASQSIS |

TABLE 6-continued

Examples of multispecific molecules of the present invention.

| SEQ ID NO: | Description | Sequence |
|---|---|---|
| | | NRLAWYQQKPGKAPKLLIYSASTLASGVPSRFSGSGSGTDFTLTISSLQPEDFATYYCQ<br>STYYGNDGNAFGCGTKVTVLG |
| 114 | CHAIN_2$_{PRO1993}$ variant | DIQMTQSPSSLSASVGDRVTITCQASQSINDYLAWYQQKPGKAPKLLIYKASTLASGVP<br>SRFSGSGSGTDFTLTISSLQPEDFATYYCQAAYIITDIDNVFGTGTKVTVLGGGGGSGG<br>GGSGGGGSGGGGSQVQLQESGPGLVKPSETLSLTCKVSGFSFSSGYDMCWIRQPPGKG<br>LEWIGCVVAGSVDITYYASWAKGRVTISVDSSKNQFSLKLSSVTAADTAVYYCARKD<br>AYSDAFNLWGQGTLVTVSSGGGGSGGGGSEVQLVESGGGLVQPGGSLRLSCAASGFS<br>FSANYYPCWVRQAPGKCLEWIGCIYGGSSDITYDANWTKGRFTISRDNSKNTVYLQM<br>NSLRAEDTAVYYCARSAWYSGWGGDLWGQGTLVTVSSGGGSGGGSEVQLVESGGG<br>LVQPGGSLRLSCAASGFSLSSNAMGWVRQAPGKGLEYIGIISVGGFTYYASWAKGRFT<br>ISRDNSKNTVYLQMNSLRAEDTATYFCARDRHGGDSSGAFYLWGQGTLVTVSS |
| | Constructs of Example 4: anti-HER2xPDL1 ($_{high\ KD}$)xHSA | |
| 115 | PRO1678 (scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>EVQLVESGGGLVQPGGSLRLSCAASGFNIKDTYIHWVRQAPGKCLEWVARIYPTNG<br>YTRYADSVKGRFTISADTSKNTAYLQMNSLRAEDTAVYYCSRWGGDGFYAMDYW<br>GQGTLVTVSSGGGGSGGGGSGGGGSGGGGSIQMTQSPSSLSASVGDRVTITCRASQD<br>VNTAVAWYQQKPGKAPKLLIYSASFLYSGVPSRFSGSRSGTDFTLTISSLQPEDFATY<br>YCQQHYTTPPTFGCGTKLTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAYSDAFNLWGQGTLVTVSSGGGGSGGGGSVVMTQSPSSL<br>SASVGDRVTITCQASQIISSRSAWYQQKPGQPPKLLIYQASKLASGVPSRFSGSGSGT<br>DFTLTISSLQPEDFATYYCQCTYIDSNFGAFGGGTKLTVLGGGGGSGGGGSGGGGSG<br>GGGSEVQLVESGGGLVQPGGSLRLSCAASGFSFSSSYWICWVRQAPGKGLEWVGCV<br>FTGDGTTYYASWAKGRFTISRDNSKNTVYLQMNSLRAEDTATYFCARPVSVYYYG<br>MDLWGQGTLVTVSS |
| 116 | PRO1679 (scDb-scFv, scMATCH3) | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSQV<br>QLQESGPGLVKPSETLSLTCKVSGFSFSSGYDMCWIRQPPGKGLEWIGCVVAGSVDI<br>TYYASWAKGRVTISVDSSKNQFSLKLSSVTAADTAVYYCARKDAYSDAFNLWGQG<br>TLVTVSSGGGGSGGGGSGGGGSGGGGSIQMTQSPSSLSASVGDRVTITCQASQSIND<br>YLAWYQQKPGKAPKLLIYKASTLASGVPSRFSGSGSGTDFTLTISSLQPEDFATYYCQ<br>AAYIITDIDNVFGTGTKVTVLGGGGGSEVQLVESGGGLVQPGGSLRLSCAASGFNIK<br>DTYIHWVRQAPGKCLEWVARIYPTNGYTRYADSVKGRFTISADTSKNTAYLQMNSL<br>RAEDTAVYYCSRWGGDGFYAMDYWGQGTLVTVSSGGGGSGGGGSVVMTQSPSSL<br>SASVGDRVTITCQASQIISSRSAWYQQKPGQPPKLLIYQASKLASGVPSRFSGSGSGT<br>DFTLTISSLQPEDFATYYCQCTYIDSNFGAFGGGTKLTVLGGGGGSGGGGSGGGGSG<br>GGGSEVQLVESGGGLVQPGGSLRLSCAASGFSFSSSYWICWVRQAPGKGLEWVGCV<br>FTGDGTTYYASWAKGRFTISRDNSKNTVYLQMNSLRAEDTATYFCARPVSVYYYG<br>MDLWGQGTLVTVSS |
| 117 | PRO1680 (scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAGYIITDIDNVFGTGTKVTVLGGGGGS<br>EVQLVESGGGLVQPGGSLRLSCAASGFNIKDTYIHWVRQAPGKCLEWVARIYPTNG<br>YTRYADSVKGRFTISADTSKNTAYLQMNSLRAEDTAVYYCSRWGGDGFYAMDYW<br>GQGTLVTVSSGGGGSGGGGSGGGGSGGGGSIQMTQSPSSLSASVGDRVTITCRASQD<br>VNTAVAWYQQKPGKAPKLLIYSASFLYSGVPSRFSGSRSGTDFTLTISSLQPEDFATY<br>YCQQHYTTPPTFGCGTKLTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAASDAFNLWGQGTLVTVSSGGGGSGGGGSVVMTQSPSSL<br>SASVGDRVTITCQASQIISSRSAWYQQKPGQPPKLLIYQASKLASGVPSRFSGSGSGT<br>DFTLTISSLQPEDFATYYCQCTYIDSNFGAFGGGTKLTVLGGGGGSGGGGSGGGGSG<br>GGGSEVQLVESGGGLVQPGGSLRLSCAASGFSFSSSYWICWVRQAPGKGLEWVGCV<br>FTGDGTTYYASWAKGRFTISRDNSKNTVYLQMNSLRAEDTATYFCARPVSVYYYG<br>MDLWGQGTLVTVSS |
| 118 | PRO1681 (scDb-scFv, scMATCH3) | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSQV<br>QLQESGPGLVKPSETLSLTCKVSGFSFSSGYDMCWIRQPPGKGLEWIGCVVAGSVDI<br>TYYASWAKGRVTISVDSSKNQFSLKLSSVTAADTAVYYCARKDAASDAFNLWGQG<br>TLVTVSSGGGGSGGGGSGGGGSGGGGSIQMTQSPSSLSASVGDRVTITCQASQSIND<br>YLAWYQQKPGKAPKLLIYKASTLASGVPSRFSGSGSGTDFTLTISSLQPEDFATYYCQ<br>AGYIITDIDNVFGTGTKVTVLGGGGGSEVQLVESGGGLVQPGGSLRLSCAASGFNIK<br>DTYIHWVRQAPGKCLEWVARIYPTNGYTRYADSVKGRFTISADTSKNTAYLQMNSL<br>RAEDTAVYYCSRWGGDGFYAMDYWGQGTLVTVSSGGGGSGGGGSVVMTQSPSSL<br>SASVGDRVTITCQASQIISSRSAWYQQKPGQPPKLLIYQASKLASGVPSRFSGSGSGT<br>DFTLTISSLQPEDFATYYCQCTYIDSNFGAFGGGTKLTVLGGGGGSGGGGSGGGGSG<br>GGGSEVQLVESGGGLVQPGGSLRLSCAASGFSFSSSYWICWVRQAPGKGLEWVGCV<br>FTGDGTTYYASWAKGRFTISRDNSKNTVYLQMNSLRAEDTATYFCARPVSVYYYG<br>MDLWGQGTLVTVSS |

TABLE 6-continued

Examples of multispecific molecules of the present invention.

| SEQ ID NO: | Description | Sequence |
|---|---|---|
| 119 | PRO1814<br>(scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>EVQLVESGGGLVQPGGSLRLSCAASGFTFTDYTMDWVRQAPGKGLEWVADVNPNS<br>GGSIYNQRFKGRFTLSVDRSKNTLYLQMNSLRAEDTAVYYCARNLGPSFYFDYWGQ<br>GTLVTVSSGGGGSGGGGSGGGGSGGGGSDIQMTQSPSSLSASVGDRVTITCKASQD<br>VSIGVAWYQQKPGKAPKLLIYSASYRYTGVPSRFSGSGSGTDFTLTISSLQPEDFATY<br>YCQQYYIYPYTFGTGTKVTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAYSDAFNLWGQGTLVTVSSGGGGSGGGGSIQMTQSPSSLS<br>ASVGDRVTITCQSSESVYSNNQLSWYQQKPGQPPKLLIYDASDLASGVPSRFSGSGS<br>GTDFTLTISSLQPEDFATYYCAGGFSSSDTAFGGGTKLTVLGGGGGSGGGGSGGGG<br>SGGGGSEVQLVESGGGLVQPGGSLRLSCAASGFSLSSNAMGWVRQAPGKGLEYIGII<br>SVGGFTYYASWAKGRFTISRDNSKNTVYLQMNSLRAEDTATYFCARDRHGGDSSG<br>AFYLWGQGTLVTVSS |
| 120 | PRO1852<br>(scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>EVQLVESGGGLVQPGGSLRLSCAASGFTFTDYTMDWVRQAPGKCLEWVADVNPNS<br>GGSIYNQRFKGRFTLSVDRSKNTLYLQMNSLRAEDTAVYYCARNLGPSFYFDYWGQ<br>GTLVTVSSGGGGSGGGGSGGGGSGGGGSDIQMTQSPSSLSASVGDRVTITCKASQD<br>VSIGVAWYQQKPGKAPKLLIYSASYRYTGVPSRFSGSGSGTDFTLTISSLQPEDFATY<br>YCQQYYIYPYTFGCGTKVTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAYSDAFNLWGQGTLVTVSSGGGGSGGGGSIQMTQSPSSLS<br>ASVGDRVTITCQSSESVYSNNQLSWYQQKPGQPPKLLIYDASDLASGVPSRFSGSGS<br>GTDFTLTISSLQPEDFATYYCAGGFSSSDTAFGGGTKLTVLGGGGGSGGGGSGGGG<br>SGGGGSEVQLVESGGGLVQPGGSLRLSCAASGFSLSSNAMGWVRQAPGKGLEYIGII<br>SVGGFTYYASWAKGRFTISRDNSKNTVYLQMNSLRAEDTATYFCARDRHGGDSSG<br>AFYLWGQGTLVTVSS |
| 121 | PRO1853<br>(scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAGYIITDIDNVFGTGTKVTVLGGGGGS<br>EVQLVESGGGLVQPGGSLRLSCAASGFTFTDYTMDWVRQAPGKGLEWVADVNPNS<br>GGSIYNQRFKGRFTLSVDRSKNTLYLQMNSLRAEDTAVYYCARNLGPSFYFDYWGQ<br>GTLVTVSSGGGGSGGGGSGGGGSGGGGSDIQMTQSPSSLSASVGDRVTITCKASQD<br>VSIGVAWYQQKPGKAPKLLIYSASYRYTGVPSRFSGSGSGTDFTLTISSLQPEDFATY<br>YCQQYYIYPYTFGTGTKVTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAASDAFNLWGQGTLVTVSSGGGGSGGGGSIQMTQSPSSLS<br>ASVGDRVTITCQSSESVYSNNQLSWYQQKPGQPPKLLIYDASDLASGVPSRFSGSGS<br>GTDFTLTISSLQPEDFATYYCAGGFSSSDTAFGGGTKLTVLGGGGGSGGGGSGGGG<br>SGGGGSEVQLVESGGGLVQPGGSLRLSCAASGFSLSSNAMGWVRQAPGKGLEYIGII<br>SVGGFTYYASWAKGRFTISRDNSKNTVYLQMNSLRAEDTATYFCARDRHGGDSSG<br>AFYLWGQGTLVTVSS |
| 122 | PRO1854<br>(scDb-scFv, scMATCH3) | DIQMTQSPSSLSASVGDRVTITCQASQSINDYLAWYQQKPGKAPKLLIYKASTLASG<br>VPSRFSGSGSGTDFTLTISSLQPEDFATYYCQAGYIITDIDNVFGTGTKVTVLGGGGGS<br>EVQLVESGGGLVQPGGSLRLSCAASGFTFTDYTMDWVRQAPGKCLEWVADVNPNS<br>GGSIYNQRFKGRFTLSVDRSKNTLYLQMNSLRAEDTAVYYCARNLGPSFYFDYWGQ<br>GTLVTVSSGGGGSGGGGSGGGGSGGGGSDIQMTQSPSSLSASVGDRVTITCKASQD<br>VSIGVAWYQQKPGKAPKLLIYSASYRYTGVPSRFSGSGSGTDFTLTISSLQPEDFATY<br>YCQQYYIYPYTFGCGTKVTVLGGGGGSQVQLQESGPGLVKPSETLSLTCKVSGFSFS<br>SGYDMCWIRQPPGKGLEWIGCVVAGSVDITYYASWAKGRVTISVDSSKNQFSLKLS<br>SVTAADTAVYYCARKDAASDAFNLWGQGTLVTVSSGGGGSGGGGSIQMTQSPSSLS<br>ASVGDRVTITCQSSESVYSNNQLSWYQQKPGQPPKLLIYDASDLASGVPSRFSGSGS<br>GTDFTLTISSLQPEDFATYYCAGGFSSSDTAFGGGTKLTVLGGGGGSGGGGSGGGG<br>SGGGGSEVQLVESGGGLVQPGGSLRLSCAASGFSLSSNAMGWVRQAPGKGLEYIGII<br>SVGGFTYYASWAKGRFTISRDNSKNTVYLQMNSLRAEDTATYFCARDRHGGDSSG<br>AFYLWGQGTLVTVSS |
| | | PRO1543 variant (MATCH4) |
| 123 | CHAIN_1$_{PRO1543}$_variant | DIQMTQSPSSLSASVGDRVTITCRASQDVNTAVAWYQQKPGKAPKLLIYSASFLYSG<br>VPSRFSGSRSGTDFTLTISSLQPEDFATYYCQQHYTTPPTFGCGTKLTVLGGGGGSGG<br>GGSGGGGSGGGGSEVQLVESGGGLVQPGGSLRLSCAASGFNIKDTYIHWVRQAPGK<br>CLEWVARIYPTNGYTRYADSVKGRFTISADTSKNTAYLQMNSLRAEDTAVYYCSR<br>WGGDGFYAMDYWGQGTLVTVSSGGGGSGGGGSDIQMTQSPSSLSASVGDRVTITC<br>QSSESVYSNNQLSWYQQKPGQPPKLLIYDASDLASGVPSRFSGSGSGTDFTLTISSLQ<br>PEDFATYYCAGGFSSSDTAFGCGTKLTVLGGGSGGSDIQMTQSPSSLSASVGDRVTI<br>TCQSSQSVFSNNYLAWFQQKPGQSPKRLIYSASTLASGVPSRFSGSGSGTDFTLTISSL<br>QPEDFATYYCLGSYACSSADCYVFGTGTKVTVLG |
| 124 | CHAIN_2$_{PRO1543}$_variant | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP |

TABLE 6-continued

Examples of multispecific molecules of the present invention.

| SEQ ID NO: | Description | Sequence |
|---|---|---|
| | | GKGLEWIGCWAGSVDITYYASWAKGRVTISVDSSKNQFSLKLSSVTAADTAVYYC<br>ARKDAYSDAFNLWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSLSSNAMGWVRQAPGKCLEYIGIISVGGFTYYASWA<br>KGRFTISRDNSKNTVYLQMNSLRAEDTATYFCARDRHGGDSSGAFYLWGQGTLVT<br>VSS |
| PRO1895 (MATCH4): pertuzumab ID diS capped scFv $(G_4S)_2$ 23-13-A01-sc02 diS_$(G_2S)_2$_28-21-D09-sc04 VL/33-03-G02-sc01 ala scan23 scFv_28-21-D09-sc04_(G3S)2_23-13-A01-sc02 diS VH | | |
| 125 | CHAIN_1$_{PRO1895}$ | DIQMTQSPSSLSASVGDRVTITCKASQDVSIGVAWYQQKPGKAPKLLIYSASYRYTG<br>VPSRFSGSGSGTDFTLTISSLQPEDFATYYCQQYYIYPYTFGCGTKVTVLGGGGGSGG<br>GGSGGGGSGGGGSEVQLVESGGGLVQPGGSLRLSCAASGFTFTDYTMDWVRQAPG<br>KCLEWVADVNPNSGGSIYNQRFKGRFTLSVDRSKNTLYLQMNSLRAEDTAVYYCA<br>RNLGPSFYFDYWGQGTLVTVSSGGGGSGGGGSDVVMTQSPSSLSASVGDRVTITCQ<br>ASQIISSRSAWYQQKPGQPPKLLIYQASKLASGVPSRFSGSGSGTDFTLTISSLQPEDF<br>ATYYCQCTYIDSNFGAFGCGTKLTVLGGGSGGSDIQMTQSPSSLSASVGDRVTITCQ<br>SSQSVFSNNYLAWFQQKPGQSPKRLIYSASTLASGVPSRFSGSGSGTDFTLTISSLQPE<br>DFATYYCLGSYACSSADCYVFGTGTKVTVLG |
| 126 | CHAIN_2$_{PRO1895}$ | DIQMTQSPSSLSASVGDRVTITCQASQSINDYLAWYQQKPGKAPKLLIYKASTLASG<br>VPSRFSGSGSGTDFTLTISSLQPEDFATYYCQAAYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCWAGSVDITYYASWAKGRVTISVDSSKNQFSLKLSSVTAADTAVYYC<br>ARKDAYSDAFNLWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSFSSSYWICWVRQAPGKCLEWVGCVFTGDGTTYYA<br>SWAKGRFTISRDNSKNTVYLQMNSLRAEDTATYFCARPVSVYYYGMDLWGQGTLV<br>TVSS |
| PRO2366 (MATCH4): pertuzumab ID diS capped scFv $(G_4S)_2$ 19-04-A10-sc06_ $(G_2S)_2$_28-21-D09-sc04 VL/33-03-G02 Q108A Y215A $(G_4S)$_28-21-D09-SC04_$(G_3S)_2$_19-04-A10-sc06 VH | | |
| 127 | CHAIN_1$_{PRO2366}$ | DIQMTQSPSSLSASVGDRVTITCKASQDVSIGVAWYQQKPGKAPKLLIYSASYRYTG<br>VPSRFSGSGSGTDFTLTISSLQPEDFATYYCQQYYIYPYTFGCGTKVTVLGGGGGSGG<br>GGSGGGGSGGGGSEVQLVESGGGLVQPGGSLRLSCAASGFTFTDYTMDWVRQAPG<br>KCLEWVADVNPNSGGSIYNQRFKGRFTLSVDRSKNTLYLQMNSLRAEDTAVYYCA<br>RNLGPSFYFDYWGQGTLVTVSSGGGGSGGGGSAFELTQSPSSLSASVGDRVTITCQA<br>SESINSRLAWYQQKPGQPPKLLIYDASDLTSGVPSRFSGSGSGTDFTLTISSLQPEDFA<br>TYYCQGYGGSSTTTFGCGTKLTVLGGGSGGSDIQMTQSPSSLSASVGDRVTITCQSS<br>QSVFSNNYLAWFQQKPGQSPKRLIYSASTLASGVPSRFSGSGSGTDFTLTISSLQPEDF<br>ATYYCLGSYACSSADCYVFGTGTKVTVLG |
| 128 | CHAIN_2$_{PRO2366}$ | DIQMTQSPSSLSASVGDRVTITCQASQSINDYLAWYQQKPGKAPKLLIYKASTLASG<br>VPSRFSGSGSGTDFTLTISSLQPEDFATYYCQAGYIITDIDNVFGTGTKVTVLGGGGGS<br>GGGGSGGGGSGGGGSQVQLQESGPGLVKPSETLSLTCKVSGFSFSSGYDMCWIRQPP<br>GKGLEWIGCVVAGSVDITYYASWAKGRVTISVDSSKNQFSLKLSSVTAADTAVYYC<br>ARKDAASDAFNLWGQGTLVTVSSGGGGSGGGGSEVQLVESGGGLVQPGGSLRLSC<br>AASGFSLSSYDMSWVRQAPGKGLAWIGASYASGPTYYASWAKGRFTISRDNSKNTV<br>YLQMNSLRAEDTATYFCARGGWTGTSHSNIWGQGTLVTVSSGGGSGGGSEVQLVE<br>SGGGLVQPGGSLRLSCAASGFSLSSYAMNWVRQAPGKCLEWIGHINAGDIAYYATW<br>AKGRFTISRDNSKNTVYLQMNSLRAEDTAVYFCARGAGGFSTGPFKLWGQGTLVTV<br>SS |
| PRO2474 (MATCH4) (PRO2366 varianti): pertuzumab ID diS capped scFv $(G_4S)_2$ 33-03-G02 Q108A Y215A diS $(G_2S)_2$ 28-21-D09-sc04 VL/19-04-A10-sc06 $(G_4S)_2$ 28-21-D09-sc04 $(G_3S)_2$ 33-03-G02 Q108A Y215A diS VH | | |
| 129 | CHAIN_1$_{PRO2474}$ | DIQMTQSPSSLSASVGDRVTITCKASQDVSIGVAWYQQKPGKAPKLLIYSASYRYTG<br>VPSRFSGSGSGTDFTLTISSLQPEDFATYYCQQYYIYPYTFGCGTKVTVLGGGGGSGG<br>GGSGGGGSGGGGSEVQLVESGGGLVQPGGSLRLSCAASGFTFTDYTMDWVRQAPG<br>KCLEWVADVNPNSGGSIYNQRFKGRFTLSVDRSKNTLYLQMNSLRAEDTAVYYCA<br>RNLGPSFYFDYWGQGTLVTVSSGGGGSGGGGSDIQMTQSPSSLSASVGDRVTITCQA<br>SQSINDYLAWYQQKPGKAPKLLIYKASTLASGVPSRFSGSGSGTDFTLTISSLQPEDF<br>ATYYCQAGYIITDIDNVFGCGTKVTVLGGGSGGSDIQMTQSPSSLSASVGDRVTITCQ<br>SSQSVFSNNYLAWFQQKPGQSPKRLIYSASTLASGVPSRFSGSGSGTDFTLTISSLQPE<br>DFATYYCLGSYACSSADCYVFGTGTKVTVLG |
| 130 | CHAIN_2$_{PRO2474}$ | AFELTQSPSSLSASVGDRVTITCQASESINSRLAWYQQKPGQPPKLLIYDASDLTSGV<br>PSRFSGSGSGTDFTLTISSLQPEDFATYYCQGYGGSSTTTFGCGTKLTVLGGGGGSGG<br>GGSGGGGSGGGGSEVQLVESGGGLVQPGGSLRLSCAASGFSLSSYAMNWVRQAPG |

TABLE 6-continued

Examples of multispecific molecules of the present invention.

| SEQ ID NO: | Description | Sequence |
|---|---|---|
| | | KCLEWIGHINAGDIAYYATWAKGRFTISRDNSKNTVYLQMNSLRAEDTAVYFCARG AGGFSTGPFKLWGQGTLVTVSSGGGGSGGGGSEVQLVESGGGLVQPGGSLRLSCAA SGFSLSSYDMSWVRQAPGKGLAWIGASYASGPTYYASWAKGRFTISRDNSKNTVYL QMNSLRAEDTATYFCARGGWTGTSHSNIWGQGTLVTVSSGGGSGGGSQVQLQESG PGLVKPSETLSLTCKVSGFSFSSGYDMCWIRQPPGKCLEWIGCVVAGSVDITYYASW AKGRVTISVDSSKNQFSLKLSSVTAADTAVYYCARKDAASDAFNLWGQGTLVTVSS |
| PRO2475 (MATCH4) (PRO2366 variant_2): 28-21-D09-sc04 $(G_4S)_2$ 19-04-A10-sc06_$(G_2S)_2$_33-03-G02 Q108A Y215A VLZ pertuzumab ID diS capped ScFv$(G_4S)_2$_33-03-G02 Q108A Y215A $(G_3S)_2$_19-04-A10-sc06 VH | | |
| 131 | CHAIN_1PRO2475 | DIQMTQSPSSLSASVGDRVTITCQSSQSVFSNNYLAWFQQKPGQSPKRLIYSASTLAS GVPSRFSGSGSGTDFTLTISSLQPEDFATYYCLGSYACSSADCYVFGTGTKVTVLGGG GGSGGGGSGGGGSGGGGSEVQLVESGGGLVQPGGSLRLSCAASGFSLSSYDMSWV RQAPGKGLAWIGASYASGPTYYASWAKGRFTISRDNSKNTVYLQMNSLRAEDTAT YFCARGGWTGTSHSNIWGQGTLVTVSSGGGGSGGGGSAFELTQSPSSLSASVGDRV TITCQASESINSRLAWYQQKPGQPPKLLIYDASDLTSGVPSRFSGSGSGTDFTLTISSL QPEDFATYYCQGYGGSSTTTFGCGTKLTVLGGGSGGSDIQMTQSPSSLSASVGDRVT ITCQASQSINDYLAWYQQKPGKAPKLLIYKASTLASGVPSRFSGSGSGTDFTLTISSLQ PEDFATYYCQAGYIITDIDNVFGTGTKVTVLG |
| 132 | CHAIN_2PRO2475 | DIQMTQSPSSLSASVGDRVTITCKASQDVSIGVAWYQQKPGKAPKLLIYSASYRYTG VPSRFSGSGSGTDFTLTISSLQPEDFATYYCQQYYIYPYTFGCGTKVTVLGGGGGSGG GGSGGGGSGGGGSEVQLVESGGGLVQPGGSLRLSCAASGFTFTDYTMDWVRQAPG KCLEWVADVNPNSGGSIYNQRFKGRFTLSVDRSKNTLYLQMNSLRAEDTAVYYCA RNLGPSFYFDYWGQGTLVTVSSGGGGSGGGGSQVQLQESGPGLVKPSETLSLTCKV SGFSFSSGYDMCWIRQPPGKGLEWIGCVVAGSVDITYYASWAKGRVTISVDSSKNQF SLKLSSVTAADTAVYYCARKDAASDAFNLWGQGTLVTVSSGGGSGGGSEVQLVES GGGLVQPGGSLRLSCAASGFSLSSYAMNWVRQAPGKCLEWIGHINAGDIAYYATW AKGRFTISRDNSKNTVYLQMNSLRAEDTAVYFCARGAGGFSTGPFKLWGQGTLVTV SS |
| PRO2476 (MATCH4) (PRO2366 variant_3): 19-04-A10-sc06 $(G_4S)_2$ pertuzumab ID diS capped_$(G_2S)_2$_33-03-G02 Q108A Y215A VL/28-21-D09-sc04_$(G_4S)_2$ 33-03-G02 Q108A Y215A_(G3S)2_pertuzumab ID diS capped VH | | |
| 133 | CHAIN_1$_{PRO2476}$ | AFELTQSPSSLSASVGDRVTITCQASESINSRLAWYQQKPGQPPKLLIYDASDLTSGV PSRFSGSGSGTDFTLTISSLQPEDFATYYCQGYGGSSTTTFGCGTKLTVLGGGGGSGG GGSGGGGSGGGGSEVQLVESGGGLVQPGGSLRLSCAASGFSLSSYAMNWVRQAPG KCLEWIGHINAGDIAYYATWAKGRFTISRDNSKNTVYLQMNSLRAEDTAVYFCARG AGGFSTGPFKLWGQGTLVTVSSGGGGSGGGGSDIQMTQSPSSLSASVGDRVTITCKA SQDVSIGVAWYQQKPGKAPKLLIYSASYRYTGVPSRFSGSGSGTDFTLTISSLQPEDF ATYYCQQYYIYPYTFGCGTKVTVLGGGSGGSDIQMTQSPSSLSASVGDRVTITCQAS QSINDYLAWYQQKPGKAPKLLIYKASTLASGVPSRFSGSGSGTDFTLTISSLQPEDFA TYYCQAGYIITDIDNVFGTGTKVTVLG |
| 134 | CHAIN_2$_{PRO2476}$ | DIQMTQSPSSLSASVGDRVTITCQSSQSVFSNNYLAWFQQKPGQSPKRLIYSASTLAS GVPSRFSGSGSGTDFTLTISSLQPEDFATYYCLGSYACSSADCYVFGTGTKVTVLGGG GGSGGGGSGGGGSGGGGSEVQLVESGGGLVQPGGSLRLSCAASGFSLSSYDMSWV RQAPGKGLAWIGASYASGPTYYASWAKGRFTISRDNSKNTVYLQMNSLRAEDTAT YFCARGGWTGTSHSNIWGQGTLVTVSSGGGGSGGGGSQVQLQESGPGLVKPSETLS LTCKVSGFSFSSGYDMCWIRQPPGKGLEWIGCVVAGSVDITYYASWAKGRVTISVD SSKNQFSLKLSSVTAADTAVYYCARKDAASDAFNLWGQGTLVTVSSGGGSGGGSE VQLVESGGGLVQPGGSLRLSCAASGFTFTDYTMDWVRQAPGKCLEWVADVNPNSG GSIYNQRFKGRFTLSVDRSKNTLYLQMNSLRAEDTAVYYCARNLGPSFYFDYWGQG TLVTVSS |
| PRO2477 (MATCH4) (PRO2366 variant_4): pertuzumab ID diS capped scFv $(G_4S)_2$ 33-03-G02 Q108A Y215A_(G2S)2_19-04-A10-sc06 VL/28-21-D09-sc04 $(G_4S)_2$ 19-04-A10-SC06_$(G_3S)_2$ 33-03-G02 Q108A Y215A VH | | |
| 135 | CHAIN_1$_{PRO2477}$ | DIQMTQSPSSLSASVGDRVTITCKASQDVSIGVAWYQQKPGKAPKLLIYSASYRYTG VPSRFSGSGSGTDFTLTISSLQPEDFATYYCQQYYIYPYTFGCGTKVTVLGGGGGSGG GGSGGGGSGGGGSEVQLVESGGGLVQPGGSLRLSCAASGFTFTDYTMDWVRQAPG KCLEWVADVNPNSGGSIYNQRFKGRFTLSVDRSKNTLYLQMNSLRAEDTAVYYCA RNLGPSFYFDYWGQGTLVTVSSGGGGSGGGGSDIQMTQSPSSLSASVGDRVTITCQA SQSINDYLAWYQQKPGKAPKLLIYKASTLASGVPSRFSGSGSGTDFTLTISSLQPEDF ATYYCQAGYIITDIDNVFGTGTKVTVLGGGSGGSAFELTQSPSSLSASVGDRVTITCQ ASESINSRLAWYQQKPGQPPKLLIYDASDLTSGVPSRFSGSGSGTDFTLTISSLQPEDF ATYYCQGYGGSSTTTFGCGTKLTVLG |
| 136 | CHAIN_2$_{PRO2477}$ | DIQMTQSPSSLSASVGDRVTITCQSSQSVFSNNYLAWFQQKPGQSPKRLIYSASTLAS GVPSRFSGSGSGTDFTLTISSLQPEDFATYYCLGSYACSSADCYVFGTGTKVTVLGGG GGSGGGGSGGGGSGGGGSEVQLVESGGGLVQPGGSLRLSCAASGFSLSSYDMSWV RQAPGKGLAWIGASYASGPTYYASWAKGRFTISRDNSKNTVYLQMNSLRAEDTAT |

TABLE 6-continued

| Examples of multispecific molecules of the present invention. | | |
|---|---|---|
| SEQ ID NO: | Description | Sequence |
| | | YFCARGGWTGTSHSNIWGQGTLVTVSSGGGGSGGGGSEVQLVESGGGLVQPGGSL RLSCAASGFSLSSYAMNWVRQAPGKCLEWIGHINAGDIAYYATWAKGRFTISRDNS KNTVYLQMNSLRAEDTAVYFCARGAGGFSTGPFKLWGQGTLVTVSSGGGGSGGGSQ VQLQESGPGLVKPSETLSLTCKVSGFSFSSGYDMCWIRQPPGKGLEWIGCVVAGSVD ITYYASWAKGRVTISVDSSKNQFSLKLSSVTAADTAVYYCARKDAASDAFNLWGQ GTLVTVSS |

TABLE 7

| Other sequences related to the present invention. | | |
|---|---|---|
| SEQ ID NO: | Description | Sequence |
| | | IL23R domain 14-11-D07 sc03 (dummy) |
| 137 | $VH_{14-11-D07\ sc03}$ | EVQLVESGGGLVQPGGSLRLSCAASGIDFNSNYYMCWVRQAPGKGLEWIGCIYVGS HVNTYYANWAKGRFTISRDNSKNTVYLQMNSLRAEDTAVYYCATSGSSVLYFKFW GQGTLVTVSS |
| 138 | $VL_{14-11-D07\ sc03}$ | DIQMTQSPSSLSASVGDRVTITCQASENIYSFLAWYQQKPGKAPKLLIYSASKLAAGV PSRFSGSGSGTDFTLTISSLQPEDFATYYCQQTNRYSNPDIYNVFGTGTKVTVLG |
| | | Linkers |
| 139 | Linker | GGGGSGGGGSGGGGSGGGGS |
| 140 | Linker sequence unit | GGGGS |
| 141 | Generic linker sequence | (GmS)n, with m being selected from 2, 3 and 4 and with n being selected from 2, 3, 4, 5 and 6 |
| | | VH and VL sequences |
| 142 | VH3 | EVQLVESGGGLVQ PGGSLRLSCAAS ***GFSFSANYYPC*** WVRQAPGKGLE WIG***CIYGGSS*** ***DITYDANWTK*** GRFTISRDNS KNTVYLQMNS LRAEDTAVYY CA ***RSAWYSGWGGDL*** GQGTLVTVSS |
| 143 | VH4 | QVQLQESGPGLVKP SETLSLTCKVS ***GFSFSNSYWIC*** WIRQPPGKGLE WIG***CTFVGSSD*** ***STYYANWAKG***R VTISVDSSKNQ FSLKLSSVTAA DTAVYYCA ***RHPSDAVYGYANNL*** WGQGTLVTVSS |
| 144 | Vkappa1 | DIQMTQSPSSL SASVGDRVTITC ***QASQSINNVLA*** YQQKPGKAPKLL IY***RASTLAS***P SRFSGSGSGTDF TLTISSLQPEDF ATYYC ***QSSYGNYGD***FGT GTKVTVLG |

TABLE 7-continued

| SEQ ID NO: | Description | Sequence |
|---|---|---|
| | | Other sequences related to the present invention. |
| | | Vlambda FR4 sequences |
| 145 | Vlambda germline-based FR4_Sk17 | FGTGTKVTVLG |
| 146 | Vlambda germline-based FR4_Sk12 | FGGGTKLTVLG |
| 147 | Vlambda germline-based FR4_1 | FGGGTQLIILG |
| 148 | Vlambda germline-based FR4_2 | FGEGTELTVLG |
| 149 | Vlambda germline-based FR4_3 | FGSGTKVTVLG |
| 150 | Vlambda germline-based FR4_4 | FGGGTQLTVLG |
| 151 | Vlambda germline-based FR4_5 | FGGGTQLTALG |
| 152 | Vlambda germline-based FR4_Sk12_G141C | FGCGTKLTVLG |
| | | Antigens |
| 153 | CD137 UniProt ID NO: Q07011 | MGNSCYNIVATLLLVLNFERTRSLQDPCSNCPAGTFCDNNRNQICSPCPPNSFSSAG GQRTCDICRQCKGVFRTRKECSSTSNAECDCTPGFHCLGAGCSMCEQDCKQGQELTK KGCKDCCFGTFNDQKRGICRPWTNCSLDGKSVLVNGTKERDVVCGPSPADLSPGAS SVTPPAPAREPGHSPQIISFFLALTSTALLFLLFFLTLRFSVVKRGRKKLLYIFKQ PFMRPVQTTQEEDGCSCRFPEEEEGGCEL |

Throughout the text of this application, should there be a discrepancy between the text of the specification (e.g., Tables 1 to 6) and the sequence listing, the text of the specification shall prevail.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

To the extent possible under the respective patent law, all patents, applications, publications, test methods, literature, and other materials cited herein are hereby incorporated by reference.

The following Examples illustrates the invention described above, but is not, however, intended to limit the scope of the invention in any way. Other test models known as such to the person skilled in the pertinent art can also determine the beneficial effects of the claimed invention.

Example 1: Generation and Testing of Low Affinity Anti-PD-L1 Molecules

Aim of the Project

The goal of the project is to identify a low affinity anti-PD-L1 antibody fragment that neutralizes the interaction between PD-L1 and PD-1. Ultimately, this domain will be combined in a multispecific molecule with a high affinity domain against a selected tumor associated antigen (TAA) coexpressed with PD-L1 on tumor cells, allowing the targeting and neutralization of PD-L1 specifically on those cancer cells. Two groups of long acting molecules, corresponding to two projects, were designed. Each group of molecules is mainly differing in the number of specificities (3 or 4) as well as in their format. Both groups of molecules contain a Her2 domain as TAA, a low affinity PD-L1 domain and a human serum albumin binding domain for half-life extension, but one group contains in addition an anti-CD3E binding domain in order to trigger T cell activation. This example describes the production and characterization of the low affinity domains as well as of the multispecific molecules that were designed in these projects.

Design and Production of scFv

In order to generate a low affinity PD-L1 antibody that neutralizes the interaction between PD-L1 and PD-1, single alanine substitutions were introduced in the CDR regions of a high affinity neutralizing anti-PD-L1 domain previously identified, clone 33-03-G02. As a first step each amino acid of the CDR3 region (highest amino acid variability) of the high affinity domain were mutated to alanine resulting in 21 mutants. In comparison to the original domain, the affinity to PD-L1 was reduced by more than 100-fold for three single mutants. Therefore, single mutations were combined go generate two double mutants. In parallel, nine additional single mutants of the most variable residues of the CDR1 and CDR2 regions were designed as well as two mutants containing combination of other single mutations of the CD3 region which only slightly reduced the affinity of the parental domain but are presumably exposed residues. Furthermore, three mutants containing up to three alanine substitutions of predicted exposed residues were expressed in addition. Data obtained for the five most interesting molecules with a 100-fold to 6'500-fold reduced affinity are presented below.

Methods:

scFv Production

Heterologous expression of the proteins was performed in *E. coli* as insoluble inclusion bodies by induced overnight expression in small scale (as indicated in Table 8 below). Inclusion bodies were isolated from the homogenized cell pellet by a centrifugation protocol that included several washing steps to remove cell debris and other host cell impurities. The purified inclusion bodies were solubilized in a denaturing buffer and the scFvs were refolded by a scalable refolding protocol that generated milligram amounts of natively folded, monomeric scFv. At this point a standardized protocol was employed to purify the scFvs. The product after refolding was captured by an affinity chromatography to yield the purified scFvs. Table 8 summarizes manufacture of scFv molecules. Expression of mammalian constructs was performed in CHO-S cells using CHOgro transient transfection kit (Mirus) (see in Table 8). Cultures were harvested after 5-7 days (cell viability <70%) of expression at 37° C. by centrifugation and proteins were purified from clarified culture supernatants by Protein L affinity chromatography followed, if needed, by a polishing step by size-exclusion chromatography. For the quality control of the manufactured material standard analytical methods, such as SE-HPLC, UV280 and SDS-PAGE were used.

Freeze-Thaw Stability Study

Compatibility of the top performing scFv molecules was assessed with respect to freeze-thawing (F/T) cycles (colloidal stability). For the F/T stability assessment the same analytical methods (SE-HPLC, UV absorbance at 280 nm) and parameters as for the storage stability study were applied to monitor the quality of the molecules over multiple F/T cycles. As no dedicated freeze-thaw study was performed, freeze-thaw data was extracted from −80° C. samples of storage stability study which was acquired over 28 days (up to 7 d storage in between F/T cycles).

Differential Scanning Fluorimetry (DSF)

The midpoint of transition for the thermal unfolding of the scFv constructs was determined by Differential Scanning Fluorimetry using the fluorescence dye SYPRO® Orange. Samples were prepared at a final protein concentration of 50 μg/mL in final buffer (50 mM NaCiP, 150 mM NaCl, pH6.4) containing a final concentration of 5×SYPRO® Orange in a total volume of 100 μl. Twenty-five microliters of prepared samples were added in triplicate to white-walled AB gene PCR plates. The assay was performed in a qPCR machine used as a thermal cycler, and the fluorescence emission was detected using the software's custom dye calibration routine. The PCR plate containing the test samples was subjected to a temperature ramp from 25° C. to 96° C. in increments of 1° C. with 30 s pauses after each temperature increment. The total assay time was about two hours. The Tm was calculated by the software GraphPad Prism using a mathematical second derivative method to calculate the inflection point of the curve. The reported Tm is an average of three measurements.

TABLE 8

Manufacture ofscFv domains based on clone with Clone ID 33-03-G02.

| PRO ID | Mutations (AHO numbering) | Expression, mg/L | Purity by SE-HPLC, StM, % mc | Purity by SE-HPLC post concentration to 10 mg/mL, % mc | Purity by SDS-PAGE | Thermo-dynamic Stability by DSF, Tm | Thermo-dynamic Stability by DSF, Tonset | Freeze/Thaw Stability, 4 cycles |
|---|---|---|---|---|---|---|---|---|
| PRO1075 | VL-Q108A | 4.2 (*E. coli*) | 97 | 93.2 | >95% | 76.9 | 71.0 | <1% |
| PRO1076 | VL-G109A | 13.2(*E. coli*) | 97 | 95.8 | >95% | 76.3 | 71.0 | <1% |
| PRO1089 | VH-Y112A | 8.4(*E. coli*) | 99 | 99.1 | >95% | 79.6 | 74.0 | <1% |
| PRO1434 | VL-Q108A/G109A | 8.2 (CHO) | 100 | 99.6 | >95% | 73.0 | 66.3 | <1% |
| PRO1494 | VL-Q108A/VH-Y112A | 17 (CHO) | 99 | 99.3 | >95% | 75.2 | 68.0 | <1% |

Affinities to PD-L1 by SPR

Method:

Affinity to PD-L1 was determined by surface plasmon resonance (SPR) measurements using a Biacore T200 device (GE Healthcare). All measurements were performed at 25° C. In this experiment, Fc-tagged human PD-L1 extracellular domain (ECD, SinoBiological, cat. 10084-H02H) was captured using the Human Antibody Capture kit from GE Healthcare (cat. BR-1008-39). After each analyte injection cycle, the anti-human Fc-specific IgG was regenerated, and new antigen was captured. For affinity determination, the scFvs were injected as analyte using a dose response multi-cycle kinetic assay with concentrations of the analyte ranging from 6.86 to 5000 nM (three-fold dilutions steps) diluted in running buffer (10 mM HEPES, 150 mM NaCl, and 0.05% Tween 20, pH 7.4). Association and dissociation time were set to 300 s and 720 s, respectively. The apparent dissociation ($k_d$) and association ($k_a$) rate constants and the apparent dissociation equilibrium constant ($K_D$) were calculated with the Biacore analysis software (BIAevaluation, GE Healthcare) using one-to-one Langmuir binding model and quality of the fits was monitored based on Chi2 and U-value, which is a measure for the quality of the curve fitting. In addition to the kinetic measurement, the value of the $K_D$ was obtained by fitting a plot of response at equilibrium against the concentration (steady-state affinity measurement).

Results:

As shown in Table 9, binding to human PD-L1 was confirmed for the humanized scFvs tested. Affinity to PD-L1 was reduced by 6,500-fold for PRO1434 compared to the parental scFv PRO830.

TABLE 9

Summary of affinities of scFv based on clone with Clone ID 33-03-G02 to hPD-L1.

| PRO ID | Mutations (AHO numbering) | Affinity to human PD-L1: kinetic analysis $k_a$ ($M^{-1}s^{-1}$) | $k_d$ ($s^{-1}$) | KD (M) | steady state analysis KD (M) |
|---|---|---|---|---|---|
| PRO830 | NA | 1.78E+06 | 1.39E−04 | 7.81E−11 | ND |
| PRO1075 | VL-Q108A | 1.67E+06 | 2.05E−02 | 1.22E−08 | ND |
| PRO1076 | VL-G109A | 1.80E+06 | 1.35E−02 | 7.52E−09 | ND |
| PRO1089 | VH-Y112A | 1.99E+06 | 3.28E−02 | 1.65E−08 | ND |
| PRO1434 | VL-Q108A/G109A | 1.09E+06 | 0.5346 | 4.92E−07 | 4.87E−07 |
| PRO1494 | VL-Q108A/VH-Y112A | ND | | | |

NA: not applicable
ND: not determined

Binding to PD-L1 Expressing Cells by FC

Method:

CHO-K1 (control cells that do not express PD-L1) and CHO-PD-L1 (Amsbio) with a high PD-L1 expression level were harvested and cell number was determined. Cell suspensions were centrifuged for 5 min at 400×g and 100 µl of cell suspensions (10'000 cells) diluted in PBS-EB (1×DPBS, 2% BCS H.I., 2 mM EDTA) were added to designated wells in a non-binding plate. After three washing steps with PBS-EB, cells were centrifuged and washing buffer was aspirated. 100 µl of the serial dilutions of samples to be tested as well as the positive control were then directly added to the plate. Positive control samples (PRO830, 33-03-G02) were diluted in PBS-EB with concentrations ranging from 3500 to 0.22 ng/ml and samples dilutions ranged from 1000 to 0.064 µg/ml. After incubation at 4° C. for 1 h, plates were washed three times using 100 µl of PBS-EB. Cell pellets were re-suspended with 100 µl Protein L-APC at a concentration of 2 µg/ml and incubated for 1 h at 4° C. Next, cells were washed again three times using 100 µl of PBS-EB. The cell pellets were re-suspended with 50 µl PBS-EB and analyzed with NovoCyte 2060 flow cytometer device. Fluorescence intensity of APC for 5'000 events was recorded for each sample and the geometric mean of fluorescence intensity MFI was calculated. The data were corrected for unspecific antibody binding (blank and CHO-K1 cell binding).

Figure 1:
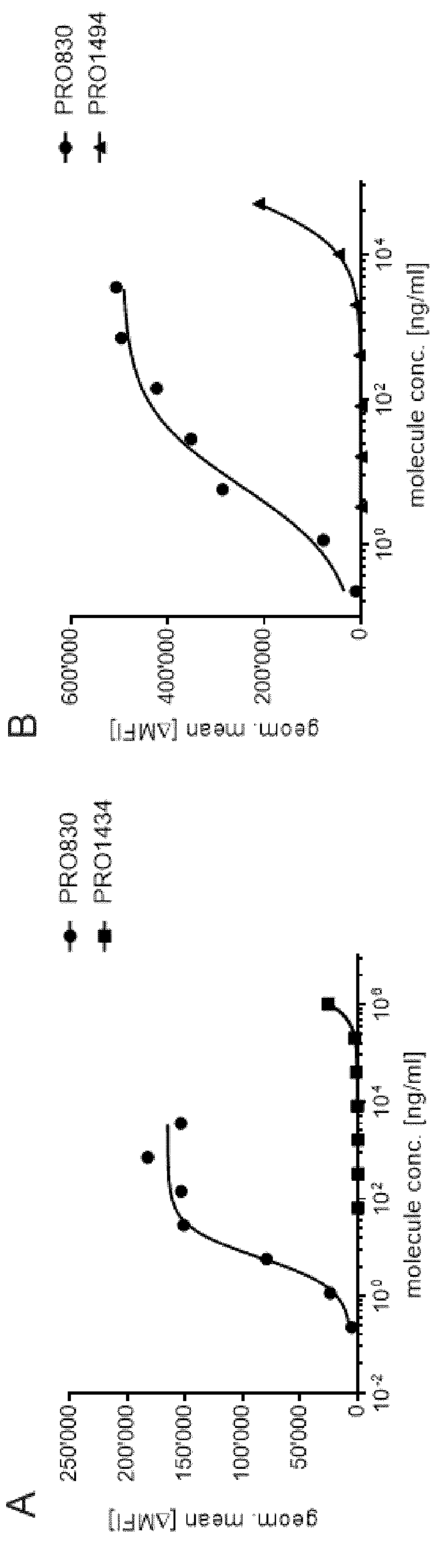
FIG. 1 Binding to PD-L1 expressing cells assessed by flow cytometry. Binding of (A) PRO1434 and (B) PRO1494 to PD-L1 expressing cells. PRO830 was used as a reference. PRO1434 showed a signal only at 100 μg/ml whereas binding was observed with 3.5 μg/ml for PRO1494.

Results:

Potency to bind cells expressing PD-L1 was assessed using flow cytometry as described above. Serial dilutions of the respective molecules to be tested as well as the reference PRO830, were added to the plates. Individual $IC_{50}$ values on each plate were calibrated against the $IC_{50}$ of the reference molecule PRO830 (high affinity PD-L1 domain) that was taken along on each plate (relative $EC_{50}$:$EC_{50}$, PRO830/ $IC_{50}$, test scFv). Potencies are summarized in Table 10 which shows that PRO1434 and PRO1494 have the weakest binding. Dose-response curves obtained for PRO1434 and PRO1494 are presented in FIG. 1.

TABLE 10

Potencies of scFvs based on clone with Clone ID 33-03-G02 to bind cells expressing hPD-L1.

| PRO ID | Mutations | Binding to cells expressing PD-L1 CHO-K1 with high PD-L1 expression: $EC_{50}$ (ng/ml) | rel. $EC_{50}$ * |
|---|---|---|---|
| PRO830 | NA | 5.5 | 1 |
| PRO1075 | VL-Q108A | 333314 | 1.42E−05 |
| PRO1076 | VL-G109A | ND | |
| PRO1089 | VH-Y112A | 51168 | 9.30E−05 |
| PRO1434 | VL-Q108A/G109A | NB | |
| PRO1494 | VL-Q108A/VH-Y112A | very low binding level | |

NA: not applicable
ND: not determined
NB: no binding at the highest tested concentration
*: $EC_{50, PRO830}$ (ng/ml)/$EC_{50, test\ molecule}$ (ng/ml)

PD-L1/PD-1 Neutralization by NFAT Reporter Gene Assay

Method:

The ability of the scFvs to neutralize the PD-L1/PD-1 interaction when both interacting molecules were expressed on the cell surface was tested using CHO/PD-L1/TCR (T cell receptor) activator and Jurkat/PD-1 cells. In this assay, CHO cells stably expressing PD-L1 and a TCR activator are incubated with Jurkat T cells stably expressing PD-1 and as a reporter gene to monitor T cell activation, firefly luciferase under the control of the NFAT response elements. Upon binding of the TCR activator on CHO cells to the Jurkat T cells, TCR signaling triggers NFAT-induced expression of firefly luciferase. The interaction between PD-L1 and PD-1 however negatively regulates such TCR signaling and thus diminishes firefly luciferase expression. Therefore, blockade of the PD-L1/PD-1 interaction in this system restores luciferase activity.

35'000 CHO/PDL1/TCR activator cells in 100 µl of cell culture medium (DMEM/F12, 10% FCS) were added to the inner wells of a white cell culture plate and incubated for 16-20 h at 37° C. and 5% $CO_2$. Next day, cell culture medium was removed from each well and 50 µl of 2-fold concentrated serial dilutions of the respective molecules to be tested (final concentrations from 162 to 0.025 µg/ml) and the reference molecule avelumab (final concentrations from 3'000 to 0.46 ng/ml) were added. Then, 50 µl of effector Jurkat cells diluted at 400'000 cell/ml in assay buffer (RPM11640 with 10% FCS) were added to each well and plates were incubated for 6 h at 37° C. and 5% $CO_2$. Finally, 50 µL luciferase substrate (BPS Bioscience) prepared according to manufacturer's protocol, was added per well and plates were incubated for 30 min in the dark, luminescence was measured using Flexstation III multi-mode microplate reader.

Figure 2:
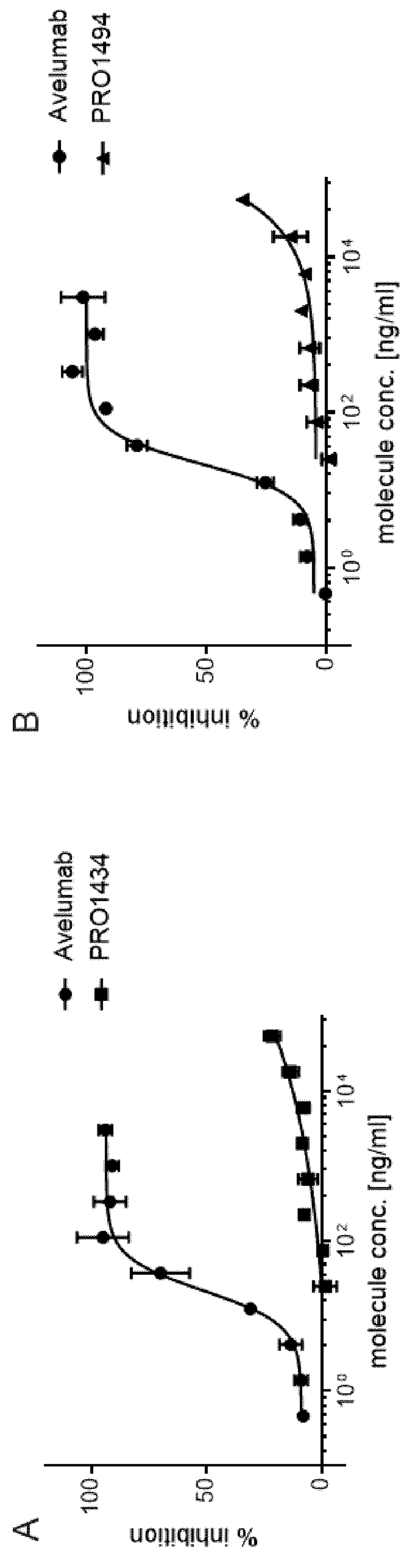
FIG. 2 Blockade of PD-1/PD-L1 interaction in NFAT reporter gene assay. PD-L1 neutralization by (A) PRO1434 and (B) PRO1494. Avelumab was used as a reference. For both molecules tested only a partial neutralization of PD-L1 interaction with PD-1 was observed with the highest concentration (162 μg/ml) tested.

Results:

Potency to neutralize PD-L1 binding to PD-1 was assessed in the cell-based reporter gene assay as described above. Serial dilutions of the respective molecules to be tested as well as the reference avelumab, were added to the plates. Individual IC50 values on each plate were calibrated against the $IC_{50}$ of the reference molecule avelumab (high affinity PD-L1 domain) that was taken along on each plate (relative $IC_{50}$: $IC_{50}$, avelumab/$IC_{50}$, test scFv). Potencies are summarized in Table 11 which shows that PRO1434 and PRO1494 have the lowest potencies. Titration curves obtained for PRO1434 and PRO1494 are presented FIG. 2.

TABLE 11

| Potencies of scFvs based on clone with Clone ID 33-03-G02 to neutralize PD-L1/PD-1 interaction in reporter gene assay. | | | |
|---|---|---|---|
| | | Neutralization of PD-L1 in NF-AT potency assay | |
| PRO ID | Mutations | $IC_{50}$ (ng/ml) | rel. $IC_{50}$* |
| PRO830 | NA | 20.36 | 1 |
| PRO1075 | VL-Q108A | 827.7 | 0.021 |
| PRO1076 | VL-G109A | ND | |
| PRO1089 | VH-Y112A | 1284 | 0.013 |
| PRO1434 | VL-Q108A/G109A | very low potency | |
| PRO1494 | VL-Q108A/VH-Y112A | 36761 | 5.89E−04 |

NA: not applicable
ND: not determined
*: $IC_{50,\ avelumab}$ (ng/ml)/$IC_{50,\ test\ molecule}$ (ng/ml)

Storage Stability Study
Method:

Humanized scFvs were subjected to stability studies such as a four-week stability study, in which the scFvs were formulated in an aqueous buffer (final buffer, 50 mM NaCiP, 150 mM NaCl, pH 6.4) at 10 mg/ml and stored at −80° C., 4° C. and 40° C. for four weeks. At the minimum, protein concentration by measurement of UV absorbance at 280 nm was measured and the fraction of monomers and oligomers in the formulation were evaluated by integration of SE-HPLC peak areas after one week, two weeks and at the end of each study. Parameters, such as % monomer content, % monomer loss, content and % content loss were recorded over time.

Results:

Table 12 and 13 compare d0, d7, d14 and endpoint measurements obtained at d28 of the study at 4° C. and 40° C. At 4° C. all molecules show less than 10% loss of monomeric content over 28 days except PRO1075 and PRO1076. At 40° C. only two molecules showed a monomeric content above 85% after 28 days, PRO1434 (86%) and PRO1494 (90%).

Example 2: Generation and Testing of Multispecific Constructs Targeting HER2 (as an Example of a TAA), PD-L1 and CD3 (as Example of an Immune Cell Antigen)

This approach is directed at a next generation multi-specific immuno-oncology program targeting HER2-expressing malignant tumors. HER2 is a clinically validated target in several cancer types with unmet medical need, most prominently breast and gastric cancer. However, the spectrum of tumors (over-) expressing HER2 is much broader but—for mechanistic reasons—not accessible to conventional antibodies like trastuzumab while amenable for the present approach, which is designed to not only effectively mediate T cell-induced lysis of HER2-expressing tumors but at the same time to avoid tumor immune-escape by concomitant blockade of immune-suppressive PD-L1 signaling. The local restriction of the two additive, likely simultaneously acting mechanisms of action to tumor tissue, is expected to provide compounds in accordance with the present approach a substantially expanded efficacy profile with anticipated clinical efficacy even in HER2 expressing tumors primarily or secondarily refractory to standard anti-HER2 therapies. The present approach should lead to i) at least as potent, and more selective blockade of PD-1/PD-L1 interaction than avelumab/Bavencio®. Specifically, compounds in accordance with the present approach should efficiently block PD-1 binding to PD-L1 on HER2/PD-L1 co-expressing target cells, while blockade of the PD-1/PD-L1 interaction on cells not expressing Her2 should be much less potent than with avelumab/Bavencio®, ii) at least as potent and more selective lysis of HER2/PD-L1 co-expressing cells by peripheral blood mononuclear cells, when compared to trastuzumab/Herceptin®, avelumab/Bavencio® and the combination of the two. More specifically, compounds in accordance with the present approach should potently lyse cells co-expressing HER2 and PD-L1 while no lysis of cells expressing PD-L1 only should occur.

Design and Production of Tribodies, DVD-Tribodies and MATCH-4 Molecules

Figure 3:
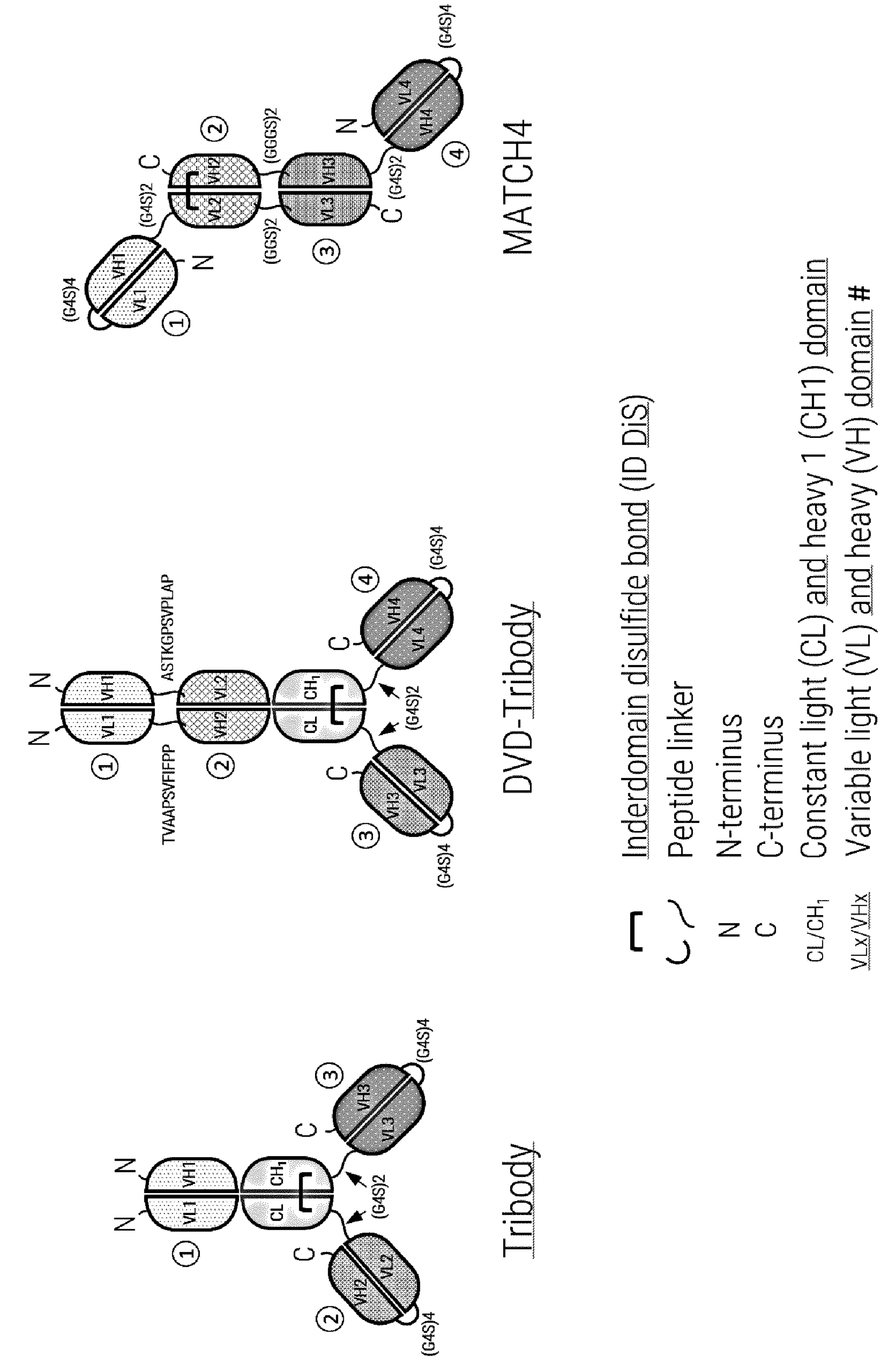
FIG. 3 Architecture of the multispecific molecules. Schematic representation and description of the three different multispecific formats Tribody, DVD-Tribody and MATCH-4. Table 14 describes the domains comprised in the different molecules produced and their positioning within the molecules. The targets for the different domains are: trastuzumab: Her2; clone 14-11-D07: IL23R; clone 23-13-A01: human/mouse serum albumin; clone 28-21-D09: CD3e; clone 33-02-G02 and mutants thereof: PD-L1. Gly-Ser linker sequences connecting individual domains are indicated in the Figure.

A description of the different formats (Tribody, DVD-Tribody and MATCH-4) designed within the present approach is presented in FIG. 3. The data regarding the production of all the molecules are detailed in Table 14, which shows a description of the domain compositions of the different molecules produced and their positioning within the molecules. The targets for the different domains are: trastuzumab: Her2; clone 14-11-D07: IL23R; clone 23-13-A01: human/mouse SA; clone 28-21-D09: CD3e; clone 33-02-G02 and mutants thereof: PD-1.

TABLE 12

| 4 w stability study scFv fragments based on clone with Clone ID 33-03-G02 at 4° C. of the scFv. | | | | | |
|---|---|---|---|---|---|
| | | Stress Stability, % mc at 4° C. | | | |
| PRO ID | Mutations | d0 | d7 | d14 | d28 |
| PRO1075 | VL-Q108A | 93.2 | 76.3 | 76.1 | 74.0 |
| PRO1076 | VL-G109A | 95.8 | 81.7 | 78.4 | 77.1 |
| PRO1089 | VH-Y112A | 99.1 | 98.0 | 97.6 | 96.5 |
| PRO1434 | VL-Q108A/G109A | 99.6 | 98.9 | 98.2 | 96.7 |
| PRO1494 | VL-Q108A/VH-Y112A | 99.3 | 98.9 | 98.8 | 98.1 |

TABLE 13

| 4 w stability study at 40° C. of the scFv. | | | | | |
|---|---|---|---|---|---|
| | | Stress Stability, % mc at 4° C. | | | |
| PRO ID | Mutations | d0 | d7 | d14 | d28 |
| PRO1075 | VL-Q108A | 93.2 | 80.0 | 80.1 | 78.8 |
| PRO1076 | VL-G109A | 95.8 | 81.9 | 81.7 | 81.4 |
| PRO1089 | VH-Y112A | 99.4 | 91.7 | 88.0 | 84.5 |
| PRO1434 | VL-Q108A/G109A | 99.6 | 87.1 | 86.6 | 86.0 |
| PRO1494 | VL-Q108A/VH-Y112A | 99.3 | 96.4 | 93.8 | 90.1 |

TABLE 14

| Composition of multispecific molecules according to the present approach | | | | | | | | | |
|---|---|---|---|---|---|---|---|---|---|
| PRO ID | Format | Domain 1 | Speci-ficity 1 | Domain 2 | Speci-ficity 2 | Domain 3 | Speci-ficity 3 | Domain 4 | Speci-ficity 4 |
| PRO1454 | Tribody | trastuzumab | Her2 | 28-21-D09 sc04 | CD3 | 33-03-G02, VL-G109A | PD-L1 | NA | NA |
| PRO1455 | Tribody | 14-11-D07-sc03 | IL23R | 28-21-D09 sc04 | CD3 | 33-03-G02, VL-G109A | PD-L1 | NA | NA |
| PRO1456 | Tribody | trastuzumab | Her2 | 28-21-D09 sc04 | CD3 | 14-11-D07-sc03 | IL23R | NA | NA |
| PRO1497 | Tribody | trastuzumab | Her2 | 28-21-D09 sc04 | CD3 | 33-03-G02, VL-Q108A, VL-G109A** | PD-L1 | NA | NA |
| PRO1498 | Tribody | 14-11-D07-sc03 | IL23R | 28-21-D09 sc04 | CD3 | 33-03-G02, VL-Q108A, VL-G109A** | PD-L1 | NA | NA |
| PRO1543 | MATCH-4 | trastuzumab, VL-G141C/H-G51C* | Her2 | 23-13-A01-sc02, VL-G141C/VH-G51C* | HSA | 28-21-D09 sc04 | CD3 | 33-03-G02, VL-Q108A, VL-G109A** | PD-L1 |
| PRO1543 variant | MATCH-4 | trastuzumab, VL-G141C/H-G51C* | Her2 | 19-01-H04-sc03 | HSA | 28-21-D09 sc04 | CD3 | 33-03-G02, VL-Q108A, VL-G109A** | PD-L1 |
| PRO1544 | MATCH-4 | 33-03-G02, VL-Q108A, VL-G109A** | PD-L1 | 23-13-A01-sc02, VL-G141C/VH-G51C* | HSA | 28-21-D09 sc04 | CD3 | trastuzumab, VL-G141C/VH-G51C* | Her2 |
| PRO1545 | MATCH-4 | 33-03-G02, VL-Q108A, VL-G109A** | PD-L1 | 23-13-A01-sc02, VL-G141C/VH-G51C* | HSA | 28-21-D09 sc04 | CD3 | 14-11-D07-sc03 | IL23R |
| PRO1546 | MATCH-4 | 14-11-D07-sc03 | IL23R | 23-13-A01-sc02, VL-G141C/VH-G51C* | HSA | 28-21-D09 sc04 | CD3 | 33-03-G02, VL-Q108A, VL-G109A** | PD-L1 |
| PRO1547 | DVD-Tribody | trastuzumab | Her2 | 23-13-A01-sc02 | HSA | 28-21-D09 sc04 | CD3 | 33-03-G02, VL-Q108A, VL-G109A** | PD-L1 |
| PRO1548 | DVD-Tribody | trastuzumab | Her2 | 23-13-A01-sc02 | HSA | 28-21-D09 sc04 | CD3 | 14-11-D07-sc03 | IL23R |
| PRO1557 | MATCH-4 | trastuzumab, VL-G141C/H-G51C* | Her2 | 23-13-A01-sc02, VL-G141C/VH-G51C* | HSA | 28-21-D09 sc04 | CD3 | 14-11-D07-sc03 | IL23R |
| PRO1558 | MATCH-4 | 14-11-D07-sc03 | IL23R | 23-13-A01-sc02, VL-G141C/VH-G51C* | HSA | 28-21-D09 sc04 | CD3 | trastuzumab, VL-G141C/VH-G51C* | Her2 |
| PRO1895 | MATCH4 | pertuzumab, VL-G141C/VH-G51C* | Her2 | 23-13-A01-sc02, VL-G141C/VH-G51C* | HSA | 28-21-D09-sc04 | CD3 | 33-03-G02. VL-Q108A, VL-G109A** (PRO1434) | PD-L1 |
| PRO2366 | MATCH4 | pertuzumab, VL-G141C/VH-G51C* | Her2 | 19-04-A10-sc06, VL-G141C/VH-G51C* | HSA | 28-21-D09-sc04 | CD3 | 33-03-G02, VL-Q108A, VL-Y215A** (PRO1494) | PD-L1 |

*VL/H interdomain disulfide bond, numbering according to A. Honegger

**mutations, numbering according to A. Honegger

Method:

Expression of Tribodies, DVD-Tribodies and MATCH-4 constructs was performed in CHO-S cells using CHOgro transient transfection kit (Mirus). Cultures were harvested after 5-7 days (cell viability <70%) of expression at 37° C. by centrifugation and proteins were purified from clarified culture supernatants by Protein L affinity chromatography followed, if needed, by a polishing step by size-exclusion chromatography. For the quality control of the manufactured material standard analytical methods, such as SE-HPLC, UV280 and SDS-PAGE were used.

Affinities to Human PD-L1, IL-23R, Her2, CD3E and Human and Mouse Serum Albumin (SA) by SPR Method:

Affinity to PD-L1 was determined by surface plasmon resonance (SPR) measurements using a Biacore T200 device (GE Healthcare) as described above. The apparent dissociation ($k_d$) and association ($k_a$) rate constants and the apparent dissociation equilibrium constant ($K_D$) were calculated with the Biacore analysis software (BIAevaluation, GE Healthcare) using one-to-one Langmuir binding model. The quality of the fits was monitored based on Chi2 and U-value. In addition to the kinetic measurement, the value of the $K_D$ was obtained by fitting a plot of response at equilibrium against the concentration (steady-state affinity measurement).

Binding affinities of multi-specific constructs towards recombinant human CD3E ECD (SinoBiological, cat. 10977-H08H), recombinant human IL-23R (custom-made by Trenzyme) and recombinant human Her2 ECD (SinoBiological, cat. 10004-HCCH) were measured by SPR using a Biacore T200 instrument. All measurements were performed at 25° C. The different proteins were immobilized on a sensor chip (CM5 sensor chip, GE healthcare) by amine-coupling to reach an immobilization level of approximately 100 response units (RUs). Serial dilutions of the multispecific molecules ranging from 0.35 to 90 nM (two-fold dilutions steps) in running buffer were injected into the flow cells at a flow rate of 30-50 μl/min for 5-7 min. Dissociation of the multispecific constructs from the CD3ε, IL-23R and Her2 on the CM5 chip was allowed to proceed for 12 min. After each injection cycle, surfaces were regenerated with one injection of 10 mM glycine HCl, pH 2. Obtained binding curves were double-referenced (empty reference channel and zero analyte injection) and the values of $k_d$, $k_a$ and $K_D$ were calculated with the Biacore analysis software using one-to-one Langmuir binding model and quality of the fits was monitored based on Chi2 and U-value. Since the fits using the one-to-one Langmuir binding model showed sub-optimal quality of curve fitting for CD3s, the $K_D$ was in addition calculated using a two-state reaction model. This model describes a 1:1 binding of analyte to immobilized ligand followed by a conformational change that stabilizes the complex.

Affinity of molecules to human serum albumin (HSA) and mouse serum albumin (MSA) was determined by SPR measurements using a Biacore T200 device (GE Healthcare). SA was directly coupled to a CM5 sensor chip (GE Healthcare) using amine coupling chemistry. After performing a regeneration scouting and surface performance test to find best assay conditions, a dose response of the molecules of interest with concentrations ranging from 0.7 to 180 nM was tested. The assay was run in a PBS-Tween buffer at pH 5.5. Association and dissociation time were set to 180 s and 720 s, respectively. Obtained binding curves were double-referenced (empty reference channel and zero analyte injection) and fitted using BiaEvaluation software (GE Healthcare) and the 1:1 Langmuir binding model. Retrieved kinetic parameters were used to calculate the apparent dissociation equilibrium constant ($K_D$).

Results:

As shown in Table 15 and Table 16, binding to CD3s, human and mouse serum albumin was similar for all molecules tested, and molecules containing the anti-IL23R domain showed comparable affinities to IL23R. Affinity determination by SPR of low affinity domains is very difficult due to the high amount of protein that has to be injected in order to cover the concentration range corresponding to the affinity of the molecules. Therefore, a reliable measurement of the affinity to PD-L1 could not be obtained for some molecules. In addition, in case of low affinity domains steady state analysis of the SPR measurement might be more adequate due to the high bulk shifts observed, which introduce artefacts in the kinetic analysis. Affinity measurement for human PD-L1 was valid for only one Tribody, PRO1498. For the MATCH-4 molecules, valid measurements were obtained using the steady state analysis. The lowest affinities to PD-L1 were around 900 nM for PRO1544, PRO1545 and PRO1547. PRO1543 and PRO1546 showed similar affinities around 300 nM. MATCH-4 proteins carrying the lambda capped trastuzumab G100C/G172C mutant anti-Her2 domain (PRO1543, PRO1544, PRO1557 and PRO1558) showed similar affinities to Her2 (300 to 400 pM), which again is comparable to the affinities of trastuzumab anti-Her2 domain incorporated in Tribody (PRO1497) and DVD-Tribody (PRO1547 and PRO1548).

TABLE 15

Summary of affinities of constructs of the present approach for binding to human PD-L1, Her2 and IL23R by SPR.

| | Affinity to human Her2 | | | Affinity to human PD-L1: kinetic analysis | | | Affinity to human PD-L1: steady state analysis | Affinity to human IL23R | | |
|---|---|---|---|---|---|---|---|---|---|---|
| PRO ID | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) | $K_D$ (M) | $k_a$ ($M^{-1}$ $s^{-1}$) | $k_d$ ($s^{-1}$) | $K_D$ (M) |
| PRO1454 | | not measured | | | not measured | | | | not measured | |
| PRO1455 | | not measured | | | not measured | | | | not measured | |
| PRO1456 | | not measured | | | not measured | | | | not measured | |
| PRO1497 | 2.07E+05 | 5.40E−05 | 2.61E−10 | | not determined | | | | no binding | |
| PRO1498 | | no binding | | 1.14E+03 | 3.79E−04 | 3.32E−07 | not measured | 4.95E+05 | 2.78E−04 | 5.63E−10 |
| PRO1543 | 1.54E+05 | 6.26E−05 | 4.06E−10 | 1.76E+04 | 3.67E−04 | 2.09E−08 | 3.47E−07 | | no binding | |
| PRO1544 | 1.57E+05 | 5.56E−05 | 3.54E−10 | 4.12E+03 | 1.17E−03 | 2.84E−07 | 8.09E−07 | | no binding | |
| PRO1545 | | no binding | | 1.95E+03 | 2.20E−03 | 1.13E−06 | 8.79E−07 | 3.09E+05 | 4.71E−04 | 1.52E−09 |
| PRO1546 | | no binding | | 2.41E+04 | 3.45E−04 | 1.43E−08 | 3.80E−07 | 4.58E+05 | 3.88E−04 | 8.48E−10 |
| PRO1547 | 1.66E+05 | 6.00E−05 | 3.61E−10 | | not determined | | 9.16E−07 | | no binding | |
| PRO1548 | 1.87E+05 | 6.06E−05 | 3.23E−10 | | | no binding | | 2.40E+05 | 2.36E−04 | 9.85E−10 |
| PRO1557 | 2.00E+05 | 6.35E−05 | 3.18E−10 | | | no binding | | 5.52E+05 | 5.14E−04 | 9.31E−10 |
| PRO1558 | 2.02E+05 | 6.07E−05 | 3.00E−10 | | | no binding | | 5.68E+05 | 4.93E−04 | 8.68E−10 |

| | Affinity by SPR measurement | | | | | | |
|---|---|---|---|---|---|---|---|
| Protein ID | Antigen | $k_a$ ($M^{-1}$ $s^{-1}$) | $k_d$ ($s^{-1}$) | $K_D$ (M) | % Binding level # | rel. Chi2 (% of Rmax) | U value |
| PRO1895 | human Her-2 | 1.96E+05 | 8.11E−05 | 4.14E−10 | 10.35 | 0.12 | 7 |

Maximum binding level achieved normalized to theoretical Rmax

TABLE 16

Summary of affinities of constructs of the present approach for binding to human $CD3_{\epsilon}$, human and mouse serum albumin (SA) by SPR.

| PRO ID | Affinity to human CD3 | | | | | | | Affinity to human SA (at pH5.5) | | | Affinity to mouse SA (at pH5.5) | | |
|---|---|---|---|---|---|---|---|---|---|---|---|---|---|
| | $k_a1$ ($M^{-1}$ $s^{-1}$) | $k_d1$ ($s^{-1}$) | $K_D1$ (M) | $k_a2$ ($M^{-1}$ $s^{-1}$) | $k_d2$ ($s^{-1}$) | $K_D2$ (M) | $K_D$ (M) | $k_a$ ($M^{-1}$ $s^{-1}$) | $k_d$ ($s^{-1}$) | $K_D$ (M) | $k_a$ ($M^{-1}$ $s^{-1}$) | $k_d$ ($s^{-1}$) | $K_D$ (M) |
| PRO1454 | not measured | | | | | | | NA | | | NA | | |
| PRO1455 | not measured | | | | | | | NA | | | NA | | |
| PRO1456 | not measured | | | | | | | NA | | | NA | | |
| PRO1497 | 2.31E+05 | 5.94E−03 | 2.57E−08 | 7.20E−04 | 2.86E−03 | 3.97E+00 | 2.06E−08 | NA | | | NA | | |
| PRO1498 | 1.97E+05 | 5.84E−03 | 2.96E−08 | 1.05E−03 | 1.98E−03 | 1.89E+00 | 1.95E−08 | NA | | | NA | | |
| PRO1543 | 1.90E+05 | 5.42E−03 | 2.85E−08 | 4.08E−03 | 5.03E−03 | 1.23E+00 | 1.57E−08 | 1.45 E+05 | 1.18 E−04 | 8.10 E−10 | 6.02 E+04 | 1.17 E−03 | 1.95 E−08 |
| PRO1544 | 2.22E+05 | 5.16E−03 | 2.32E−08 | 3.49E−03 | 4.20E−03 | 1.20E+00 | 1.27E−08 | 1.39 E+05 | 1.21 E−04 | 8.70 E−10 | 5.75 E+04 | 1.12 E−03 | 1.95 E−08 |
| PRO1545 | 1.69E+05 | 6.45E−03 | 3.82E−08 | 5.51E−03 | 4.32E−03 | 7.84E−01 | 1.67E−08 | 1.71 E+05 | 1.19 E−04 | 6.93 E−10 | 6.79 E+04 | 1.08 E−03 | 1.59 E−08 |
| PRO1546 | 1.97E+05 | 7.52E−03 | 3.82E−08 | 5.77E−03 | 5.33E−03 | 9.24E−01 | 1.83E−08 | 1.68 E+05 | 1.34 E−04 | 7.97 E−10 | 6.70 E+04 | 1.16 E−03 | 1.73 E−08 |
| PRO1547 | 1.97E+05 | 4.97E−03 | 2.52E−08 | 6.04E−04 | 8.19E−04 | 1.36E+00 | 1.45E−08 | not measured | | | not measured | | |
| PRO1548 | 2.82E+05 | 4.06E−03 | 1.44E−08 | 9.47E−04 | 1.29E−03 | 1.36E+00 | 8.28E−09 | not measured | | | not measured | | |
| PRO1557 | 2.83E+05 | 5.29E−03 | 1.87E−08 | 4.35E−03 | 3.56E−03 | 8.18E−01 | 8.43E−09 | 2.40 E+05 | 1.20 E−04 | 4.98 E−10 | 9.56 E+04 | 1.07 E−03 | 1.12 E−08 |
| PRO1558 | 3.15E+05 | 4.96E−03 | 1.57E−08 | 3.27E−03 | 3.35E−03 | 1.02E+00 | 7.95E−09 | 2.45 E+05 | 1.23 E−04 | 5.01 E−10 | 9.58 E+04 | 1.10 E−03 | 1.15 E−08 |

NA: not applicable

PD-L1/PD-1 Neutralization by FC

Method:

These assays were conducted to assess the ability of the multi-specific low affinity PD-L1x/Her2 constructs to neutralize the interaction between PD-1 and PD-L1 expressed on HCC1954 cells, which also express Her2. Specifically, the molecules should efficiently block PD-1 binding to PD-L1 on Her2/PD-L1 co-expressing target cells (HCC1954), while blockade of the PD-1/PD-L1 interaction on cells not expressing Her2 (HCC827) should be much less potent than with avelumab/Bavencio© or nivolumab/Opdivo©. Blockade of PD-1 binding to the cells was analyzed by FC and compared to the reference IgG avelumab. Moreover, HCC827 cells were used as an additional control as these cells express PD-L1 at comparable levels than HCC1954 cells but lack significant expression of Her2.

HCC1954 and HCC827 cells were stimulated with 10 ng/ml human IFNγ for 24 h to further induce the expression of PD-L1. Next day, HCC827 and HCC1954 cells were detached, centrifuged for 4 min with 200 g, re-suspended in PBS/2% FCS/2 mM EDTA (staining buffer) and seeded into 96 well PP microplates (50 μl/well). Dilution series of three-fold steps of the multi-specific molecules and of avelumab starting at 20 μg/ml and 5 μg/ml, respectively, were prepared in staining buffer containing 500 ng/ml biotinylated PD 1. Plates of HCC827 and HCC1954 were centrifuged for 4 min with 200 g and the dilution series were added to the cells (100 μl/well) and incubated for 30 min at RT. Next, plates were washed once with 150 μl staining buffer and Streptavidin-PE solution was added to the cells (100 μl/well) and incubated for 30 min at 4° C. As a next step, cells were washed again as indicated above and then cells were re-suspended in 100 μl of staining buffer. Re-suspended cells were then processed for fluorescence measurement using NovoCyte flow cytometer (ACEA Bioscience Inc.). Mean fluorescence intensity of PE-labeled PD-1 was reported and data were fitted using sigmoidal 4PL fit (GraphPad Prism). Individual $IC_{50}$ values on each plate were calibrated against the $IC_{50}$ of the reference molecule avelumab that was taken along on each plate (relative $IC_{50}$:$IC_{50}$, avelumab/$IC_{50}$, test molecule). In addition, the ratio between the relative $IC_{50}$ values found on high Her2 expressing HCC1954 and low Her2 expressing HCC827 cells was calculated.

Figure 4:
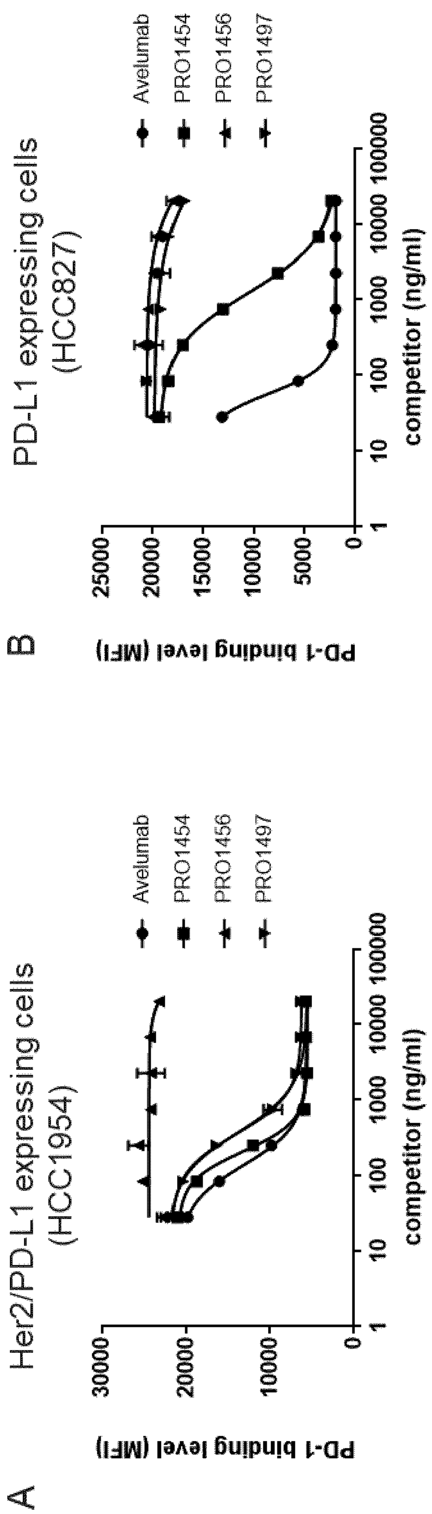
FIG. 4 Blockade of PD-1/PD-L1 interaction on Her2 expressing cells. Inhibition of PD-1 binding to (A) cells expressing PD-L1 and Her2 (HCC1954) or (B) cells expressing PD-L1 without significant expression of Her2 (HCC827) in presence of increasing concentrations of avelumab, PRO1454, PRO1456 and PRO1497. PRO1454 inhibits PD-1 binding to PD-L1 on PD-L1/high Her2 expressing cells (HCC1954) with an $IC_{50}$ of 205 ng/ml as well as on PD-L1 expressing cells (HCC827) with an $IC_{50}$ of 1204 ng/ml. PRO1497 containing the anti-PD-L1 domain with a 50-fold lower affinity inhibited PD-1 binding to Her2/PD-L1 expressing cells with comparable potency as PRO1454 but showed only very weak inhibition of PD-1 binding to cells expressing only PD-L1 at the concentrations tested. PRO1456 which does not contain an anti-PD-L1 domain did not affect PD-1 binding on both cell lines. Data were fitted using sigmoidal 4PL fit (GraphPad Prism).

Results:

Obtained potencies of constructs according to the present approach to neutralize PD-1/PD-L1 interaction are summarized in Table 17. On HCC1954 cells expressing high levels of Her2 and PD-L1, the Tribody PRO1454 carrying the single alanine mutant PD-L1 domain (33-03-G02 G109A) showed a similar potency as avelumab whereas on cells expressing only PD-L1 (HCC827) the potency of PRO1454 was 14-fold lower. The Tribody PRO1497 carrying the double alanine mutant 33-03-G02 Q108A/G109A neutralized PD-1/PD-L1 interaction on Her2/PD-L1 positive cells (HCC1954) almost as efficient as PRO1454 as shown by similar relative $IC_{50}$ values (PRO1454: 0.66, PRO1497: 0.38). However, in contrast to PRO1454, PRO1497 demonstrated only very weak neutralization potency on PD-L1 expressing cells (HCC827) (FIG. 4). This finding shows the potentially larger therapeutic window of molecules such as PRO1497 containing a PD-L1 domain with an affinity equivalent to the domain carrying both mutations (Q108A/G109A) versus a domain with an affinity similar to the single alanine mutant (G109A).

All MATCH-4 molecules containing trastuzumab anti-Her2 domain and the anti-PD-L1 domain carrying both mutations (Q108A/G109A) had similar potencies (rel. $IC_{50}$ values, PRO1543: 0.28, PRO1544: 0.24) when compared to the Tribody PRO1497. Titration curves obtained for PRO1543 and PRO1546 are presented in FIG. 5. Along that line, the DVD-Tribody PRO1547 containing trastuzumab anti-Her2 domain and the anti-PD-L1 domain carrying both mutations (Q108A/G109A) neutralized PD-1/PD-L1 interaction with a potency similar to PRO1497 (rel. IC50 values, PRO1547: 0.25).

TABLE 17

Potencies of multi-specific molecules to neutralize PD-L1/PD-1 interaction in flow cytometry assay. Neutralization of PD-L1/PD-1 interaction in FC based assay

| | High Her2 expressing cells (HCC1954) | | Low Her2 expressing cells (HCC827) | | Ratio |
|---|---|---|---|---|---|
| PRO ID | $IC_{50}$ (ng/ml) | rel. $IC_{50}$* | $IC_{50}$ (ng/ml) | rel. $IC_{50}$* | rel. $IC_{50}$ (high Her2)/ rel. $IC_{50}$ (low Her2) |
| PRO1454 | 205.5 | 0.66 | 1240 | 0.05 | 14.04 |
| PRO1455 | 2846 | 0.06 | 2796 | 0.01 | 4.83 |
| PRO1456 | no inhibition | | no inhibition | | NA |
| PRO1497 | 352.2 | 0.38 | 719036 | 0.00 | 4886 |
| PRO1498 | 7046 | 0.02 | 8537 | 0.01 | 2.9 |
| PRO1543 | 600.5 | 0.28 | 59224 | 0.00 | 272.4 |
| PRO1544 | 527.7 | 0.24 | 45995 | 0.00 | 232.6 |
| PRO1545 | 4136 | 0.03 | 88075 | 0.00 | 55.66 |
| PRO1546 | 51902 | 0.00 | 254254 | 0.00 | 10.31 |
| PRO1547 | 522.3 | 0.25 | no inhibition | | NA |
| PRO1548 | not measured | | | | NA |
| PRO1557 | not measured | | | | NA |
| PRO1558 | not measured | | | | NA |
| avelumab | 127.7 | 1 | 46.03 | 1 | 1 |
| nivolumab | 43.48 | 2.94 | 39.77 | 1.16 | 2.54 |

NA: not applicable
*$IC_{50,\ avelumab}$ (ng/ml)/$IC_{50,\ test\ molecule}$ (ng/ml)

CD3 Activation and PD-L1/PD-1 Interaction Blockade by NFAT Reporter Gene Assay

Method:

T-cell activation was tested in an NFAT (nuclear factor of activated T-cells) assay to assess simultaneous effects of the molecules on CD3 cross-linking and PD-1/PD-L1 blockade. Specifically, the molecules should efficiently induce CD3 activation and block PD-1 binding to PD-L1 on HER2/PD-L1 co-expressing target cells (HCC1954), while CD3 activation and blockade of the PD-1/PD-L1 interaction on cells not expressing Her2 (CHO-PD-L1) should be much less potent. The Jurkat PD-1 NFAT reporter T cell line expresses the luciferase reporter gene under control of the NFAT response elements from the IL-2 promoter. The transcription factor NFAT is activated upon cross-linking of CD3e and induces a number of genes involved in T cell activation. In this system, cross-linking of CD36 induces expression of the luciferase reporter gene. In addition, the interaction between PD-L1 and PD-1 negatively regulates such CD3e signaling and thus diminishes firefly luciferase expression. Therefore, blockade of the PD-L1/PD-1 interaction in this system leads to increased luciferase activity. HCC1954 cells stimulated for 24 h with 10 ng/ml IFNy to increase PD-L1 expression and PD-L1 expressing CHO-K1 cells (clone A2) were used as target cells and seeded at 25'000 cells per well in 50 μl on 96-well culture plates. Serial dilutions of the molecules to be tested were prepared in assay medium containing 50 mg/ml HSA and 25 μl were added to the cells (final concentrations range from 250 nM to 0.026 pM). PD-1 expressing Jurkat NFAT reporter cells were prepared in assay medium containing HSA at 50 mg/ml and added at a cell density of 50'000 cells per well. Luciferase expression was detected by addition of Luciferase reagent and was read by a luminescence reader 5 or 22 h after addition of Jurkat PD-1 NFAT reporter cells. Relative luminescence units (RLU) are presented. Potency of PRO1497 which is a HER2×PD-$L1_{high\ KD}$×CD3 scDb-scFv was used as a reference for calculation of the relative potency of the extended half-life molecules.

Results:

Potency to trigger CD3 activation and PD-L1/PD-1 interaction blockade concomitantly was assessed by NFAT reporter gene assay and the results are presented in Table 18. Serial dilutions of the respective molecules to be tested as well as the reference scDb-scFv Her2×CD3×PD-$L1_{low\ affinity}$ (PRO1497) were added to the plates. Individual $IC_{50}$ values and maximal activation were normalized to the $IC_{50}$ and maximal activation of the reference molecule PRO1497 in presence of Her2 and PD-L1 expressing cells HCC1954 (relative $IC_{50}$ or Max. act.: $IC_{50}$ or Max. Act., PRO1497 on HCC1954/$IC_{50}$ or Max act., test molecule). In the presence of PD-1/Her2 expressing cells (HCC1954), Tribodies PRO1454, PRO1497 and PRO1456 activated CD3 signaling in Jurkat cells with similar $EC_{50}$ but the maximal activation was higher for PRO1454 and PRO1497, i.e. for molecules carrying the low affinity anti-PD-L1 domain, compared to PRO1456 containing an anti-IL-23R dummy domain instead of the anti-PD-L1 domain (FIG. 6). This suggests that PRO1454 and PRO1497 simultaneously block PD-L1 and activate CD3 within the immunological synapse in presence of cells co-expressing Her2 and PD-L1. 27-fold weaker activation was observed with PRO1455 compared to PRO1454 and even 475-fold weaker with PRO1498 compared to PRO1497, i.e. molecules carrying no anti-Her2 domain but the low affinity anti-PD-L1 domain 33-03-G02 G109A or 33-03-G02 Q108A/G109A, respectively. This finding shows the potentially larger therapeutic window of molecules containing a PD-L1 domain with an affinity equivalent to the domain carrying both mutations (Q108A/G109A) versus a domain with an affinity similar to the single alanine mutant (G109A) both molecules being of similar potency as the molecule carrying no PD-L1 domain (PRO1456). Potencies are summarized in Table 18 which shows that PRO1543 had the best potency on Her 2/PD-L1 expressing cells (HCC1954) and one of the lowest in presence of PD-L1/very low Her2 expressing cells (HCC827). Titration curves obtained for PRO1543 and the control molecules PRO1546 and PRO1557 in presence or absence of 1 μg/ml nivolumab and PRO1557 in combination with the low affinity PD-L1 domain PRO1434 are presented in FIG. 7.

TABLE 18

Potencies of molecules to trigger CD3 activation and neutralize PD-L1/PD-1 interaction in NFAT reporter gene assay.

| | Neutralization of PD-L1/PD-1 interaction in NFAT reporter gene assay | | | | | |
|---|---|---|---|---|---|---|
| | High Her2 expressing cells (HCC1954) | | | negative Her2 cells (CHO-PD-L1; A2 clone) | | |
| PRO ID | $IC_{50}$ (pM) | rel. $IC_{50}$* | rel. max. activation (%)$ | $IC_{50}$ (pM) | rel. $IC_{50}$* | rel. max. activation (%)$ |
| PRO1454 | 148 | 1** | 100$$ | | not measured | |
| PRO1455 | 4071 | 0.036** | 598$ | | not measured | |
| PRO1456 | 291 | 1.24 | 75 | | not measured | |
| PRO1497 | 361 | 1 | 100 | | not measured | |
| PRO1498 | 172108 | 0.002 | 71 | | not measured | |
| PRO1543 | 402 | 0.32 | 102 | 29196 | 0.004 | 62 |
| PRO1543 + nivolumab | 125 | 4.75*** | 107$$$ | | no activation | |
| PRO1544 | 2290 | 0.08 | 78 | 10544 | 0.02 | 42 |
| PRO1545 | 12246 | 0.010 | 67 | 25996 | 0.006 | 59 |
| PRO1546 | 95436 | 0.001 | 28 | 31494 | 0.004 | 60 |
| PRO1546 + nivolumab | | no activation | | | no activation | |
| PRO1547 | 779 | 0.2 | 106 | 142091 | 0.001 | 19 |
| PRO1548 | 325 | 0.5 | 86 | | no activation | |
| PRO1557 | 391 | 0.30 | 82 | | no activation | |
| PRO1557 + nivolumab | 319 | 1.86*** | 115$$$ | | no activation | |
| PRO1557 + PRO1434 | 671 | 0.88*** | 75$$$ | | no activation | |
| RO1558 | 2714 | 0.06 | 53 | | no activation | |

NA: not applicable

*$IC_{50,\ PRO1497\ on\ HCC1954}$ (pM)/$IC_{50,\ test\ molecule}$ (pM)

$Max. activation, $_{PRO1497\ on\ HCC1954}$ (RLU)/Max. activation, $_{test\ molecule}$ (RLU)

**$IC_{50,\ PRO1454\ on\ HCC1954}$ (pM)/$IC_{50,\ test\ molecule}$ (pM)

$$Max. activation, $_{PRO1454\ on\ HCC1954}$ (RLU)/Max. activation, $_{test\ molecule}$ (RLU)

***$IC_{50,\ PRO1543\ on\ HCC1954}$ (pM)/$IC_{50,\ test\ molecule}$ (pM)

$$$Max. activation, $_{PRO1543\ on\ HCC1954}$ (RLU)/Max. activation, $_{test\ molecule}$ (RLU)

Cytotoxicity Assay (T-Cell Driven Target Cell Depletion)

To assess the ability of the compounds of the present approach to selectively direct T cells to Her2 and PD-L1 co-expressing cells, a cytotoxicity assay using Her2 and PD-L1 positive cell lines (HCC1954) were performed, in the presence of human PBMCs. Simultaneous binding to both targets by the compounds of the present approach lead to cross-linking of CD38 on T cells and activated a signaling cascade that triggers T cell activation (CD69 upregulation, cytokine secretion) and the release of cytotoxic granules, which ultimately resulted in target cell killing. In contrast to the combination of avelumab/Bavencio© and trastuzumab/Herceptin©, the compounds of the present approach should selectively lyse cells co-expressing PD-L1 and HER2 while no lysis of cells solely expressing PD-L1 (CHO.PD-L1 transfectants) should be observed.

Methods:

Blood Cells Fractionation:

Peripheral blood mononuclear cells (PBMC) were isolated from fresh blood of healthy volunteers using the lymphocyte separation medium Lymphoprep (Stemcell technologies) according to manufacturer's instructions. Briefly, blood was diluted 1:2 with human PBMC isolation buffer (PBS, 2% FCS, 2 mM EDTA) or cynomolgus PBMCs isolation buffer (PBS, 5% FCS, 2 mM EDTA) and applied to Leucosep tubes containing recommended amount of Lymphoprep medium. LeucoSep tubes were centrifuged 30 min at 800 g (human blood) or 2000 g (cynomolgus blood) without brakes at RT. Then, the cell layer containing PBMCs was collected and washed twice with human PBMCs isolation buffer and red blood cells were lysed using red blood cells lysis buffer for 5 min at RT. Isolated human cells were then washed once with their respective isolation buffer and once with assay medium (RPMI-1640, 10% FCS). After platelet removal, isolated PBMCs were resuspended in assay medium at a density of $3\times10^6$ viable cells per ml.

Flow Cytometry-Based In Vitro Cytotoxicity Assay (FC Assay), CD8+ T Cells Activation and CD11c+, CD4+ T Cells, CD8+ T Cells Viability:

Two cell lines were used as target cells, HCC1954 (co-expressing high levels of HER2 and PD-L1) and HCC827 cells (co-expressing low levels of HER2 and PD-L1) stimulated for 24 h with 10 ng/ml IFNγ to increase PD-L1 expression as well as CHO-PD-L1 (no Her2 and high PD-L1) and CHO-K1 cell line used as negative control cell line. 5'000 viable target cells previously labelled with PKH67 and diluted in 75 μl of assay medium (RPMI-1640, 10% FCS) were added to 96-well plates. 25 μl of 6 times concentrated test proteins diluted in assay medium were added to appropriate wells. 150'000 viable effector cells (PBMCs) diluted in 50 μl assay medium were added to each well (E:T ratio of 30:1) and plates were mixed on a nutating mixer at RT prior to their incubation at 37° C., 5% C02. After 16 h or 40 h, cells were trypsinized, resuspended in staining buffer (PBS, 2% BCS, 2 mM EDTA) and transferred into non-binding plates.

Cells were stained for different markers such as CD69, CD8, CD4, CD11c and Annexin-V. For analysis, the focus was on apoptotic and dead target cells and activated CD8+ T cells. Thereby, target cells were identified by green fluorescence (PKH67) and their viability was analyzed by Annexin-V APC. Effector cells (CD8+ cells) were identified by detecting CD8 on their surface (anti-CD8 PerCP-Cy5.5). Activation of CD8+ T cells was finally detected by quantification of CD69 expression (anti-CD69 PE). CD4 was used to better discriminate CD8+ and CD4+ T cells. CD11c was used to stain monocytes and dendritic cells. For each marker except Annexin-V antibodies were incubated 30 min at RT under gentle agitation. Cells were washed once with staining buffer, once with Annexin binding buffer and Annexin-V staining was carried on for 30 min at RT under agitation. Cells were washed once with Annexin-V binding buffer and flow cytometry analysis was done on a Novocyte Flow Cytometer.

The percentage of specific target cells lysis was calculated according to the following equation:

$$\text{Specific lysis of target cells [in \%]} = \left[1 - \frac{\text{Viability target cells of sample}}{\text{average viability of control samples}}\right] \times 100$$

The percentage of activated CD8+ T cells corresponds to the proportion of CD69+ CD8+ T cells.

The percentage of viable CD4+, CD8+ T cells and CD11c+ cells correspond to the proportion of Annexin-V negative cells within the different cell populations.

Results:

Cytotoxic potential of the selected MATCH-4 molecules PRO1543 and PRO1895 was assessed using the flow cytometry-based cytotoxicity assay. Data obtained are presented in Table 19 and titration curves for PRO1543 and PRO1895 and control molecule PRO2290 are presented in FIGS. 8 and 9. PRO1543 and PRO1895 bearing the anti-Her2 and the low affinity anti-PD-L1 domains are similarly potent to each other and are more potent than PRO2290, which carries the pertuzumab epitope anti-Her2 domain but contains no low affinity anti-PD-L1 domain. This data shows the additional effect of PD-L1 targeting within the immunological synapse leading to improved target cell lysis.

TABLE 19

Potencies of PRO1543 for target cell lysis.

| PRO ID | High Her2 expressing cells (HCC1954) T cell activation IC50 (pM) | Low Her2PD-L1$^+$ HCC827 T cell activation IC50 (pM) |
|---|---|---|
| PRO1543 | 49 | 136 |
| PRO1895 | 27 | 153 |
| PRO2290 | 220 | 1002 |

CD4+ and CD8+ T cell viability was analyzed after 16 and 40 h. This gives a safety read-out as activated CD4+ and CD8+ T cells are expressing PD-L1 but not Her2 and might be targeted as well by PRO1543. As summarized in Table 21 and illustrated in FIG. 10, PRO1543 decreased CD4+ and CD8+ T cell viability by 5 to 10% and only at the highest concentrations tested. This can be considered as a minor effect on cell viability.

Cytotoxicity Assay on Cell Expressing Different Her2 and PD-L1 Levels (T-Cell Driven Target Cell Depletion)

Method:

Same method as in the example above was used. Four cell lines were used as target cells, HCC1954 (co-expressing high levels of HER2 and PD-L1), HCC1827 (expressing very low levels of HER2 and high levels of PD-L1) stimulated for 24 h with 10 ng/ml IFNy to increase PD-L1 expression, MCF-7 (expressing low levels of HER2 and very low PD-L1 levels) as well as CHO-PD-L1 (no Her2 and high PD-L1, purchased at BPS Bioscience. Please note that this cell line expresses PD-L1 at a about 9 times lower level compared to the CHO-PD-L1 clone A2 cell line used for the experiments shown in Tables 18 and 19, FIGS. 8 and 9).

Results:

The results of the cytotoxicity assay are shown in Table 22 and in FIGS. 11 and 12. The results demonstrate that the molecule comprising the low affinity PD-L1 domain, PRO1543, has superior potency over PRO1557 and PRO957 to kill cells expressing HER2 and PD-L1 while it does not kill cells expressing no HER2. Co-expression of HER2 and PD-L1 occurs only on cancer cells. PRO1543 furthermore mediates lysis of HER2/PD-L1 double-positive cancer cells more potently than _normal cells expressing only HER2. Thus, PRO1543 in contrast to a molecule not containing a PD-L1 binding domain, reveals selectivity for double-positive cells and spares normal cells expressing HER2. Due to the absence of a PD-L1 binding domain, PRO1557 and PRO957 have no such selectivity and their potency is solely determined by the HER2 expression level of the target cell.

TABLE 21

Percentage of viable CD4+ and CD8+ T cells after 40 h

| | High her2 expressing cells (HCC1954) | | Low Her2 expressing cells (HCC827) | | No Her2/PD-L1 cells (CHO-K1) | |
|---|---|---|---|---|---|---|
| PRO ID | CD4$^+$ cell viability range (%) | CD8$^+$ cell viability range (%) | CD4$^+$ cell viability range (%) | CD8$^+$ cell viability range (%) | CD4$^+$ cell viability range (%) | CD8$^+$ cell viability range (%) |
| PRO1543 | 82-93 | 92-96 | 84-92 | 93-97 | 94-95 | 96-97 |
| PRO1546 | 86-94 | 92-98 | 90.9 | 95-98 | 93-94 | 97-98 |
| PRO1557 | 81-94 | 88-97 | 88-92 | 93-96 | 93-94 | 94-97 |

TABLE 22

Potencies of PRO1543 for killing of different target cell lines

| PRO ID | High Her2 expressing cells (HCC1954) IC$_{50}$ (pM) 16 h | High Her2 expressing cells (HCC1954) max. lysis (%) 16 h | Her2$^+$/PD-L1$^-$ MCF-7 IC$_{50}$ (pM) 16 h | Her2$^+$/PD-L1$^-$ MCF-7 max. lysis (%) 16 h | Her2$^{+/-}$/PD-L1$^+$ CHO-PD-L1 IC$_{50}$ (pM) 16 h | Her2$^{+/-}$/PD-L1$^+$ CHO-PD-L1 max. lysis (%) 16 h | Her2$^-$/7PD-L1$^+$ CHO-PD-L1 (BPS Bioscience) IC$_{50}$ (pM) 16 h | Her2$^-$/7PD-L1$^+$ CHO-PD-L1 (BPS Bioscience) max. lysis (%) 16 h |
|---|---|---|---|---|---|---|---|---|
| PRO1543 | 0.23 | 76.81 | 3.11 | 90.38 | 5.30 | 77.94 | no target cell killing | |
| PRO1557 | 2.79 | 77.49 | 18.14 | 90.78 | 449.30 | 81.77 | no target cell killing | |
| PRO957 | 11.78 | 69.97 | 52.58 | 82.70 | 430.20 | 51.64 | no target cell killing | |
| trastuzumab + nivolumab | 127.80 | 72.43 | 14.46 | 26.94 | no target cell killing | | no target cell killing | |

Assessment of the Anti-Tumor Efficacy of PD-L1 Blockade and Concomitant Localized Stimulation of CD3 in the Human Cell Line-Derived Ductal Breast Carcinoma Xenograft Model HCC1954

The anti-tumor activity of the compounds of the present approach was compared to anti-PD-1 therapy and anti-PD-1 anti-Her2 combined therapy in human HCC1954 ductal breast carcinoma xenografts using the immunodeficient NOG mice strain from Taconic and allogeneic human peripheral blood mononuclear cells. Effects of PRO1678 (scMATCH3) and PRO1543 (MATCH4) on tumor volume were compared to treatment with the anti-PD-1 antibody (nivolumab) and the nivolumab/anti Her2 antibody (trastuzumab) combo. An irrelevant IgG palivizumab was used as a control IgG. Animal body weight was followed as well.

Study Set-Up and Treatment Schedule:

Female NOG mice received unilateral injections of 5×106 HCC1954 cells. Cells were injected in a mixture of 50% cell suspension in PBS and 50% Matrigel in a total injection volume of 100 μl. After injection of tumor cells into NOG mice and successful tumor engraftment (median group tumor volume of 80-100 mm3), mice were substituted with 5×106 human PBMCs by intravenous injection. On the day of randomization, four mice of each group were reconstituted with PBMCs of donor A and another four mice with PBMCs of donor B. Treatment will start 1-2 hours after the injection of PBMCs and were applied as follows.

| group ID | compound | total daily dose [mg] | dosing days | route | no. of mice |
|---|---|---|---|---|---|
| 1 | palivizumab | 0.1 | 0, 5, 10, 15, 20, 25, 30 | ip | 8 |
| 2 | nivolumab | 0.1 | 0, 5, 10, 15, 20, 25, 30 | ip | 8 |
| 3 | PRO1678 low dose | 0.1 | 0, 5, 10, 15, 20, 25, 30 | ip | 8 |
| 4 | PRO1678 high dose | 0.5 | 0, 5, 10, 15, 20, 25, 30 | ip | 8 |
| 5 | PRO1543 | 0.05 | 0, 5, 10, 15, 20, 25, 30 | ip | 8 |
| 6 | trastuzumab + nivolumab | 0.1 + 0.1 | 0, 5, 10, 15, 20, 25, 30 | ip | 8 |

Body weights (Table 24) and tumor volume by caliper measurement (Table 23 and FIG. 13) were performed twice weekly. Animals were terminated at day 33. In some few groups few animals died already at day 27 onwards. No body weight loss was observed.

TABLE 231

Relative tumor volume

| Molecule | Dose | Grp | | Day 0 | 2 | 6 | 9 | 13 | 16 | 20 | 23 | 27 | 30 | 33 |
|---|---|---|---|---|---|---|---|---|---|---|---|---|---|---|
| palivizumab | 0.1 | 1 | mean (%) | 100.0 | 125.0 | 195.6 | 267.8 | 319.8 | 402.6 | 521.5 | 635.2 | 740.9 | 840.9 | 1090.8 |
| | | | SD (%) | 0.0 | 10.6 | 37.9 | 56.3 | 65.0 | 86.6 | 117.7 | 152.1 | 157.1 | 178.7 | 275.7 |
| | | | N | 8.0 | 8.0 | 8.0 | 8.0 | 8.0 | 8.0 | 8.0 | 8.0 | 8.0 | 6.0 | 4.0 |
| nivolumab | 0.1 | 2 | mean (%) | 100.0 | 107.9 | 129.7 | 174.0 | 218.8 | 267.9 | 313.3 | 332.2 | 426.8 | 518.5 | 615.4 |
| | | | SD (%) | 0.0 | 16.5 | 41.4 | 65.3 | 77.3 | 91.9 | 127.9 | 132.7 | 178.8 | 168.4 | 252.3 |
| | | | N | 8.0 | 8.0 | 8.0 | 8.0 | 8.0 | 8.0 | 8.0 | 8.0 | 7.0 | 6.0 | 5.0 |
| PRO1678 | 0.1 | 3 | mean (%) | 100.0 | 115.4 | 156.1 | 182.0 | 204.7 | 242.0 | 287.8 | 368.4 | 428.0 | 512.2 | 489.0 |
| | | | SD (%) | 0.0 | 12.4 | 40.8 | 61.9 | 86.9 | 94.0 | 128.3 | 153.9 | 213.3 | 245.1 | 236.9 |
| | | | N | 8.0 | 8.0 | 8.0 | 8.0 | 8.0 | 8.0 | 8.0 | 8.0 | 8.0 | 8.0 | 7.0 |
| PRO1678 | 0.5 | 4 | mean (%) | 100.0 | 114.8 | 118.9 | 138.5 | 145.6 | 164.5 | 193.7 | 213.4 | 261.8 | 312.3 | 388.7 |
| | | | SD (%) | 0.0 | 8.3 | 21.8 | 32.0 | 32.7 | 45.6 | 45.0 | 61.7 | 57.2 | 102.3 | 162.7 |
| | | | N | 8.0 | 8.0 | 8.0 | 8.0 | 8.0 | 8.0 | 8.0 | 8.0 | 8.0 | 7.0 | 5.0 |
| PRO1543 | 0.05 | 6 | mean (%) | 100.0 | 101.7 | 136.9 | 129.0 | 59.9 | 36.5 | 28.1 | 26.8 | 21.7 | 20.5 | 20.5 |
| | | | SD (%) | 0.0 | 13.2 | 53.5 | 59.5 | 24.4 | 13.2 | 14.5 | 15.9 | 18.0 | 22.3 | 23.3 |
| | | | N | 8.0 | 8.0 | 8.0 | 8.0 | 8.0 | 8.0 | 8.0 | 8.0 | 8.0 | 7.0 | 7.0 |
| trastuzumab + nivolumab | 0.1 + 0.1 | 7 | mean (%) | 100.0 | 100.1 | 94.2 | 93.8 | 106.8 | 110.8 | 118.5 | 132.6 | 141.7 | 170.1 | 237.9 |
| | | | SD (%) | 0.0 | 21.3 | 30.5 | 35.3 | 42.2 | 47.6 | 53.2 | 67.7 | 74.3 | 81.1 | 102.3 |
| | | | N | 8.0 | 8.0 | 8.0 | 8.0 | 8.0 | 8.0 | 8.0 | 8.0 | 8.0 | 8.0 | 6.0 |

TABLE 24

| Relative body weight | | | | | | | | | | | | | | |
|---|---|---|---|---|---|---|---|---|---|---|---|---|---|---|
| | | | | Day | | | | | | | | | | |
| Molecule | Dose | Grp | | 0 | 2 | 6 | 9 | 13 | 16 | 20 | 23 | 27 | 30 | 33 |
| palivizumab | 0.1 | 1 | mean (%) | 100.0 | 100.1 | 102.3 | 106.4 | 106.3 | 109.6 | 112.7 | 110.0 | 107.4 | 112.6 | 117.8 |
| | | | SD (%) | 0.0 | 1.3 | 3.1 | 4.2 | 4.7 | 7.1 | 8.6 | 8.6 | 10.9 | 10.4 | 5.2 |
| | | | N | 8.0 | 8.0 | 8.0 | 8.0 | 8.0 | 8.0 | 8.0 | 8.0 | 8.0 | 6.0 | 4.0 |
| nivolumab | 0.1 | 4 | mean (%) | 100.0 | 100.4 | 102.0 | 106.3 | 105.2 | 107.3 | 105.9 | 105.4 | 106.7 | 107.1 | 113.6 |
| | | | SD (%) | 0.0 | 1.7 | 2.4 | 4.1 | 4.1 | 5.9 | 8.2 | 10.4 | 7.3 | 6.3 | 10.8 |
| | | | N | 8.0 | 8.0 | 8.0 | 8.0 | 8.0 | 8.0 | 8.0 | 8.0 | 7.0 | 6.0 | 5.0 |
| PRO1678 | 0.1 | 2 | mean (%) | 100.0 | 99.3 | 101.4 | 105.3 | 106.0 | 111.4 | 115.6 | 114.4 | 111.1 | 109.2 | 108.1 |
| | | | SD (%) | 0.0 | 2.9 | 4.7 | 3.1 | 4.2 | 6.6 | 7.0 | 5.9 | 6.2 | 9.5 | 11.0 |
| | | | N | 8.0 | 8.0 | 8.0 | 8.0 | 8.0 | 8.0 | 8.0 | 8.0 | 8.0 | 8.0 | 7.0 |
| PRO1678 | 0.5 | 3 | mean (%) | 100.0 | 99.3 | 102.6 | 106.9 | 105.1 | 111.6 | 111.7 | 110.4 | 106.1 | 106.6 | 106.0 |
| | | | SD (%) | 0.0 | 1.1 | 1.8 | 3.1 | 3.9 | 4.2 | 3.7 | 2.8 | 5.8 | 11.3 | 11.0 |
| | | | N | 8.0 | 8.0 | 8.0 | 8.0 | 8.0 | 8.0 | 8.0 | 8.0 | 8.0 | 7.0 | 5.0 |
| PRO1543 | 0.05 | 9 | mean (%) | 100.0 | 100.0 | 101.8 | 105.1 | 103.8 | 107.0 | 110.3 | 111.8 | 109.4 | 110.4 | 107.8 |
| | | | SD (%) | 0.0 | 2.1 | 2.8 | 6.8 | 5.8 | 5.1 | 5.0 | 6.1 | 7.8 | 7.7 | 11.4 |
| | | | N | 8.0 | 8.0 | 8.0 | 8.0 | 8.0 | 8.0 | 8.0 | 8.0 | 8.0 | 7.0 | 7.0 |
| trastuzumab + | 0.1 + 0.1 | 14 | mean (%) | 100.0 | 101.5 | 101.1 | 103.9 | 100.3 | 103.0 | 104.4 | 105.2 | 104.8 | 101.3 | 104.7 |
| nivolumab | | | SD (%) | 0.0 | 2.3 | 3.6 | 5.8 | 5.5 | 7.2 | 6.0 | 7.0 | 7.3 | 7.0 | 2.5 |
| | | | N | 8.0 | 8.0 | 8.0 | 8.0 | 8.0 | 8.0 | 8.0 | 8.0 | 8.0 | 8.0 | 6.0 |

Example 3: Generation and Testing of Multispecific Constructs Targeting HER2 (as an Example of a TAA). PD-L1 and CD173 (as Example of a Costimulatory Immune Cell Antigen)

Design and Production of MATCH4 Molecules:

A description of the MATCH-4 molecules designed within this part of the current approach is shown in FIG. 14. Molecule composition is shown in Table 25.

TABLE 25

| Composition of multispecific molecules | | | | | | | | | |
|---|---|---|---|---|---|---|---|---|---|
| PRO ID | Format | Domain 1 | Specificity 1 | Domain 2 | Specificity 2 | Domain 3 | Specificity 3 | Domain 4 | Specificity 4 |
| PRO1778 | MATCH4 | trastuzumab, VL-G141C/ VH-G51C* | Her2 | 38-27-A11 sc07, VL-G141C/ VH-G51C* | CD137 | 33-03-G02, VL-Q108A, VL-G109A** | PD-L1 | 23-13-A01-sc02 | HSA |
| PRO1780 | MATCH4 | trastuzumab, VL-G141C/ VH-G51C* | Her2 | 23-13-A01-sc03 (23-13-A01-sc02 diS, VL-G141C/ VH-G51C)* | HSA | 33-03-G02, VL-Q108A, VL-G109A** | PD-L1 | 38-27-A11 sc07, VL-G141C/VH-G51C* | CD137 |
| PRO1992 | MATCH4 | 23-13-A01-sc02 | HSA | pertuzumab, VL-G141C/ VH-G51C* | Her2 | 33-03-G02, VL-Q108A, VL-G109A** | PD-L1 | 38-27-A11-sc07, VL-G141C/VH-G51C* | CD137 |
| PRO1993 | MATCH4 | pertuzumab, VL-G141C/ VH-G51C* | Her2 | 23-13-A01-sc02 | HSA | 38-27-A11-sc07, VL-G141C/ VH-G51C* | CD137 | 33-03-G02, VL-Q108A, VL-G109A** | PD-L1 |

*VL/VH interdomain disulfide bond, numbering according to A. Honegger

**mutations, numbering according to A. Honegger

Method:

Expression of MATCH4 constructs was performed in CHO-S cells using CHOgro transient transfection kit (Mirus). Cultures were harvested after 5-7 days (cell viability <70%) of expression at 37° C. by centrifugation and proteins were purified from clarified culture supernatants by Protein L affinity chromatography followed, if needed, by a polishing step by size-exclusion chromatography. For the quality control of the manufactured material standard analytical methods, such as SE-HPLC, UV280 and SDS-PAGE were used.

Assessment of the CD137 Agonistic Effect of Anti-Her2×CD137×HSA×PD-L1$_{(Low\ affinity)}$ MATCH4 Molecules by Using a Cell-Based Assay of Transgenic NF-kB Jurkat Reporter Cell Line Expressing CD137

In this assay the activation of CD137 signaling in Jurkat cells was assessed. The activity of CD137 signaling is reported by measurement of Luciferase expression which is driven by CD137 induced NF-kB activation in a Jurkat reporter cell line. The expression of Luciferase directly correlates with the activity of CD137. Moreover, clustering of CD137, which is required for activation of the signal pathway, is facilitated via the formation of an immunological synapse between the Jurkat cells and a Her2 expressing cell line. Therefore, Her2 expression is needed for clustering and activation of CD137 on the reporter cell line.

Method:

Cancer cell lines HCC1954 (high levels of expression for Her2 and PD-L1) and HCC827 (low levels of expression for Her2 but high levels for PD-L1) were seeded at 25'000 cells per well on 96-well culture plates. Then, seeded cells were either stimulated with 10 ng/ml IFNy for 24 h or left unstimulated. Next, serial dilutions of MATCH4 molecules of interest as well as the internal reference molecules PRO1186 or PRO1430 (both anti-CD137×HSA×PD-L1 (high affinity) scMATCH3) were prepared and added to the cells. After addition of molecules of interest, Jurkat reporter cells were prepared in assay medium containing HSA at 25 mg/ml and added at a cell density of 40'000 cells per well. Luciferase expression was detected by addition of Luciferase reagent and was read by a luminescence reader 24 h after addition of Jurkat cells. Data were presented by plotting the relative luminescence units (RLU) of the test samples as a function of test sample concentration and fitted using a sigmoidal 4PL fit (GraphPad Prism).

Results:

As shown in FIG. 15, PRO1993 was found to induce CD137 signaling in the Jurkat reporter cell line when cultured in the presence of HCC1954 cancer cells, whereas in the presence of HCC827 cancer cells only a slight activation of CD137 was observed. Data of NF-kB reporter gene assay of ND029 molecules are shown in Table 26.

PD-L1/PD-1 Neutralization by FC

Method:

These assays were conducted to assess the ability of the multi-specific low affinity PD-L1x/Her2 constructs to neutralize the interaction between PD-1 and PD-L1 expressed on HCC1954 cells, which also express Her2. Specifically, the molecules should efficiently block PD-1 binding to PD-L1 on HER2/PD-L1 co-expressing target cells (HCC1954), while blockade of the PD-1/PD-L1 interaction on cells not expressing Her2 (HCC827) should be much less potent than with avelumab/Bavencio® or nivolumab/Opdivo®. Blockade of PD-1 binding to the cells was analyzed by flow cytometry in presence of human SA as described above. Serial dilutions of the respective molecules to be tested as well as the reference avelumab were added to the plates. Individual $IC_{50}$ values on each plate were calibrated against the $IC_{50}$ of the reference molecule avelumab that was taken along on each plate (relative $IC_{50}$:$IC_{50}$, avelumab/$IC_{50}$, test molecule). In addition, the ratio between the relative $IC_{50}$ values found on high Her2 expressing HCC1954 and low Her2 expressing HCC827 cells was calculated.

Results:

Potencies of MATCH4 constructs of the present approach are summarized in Table 27. PD-L1 inhibition curve obtained for PRO1993 is shown in FIG. 16.

TABLE 26

Potencies of ND029 molecules in NF-kB reporter gene assay (CD137 activity assay).

| | NFkB reporter gene assay | | | | | |
|---|---|---|---|---|---|---|
| | High her2 expressing cells (HCC1954) | | | Low Her2 expressing cells (HCC827) | | |
| PRO ID | $EC_{50}$ (pM) | rel. EC50 | rel. activation (%) | $EC_{50}$ (pM) | rel. EC50 | rel. activation (%) |
| PRO1715 | 448.4 | 0.24* | 12.5$^{\$}$ | | no activation | |
| PRO1716 | | no activation | | | no activation | |
| PRO1717 | 130247 | 0.001* | 31.8$^{\$}$ | | no activation | |
| PRO1718 | 2662 | 0.040* | 19.0$^{\$}$ | | no activation | |
| PRO1719 | | no activation | | | no activation | |
| PRO1720 | | no activation | | | no activation | |
| PRO1721 | | no activation | | | no activation | |
| PRO1722 | | no activation | | | no activation | |
| PRO1778 | 661.0 | 0.14** | 50.1$^{\$\$}$ | | no activation | |
| PRO1779 | 1881.0 | 0.05** | 61.1$^{\$\$}$ | | no activation | |
| PRO1780 | 603.1 | 0.15** | 75.4$^{\$\$}$ | | no activation | |
| PRO1186 | 125.6 | 1 | 100 | 127.3 | 1 | 100 |
| PRO1430 | 80.4 | 1 | 100 | 85.3 | 1 | 100 |
| PRO1992 | 82.4 | 2.18* | 44.9$^{\$}$ | 252.5 | 0.47* | 9.7$^{\$}$ |
| PRO1993 | 167.7 | 1.07* | 36.4$^{\$}$ | 287.3 | 0.41* | 10.4$^{\$}$ |

*$IC_{50,\ PRO1430}$ (pM)/$IC_{50,\ test\ molecule}$ (pM)

**$IC_{50,\ PRO1186}$ (pM)/$IC_{50,\ test\ molecule}$ (pM)

$^{\$}$rel. to PRO1430

$^{\$\$}$rel. to PRO1186

TABLE 27

Potencies of multi-specific molecules in PD-L1/PD-1 neutralization by flow cytometry.

| | Neutralization of PD-L1/PD-1 interaction in FC based assay | | | | |
|---|---|---|---|---|---|
| | High Her2 expressing cells (HCC1954) | | Low Her2 expressing cells (HCC827) | | Ratio |
| PRO ID | $IC_{50}$ (ng/ml) | rel. $IC_{50}$* | $IC_{50}$ (ng/ml) | rel. $IC_{50}$* | rel. $IC_{50}$ (high Her2)/ rel. $IC_{50}$ (low Her2) |
| PRO1778 | 1418 | 0.09 | 6725 | 0.01 | 13.2 |
| PRO1780 | 695.4 | 0.18 | 32646 | 1.41E−03 | 130.2 |
| PRO1992 | 591.6 | 0.22 | no inhibition | | NA |
| PRO1993 | 166.7 | 0.77 | no inhibition | | NA |
| avelumab | 127.7 | 1 | 46.03 | 1 | 1 |
| nivolumab | 43.48 | 2.94 | 39.77 | 1.16 | 2.54 |

NA: not applicable

*$IC_{50,\ avelumab}$ (ng/ml)/$IC_{50,\ test\ molecule}$ (ng/ml)

Example 4: Generation and Testing of Multispecific Constructs Targeting HER2 (as an Example of a TAA) and PD-L1

Design and Production of scDb-scFv:

A description of the different scDb-scFv (scMATCH3) molecules designed within this aspect of the present approach is shown in FIG. 17. The data regarding the production of all the molecules are detailed in Table 28, which describes the domains composing of the different molecules produced and their positioning within the molecules.

Method:

Expression of scDb-scFv constructs was performed in CHO-S cells using CHOgro transient transfection kit (Mirus). Cultures were harvested after 5-7 days (cell viability <70%) of expression at 37° C. by centrifugation and proteins were purified from clarified culture supernatants by Protein L affinity chromatography followed, if needed, by a polishing step by size-exclusion chromatography. For the quality control of the manufactured material standard analytical methods, such as SE-HPLC, UV280 and SDS-PAGE were used.

TABLE 28

Composition of multispecific constructs of the present approach

| PRO ID | Format | Domain 1 | Specificity 1 | Domain 2 | Specificity 2 | Domain 3 | Specificity 3 | Domain 4 | Specificity 4 |
|---|---|---|---|---|---|---|---|---|---|
| PRO 1678 | scDb-scFv | trastuzumab, VL-G141C/VH-G51C* | Her2 | 33-03-G02, VL-Q108A, VL-G109A** | PD-L1 | 23-13-A01-sc02 | HSA | NA | NA |
| PRO 1679 | scDb-scFv | 33-03-G02, VL-Q108A, VL-G109A** | PD-L1 | trastuzumab, VL-G141C/VH-G51C* | Her2 | 23-13-A01-sc02 | HSA | NA | NA |
| PRO 1680 | scDb-scFv | trastuzumab, VL-G141C/VH-G51C* | Her2 | 33-03-G02, VL-Q108A, VH-Y112A** | PD-L1 | 23-13-A01-sc02 | HSA | NA | NA |
| PRO 1681 | scDb-scFv | 33-03-G02, VL-Q108A, VH-Y112A** | PD-L1 | trastuzumab, VL-G141C/VH-G51C* | Her2 | 23-13-A01-sc02 | HSA | NA | NA |
| PRO 1814 | scDb-scFv | pertuzumab | Her2 | 33-03-G02, VL-Q108A, VL-G109A** | PD-L1 | 19-01-H04-sc03 | HSA | NA | NA |
| PRO 1852 | scDb-scFv | pertuzumab, VL-G141C/VH-G51C* | Her2 | 33-03-G02, VL-Q108A, VL-G109A** | PD-L1 | 19-01-H04-sc03 | HSA | NA | NA |
| PRO 1853 | scDb-scFv | pertuzumab | Her2 | 33-03-G02, VL-Q108A, VH-Y112A** | PD-L1 | 19-01-H04-sc03 | HSA | NA | NA |
| PRO 1854 | scDb-scFv | pertuzumab, VL-G141C/VH-G51C* | Her2 | 33-03-G02, VL-Q108A VH-Y112A** | PD-L1 | 19-01-H04-sc03 | HSA | NA | NA |

*VL/VH interdomain disulfide bond, numbering according to A. Honegger

**mutations, numbering according to A. Honegger

Affinities to Human Her2, PD-L1 and Human and Mouse Serum Albumin (SA) by SPR

Method:

Affinity to human PD-L1, Her2 and human and mouse serum albumin (SA) was determined by SPR using a Biacore T200 device (GE Healthcare) as described above.

Obtained SPR sensorgrams were double-referenced (empty reference channel and zero analyte injection) and fitted using BiaEvaluation software (GE Healthcare) and the 1:1 Langmuir binding model. Quality of the fits was monitored based on Chi2 and U-value (Biacore). Retrieved kinetic parameters were used to calculate the apparent dissociation equilibrium constant ($K_D$). In addition to the kinetic measurement, the value of the $K_D$ for the low affinity PD-L1 measurements was obtained by fitting a plot of response at equilibrium against the concentration (steady-state affinity measurement).

Results:

As shown in Table 29, binding to Her2 and human SA was similar for all molecules tested. Affinity to PD-L1 could be determined only for the molecules PRO1678 and PRO1679 using the steady state analysis and for both proteins, the affinity found was comparable ($K_D$ values, PRO1678: 156 nM, PRO1679: 122 nM).

TABLE 29

Summary of affinities of scMATCH3 constructs of the present approach directed at human Her2, PD-L1 and human and mouse serum albumin (SA) at pH5.5.

| | Affinity to human Her2 | | | Affinity to human PD-L1: kinetic analysis | | | Affinity to human PD-L1: steady state analysis | Affinity to human SA (at pH5.5) | | | Affinity to mouse SA (at pH5.5) | | |
|---|---|---|---|---|---|---|---|---|---|---|---|---|---|
| PRO ID | $k_a$ ($M^{-1}s^{-1}$) | $k_d$ ($s^{-1}$) | $K_D$ (M) | $k_a$ ($M^{-1}s^{-1}$) | $k_d$ ($s^{-1}$) | $K_D$ (M) | $K_D$ (M) | $k_a$ ($M^{-1}s^{-1}$) | $k_d$ ($s^{-1}$) | $K_D$ (M) | $k_a$ ($M^{-1}s^{-1}$) | $k_d$ ($s^{-1}$) | $K_D$ (M) |
| PRO1678 | 2.13E+05 | 7.11E−05 | 3.34E−10 | not determined | | | 1.56E−07 | 2.21E+05 | 7.62E−04 | 3.45E−09 | 1.37E+05 | 5.18E−03 | 3.78E−08 |
| PRO1679 | 2.00E+05 | 6.49E−05 | 3.24E−10 | not determined | | | 1.22E−07 | 1.88E+05 | 7.33E−04 | 3.89E−09 | not determined | | |
| PRO1680 | 2.15E+05 | 6.87E−05 | 3.19E−10 | not determined | | | | 1.88E+05 | 7.32E−04 | 3.00E−09 | not determined | | |
| PRO1681 | 1.96E+05 | 6.26E−05 | 3.19E−10 | not determined | | | | 1.91E+05 | 7.37E−04 | 3.85E−09 | not determined | | |
| PRO1814 | not measured | | | not measured | | | | not measured | | | not measured | | |
| PRO1852 | not measured | | | not measured | | | | not measured | | | not measured | | |
| PRO1853 | not measured | | | not measured | | | | not measured | | | not measured | | |
| PRO1854 | not measured | | | not measured | | | | not measured | | | not measured | | |
| avelumab | NA | | | 4.91E+05 | 1.21E−05 | | 2.47E−11 | NA | | | NA | | |
| nivolumab | NA | | | not measured | | | | NA | | | NA | | |

NA: not applicable

PD-L1/PD-1 Neutralization by FC

Method:

The assay was conducted to assess the ability of the multi-specific low affinity PD-L1x/Her2 constructs to neutralize the interaction between PD-1 and PD-L1 expressed on HCC1954 cells, which also express Her2. Specifically, the molecules should efficiently block PD-1 binding to PD-L1 on Her2/PD-L1 co-expressing target cells (HCC1954), while blockade of the PD-1/PD-L1 interaction on cells not expressing Her2 (HCC827) should be much less potent than with avelumab/Bavencio® or nivolumab/Opdivo®. Blockade of PD-1 binding to the cells was analyzed by flow cytometry in presence of human SA as described above. Individual $IC_{50}$ values on each plate were calibrated against the $IC_{50}$ of the reference molecule avelumab that was taken along on each plate (relative $IC_{50}$:$IC_{50}$, avelumab/$IC_{50}$, test molecule). In addition, the ratio between the relative $IC_{50}$ values found on high Her2 expressing HCC1954 and low Her2 expressing HCC827 cells was calculated.

Results:

Potencies of scMATCH3 constructs of the present approach are summarized in Table 30.

TABLE 30

Potencies of constructs of the present approach to neutralize PD-L1/PD-1 interaction in flow cytometry assay.

| | Neutralization of PD-L1/PD-1 interaction in FC based assay: High Her2 expressing cells (HCC1954) | | Low Her2 expressing cells (HCC827) | | Ratio rel. $IC_{50}$ (high Her2)/ |
|---|---|---|---|---|---|
| PRO ID | $IC_{50}$ (ng/ml) | rel. $IC_{50}$* | $IC_{50}$ (ng/ml) | rel. $IC_{50}$* | rel. $IC_{50}$ (low Her2) |
| PRO1678 | 428.3 | 0.29 | 43466 | 2.89E−03 | 100.4 |
| PRO1679 | 652.4 | 0.19 | 118941 | 1.06E−03 | 179.7 |
| PRO1680 | 1146 | 0.11 | 2.10E+06 | 5.98E−05 | 1840.9 |

TABLE 30-continued

Potencies of constructs of the present approach to neutralize PD-L1/PD-1 interaction in flow cytometry assay.

| | Neutralization of PD-L1/PD-1 interaction in FC based assay: High Her2 expressing cells (HCC1954) | | Low Her2 expressing cells (HCC827) | | Ratio rel. $IC_{50}$ (high Her2)/ |
|---|---|---|---|---|---|
| PRO ID | $IC_{50}$ (ng/ml) | rel. $IC_{50}$* | $IC_{50}$ (ng/ml) | rel. $IC_{50}$* | rel. $IC_{50}$ (low Her2) |
| PRO1681 | 2011 | 0.06 | 1.52E+06 | 8.27E−05 | 725.9 |
| PRO1814 | 52.53 | 0.86 | 53797 | 1.02E−03 | 841.7 |
| PRO1852 | 55.55 | 0.81 | 16835 | 3.26E−03 | 249.1 |

TABLE 30-continued

Potencies of constructs of the present approach to neutralize PD-L1/PD-1 interaction in flow cytometry assay.

| | Neutralization of PD-L1/PD-1 interaction in FC based assay | | | | |
|---|---|---|---|---|---|
| | High Her2 expressing cells (HCC1954) | | Low Her2 expressing cells (HCC827) | | Ratio rel. $IC_{50}$ (high Her2)/ |
| PRO ID | $IC_{50}$ (ng/ml) | rel. $IC_{50}$* | $IC_{50}$ (ng/ml) | rel. $IC_{50}$* | rel. $IC_{50}$ (low Her2) |
| PRO1853 | 69.48 | 0.65 | 88234 | 6.22E−04 | 1043.7 |
| PRO1854 | 56.06 | 0.80 | 53489 | 1.03E−03 | 784.2 |
| avelumab | 127.7 | 1 | 46.03 | 1 | 1 |
| nivolumab | 43.48 | 2.94 | 39.77 | 1.16 | 2.54 |

NA: not applicable

*$IC_{50,\ avelumab}$ (ng/ml)/$IC_{50,\ test\ molecule}$ (ng/ml)

Binding to Her2 Expressing SK-OV3 and MCF-7 Cells by Flow Cytometry

Method:

SK-OV3 cells (from ATCC, cat. HTB-77, human ovarian adenocarcinoma cells that express very high levels of HER2 and very low PD-L1 levels), MCF-7 (human breast cancer cells that express low levels of HER2 and very low PD-L1 levels) and CHO PD-L1 (from Amsbio, control cells that express high levels of PD-L1 and do not express human Her2) were harvested and cell number was determined. Cell suspensions were centrifuged for 5 min at 400×g and 100 µl of cell suspensions (50'000 cells) diluted in PBS-EB (1×DPBS, 2% BCS H.I., 2 mM EDTA) were added to designated wells in a non-binding plate. After three washing steps with PBS-EB, cells were centrifuged and washing buffer was aspirated. 100 µl of serial dilutions starting at a concentration of 50 nM of samples to be tested (MATCH4 molecules: anti-HER2 trastuzumab-based PRO1543 and anti-HER2 pertuzumab-based PRO1895) as well as the reference antibodies trastuzumab and pertuzumab were then directly added to the plate. After incubation at 4° C. for 1 h, plates were washed three times using 100 µl of PBS-EB. Cell pellets incubated with MATCH4 molecules were re-suspended with 100 µl of Numab's framework specific detection antibody which subsequentially was detected by the addition of anti-rabbit IgG antibody labeled with APC at a concentration of 2 µg/ml and incubated for 1 h at 4° C. Cell pellets incubated with reference antibodies trastuzumab and pertuzumab molecules were re-suspended with 100 µl of anti-human Fc antibody labeled with RPE at a concentration of 5 µg/ml and incubated for 1 h at 4° C.

Next, cells were washed again three times using 100 µl of PBS-EB. The cell pellets were re-suspended with 50 µl PBS-EB and analyzed with NovoCyte 2060 flow cytometer device. Fluorescence intensity of APC and RPE channel for 5,000 events was recorded for each sample and the geometric mean of fluorescence intensity MFI was calculated. The data were single-referenced (subtracted for fluorescence intensity found on cells incubated with buffer and detection antibody only) and obtained concentration-response curves were fitted using a 4-PL fit (GraphPad prism software).

Results:

The apparent binding affinity to bind SK-OV3, MCF-7 and CHO PD-L1 was assessed using flow cytometry. Individual $EC_{50}$ values on each plate were calibrated against the $EC_{50}$ of the respective reference molecule (i.e. trastuzumab for PRO1543 and pertuzumab for PRO1895). Obtained $EC_{50}$ and relative $EC_{50}$ as well as maximum binding in flow cytometry are shown in Table 31. Concentration-response curves are depicted in FIG. 19.

As shown in Table 31, MATCH4 molecules bound to SK-OV3 cells expressing high levels of HER2 with an apparent binding affinity comparable to the clinical stage antibodies trastuzumab and pertuzumab. This result indicates that MATCH4 molecules can catch up with the apparent binding affinity of bivalent anti-HER2 antibodies trastuzumab and pertuzumab when binding to cells that express high levels of HER2 and PD-L1 (even if the expression is very low) is tested due to avidity effects (binding to HER2 and PD-L1).

On the other hand, the apparent binding affinity of MATCH4 is inferior to the binding affinity of clinical stage antibodies when binding to cells is assessed that express both antigens at very low levels (e.g. MCF-7 cells) caused by the lack of avidity of MATCH4 molecules. Residual binding to CHO PD-L1 cells was found for pertuzumab and pertuzumab-based MATCH4 molecule PRO1895, which contrasts with non-binding of trastuzumab and trastuzumab-based MATCH4 molecule PRO1543. One might speculate that pertuzumab is able to binds to hamster HER2 whereas trastuzumab, which binds to a different epitope, cannot. In any case, these data indicate that the low affinity anti-PD-L1 moiety incorporated in MATCH4 molecules is not able to bind to cells that express PD-L1 only.

Binding to Her2 Expressing HCC1954 and HCC827 Cells by Flow Cytometry

Method:

Assessment of the apparent affinity of PRO1543 and PRO1895 as well as clinical stage anti-HER2 antibody trastuzumab and pertuzumab to bind HCC1954 (high levels of expression for Her2 and PD-L1) and HCC827 (low levels of expression for Her2 but high levels for PD-L1) was done in flow cytometry. HCC827 and HCC1954

TABLE 31

Plasmamembranous binding of MATCH4 molecules PRO1543 and PRO1895 to SK-OV3, MCF-7 and CHO PD-L1 cells. Table shows $EC_{50}$ and relative $EC_{50}$ (normalized to respective reference antibodies trastuzumab or pertuzumab) as well as maximum binding obtained by flow cytometry

| | | | | Plasmamembranous binding in flow cytometry | | |
|---|---|---|---|---|---|---|
| Protein ID | Target cells | Expression levels of HER2 | Expression levels of PD-L1 | $EC_{50}$ [nM] | rel. $EC_{50}$ ($EC_{50}$, reference/$EC_{50}$, sample) | Maximum binding in flow cytometry [ΔMFI] |
| trastuzumab | SK-OV3 | very high | very low | 2.63 | 1.00 | 991744 |
| PRO1543 | SK-OV3 | | | 3.32 | 0.79 | 631217 |
| pertuzumab | SK-OV3 | | | 1.96 | 1.00 | 1087428 |
| PRO1895 | SK-OV3 | | | 1.87 | 1.05 | 673880 |

TABLE 31-continued

Plasmamembranous binding of MATCH4 molecules PRO1543 and PRO1895 to SK-OV3, MCF-7 and CHO PD-L1 cells. Table shows $EC_{50}$ and relative $EC_{50}$ (normalized to respective reference antibodies trastuzumab or pertuzumab) as well as maximum binding obtained by flow cytometry

| | | | | Plasmamembranous binding in flow cytometry | | |
|---|---|---|---|---|---|---|
| Protein ID | Target cells | Expression levels of HER2 | Expression levels of PD-L1 | $EC_{50}$ [nM] | rel. $EC_{50}$ ($EC_{50}$, reference/$EC_{50}$, sample) | Maximum binding in flow cytometry [ΔMFI] |
| trastuzumab | MCF-7 | low | very low | 0.74 | 1.00 | 58328 |
| PRO1543 | MCF-7 | | | 28.63 | 0.03 | 109245 |
| pertuzumab | MCF-7 | | | 0.96 | 1.00 | 61798 |
| PRO1895 | MCF-7 | | | 5.35 | 0.18 | 101349 |
| trastuzumab | CHO PD-L1 | no | high | no binding | | 144 |
| PRO1543 | CHO PD-L1 | expression | | no binding | | 1393 |
| pertuzumab | CHO PD-L1 | | | 1.29 | 1.00 | 27740 |
| PRO1895 | CHO PD-L1 | | | 97.30 | 0.01 | 9684 |

cells were stimulated with IFNy for 24 h to further increase PD-L1 expression and were then tested in flow cytometry experiment as described above with the exception the dilution series of proteins started at 150 nM.

Results:

Individual $EC_{50}$ values on each plate were calibrated against the $EC_{50}$ value of the respective reference molecule (i.e. trastuzumab for PRO1543 and pertuzumab for PRO1895). Obtained $EC_{50}$ and relative $EC_{50}$ as well as maximum binding in flow cytometry are shown in Table 32. Concentration-response curves are depicted in FIG. 20.

As shown in Table 32, MATCH4 molecules bound to IFNy-stimulated HCC827 cells expressing high levels of PD-L1 and low levels of HER2 with an apparent binding affinity comparable to the clinical stage antibodies trastuzumab and pertuzumab. On the other hand, the apparent binding affinity of MATCH4 is inferior to the binding affinity of clinical stage antibodies when binding to cells is assessed that express both antigens at high levels (IFNy-stimulated HCC1954 cells).

Concomitant Binding of PRO1543 and Pertuzumab as Well as PRO1895 and Trastuzumab to SK-OV3 Cells in Flow Cytometry Method:

The ability of MATCH4 molecules to bind to HER2-expressing SK-OV3 cells in presence of saturating concentration of trastuzumab and pertuzumab was assessed by flow cytometry. Instead of testing a serial dilution of trastuzumab and pertuzumab, a high concentration of the antibodies that resulted in saturated binding to SK-OV3 cells (50 nM) was added to the cells prior the addition of MATCH4 molecules. After the incubation of cells with trastuzumab or pertuzumab for 1 h at 4° C., serial dilution of MATCH4 molecules starting at 50 nM were added to the cells.

Plasmamembranous binding of MATCH4 molecules PRO1543 and PRO1895 was then assessed by flow cytometry as described above.

Results:

Individual $EC_{50}$ values on each plate were calibrated against the $EC_{50}$ value of the respective control (i.e. binding of MATCH4 molecules without the addition of anti-HER2 antibodies trastuzumab and pertuzumab). Obtained $EC_{50}$ and relative $EC_{50}$ as well as maximum binding in flow cytometry are shown in Table 33. Concentration-response curves are depicted in FIG. 21.

As shown in Table 33 and in FIG. 21, MATCH4 molecules bound to SK-OV3 cells in the absence of the antibodies trastuzumab and pertuzumab with an apparent binding affinity comparable to the affinities found in the experiment described before (see Table 31). Of note, PRO1543 could also bind to the cells in presence of pertuzumab and PRO1895 in the presence of trastuzumab with binding affinities similar to the ones obtained in the absence of the respective antibody (compare relative $EC_{50}$ values). On the other hand, no binding of PRO1543 and PRO1895 was found when SK-OV3 cells were incubated with trastuzumab and pertuzumab prior the addition of MATCH4 molecules, respectively. As PRO1543 contains the anti-HER2 binding moiety of trastuzumab and PRO1895 the one of pertuzumab, binding of PRO1543 in presence of pertuzumab and PRO1895 in the presence of trastuzumab was expected and demonstrated in this experiment. Trastuzumab and pertuzumab bind to different, non-overlapping epitopes on human HER2.

TABLE 32

Plasmamembranous binding of MATCH4 molecules PRO1543 and PRO1895 to HCC1954 and HCC827 cells. Table shows $EC_{50}$ and relative $EC_{50}$ (normalized to respective reference antibodies trastuzumab or pertuzumab) as well as maximum binding obtained by flow cytometry.

| | | | | Plasmamembranous binding in flow cytometry | | |
|---|---|---|---|---|---|---|
| Protein ID | Target cells | Expression levels of HER2 | Expression levels of PD-L1 | $EC_{50}$ [nM] | rel. $EC_{50}$ ($EC_{50}$, reference/$EC_{50}$, sample) | Maximum binding in flow cytometry [ΔMFI] |
| trastuzumab | HCC1954 (IFNy) | high | high | 4.14 | 1.00 | 1648270 |
| PRO1543 | HCC1954 (IFNy) | | | 27.82 | 0.15 | 1898099 |
| pertuzumab | HCC1954 (IFNy) | | | 2.51 | 1.00 | 1854851 |
| PRO1895 | HCC1954 (IFNy) | | | 17.30 | 0.15 | 2444712 |

TABLE 32-continued

Plasmamembranous binding of MATCH4 molecules PRO1543 and PRO1895 to HCC1954 and HCC827 cells. Table shows $EC_{50}$ and relative $EC_{50}$ (normalized to respective reference antibodies trastuzumab or pertuzumab) as well as maximum binding obtained by flow cytometry.

| | | | | Plasmamembranous binding in flow cytometry | | |
|---|---|---|---|---|---|---|
| Protein ID | Target cells | Expression levels of HER2 | Expression levels of PD-L1 | $EC_{50}$ [nM] | rel. $EC_{50}$ ($EC_{50}$, reference/$EC_{50}$, sample) | Maximum binding in flow cytometry [ΔMFI] |
| trastuzumab | HCC827 (IFNy) | low | high | 1.01 | 1.00 | 30842 |
| PRO1543 | HCC827 (IFNy) | | | 3.90 | 0.26 | 52280 |
| pertuzumab | HCC827 (IFNy) | | | 1.39 | 1.00 | 33841 |
| PRO1895 | HCC827 (IFNy) | | | 1.34 | 1.04 | 45391 |

TABLE 33

Plasmamembranous binding of MATCH4 molecules PRO1543 and PRO1895 to SK-OV3 cells in presence of trastuzumab and pertuzumab. Table shows $EC_{50}$ and relative $EC_{50}$ (normalized to respective reference sample without trastuzumab or pertuzumab) as well as maximum binding obtained by flow cytometry.

| | | | | Plasmamembranous binding in flow cytometry | | |
|---|---|---|---|---|---|---|
| Protein ID | Target cells | Addition of trastuzumab | Addition of pertuzumab | $EC_{50}$ [nM] | rel. $EC_{50}$ ($EC_{50}$, reference/$EC_{50}$, sample) | Maximum binding in flow cytometry [ΔMFI] |
| PRO1543 | SKOV-3 | no | no | 4.09 | 1.00 | 399122 |
| PRO1543 | SKOV-3 | no | yes | 4.16 | 0.98 | 268242 |
| PRO1543 | SKOV-3 | yes | no | | no binding | |
| PRO1895 | SKOV-3 | no | no | 2.02 | 1.00 | 295834 |
| PRO1895 | SKOV-3 | yes | no | 4.55 | 0.44 | 345985 |
| PRO1895 | SKOV-3 | no | yes | | no binding | |

The invention claimed is:

1. An antibody or antigen-binding fragment thereof specifically binding to human serum albumin (HSA), that comprises HCDR1, HCDR2, and HCDR3 sequences of SEQ ID NOs: 61, 62 and 63, respectively, and LCDR1, LCDR2, and LCDR3 sequences of SEQ ID NOs: 64, 65 and 66, respectively.

2. The antibody or antigen-binding fragment thereof of claim 1, wherein said antibody or antigen-binding fragment thereof comprises (i) a VH domain having an amino acid sequence that is in the framework sequences at least 90 percent identical to the amino acid sequence of SEQ ID NO: 67; and a VL domain having an amino acid sequence that is in the framework sequences at least 90 percent identical to the amino acid sequence of SEQ ID NO: 69; or (ii) a VH domain having an amino acid sequence that is in the framework sequences at least 90 percent identical to the amino acid sequence of SEQ ID NO: 68; and a VL domain having an amino acid sequence that is in the framework sequences at least 90 percent identical to the amino acid sequence of SEQ ID NO: 70.

3. The antibody or antigen-binding fragment thereof of claim 2 comprising (i) a VH domain of SEQ ID NO: 67 and a VL domain of SEQ ID NO: 69; or (ii) a VH domain of SEQ ID NO: 68 and a VL domain of SEQ ID NO: 70.

4. A multispecific antibody comprising (i) at least one antibody or antigen-binding fragment thereof of claim 1, and (ii) at least one antibody or antigen-binding fragments thereof with specificity for a target different from HSA.

5. The multispecific antibody of claim 4, wherein said target different from HSA is a tumor-associated immune checkpoint antigen.

6. The multispecific antibody of claim 5, wherein said tumor-associated immune checkpoint antigen is selected from the group consisting of PD-L1, PD-L2, CD80, CD86, CD276 (B7-H3), and VTCN1 (B7-H4).

7. The multispecific antibody of claim 5, wherein said tumor-associated immune checkpoint antigen is an inhibitory immune cell antigen selected from group consisting of CTLA4, PD-1, lymphocyte-activation gene 3, T-cell immunoglobulin mucin-3, BTLA, TIM3, TIGIT, CD160, LAG3, and LAIR1.

8. The multispecific antibody of claim 4, wherein said target different from HSA is a tumor-associated antigen (TAA).

9. The multispecific antibody of claim 8, wherein said TAA is selected from of the group of EGFRvIII, 5T4, CD19, CD20, CD22, CD38, BCMA, IL4RA, mesothelin, GD2, Tn antigen, sTn antigen, Tn-O-Glycopeptide, sTn-O-Glycopeptide, PSMA, CD97, TAG72, CD44v6, CEA, EPCAM, KIT, IL-13Ra2, leguman, GD3, CD171, IL-11Ra, IL13RA2, ROR1, PSCA, MAD-CT-1, MAD-CT-2, VEGFR2, CLEC12A, LewisY, CD24, PDGFR-beta, SSEA-4, folate receptor alpha, Her2/neu (HER2), MUC1, MUC16, EGFR, NCAM, Ephrin B2, CAIX, LMP2, sLe, HMWMAA, o-acetyl-GD2, folate receptor beta, TEM1/CD248, CD33, CD123, CD133, CD135, TEM7R, FAP, legumain, HPV E6 or E7, ML-IAP, CLDN6, TSHR, GPRC5D, ALK, polysialic acid, Fos-related antigen, neutrophil elastase, TRP-2, CYP1B1, sperm protein 17, beta human chorionic gonadotropin, AFP, thyroglobulin, PLAC1, globoH, RAGE1, MN-CA IX, human telomerase reverse transcriptase, intestinal carboxyl esterase, mut hsp70-2, NA-17, NY-BR-1, UPK2, HAVCR1, ADRB3, PANX3, NY-ESO-1, GPR20, Ly6k, OR51E2, TARP, GFRalpha4, GPC3, CDH3, FGFR1, SSTR2, CECAM6, GA733, and gp120.

10. The multispecific antibody of claim 4, further comprising (iii) at least one antibody or antigen-binding fragments thereof with specificity for an immune cell antigen.

11. The multispecific antibody of claim 10, wherein said immune cell antigen is a stimulatory immune cell antigen selected from the group consisting of CD3 and CD16.

12. The multispecific antibody of claim 10, wherein said immune cell antigen is a costimulatory immune cell antigen selected from the group consisting of is CD137, CD28, ICOS, HVEM, CD27, OX40, DR3, GITR, CD30, SLAM, CD2, 2B4, TIM1, TIM2, and CD226.

13. A pharmaceutical composition comprising the multispecific antibody of claim 4, and a pharmaceutically acceptable carrier.

14. The multispecific antibody of claim 2, wherein said antibody or antigen-binding fragment thereof comprises a VH domain having an amino acid sequence that is in the framework sequences at least 95 percent identical to the amino acid sequence of SEQ ID NO: 67 and a VL domain having an amino acid sequence that is in the framework sequences at least 95 percent identical to the amino acid sequence of SEQ ID NO: 69.

15. The multispecific antibody of claim 2, wherein said antibody or antigen-binding fragment thereof comprises a VH domain having an amino acid sequence that is in the framework sequences at least 95 percent identical to the amino acid sequence of SEQ ID NO: 68 and a VL domain having an amino acid sequence that is in the framework sequences at least 95 percent identical to the amino acid sequence of SEQ ID NO: 70.

* * * * *

SEQUENCE LISTING

```
<160> NUMBER OF SEQ ID NOS: 153

<210> SEQ ID NO 1
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 1

Gly Phe Ser Phe Ser Ser Gly Tyr Asp Met Cys
1               5                   10


<210> SEQ ID NO 2
<211> LENGTH: 18
<212> TYPE: PRT
<213> ORGANISM: Artificial sequence
<220> FEATURE:
<223> OTHER INFORMATION: artificial antibody-based sequence

<400> SEQUENCE: 2

Cys Val Val Ala Gly Ser Val Asp Ile Thr Tyr Tyr Ala Ser Trp Ala
1               5                   10                  15

Lys Gly


<210> SEQ ID NO 3
<211> LENGTH: 11
<212> TYPE: PRT
<213> ORGANISM: Artificial sequence
```

-continued

<220> FEATURE:
<223> OTHER INFORMATION: artificial antibody-based sequence

<400> SEQUENCE: 3

Arg Lys Asp Ala Tyr Ser Asp Ala Phe Asn Leu
1 5 10

<210> SEQ ID NO 4
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 4

Arg Lys Asp Ala Ala Ser Asp Ala Phe Asn Leu
1 5 10

<210> SEQ ID NO 5
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 5

Gln Ala Ser Gln Ser Ile Asn Asp Tyr Leu Ala
1 5 10

<210> SEQ ID NO 6
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 6

Lys Ala Ser Thr Leu Ala Ser
1 5

<210> SEQ ID NO 7
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 7

Gln Gln Gly Tyr Ile Ile Thr Asp Ile Asp Asn Val
1 5 10

<210> SEQ ID NO 8
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 8

Gln Ala Gly Tyr Ile Ile Thr Asp Ile Asp Asn Val
1 5 10

<210> SEQ ID NO 9
<211> LENGTH: 12
<212> TYPE: PRT
<213> ORGANISM: Artificial sequence
<220> FEATURE:

```
<223> OTHER INFORMATION: artificial antibody-based sequence

<400> SEQUENCE: 9

Gln Gln Ala Tyr Ile Ile Thr Asp Ile Asp Asn Val
1               5                   10


<210> SEQ ID NO 10
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 10

Gln Ala Ala Tyr Ile Ile Thr Asp Ile Asp Asn Val
1               5                   10


<210> SEQ ID NO 11
<211> LENGTH: 121
<212> TYPE: PRT
<213> ORGANISM: Artificial sequence
<220> FEATURE:
<223> OTHER INFORMATION: artificial antibody-based sequence

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg Lys Asp Ala Tyr Ser Asp Ala Phe Asn Leu Trp Gly
            100                 105                 110

Gln Gly Thr Leu Val Thr Val Ser Ser
        115                 120


<210> SEQ ID NO 12
<211> LENGTH: 121
<212> TYPE: PRT
<213> ORGANISM: Artificial sequence
<220> FEATURE:
<223> OTHER INFORMATION: artificial antibody-based sequence

<400> SEQUENCE: 12

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Ser Gly
            20                  25                  30

Tyr Asp Met Cys Trp Ile Arg Gln Pro Pro Gly Lys Gly Leu Glu Trp
        35                  40                  45

Ile Gly Cys Val Val Ala Gly Ser Val Asp Ile Thr Tyr Tyr Ala Ser
    50                  55                  60

Trp Ala Lys Gly Arg Val Thr Ile Ser Val Asp Ser Ser Lys Asn Gln
65                  70                  75                  80
```

-continued

```
Phe Ser Leu Lys Leu Ser Ser Val Thr Ala Ala Asp Thr Ala Val Tyr
                85                  90                  95

Tyr Cys Ala Arg Lys Asp Ala Ala Ser Asp Ala Phe Asn Leu Trp Gly
            100                 105                 110

Gln Gly Thr Leu Val Thr Val Ser Ser
        115                 120


<210> SEQ ID NO 13
<211> LENGTH: 111
<212> TYPE: PRT
<213> ORGANISM: Artificial sequence
<220> FEATURE:
<223> OTHER INFORMATION: artificial antibody-based sequence

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Ile Ile Thr Asp
                85                  90                  95

Ile Asp Asn Val Phe Gly Thr Gly Thr Lys Val Thr Val Leu Gly
            100                 105                 110


<210> SEQ ID NO 14
<211> LENGTH: 111
<212> TYPE: PRT
<213> ORGANISM: Artificial sequence
<220> FEATURE:
<223> OTHER INFORMATION: artificial antibody-based sequence

<400> SEQUENCE: 14

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly Tyr Ile Ile Thr Asp
                85                  90                  95

Ile Asp Asn Val Phe Gly Thr Gly Thr Lys Val Thr Val Leu Gly
            100                 105                 110


<210> SEQ ID NO 15
<211> LENGTH: 111
<212> TYPE: PRT
<213> ORGANISM: Artificial sequence
<220> FEATURE:
<223> OTHER INFORMATION: artificial antibody-based sequence
```

<400> SEQUENCE: 15

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Tyr Ile Ile Thr Asp
                85                  90                  95

Ile Asp Asn Val Phe Gly Thr Gly Thr Lys Val Thr Val Leu Gly
            100                 105                 110

<210> SEQ ID NO 16
<211> LENGTH: 111
<212> TYPE: PRT
<213> ORGANISM: Artificial sequence
<220> FEATURE:
<223> OTHER INFORMATION: artificial antibody-based sequence

<400> SEQUENCE: 16

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly
            100                 105                 110

<210> SEQ ID NO 17
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 17

Gly Phe Asn Ile Lys Asp Thr Tyr Ile His
1               5                   10

<210> SEQ ID NO 18
<211> LENGTH: 17
<212> TYPE: PRT
<213> ORGANISM: Artificial sequence
<220> FEATURE:
<223> OTHER INFORMATION: artificial antibody-based sequence

<400> SEQUENCE: 18

Arg Ile Tyr Pro Thr Asn Gly Tyr Thr Arg Tyr Ala Asp Ser Val Lys
1               5                   10                  15

-continued

Gly

<210> SEQ ID NO 19
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 19

Arg Trp Gly Gly Asp Gly Phe Tyr Ala Met Asp Tyr
1 5 10

<210> SEQ ID NO 20
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 20

Arg Ala Ser Gln Asp Val Asn Thr Ala Val Ala
1 5 10

<210> SEQ ID NO 21
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 21

Ser Ala Ser Phe Leu Tyr Ser
1 5

<210> SEQ ID NO 22
<211> LENGTH: 9
<212> TYPE: PRT
<213> ORGANISM: Artificial sequence
<220> FEATURE:
<223> OTHER INFORMATION: artificial antibody-based sequence

<400> SEQUENCE: 22

Gln Gln His Tyr Thr Thr Pro Pro Thr
1 5

<210> SEQ ID NO 23
<211> LENGTH: 120
<212> TYPE: PRT
<213> ORGANISM: Artificial sequence
<220> FEATURE:
<223> OTHER INFORMATION: artificial antibody-based sequence

<400> SEQUENCE: 23

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 24
<211> LENGTH: 120
<212> TYPE: PRT
<213> ORGANISM: Artificial sequence
<220> FEATURE:
<223> OTHER INFORMATION: artificial antibody-based sequence

<400> SEQUENCE: 24

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Cys Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser
115 120

<210> SEQ ID NO 25
<211> LENGTH: 108
<212> TYPE: PRT
<213> ORGANISM: Artificial sequence
<220> FEATURE:
<223> OTHER INFORMATION: artificial antibody-based sequence

<400> SEQUENCE: 25

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Gly Gly Thr Lys Leu Thr Val Leu Gly
100 105

<210> SEQ ID NO 26
<211> LENGTH: 108
<212> TYPE: PRT

```
<213> ORGANISM: Artificial sequence
<220> FEATURE:
<223> OTHER INFORMATION: artificial antibody-based sequence

<400> SEQUENCE: 26

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly
            100                 105


<210> SEQ ID NO 27
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 27

Gly Phe Thr Phe Thr Asp Tyr Thr Met Asp
1               5                   10


<210> SEQ ID NO 28
<211> LENGTH: 17
<212> TYPE: PRT
<213> ORGANISM: Artificial sequence
<220> FEATURE:
<223> OTHER INFORMATION: artificial antibody-based sequence

<400> SEQUENCE: 28

Asp Val Asn Pro Asn Ser Gly Gly Ser Ile Tyr Asn Gln Arg Phe Lys
1               5                   10                  15

Gly


<210> SEQ ID NO 29
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 29

Arg Asn Leu Gly Pro Ser Phe Tyr Phe Asp Tyr
1               5                   10


<210> SEQ ID NO 30
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 30

Lys Ala Ser Gln Asp Val Ser Ile Gly Val Ala
```

1 5 10

<210> SEQ ID NO 31
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 31

Ser Ala Ser Tyr Arg Tyr Thr
1 5

<210> SEQ ID NO 32
<211> LENGTH: 9
<212> TYPE: PRT
<213> ORGANISM: Artificial sequence
<220> FEATURE:
<223> OTHER INFORMATION: artificial antibody-based sequence

<400> SEQUENCE: 32

Gln Gln Tyr Tyr Ile Tyr Pro Tyr Thr
1 5

<210> SEQ ID NO 33
<211> LENGTH: 119
<212> TYPE: PRT
<213> ORGANISM: Artificial sequence
<220> FEATURE:
<223> OTHER INFORMATION: artificial antibody-based sequence

<400> SEQUENCE: 33

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser
115

<210> SEQ ID NO 34
<211> LENGTH: 119
<212> TYPE: PRT
<213> ORGANISM: Artificial sequence
<220> FEATURE:
<223> OTHER INFORMATION: artificial antibody-based sequence

<400> SEQUENCE: 34

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Cys Leu Glu Trp Val

-continued

```
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115


<210> SEQ ID NO 35
<211> LENGTH: 108
<212> TYPE: PRT
<213> ORGANISM: Artificial sequence
<220> FEATURE:
<223> OTHER INFORMATION: artificial antibody-based sequence

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Thr Gly Thr Lys Val Thr Val Leu Gly
            100                 105


<210> SEQ ID NO 36
<211> LENGTH: 108
<212> TYPE: PRT
<213> ORGANISM: Artificial sequence
<220> FEATURE:
<223> OTHER INFORMATION: artificial antibody-based sequence

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly
            100                 105
```

<210> SEQ ID NO 37
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 37

Gly Phe Ser Leu Ser Ser Tyr Asp Met Ser
1               5                   10

<210> SEQ ID NO 38
<211> LENGTH: 16
<212> TYPE: PRT
<213> ORGANISM: Artificial sequence
<220> FEATURE:
<223> OTHER INFORMATION: artificial antibody-based sequence

<400> SEQUENCE: 38

Ala Ser Tyr Ala Ser Gly Pro Thr Tyr Tyr Ala Ser Trp Ala Lys Gly
1               5                   10                  15

<210> SEQ ID NO 39
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 39

Arg Gly Gly Trp Thr Gly Thr Ser His Ser Asn Ile
1               5                   10

<210> SEQ ID NO 40
<211> LENGTH: 13
<212> TYPE: PRT
<213> ORGANISM: Artificial sequence
<220> FEATURE:
<223> OTHER INFORMATION: artificial antibody-based sequence

<400> SEQUENCE: 40

Gln Ser Ser Gln Ser Val Phe Ser Asn Asn Tyr Leu Ala
1               5                   10

<210> SEQ ID NO 41
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 41

Ser Ala Ser Thr Leu Ala Ser
1               5

<210> SEQ ID NO 42
<211> LENGTH: 13
<212> TYPE: PRT
<213> ORGANISM: Artificial sequence
<220> FEATURE:
<223> OTHER INFORMATION: artificial antibody-based sequence

<400> SEQUENCE: 42

Leu Gly Ser Tyr Ala Cys Ser Ser Ala Asp Cys Tyr Val
1               5                   10

-continued

```
<210> SEQ ID NO 43
<211> LENGTH: 119
<212> TYPE: PRT
<213> ORGANISM: Artificial sequence
<220> FEATURE:
<223> OTHER INFORMATION: artificial antibody-based sequence

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Asp Met Ser Trp Val Arg Gln Ala Pro Gly Lys Gly Leu Ala Trp Ile
        35                  40                  45

Gly Ala Ser Tyr Ala Ser Gly Pro Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Gly Gly Trp Thr Gly Thr Ser His Ser Asn Ile Trp Gly Gln Gly
            100                 105                 110

Thr Leu Val Thr Val Ser Ser
        115


<210> SEQ ID NO 44
<211> LENGTH: 114
<212> TYPE: PRT
<213> ORGANISM: Artificial sequence
<220> FEATURE:
<223> OTHER INFORMATION: artificial antibody-based sequence

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly


<210> SEQ ID NO 45
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 45

Gly Phe Ser Leu Ser Ser Asn Ala Met Gly
1               5                   10
```

<210> SEQ ID NO 46
<211> LENGTH: 16
<212> TYPE: PRT
<213> ORGANISM: Artificial sequence
<220> FEATURE:
<223> OTHER INFORMATION: artificial antibody-based sequence

<400> SEQUENCE: 46

Ile Ile Ser Val Gly Gly Phe Thr Tyr Tyr Ala Ser Trp Ala Lys Gly
1 5 10 15

<210> SEQ ID NO 47
<211> LENGTH: 14
<212> TYPE: PRT
<213> ORGANISM: Artificial sequence
<220> FEATURE:
<223> OTHER INFORMATION: artificial antibody-based sequence

<400> SEQUENCE: 47

Arg Asp Arg His Gly Gly Asp Ser Ser Gly Ala Phe Tyr Leu
1 5 10

<210> SEQ ID NO 48
<211> LENGTH: 13
<212> TYPE: PRT
<213> ORGANISM: Artificial sequence
<220> FEATURE:
<223> OTHER INFORMATION: artificial antibody-based sequence

<400> SEQUENCE: 48

Gln Ser Ser Glu Ser Val Tyr Ser Asn Asn Gln Leu Ser
1 5 10

<210> SEQ ID NO 49
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 49

Asp Ala Ser Asp Leu Ala Ser
1 5

<210> SEQ ID NO 50
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 50

Ala Gly Gly Phe Ser Ser Ser Ser Asp Thr Ala
1 5 10

<210> SEQ ID NO 51
<211> LENGTH: 121
<212> TYPE: PRT
<213> ORGANISM: Artificial sequence
<220> FEATURE:
<223> OTHER INFORMATION: artificial antibody-based sequence

<400> SEQUENCE: 51

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Asn

-continued

```
            20                  25                  30

Ala Met Gly Trp Val Arg Gln Ala Pro Gly Lys Gly Leu Glu Tyr Ile
        35                  40                  45

Gly Ile Ile Ser Val Gly Gly Phe Thr Tyr Tyr Ala Ser Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Thr Tyr Phe Cys Ala
                85                  90                  95

Arg Asp Arg His Gly Gly Asp Ser Ser Gly Ala Phe Tyr Leu Trp Gly
            100                 105                 110

Gln Gly Thr Leu Val Thr Val Ser Ser
        115                 120


<210> SEQ ID NO 52
<211> LENGTH: 112
<212> TYPE: PRT
<213> ORGANISM: Artificial sequence
<220> FEATURE:
<223> OTHER INFORMATION: artificial antibody-based sequence

<400> SEQUENCE: 52

Asp Ile Gln Met Thr Gln Ser Pro Ser Ser Leu Ser Ala Ser Val Gly
1               5                   10                  15

Asp Arg Val Thr Ile Thr Cys Gln Ser Ser Glu Ser Val Tyr Ser Asn
            20                  25                  30

Asn Gln Leu Ser Trp Tyr Gln Gln Lys Pro Gly Gln Pro Pro Lys Leu
        35                  40                  45

Leu Ile Tyr Asp Ala Ser Asp Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Ala Gly Gly Phe Ser Ser
                85                  90                  95

Ser Ser Asp Thr Ala Phe Gly Gly Gly Thr Lys Leu Thr Val Leu Gly
            100                 105                 110


<210> SEQ ID NO 53
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 53

Gly Phe Ser Phe Ser Ser Ser Tyr Trp Ile Cys
1               5                   10


<210> SEQ ID NO 54
<211> LENGTH: 17
<212> TYPE: PRT
<213> ORGANISM: Artificial sequence
<220> FEATURE:
<223> OTHER INFORMATION: artificial antibody-based sequence

<400> SEQUENCE: 54

Cys Val Phe Thr Gly Asp Gly Thr Thr Tyr Tyr Ala Ser Trp Ala Lys
1               5                   10                  15

Gly
```

-continued

<210> SEQ ID NO 55
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 55

```
Arg Pro Val Ser Val Tyr Tyr Tyr Gly Met Asp Leu
1               5                   10
```

<210> SEQ ID NO 56
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 56

```
Gln Ala Ser Gln Ile Ile Ser Ser Arg Ser Ala
1               5                   10
```

<210> SEQ ID NO 57
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 57

```
Gln Ala Ser Lys Leu Ala Ser
1               5
```

<210> SEQ ID NO 58
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 58

```
Gln Cys Thr Tyr Ile Asp Ser Asn Phe Gly Ala
1               5                   10
```

<210> SEQ ID NO 59
<211> LENGTH: 121
<212> TYPE: PRT
<213> ORGANISM: Artificial sequence
<220> FEATURE:
<223> OTHER INFORMATION: artificial antibody-based sequence

<400> SEQUENCE: 59

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ser Ser
            20                  25                  30

Tyr Trp Ile Cys Trp Val Arg Gln Ala Pro Gly Lys Gly Leu Glu Trp
        35                  40                  45

Val Gly Cys Val Phe Thr Gly Asp Gly Thr Thr Tyr Tyr Ala Ser Trp
    50                  55                  60

Ala Lys Gly Arg Phe Thr Ile Ser Arg Asp Asn Ser Lys Asn Thr Val
65                  70                  75                  80

Tyr Leu Gln Met Asn Ser Leu Arg Ala Glu Asp Thr Ala Thr Tyr Phe
                85                  90                  95
```

```
Cys Ala Arg Pro Val Ser Val Tyr Tyr Tyr Gly Met Asp Leu Trp Gly
            100                 105                 110

Gln Gly Thr Leu Val Thr Val Ser Ser
        115                 120


<210> SEQ ID NO 60
<211> LENGTH: 110
<212> TYPE: PRT
<213> ORGANISM: Artificial sequence
<220> FEATURE:
<223> OTHER INFORMATION: artificial antibody-based sequence

<400> SEQUENCE: 60

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ile Ile Ser Ser Arg
            20                  25                  30

Ser Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Ile Asp Ser Asn
                85                  90                  95

Phe Gly Ala Phe Gly Gly Gly Thr Lys Leu Thr Val Leu Gly
            100                 105                 110


<210> SEQ ID NO 61
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 61

Gly Phe Ser Leu Ser Ser Tyr Ala Met Asn
1               5                   10


<210> SEQ ID NO 62
<211> LENGTH: 16
<212> TYPE: PRT
<213> ORGANISM: Artificial sequence
<220> FEATURE:
<223> OTHER INFORMATION: artificial antibody-based sequence

<400> SEQUENCE: 62

His Ile Asn Ala Gly Asp Ile Ala Tyr Tyr Ala Thr Trp Ala Lys Gly
1               5                   10                  15


<210> SEQ ID NO 63
<211> LENGTH: 13
<212> TYPE: PRT
<213> ORGANISM: Artificial sequence
<220> FEATURE:
<223> OTHER INFORMATION: artificial antibody-based sequence

<400> SEQUENCE: 63

Arg Gly Ala Gly Gly Phe Ser Thr Gly Pro Phe Lys Leu
1               5                   10


<210> SEQ ID NO 64
```

<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 64

Gln Ala Ser Glu Ser Ile Asn Ser Arg Leu Ala
1 5 10

<210> SEQ ID NO 65
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 65

Asp Ala Ser Asp Leu Thr Ser
1 5

<210> SEQ ID NO 66
<211> LENGTH: 10
<212> TYPE: PRT
<213> ORGANISM: Artificial sequence
<220> FEATURE:
<223> OTHER INFORMATION: artificial antibody-based sequence

<400> SEQUENCE: 66

Gln Gly Tyr Gly Gly Ser Ser Thr Thr Thr
1 5 10

<210> SEQ ID NO 67
<211> LENGTH: 120
<212> TYPE: PRT
<213> ORGANISM: Artificial sequence
<220> FEATURE:
<223> OTHER INFORMATION: artificial antibody-based sequence

<400> SEQUENCE: 67

Glu Val Gln Leu Val Glu Ser Gly Gly Gly Leu Val Gln Pro Gly Gly
1 5 10 15

Ser Leu Arg Leu Ser Cys Ala Ala Ser Gly Phe Ser Leu Ser Ser Tyr
20 25 30

Ala Met Asn Trp Val Arg Gln Ala Pro Gly Lys Gly Leu Glu Trp Ile
35 40 45

Gly His Ile Asn Ala Gly Asp Ile Ala Tyr Tyr Ala Thr Trp Ala Lys
50 55 60

Gly Arg Phe Thr Ile Ser Arg Asp Asn Ser Lys Asn Thr Val Tyr Leu
65 70 75 80

Gln Met Asn Ser Leu Arg Ala Glu Asp Thr Ala Val Tyr Phe Cys Ala
85 90 95

Arg Gly Ala Gly Gly Phe Ser Thr Gly Pro Phe Lys Leu Trp Gly Gln
100 105 110

Gly Thr Leu Val Thr Val Ser Ser
115 120

<210> SEQ ID NO 68
<211> LENGTH: 120
<212> TYPE: PRT
<213> ORGANISM: Artificial sequence
<220> FEATURE:
<223> OTHER INFORMATION: artificial antibody-based sequence

<400> SEQUENCE: 68

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Ser Ser Tyr
            20                  25                  30

Ala Met Asn Trp Val Arg Gln Ala Pro Gly Lys Cys Leu Glu Trp Ile
        35                  40                  45

Gly His Ile Asn Ala Gly Asp Ile Ala Tyr Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Phe Cys Ala
                85                  90                  95

Arg Gly Ala Gly Gly Phe Ser Thr Gly Pro Phe Lys Leu Trp Gly Gln
            100                 105                 110

Gly Thr Leu Val Thr Val Ser Ser
        115                 120

<210> SEQ ID NO 69
<211> LENGTH: 109
<212> TYPE: PRT
<213> ORGANISM: Artificial sequence
<220> FEATURE:
<223> OTHER INFORMATION: artificial antibody-based sequence

<400> SEQUENCE: 69

Ala Phe Glu Leu Thr Gln Ser Pro Ser Ser Leu Ser Ala Ser Val Gly
1               5                   10                  15

Asp Arg Val Thr Ile Thr Cys Gln Ala Ser Glu Ser Ile Asn Ser Arg
            20                  25                  30

Leu Ala Trp Tyr Gln Gln Lys Pro Gly Gln Pro Pro Lys Leu Leu Ile
        35                  40                  45

Tyr Asp Ala Ser Asp Leu Thr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Gly Gly Ser Ser Thr
                85                  90                  95

Thr Thr Phe Gly Gly Gly Thr Lys Leu Thr Val Leu Gly
            100                 105

<210> SEQ ID NO 70
<211> LENGTH: 109
<212> TYPE: PRT
<213> ORGANISM: Artificial sequence
<220> FEATURE:
<223> OTHER INFORMATION: artificial antibody-based sequence

<400> SEQUENCE: 70

Ala Phe Glu Leu Thr Gln Ser Pro Ser Ser Leu Ser Ala Ser Val Gly
1               5                   10                  15

Asp Arg Val Thr Ile Thr Cys Gln Ala Ser Glu Ser Ile Asn Ser Arg
            20                  25                  30

Leu Ala Trp Tyr Gln Gln Lys Pro Gly Gln Pro Pro Lys Leu Leu Ile
        35                  40                  45

Tyr Asp Ala Ser Asp Leu Thr Ser Gly Val Pro Ser Arg Phe Ser Gly
    50                  55                  60

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Gly Gly Ser Ser Thr
                85                  90                  95

Thr Thr Phe Gly Cys Gly Thr Lys Leu Thr Val Leu Gly
            100                 105


<210> SEQ ID NO 71
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 71

Gly Phe Ser Phe Ser Ala Asn Tyr Tyr Pro Cys
1               5                   10


<210> SEQ ID NO 72
<211> LENGTH: 18
<212> TYPE: PRT
<213> ORGANISM: Artificial sequence
<220> FEATURE:
<223> OTHER INFORMATION: artificial antibody-based sequence

<400> SEQUENCE: 72

Cys Ile Tyr Gly Gly Ser Ser Asp Ile Thr Tyr Asp Ala Asn Trp Thr
1               5                   10                  15

Lys Gly


<210> SEQ ID NO 73
<211> LENGTH: 12
<212> TYPE: PRT
<213> ORGANISM: Artificial sequence
<220> FEATURE:
<223> OTHER INFORMATION: artificial antibody-based sequence

<400> SEQUENCE: 73

Arg Ser Ala Trp Tyr Ser Gly Trp Gly Gly Asp Leu
1               5                   10


<210> SEQ ID NO 74
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 74

Gln Ala Ser Gln Ser Ile Ser Asn Arg Leu Ala
1               5                   10


<210> SEQ ID NO 75
<211> LENGTH: 7
<212> TYPE: PRT
<213> ORGANISM: Artificial sequence
<220> FEATURE:
<223> OTHER INFORMATION: artificial antibody-based sequence

<400> SEQUENCE: 75

Ser Ala Ser Thr Leu Ala Ser
1               5


<210> SEQ ID NO 76
<211> LENGTH: 11
```

```
<212> TYPE: PRT
<213> ORGANISM: Artificial sequence
<220> FEATURE:
<223> OTHER INFORMATION: artificial antibody-based sequence

<400> SEQUENCE: 76

Gln Ser Thr Tyr Tyr Gly Asn Asp Gly Asn Ala
1               5                   10


<210> SEQ ID NO 77
<211> LENGTH: 122
<212> TYPE: PRT
<213> ORGANISM: Artificial sequence
<220> FEATURE:
<223> OTHER INFORMATION: artificial antibody-based sequence

<400> SEQUENCE: 77

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Cys Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Ala Trp Tyr Ser Gly Trp Gly Gly Asp Leu Trp
            100                 105                 110

Gly Gln Gly Thr Leu Val Thr Val Ser Ser
        115                 120


<210> SEQ ID NO 78
<211> LENGTH: 110
<212> TYPE: PRT
<213> ORGANISM: Artificial sequence
<220> FEATURE:
<223> OTHER INFORMATION: artificial antibody-based sequence

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Cys Gly Thr Lys Val Thr Val Leu Gly
            100                 105                 110


<210> SEQ ID NO 79
<211> LENGTH: 477
<212> TYPE: PRT
```

```
<213> ORGANISM: Artificial sequence
<220> FEATURE:
<223> OTHER INFORMATION: artificial antibody-based sequence

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Gln Ser Ser Gln Ser Val Phe Ser Asn
                245                 250                 255

Asn Tyr Leu Ala Trp Phe Gln Gln Lys Pro Gly Gln Ser Pro Lys Arg
            260                 265                 270

Leu Ile Tyr Ser Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Leu Gly Ser Tyr Ala Cys
305                 310                 315                 320

Ser Ser Ala Asp Cys Tyr Val Phe Gly Thr Gly Thr Lys Val Thr Val
                325                 330                 335

Leu Gly Gly Gly Gly Gly Ser Gly Gly Gly Gly Ser Gly Gly Gly Gly
            340                 345                 350

Ser Gly Gly Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Ser Leu Ser Ser Tyr Asp Met Ser Trp Val Arg Gln Ala Pro Gly
```

385 390 395 400

Lys Gly Leu Ala Trp Ile Gly Ala Ser Tyr Ala Ser Gly Pro Thr Tyr
405 410 415

Tyr Ala Ser Trp Ala Lys Gly Arg Phe Thr Ile Ser Arg Asp Asn Ser
420 425 430

Lys Asn Thr Val Tyr Leu Gln Met Asn Ser Leu Arg Ala Glu Asp Thr
435 440 445

Ala Thr Tyr Phe Cys Ala Arg Gly Gly Trp Thr Gly Thr Ser His Ser
450 455 460

Asn Ile Trp Gly Gln Gly Thr Leu Val Thr Val Ser Ser
465 470 475

<210> SEQ ID NO 80
<211> LENGTH: 485
<212> TYPE: PRT
<213> ORGANISM: Artificial sequence
<220> FEATURE:
<223> OTHER INFORMATION: artificial antibody-based sequence

<400> SEQUENCE: 80

Glu Val Gln Leu Val Glu Ser Gly Gly Gly Leu Val Gln Pro Gly Gly
1 5 10 15

Ser Leu Arg Leu Ser Cys Ala Ala Ser Gly Phe Asn Ile Lys Asp Thr
20 25 30

Tyr Ile His Trp Val Arg Gln Ala Pro Gly Lys Gly Leu Glu Trp Val
35 40 45

Ala Arg Ile Tyr Pro Thr Asn Gly Tyr Thr Arg Tyr Ala Asp Ser Val
50 55 60

Lys Gly Arg Phe Thr Ile Ser Ala Asp Thr Ser Lys Asn Thr Ala Tyr
65 70 75 80

Leu Gln Met Asn Ser Leu Arg Ala Glu Asp Thr Ala Val Tyr Tyr Cys
85 90 95

Ser Arg Trp Gly Gly Asp Gly Phe Tyr Ala Met Asp Tyr Trp Gly Gln
100 105 110

Gly Thr Leu Val Thr Val Ser Ser Ala Ser Thr Lys Gly Pro Ser Val
115 120 125

Phe Pro Leu Ala Pro Ser Ser Lys Ser Thr Ser Gly Gly Thr Ala Ala
130 135 140

Leu Gly Cys Leu Val Lys Asp Tyr Phe Pro Glu Pro Val Thr Val Ser
145 150 155 160

Trp Asn Ser Gly Ala Leu Thr Ser Gly Val His Thr Phe Pro Ala Val
165 170 175

Leu Gln Ser Ser Gly Leu Tyr Ser Leu Ser Ser Val Val Thr Val Pro
180 185 190

Ser Ser Ser Leu Gly Thr Gln Thr Tyr Ile Cys Asn Val Asn His Lys
195 200 205

Pro Ser Asn Thr Lys Val Asp Lys Lys Val Glu Pro Lys Ser Cys Gly
210 215 220

Gly Gly Gly Ser Gly Gly Gly Gly Ser Asp Ile Gln Met Thr Gln Ser
225 230 235 240

Pro Ser Ser Leu Ser Ala Ser Val Gly Asp Arg Val Thr Ile Thr Cys
245 250 255

Gln Ala Ser Gln Ser Ile Asn Asp Tyr Leu Ala Trp Tyr Gln Gln Lys
260 265 270

Pro Gly Lys Ala Pro Lys Leu Leu Ile Tyr Lys Ala Ser Thr Leu Ala

-continued

```
        275                 280                 285

Ser Gly Val Pro Ser Arg Phe Ser Gly Ser Gly Ser Gly Thr Asp Phe
    290                 295                 300

Thr Leu Thr Ile Ser Ser Leu Gln Pro Glu Asp Phe Ala Thr Tyr Tyr
305                 310                 315                 320

Cys Gln Gln Ala Tyr Ile Ile Thr Asp Ile Asp Asn Val Phe Gly Thr
                325                 330                 335

Gly Thr Lys Val Thr Val Leu Gly Gly Gly Gly Ser Gly Gly Gly
            340                 345                 350

Gly Ser Gly Gly Gly Gly Ser Gly Gly Gly Gly Ser Gln Val Gln Leu
        355                 360                 365

Gln Glu Ser Gly Pro Gly Leu Val Lys Pro Ser Glu Thr Leu Ser Leu
    370                 375                 380

Thr Cys Lys Val Ser Gly Phe Ser Phe Ser Ser Gly Tyr Asp Met Cys
385                 390                 395                 400

Trp Ile Arg Gln Pro Pro Gly Lys Gly Leu Glu Trp Ile Gly Cys Val
                405                 410                 415

Val Ala Gly Ser Val Asp Ile Thr Tyr Tyr Ala Ser Trp Ala Lys Gly
            420                 425                 430

Arg Val Thr Ile Ser Val Asp Ser Ser Lys Asn Gln Phe Ser Leu Lys
        435                 440                 445

Leu Ser Ser Val Thr Ala Ala Asp Thr Ala Val Tyr Tyr Cys Ala Arg
    450                 455                 460

Lys Asp Ala Tyr Ser Asp Ala Phe Asn Leu Trp Gly Gln Gly Thr Leu
465                 470                 475                 480

Val Thr Val Ser Ser
                485


<210> SEQ ID NO 81
<211> LENGTH: 482
<212> TYPE: PRT
<213> ORGANISM: Artificial sequence
<220> FEATURE:
<223> OTHER INFORMATION: artificial antibody-based sequence

<400> SEQUENCE: 81

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
```

```
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys Gly Gly Gly Gly Ser
    210                 215                 220

Gly Gly Gly Gly Ser Asp Ile Gln Met Thr Gln Ser Pro Ser Ser Leu
225                 230                 235                 240

Ser Ala Ser Val Gly Asp Arg Val Thr Ile Thr Cys Gln Ser Ser Gln
                245                 250                 255

Ser Val Phe Ser Asn Asn Tyr Leu Ala Trp Phe Gln Gln Lys Pro Gly
            260                 265                 270

Gln Ser Pro Lys Arg Leu Ile Tyr Ser Ala Ser Thr Leu Ala Ser Gly
        275                 280                 285

Val Pro Ser Arg Phe Ser Gly Ser Gly Ser Gly Thr Asp Phe Thr Leu
    290                 295                 300

Thr Ile Ser Ser Leu Gln Pro Glu Asp Phe Ala Thr Tyr Tyr Cys Leu
305                 310                 315                 320

Gly Ser Tyr Ala Cys Ser Ser Ala Asp Cys Tyr Val Phe Gly Thr Gly
                325                 330                 335

Thr Lys Val Thr Val Leu Gly Gly Gly Gly Gly Ser Gly Gly Gly Gly
            340                 345                 350

Ser Gly Gly Gly Gly Ser Gly Gly Gly Gly Ser Glu Val Gln Leu Val
        355                 360                 365

Glu Ser Gly Gly Gly Leu Val Gln Pro Gly Gly Ser Leu Arg Leu Ser
    370                 375                 380

Cys Ala Ala Ser Gly Phe Ser Leu Ser Ser Tyr Asp Met Ser Trp Val
385                 390                 395                 400

Arg Gln Ala Pro Gly Lys Gly Leu Ala Trp Ile Gly Ala Ser Tyr Ala
                405                 410                 415

Ser Gly Pro Thr Tyr Tyr Ala Ser Trp Ala Lys Gly Arg Phe Thr Ile
            420                 425                 430

Ser Arg Asp Asn Ser Lys Asn Thr Val Tyr Leu Gln Met Asn Ser Leu
        435                 440                 445

Arg Ala Glu Asp Thr Ala Thr Tyr Phe Cys Ala Arg Gly Gly Trp Thr
    450                 455                 460

Gly Thr Ser His Ser Asn Ile Trp Gly Gln Gly Thr Leu Val Thr Val
465                 470                 475                 480

Ser Ser
```

<210> SEQ ID NO 82
<211> LENGTH: 486
<212> TYPE: PRT
<213> ORGANISM: Artificial sequence
<220> FEATURE:
<223> OTHER INFORMATION: artificial antibody-based sequence

<400> SEQUENCE: 82

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30
```

-continued

```
Tyr Tyr Met Cys Trp Val Arg Gln Ala Pro Gly Lys Gly Leu Glu Trp
        35                  40                  45

Ile Gly Cys Ile Tyr Val Gly Ser His Val Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Gly Ser Gly Gly Gly Gly Ser Asp Ile Gln Met Thr Gln
225                 230                 235                 240

Ser Pro Ser Ser Leu Ser Ala Ser Val Gly Asp Arg Val Thr Ile Thr
                245                 250                 255

Cys Gln Ala Ser Gln Ser Ile Asn Asp Tyr Leu Ala Trp Tyr Gln Gln
            260                 265                 270

Lys Pro Gly Lys Ala Pro Lys Leu Leu Ile Tyr Lys Ala Ser Thr Leu
        275                 280                 285

Ala Ser Gly Val Pro Ser Arg Phe Ser Gly Ser Gly Ser Gly Thr Asp
    290                 295                 300

Phe Thr Leu Thr Ile Ser Ser Leu Gln Pro Glu Asp Phe Ala Thr Tyr
305                 310                 315                 320

Tyr Cys Gln Gln Ala Tyr Ile Ile Thr Asp Ile Asp Asn Val Phe Gly
                325                 330                 335

Thr Gly Thr Lys Val Thr Val Leu Gly Gly Gly Gly Ser Gly Gly
            340                 345                 350

Gly Gly Ser Gly Gly Gly Gly Ser Gly Gly Gly Gly Ser Gln Val Gln
        355                 360                 365

Leu Gln Glu Ser Gly Pro Gly Leu Val Lys Pro Ser Glu Thr Leu Ser
    370                 375                 380

Leu Thr Cys Lys Val Ser Gly Phe Ser Phe Ser Ser Gly Tyr Asp Met
385                 390                 395                 400

Cys Trp Ile Arg Gln Pro Pro Gly Lys Gly Leu Glu Trp Ile Gly Cys
                405                 410                 415

Val Val Ala Gly Ser Val Asp Ile Thr Tyr Tyr Ala Ser Trp Ala Lys
            420                 425                 430

Gly Arg Val Thr Ile Ser Val Asp Ser Ser Lys Asn Gln Phe Ser Leu
        435                 440                 445
```

```
Lys Leu Ser Ser Val Thr Ala Ala Asp Thr Ala Val Tyr Tyr Cys Ala
    450                 455                 460

Arg Lys Asp Ala Tyr Ser Asp Ala Phe Asn Leu Trp Gly Gln Gly Thr
465                 470                 475                 480

Leu Val Thr Val Ser Ser
                485


<210> SEQ ID NO 83
<211> LENGTH: 477
<212> TYPE: PRT
<213> ORGANISM: Artificial sequence
<220> FEATURE:
<223> OTHER INFORMATION: artificial antibody-based sequence

<400> SEQUENCE: 83

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Gln Ser Ser Gln Ser Val Phe Ser Asn
                245                 250                 255

Asn Tyr Leu Ala Trp Phe Gln Gln Lys Pro Gly Gln Ser Pro Lys Arg
            260                 265                 270

Leu Ile Tyr Ser Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Leu Gly Ser Tyr Ala Cys
305                 310                 315                 320
```

```
Ser Ser Ala Asp Cys Tyr Val Phe Gly Thr Gly Thr Lys Val Thr Val
                325                 330                 335

Leu Gly Gly Gly Gly Gly Ser Gly Gly Gly Gly Ser Gly Gly Gly Gly
            340                 345                 350

Ser Gly Gly Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Ser Leu Ser Ser Tyr Asp Met Ser Trp Val Arg Gln Ala Pro Gly
385                 390                 395                 400

Lys Gly Leu Ala Trp Ile Gly Ala Ser Tyr Ala Ser Gly Pro Thr Tyr
                405                 410                 415

Tyr Ala Ser Trp Ala Lys Gly Arg Phe Thr Ile Ser Arg Asp Asn Ser
            420                 425                 430

Lys Asn Thr Val Tyr Leu Gln Met Asn Ser Leu Arg Ala Glu Asp Thr
        435                 440                 445

Ala Thr Tyr Phe Cys Ala Arg Gly Gly Trp Thr Gly Thr Ser His Ser
    450                 455                 460

Asn Ile Trp Gly Gln Gly Thr Leu Val Thr Val Ser Ser
465                 470                 475


<210> SEQ ID NO 84
<211> LENGTH: 487
<212> TYPE: PRT
<213> ORGANISM: Artificial sequence
<220> FEATURE:
<223> OTHER INFORMATION: artificial antibody-based sequence

<400> SEQUENCE: 84

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205
```

-continued

```
Pro Ser Asn Thr Lys Val Asp Lys Lys Val Glu Pro Lys Ser Cys Gly
    210                 215                 220

Gly Gly Gly Ser Gly Gly Gly Gly Ser Asp Ile Gln Met Thr Gln Ser
225                 230                 235                 240

Pro Ser Ser Leu Ser Ala Ser Val Gly Asp Arg Val Thr Ile Thr Cys
                245                 250                 255

Gln Ala Ser Glu Asn Ile Tyr Ser Phe Leu Ala Trp Tyr Gln Gln Lys
            260                 265                 270

Pro Gly Lys Ala Pro Lys Leu Leu Ile Tyr Ser Ala Ser Lys Leu Ala
        275                 280                 285

Ala Gly Val Pro Ser Arg Phe Ser Gly Ser Gly Ser Gly Thr Asp Phe
    290                 295                 300

Thr Leu Thr Ile Ser Ser Leu Gln Pro Glu Asp Phe Ala Thr Tyr Tyr
305                 310                 315                 320

Cys Gln Gln Thr Asn Arg Tyr Ser Asn Pro Asp Ile Tyr Asn Val Phe
                325                 330                 335

Gly Thr Gly Thr Lys Val Thr Val Leu Gly Gly Gly Gly Gly Ser Gly
            340                 345                 350

Gly Gly Gly Ser Gly Gly Gly Gly Ser Gly Gly Gly Gly Ser Glu Val
        355                 360                 365

Gln Leu Val Glu Ser Gly Gly Gly Leu Val Gln Pro Gly Gly Ser Leu
    370                 375                 380

Arg Leu Ser Cys Ala Ala Ser Gly Ile Asp Phe Asn Ser Asn Tyr Tyr
385                 390                 395                 400

Met Cys Trp Val Arg Gln Ala Pro Gly Lys Gly Leu Glu Trp Ile Gly
                405                 410                 415

Cys Ile Tyr Val Gly Ser His Val Asn Thr Tyr Tyr Ala Asn Trp Ala
            420                 425                 430

Lys Gly Arg Phe Thr Ile Ser Arg Asp Asn Ser Lys Asn Thr Val Tyr
        435                 440                 445

Leu Gln Met Asn Ser Leu Arg Ala Glu Asp Thr Ala Val Tyr Tyr Cys
    450                 455                 460

Ala Thr Ser Gly Ser Ser Val Leu Tyr Phe Lys Phe Trp Gly Gln Gly
465                 470                 475                 480

Thr Leu Val Thr Val Ser Ser
                485


<210> SEQ ID NO 85
<211> LENGTH: 477
<212> TYPE: PRT
<213> ORGANISM: Artificial sequence
<220> FEATURE:
<223> OTHER INFORMATION: artificial antibody-based sequence

<400> SEQUENCE: 85

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80
```

-continued

```
Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Gly Ser Gly Gly Gly Gly Ser
    210                 215                 220

Asp Ile Gln Met Thr Gln Ser Pro Ser Ser Leu Ser Ala Ser Val Gly
225                 230                 235                 240

Asp Arg Val Thr Ile Thr Cys Gln Ser Ser Gln Ser Val Phe Ser Asn
                245                 250                 255

Asn Tyr Leu Ala Trp Phe Gln Gln Lys Pro Gly Gln Ser Pro Lys Arg
            260                 265                 270

Leu Ile Tyr Ser Ala Ser Thr Leu Ala Ser Gly Val Pro Ser Arg Phe
        275                 280                 285

Ser Gly Ser Gly Ser Gly Thr Asp Phe Thr Leu Thr Ile Ser Ser Leu
    290                 295                 300

Gln Pro Glu Asp Phe Ala Thr Tyr Tyr Cys Leu Gly Ser Tyr Ala Cys
305                 310                 315                 320

Ser Ser Ala Asp Cys Tyr Val Phe Gly Thr Gly Thr Lys Val Thr Val
                325                 330                 335

Leu Gly Gly Gly Gly Gly Ser Gly Gly Gly Gly Ser Gly Gly Gly Gly
            340                 345                 350

Ser Gly Gly Gly Gly Ser Glu Val Gln Leu Val Glu Ser Gly Gly Gly
        355                 360                 365

Leu Val Gln Pro Gly Gly Ser Leu Arg Leu Ser Cys Ala Ala Ser Gly
    370                 375                 380

Phe Ser Leu Ser Ser Tyr Asp Met Ser Trp Val Arg Gln Ala Pro Gly
385                 390                 395                 400

Lys Gly Leu Ala Trp Ile Gly Ala Ser Tyr Ala Ser Gly Pro Thr Tyr
                405                 410                 415

Tyr Ala Ser Trp Ala Lys Gly Arg Phe Thr Ile Ser Arg Asp Asn Ser
            420                 425                 430

Lys Asn Thr Val Tyr Leu Gln Met Asn Ser Leu Arg Ala Glu Asp Thr
        435                 440                 445

Ala Thr Tyr Phe Cys Ala Arg Gly Gly Trp Thr Gly Thr Ser His Ser
    450                 455                 460

Asn Ile Trp Gly Gln Gly Thr Leu Val Thr Val Ser Ser
465                 470                 475
```

<210> SEQ ID NO 86
<211> LENGTH: 485
<212> TYPE: PRT

<213> ORGANISM: Artificial sequence
<220> FEATURE:
<223> OTHER INFORMATION: artificial antibody-based sequence

<400> SEQUENCE: 86

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Gly
    210                 215                 220

Gly Gly Gly Ser Gly Gly Gly Gly Ser Asp Ile Gln Met Thr Gln Ser
225                 230                 235                 240

Pro Ser Ser Leu Ser Ala Ser Val Gly Asp Arg Val Thr Ile Thr Cys
                245                 250                 255

Gln Ala Ser Gln Ser Ile Asn Asp Tyr Leu Ala Trp Tyr Gln Gln Lys
            260                 265                 270

Pro Gly Lys Ala Pro Lys Leu Leu Ile Tyr Lys Ala Ser Thr Leu Ala
        275                 280                 285

Ser Gly Val Pro Ser Arg Phe Ser Gly Ser Gly Ser Gly Thr Asp Phe
    290                 295                 300

Thr Leu Thr Ile Ser Ser Leu Gln Pro Glu Asp Phe Ala Thr Tyr Tyr
305                 310                 315                 320

Cys Gln Ala Ala Tyr Ile Ile Thr Asp Ile Asp Asn Val Phe Gly Thr
                325                 330                 335

Gly Thr Lys Val Thr Val Leu Gly Gly Gly Gly Gly Ser Gly Gly Gly
            340                 345                 350

Gly Ser Gly Gly Gly Gly Ser Gly Gly Gly Gly Ser Gln Val Gln Leu
        355                 360                 365

Gln Glu Ser Gly Pro Gly Leu Val Lys Pro Ser Glu Thr Leu Ser Leu
    370                 375                 380

Thr Cys Lys Val Ser Gly Phe Ser Phe Ser Ser Gly Tyr Asp Met Cys
```

385 390 395 400

Trp Ile Arg Gln Pro Pro Gly Lys Gly Leu Glu Trp Ile Gly Cys Val
405 410 415

Val Ala Gly Ser Val Asp Ile Thr Tyr Tyr Ala Ser Trp Ala Lys Gly
420 425 430

Arg Val Thr Ile Ser Val Asp Ser Ser Lys Asn Gln Phe Ser Leu Lys
435 440 445

Leu Ser Ser Val Thr Ala Ala Asp Thr Ala Val Tyr Tyr Cys Ala Arg
450 455 460

Lys Asp Ala Tyr Ser Asp Ala Phe Asn Leu Trp Gly Gln Gly Thr Leu
465 470 475 480

Val Thr Val Ser Ser
485

<210> SEQ ID NO 87
<211> LENGTH: 482
<212> TYPE: PRT
<213> ORGANISM: Artificial sequence
<220> FEATURE:
<223> OTHER INFORMATION: artificial antibody-based sequence

<400> SEQUENCE: 87

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Ser Ala Ser Lys Leu Ala Ala Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Asn Arg Tyr Ser Asn
85 90 95

Pro Asp Ile Tyr Asn Val Phe Gly Thr Gly Thr Lys Val Thr Val Leu
100 105 110

Gly Thr Val Ala Ala Pro Ser Val Phe Ile Phe Pro Pro Ser Asp Glu
115 120 125

Gln Leu Lys Ser Gly Thr Ala Ser Val Val Cys Leu Leu Asn Asn Phe
130 135 140

Tyr Pro Arg Glu Ala Lys Val Gln Trp Lys Val Asp Asn Ala Leu Gln
145 150 155 160

Ser Gly Asn Ser Gln Glu Ser Val Thr Glu Gln Asp Ser Lys Asp Ser
165 170 175

Thr Tyr Ser Leu Ser Ser Thr Leu Thr Leu Ser Lys Ala Asp Tyr Glu
180 185 190

Lys His Lys Val Tyr Ala Cys Glu Val Thr His Gln Gly Leu Ser Ser
195 200 205

Pro Val Thr Lys Ser Phe Asn Arg Gly Glu Cys Gly Gly Gly Gly Ser
210 215 220

Gly Gly Gly Gly Ser Asp Ile Gln Met Thr Gln Ser Pro Ser Ser Leu
225 230 235 240

Ser Ala Ser Val Gly Asp Arg Val Thr Ile Thr Cys Gln Ser Ser Gln
245 250 255

Ser Val Phe Ser Asn Asn Tyr Leu Ala Trp Phe Gln Gln Lys Pro Gly

```
            260                 265                 270

Gln Ser Pro Lys Arg Leu Ile Tyr Ser Ala Ser Thr Leu Ala Ser Gly
        275                 280                 285

Val Pro Ser Arg Phe Ser Gly Ser Gly Ser Gly Thr Asp Phe Thr Leu
    290                 295                 300

Thr Ile Ser Ser Leu Gln Pro Glu Asp Phe Ala Thr Tyr Tyr Cys Leu
305                 310                 315                 320

Gly Ser Tyr Ala Cys Ser Ser Ala Asp Cys Tyr Val Phe Gly Thr Gly
                325                 330                 335

Thr Lys Val Thr Val Leu Gly Gly Gly Gly Gly Ser Gly Gly Gly Gly
            340                 345                 350

Ser Gly Gly Gly Gly Ser Gly Gly Gly Gly Ser Glu Val Gln Leu Val
        355                 360                 365

Glu Ser Gly Gly Gly Leu Val Gln Pro Gly Gly Ser Leu Arg Leu Ser
    370                 375                 380

Cys Ala Ala Ser Gly Phe Ser Leu Ser Ser Tyr Asp Met Ser Trp Val
385                 390                 395                 400

Arg Gln Ala Pro Gly Lys Gly Leu Ala Trp Ile Gly Ala Ser Tyr Ala
                405                 410                 415

Ser Gly Pro Thr Tyr Tyr Ala Ser Trp Ala Lys Gly Arg Phe Thr Ile
            420                 425                 430

Ser Arg Asp Asn Ser Lys Asn Thr Val Tyr Leu Gln Met Asn Ser Leu
        435                 440                 445

Arg Ala Glu Asp Thr Ala Thr Tyr Phe Cys Ala Arg Gly Gly Trp Thr
    450                 455                 460

Gly Thr Ser His Ser Asn Ile Trp Gly Gln Gly Thr Leu Val Thr Val
465                 470                 475                 480

Ser Ser


<210> SEQ ID NO 88
<211> LENGTH: 486
<212> TYPE: PRT
<213> ORGANISM: Artificial sequence
<220> FEATURE:
<223> OTHER INFORMATION: artificial antibody-based sequence

<400> SEQUENCE: 88

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30

Tyr Tyr Met Cys Trp Val Arg Gln Ala Pro Gly Lys Gly Leu Glu Trp
        35                  40                  45

Ile Gly Cys Ile Tyr Val Gly Ser His Val Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140
```

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
    210                 215                 220

Gly Gly Gly Gly Ser Gly Gly Gly Gly Ser Asp Ile Gln Met Thr Gln
225                 230                 235                 240

Ser Pro Ser Ser Leu Ser Ala Ser Val Gly Asp Arg Val Thr Ile Thr
                245                 250                 255

Cys Gln Ala Ser Gln Ser Ile Asn Asp Tyr Leu Ala Trp Tyr Gln Gln
            260                 265                 270

Lys Pro Gly Lys Ala Pro Lys Leu Leu Ile Tyr Lys Ala Ser Thr Leu
        275                 280                 285

Ala Ser Gly Val Pro Ser Arg Phe Ser Gly Ser Gly Ser Gly Thr Asp
    290                 295                 300

Phe Thr Leu Thr Ile Ser Ser Leu Gln Pro Glu Asp Phe Ala Thr Tyr
305                 310                 315                 320

Tyr Cys Gln Ala Ala Tyr Ile Ile Thr Asp Ile Asp Asn Val Phe Gly
                325                 330                 335

Thr Gly Thr Lys Val Thr Val Leu Gly Gly Gly Gly Gly Ser Gly Gly
            340                 345                 350

Gly Gly Ser Gly Gly Gly Gly Ser Gly Gly Gly Gly Ser Gln Val Gln
        355                 360                 365

Leu Gln Glu Ser Gly Pro Gly Leu Val Lys Pro Ser Glu Thr Leu Ser
    370                 375                 380

Leu Thr Cys Lys Val Ser Gly Phe Ser Phe Ser Ser Gly Tyr Asp Met
385                 390                 395                 400

Cys Trp Ile Arg Gln Pro Pro Gly Lys Gly Leu Glu Trp Ile Gly Cys
                405                 410                 415

Val Val Ala Gly Ser Val Asp Ile Thr Tyr Tyr Ala Ser Trp Ala Lys
            420                 425                 430

Gly Arg Val Thr Ile Ser Val Asp Ser Ser Lys Asn Gln Phe Ser Leu
        435                 440                 445

Lys Leu Ser Ser Val Thr Ala Ala Asp Thr Ala Val Tyr Tyr Cys Ala
    450                 455                 460

Arg Lys Asp Ala Tyr Ser Asp Ala Phe Asn Leu Trp Gly Gln Gly Thr
465                 470                 475                 480

Leu Val Thr Val Ser Ser
                485


<210> SEQ ID NO 89
<211> LENGTH: 488
<212> TYPE: PRT
<213> ORGANISM: Artificial sequence
<220> FEATURE:
<223> OTHER INFORMATION: artificial antibody-based sequence

<400> SEQUENCE: 89

Asp Ile Gln Met Thr Gln Ser Pro Ser Ser Leu Ser Ala Ser Val Gly
1               5                   10                  15
```

-continued

```
Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Asp Val Val Met Thr Gln Ser Pro Ser Ser Leu Ser Ala Ser
            260                 265                 270

Val Gly Asp Arg Val Thr Ile Thr Cys Gln Ala Ser Gln Ile Ile Ser
        275                 280                 285

Ser Arg Ser Ala Trp Tyr Gln Gln Lys Pro Gly Gln Pro Pro Lys Leu
    290                 295                 300

Leu Ile Tyr Gln Ala Ser Lys Leu Ala Ser Gly Val Pro Ser Arg Phe
305                 310                 315                 320

Ser Gly Ser Gly Ser Gly Thr Asp Phe Thr Leu Thr Ile Ser Ser Leu
                325                 330                 335

Gln Pro Glu Asp Phe Ala Thr Tyr Tyr Cys Gln Cys Thr Tyr Ile Asp
            340                 345                 350

Ser Asn Phe Gly Ala Phe Gly Cys Gly Thr Lys Leu Thr Val Leu Gly
        355                 360                 365

Gly Gly Ser Gly Gly Ser Asp Ile Gln Met Thr Gln Ser Pro Ser Ser
    370                 375                 380

Leu Ser Ala Ser Val Gly Asp Arg Val Thr Ile Thr Cys Gln Ser Ser
385                 390                 395                 400

Gln Ser Val Phe Ser Asn Asn Tyr Leu Ala Trp Phe Gln Gln Lys Pro
                405                 410                 415

Gly Gln Ser Pro Lys Arg Leu Ile Tyr Ser Ala Ser Thr Leu Ala Ser
            420                 425                 430
```

Gly Val Pro Ser Arg Phe Ser Gly Ser Gly Ser Gly Thr Asp Phe Thr
435 440 445

Leu Thr Ile Ser Ser Leu Gln Pro Glu Asp Phe Ala Thr Tyr Tyr Cys
450 455 460

Leu Gly Ser Tyr Ala Cys Ser Ser Ala Asp Cys Tyr Val Phe Gly Thr
465 470 475 480

Gly Thr Lys Val Thr Val Leu Gly
485

<210> SEQ ID NO 90
<211> LENGTH: 510
<212> TYPE: PRT
<213> ORGANISM: Artificial sequence
<220> FEATURE:
<223> OTHER INFORMATION: artificial antibody-based sequence

<400> SEQUENCE: 90

Asp Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asp Tyr
20 25 30

Leu Ala Trp Tyr Gln Gln Lys Pro Gly Lys Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Ala Ala Tyr Ile Ile Thr Asp
85 90 95

Ile Asp Asn Val Phe Gly Thr Gly Thr Lys Val Thr Val Leu Gly Gly
100 105 110

Gly Gly Gly Ser Gly Gly Gly Gly Ser Gly Gly Gly Gly Ser Gly Gly
115 120 125

Gly Gly Ser Gln Val Gln Leu Gln Glu Ser Gly Pro Gly Leu Val Lys
130 135 140

Pro Ser Glu Thr Leu Ser Leu Thr Cys Lys Val Ser Gly Phe Ser Phe
145 150 155 160

Ser Ser Gly Tyr Asp Met Cys Trp Ile Arg Gln Pro Pro Gly Lys Gly
165 170 175

Leu Glu Trp Ile Gly Cys Val Val Ala Gly Ser Val Asp Ile Thr Tyr
180 185 190

Tyr Ala Ser Trp Ala Lys Gly Arg Val Thr Ile Ser Val Asp Ser Ser
195 200 205

Lys Asn Gln Phe Ser Leu Lys Leu Ser Ser Val Thr Ala Ala Asp Thr
210 215 220

Ala Val Tyr Tyr Cys Ala Arg Lys Asp Ala Tyr Ser Asp Ala Phe Asn
225 230 235 240

Leu Trp Gly Gln Gly Thr Leu Val Thr Val Ser Ser Gly Gly Gly Gly
245 250 255

Ser Gly Gly Gly Gly Ser Glu Val Gln Leu Val Glu Ser Gly Gly Gly
260 265 270

Leu Val Gln Pro Gly Gly Ser Leu Arg Leu Ser Cys Ala Ala Ser Gly
275 280 285

Phe Ser Leu Ser Ser Tyr Asp Met Ser Trp Val Arg Gln Ala Pro Gly
290 295 300

-continued

```
Lys Gly Leu Ala Trp Ile Gly Ala Ser Tyr Ala Ser Gly Pro Thr Tyr
305                 310                 315                 320

Tyr Ala Ser Trp Ala Lys Gly Arg Phe Thr Ile Ser Arg Asp Asn Ser
                325                 330                 335

Lys Asn Thr Val Tyr Leu Gln Met Asn Ser Leu Arg Ala Glu Asp Thr
            340                 345                 350

Ala Thr Tyr Phe Cys Ala Arg Gly Gly Trp Thr Gly Thr Ser His Ser
        355                 360                 365

Asn Ile Trp Gly Gln Gly Thr Leu Val Thr Val Ser Ser Gly Gly Gly
    370                 375                 380

Ser Gly Gly Gly Ser Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Ser Phe Ser Ser Ser Tyr Trp Ile Cys Trp Val Arg Gln Ala Pro Gly
            420                 425                 430

Lys Cys Leu Glu Trp Val Gly Cys Val Phe Thr Gly Asp Gly Thr Thr
        435                 440                 445

Tyr Tyr Ala Ser Trp Ala Lys Gly Arg Phe Thr Ile Ser Arg Asp Asn
    450                 455                 460

Ser Lys Asn Thr Val Tyr Leu Gln Met Asn Ser Leu Arg Ala Glu Asp
465                 470                 475                 480

Thr Ala Thr Tyr Phe Cys Ala Arg Pro Val Ser Val Tyr Tyr Tyr Gly
                485                 490                 495

Met Asp Leu Trp Gly Gln Gly Thr Leu Val Thr Val Ser Ser
            500                 505                 510
```

<210> SEQ ID NO 91
<211> LENGTH: 492
<212> TYPE: PRT
<213> ORGANISM: Artificial sequence
<220> FEATURE:
<223> OTHER INFORMATION: artificial antibody-based sequence

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160
```

-continued

```
Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Asp Val Val Met Thr Gln Ser Pro Ser Ser
            260                 265                 270

Leu Ser Ala Ser Val Gly Asp Arg Val Thr Ile Thr Cys Gln Ala Ser
        275                 280                 285

Gln Ile Ile Ser Ser Arg Ser Ala Trp Tyr Gln Gln Lys Pro Gly Gln
    290                 295                 300

Pro Pro Lys Leu Leu Ile Tyr Gln Ala Ser Lys Leu Ala Ser Gly Val
305                 310                 315                 320

Pro Ser Arg Phe Ser Gly Ser Gly Ser Gly Thr Asp Phe Thr Leu Thr
                325                 330                 335

Ile Ser Ser Leu Gln Pro Glu Asp Phe Ala Thr Tyr Tyr Cys Gln Cys
            340                 345                 350

Thr Tyr Ile Asp Ser Asn Phe Gly Ala Phe Gly Cys Gly Thr Lys Leu
        355                 360                 365

Thr Val Leu Gly Gly Gly Ser Gly Gly Ser Asp Ile Gln Met Thr Gln
    370                 375                 380

Ser Pro Ser Ser Leu Ser Ala Ser Val Gly Asp Arg Val Thr Ile Thr
385                 390                 395                 400

Cys Gln Ser Ser Gln Ser Val Phe Ser Asn Asn Tyr Leu Ala Trp Phe
                405                 410                 415

Gln Gln Lys Pro Gly Gln Ser Pro Lys Arg Leu Ile Tyr Ser Ala Ser
            420                 425                 430

Thr Leu Ala Ser Gly Val Pro Ser Arg Phe Ser Gly Ser Gly Ser Gly
        435                 440                 445

Thr Asp Phe Thr Leu Thr Ile Ser Ser Leu Gln Pro Glu Asp Phe Ala
    450                 455                 460

Thr Tyr Tyr Cys Leu Gly Ser Tyr Ala Cys Ser Ser Ala Asp Cys Tyr
465                 470                 475                 480

Val Phe Gly Thr Gly Thr Lys Val Thr Val Leu Gly
                485                 490


<210> SEQ ID NO 92
<211> LENGTH: 506
<212> TYPE: PRT
<213> ORGANISM: Artificial sequence
<220> FEATURE:
<223> OTHER INFORMATION: artificial antibody-based sequence

<400> SEQUENCE: 92

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30
```

-continued

```
Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Ser Leu Ser
        275                 280                 285

Ser Tyr Asp Met Ser Trp Val Arg Gln Ala Pro Gly Lys Gly Leu Ala
    290                 295                 300

Trp Ile Gly Ala Ser Tyr Ala Ser Gly Pro Thr Tyr Tyr Ala Ser Trp
305                 310                 315                 320

Ala Lys Gly Arg Phe Thr Ile Ser Arg Asp Asn Ser Lys Asn Thr Val
                325                 330                 335

Tyr Leu Gln Met Asn Ser Leu Arg Ala Glu Asp Thr Ala Thr Tyr Phe
            340                 345                 350

Cys Ala Arg Gly Gly Trp Thr Gly Thr Ser His Ser Asn Ile Trp Gly
        355                 360                 365

Gln Gly Thr Leu Val Thr Val Ser Ser Gly Gly Gly Ser Gly Gly Gly
    370                 375                 380

Ser Glu Val Gln Leu Val Glu Ser Gly Gly Gly Leu Val Gln Pro Gly
385                 390                 395                 400

Gly Ser Leu Arg Leu Ser Cys Ala Ala Ser Gly Phe Ser Phe Ser Ser
                405                 410                 415

Ser Tyr Trp Ile Cys Trp Val Arg Gln Ala Pro Gly Lys Cys Leu Glu
            420                 425                 430

Trp Val Gly Cys Val Phe Thr Gly Asp Gly Thr Thr Tyr Tyr Ala Ser
        435                 440                 445

Trp Ala Lys Gly Arg Phe Thr Ile Ser Arg Asp Asn Ser Lys Asn Thr
```

-continued

```
    450                 455                 460

Val Tyr Leu Gln Met Asn Ser Leu Arg Ala Glu Asp Thr Ala Thr Tyr
465                 470                 475                 480

Phe Cys Ala Arg Pro Val Ser Val Tyr Tyr Tyr Gly Met Asp Leu Trp
                485                 490                 495

Gly Gln Gly Thr Leu Val Thr Val Ser Ser
            500                 505


<210> SEQ ID NO 93
<211> LENGTH: 492
<212> TYPE: PRT
<213> ORGANISM: Artificial sequence
<220> FEATURE:
<223> OTHER INFORMATION: artificial antibody-based sequence

<400> SEQUENCE: 93

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Asp Val Val Met Thr Gln Ser Pro Ser Ser
            260                 265                 270

Leu Ser Ala Ser Val Gly Asp Arg Val Thr Ile Thr Cys Gln Ala Ser
        275                 280                 285

Gln Ile Ile Ser Ser Arg Ser Ala Trp Tyr Gln Gln Lys Pro Gly Gln
    290                 295                 300

Pro Pro Lys Leu Leu Ile Tyr Gln Ala Ser Lys Leu Ala Ser Gly Val
```

-continued 305 310 315 320

Pro Ser Arg Phe Ser Gly Ser Gly Ser Gly Thr Asp Phe Thr Leu Thr
325 330 335

Ile Ser Ser Leu Gln Pro Glu Asp Phe Ala Thr Tyr Tyr Cys Gln Cys
340 345 350

Thr Tyr Ile Asp Ser Asn Phe Gly Ala Phe Gly Cys Gly Thr Lys Leu
355 360 365

Thr Val Leu Gly Gly Gly Ser Gly Gly Ser Asp Ile Gln Met Thr Gln
370 375 380

Ser Pro Ser Ser Leu Ser Ala Ser Val Gly Asp Arg Val Thr Ile Thr
385 390 395 400

Cys Gln Ser Ser Gln Ser Val Phe Ser Asn Asn Tyr Leu Ala Trp Phe
405 410 415

Gln Gln Lys Pro Gly Gln Ser Pro Lys Arg Leu Ile Tyr Ser Ala Ser
420 425 430

Thr Leu Ala Ser Gly Val Pro Ser Arg Phe Ser Gly Ser Gly Ser Gly
435 440 445

Thr Asp Phe Thr Leu Thr Ile Ser Ser Leu Gln Pro Glu Asp Phe Ala
450 455 460

Thr Tyr Tyr Cys Leu Gly Ser Tyr Ala Cys Ser Ser Ala Asp Cys Tyr
465 470 475 480

Val Phe Gly Thr Gly Thr Lys Val Thr Val Leu Gly
485 490

<210> SEQ ID NO 94
<211> LENGTH: 512
<212> TYPE: PRT
<213> ORGANISM: Artificial sequence
<220> FEATURE:
<223> OTHER INFORMATION: artificial antibody-based sequence

<400> SEQUENCE: 94

Asp Ile Gln Met Thr Gln Ser Pro Ser Ser Leu Ser Ala Ser Val Gly
1 5 10 15

Asp Arg Val Thr Ile Thr Cys Gln Ala Ser Glu Asn Ile Tyr Ser Phe
20 25 30

Leu Ala Trp Tyr Gln Gln Lys Pro Gly Lys Ala Pro Lys Leu Leu Ile
35 40 45

Tyr Ser Ala Ser Lys Leu Ala Ala Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Thr Asn Arg Tyr Ser Asn
85 90 95

Pro Asp Ile Tyr Asn Val Phe Gly Thr Gly Thr Lys Val Thr Val Leu
100 105 110

Gly Gly Gly Gly Gly Ser Gly Gly Gly Gly Ser Gly Gly Gly Gly Ser
115 120 125

Gly Gly Gly Gly Ser Glu Val Gln Leu Val Glu Ser Gly Gly Gly Leu
130 135 140

Val Gln Pro Gly Gly Ser Leu Arg Leu Ser Cys Ala Ala Ser Gly Ile
145 150 155 160

Asp Phe Asn Ser Asn Tyr Tyr Met Cys Trp Val Arg Gln Ala Pro Gly
165 170 175

Lys Gly Leu Glu Trp Ile Gly Cys Ile Tyr Val Gly Ser His Val Asn

-continued

```
            180                 185                 190

Thr Tyr Tyr Ala Asn Trp Ala Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Ala Thr Ser Gly Ser Ser Val Leu Tyr
225                 230                 235                 240

Phe Lys Phe Trp Gly Gln Gly Thr Leu Val Thr Val Ser Ser Gly Gly
                245                 250                 255

Gly Gly Ser Gly Gly Gly Gly Ser Glu Val Gln Leu Val Glu Ser Gly
            260                 265                 270

Gly Gly Leu Val Gln Pro Gly Gly Ser Leu Arg Leu Ser Cys Ala Ala
        275                 280                 285

Ser Gly Phe Ser Leu Ser Ser Tyr Asp Met Ser Trp Val Arg Gln Ala
    290                 295                 300

Pro Gly Lys Gly Leu Ala Trp Ile Gly Ala Ser Tyr Ala Ser Gly Pro
305                 310                 315                 320

Thr Tyr Tyr Ala Ser Trp Ala Lys Gly Arg Phe Thr Ile Ser Arg Asp
                325                 330                 335

Asn Ser Lys Asn Thr Val Tyr Leu Gln Met Asn Ser Leu Arg Ala Glu
            340                 345                 350

Asp Thr Ala Thr Tyr Phe Cys Ala Arg Gly Gly Trp Thr Gly Thr Ser
        355                 360                 365

His Ser Asn Ile Trp Gly Gln Gly Thr Leu Val Thr Val Ser Ser Gly
    370                 375                 380

Gly Gly Ser Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
                405                 410                 415

Gly Phe Ser Phe Ser Ser Ser Tyr Trp Ile Cys Trp Val Arg Gln Ala
            420                 425                 430

Pro Gly Lys Cys Leu Glu Trp Val Gly Cys Val Phe Thr Gly Asp Gly
        435                 440                 445

Thr Thr Tyr Tyr Ala Ser Trp Ala Lys Gly Arg Phe Thr Ile Ser Arg
    450                 455                 460

Asp Asn Ser Lys Asn Thr Val Tyr Leu Gln Met Asn Ser Leu Arg Ala
465                 470                 475                 480

Glu Asp Thr Ala Thr Tyr Phe Cys Ala Arg Pro Val Ser Val Tyr Tyr
                485                 490                 495

Tyr Gly Met Asp Leu Trp Gly Gln Gly Thr Leu Val Thr Val Ser Ser
            500                 505                 510


<210> SEQ ID NO 95
<211> LENGTH: 494
<212> TYPE: PRT
<213> ORGANISM: Artificial sequence
<220> FEATURE:
<223> OTHER INFORMATION: artificial antibody-based sequence

<400> SEQUENCE: 95

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
```

-continued

```
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
                165                 170                 175

Lys Gly Leu Glu Trp Ile Gly Cys Ile Tyr Val Gly Ser His Val Asn
            180                 185                 190

Thr Tyr Tyr Ala Asn Trp Ala Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Ala Thr Ser Gly Ser Ser Val Leu Tyr
225                 230                 235                 240

Phe Lys Phe Trp Gly Gln Gly Thr Leu Val Thr Val Ser Ser Gly Gly
                245                 250                 255

Gly Gly Ser Gly Gly Gly Gly Ser Asp Val Val Met Thr Gln Ser Pro
            260                 265                 270

Ser Ser Leu Ser Ala Ser Val Gly Asp Arg Val Thr Ile Thr Cys Gln
        275                 280                 285

Ala Ser Gln Ile Ile Ser Ser Arg Ser Ala Trp Tyr Gln Gln Lys Pro
    290                 295                 300

Gly Gln Pro Pro Lys Leu Leu Ile Tyr Gln Ala Ser Lys Leu Ala Ser
305                 310                 315                 320

Gly Val Pro Ser Arg Phe Ser Gly Ser Gly Ser Gly Thr Asp Phe Thr
                325                 330                 335

Leu Thr Ile Ser Ser Leu Gln Pro Glu Asp Phe Ala Thr Tyr Tyr Cys
            340                 345                 350

Gln Cys Thr Tyr Ile Asp Ser Asn Phe Gly Ala Phe Gly Cys Gly Thr
        355                 360                 365

Lys Leu Thr Val Leu Gly Gly Gly Ser Gly Gly Ser Asp Ile Gln Met
    370                 375                 380

Thr Gln Ser Pro Ser Ser Leu Ser Ala Ser Val Gly Asp Arg Val Thr
385                 390                 395                 400

Ile Thr Cys Gln Ser Ser Gln Ser Val Phe Ser Asn Asn Tyr Leu Ala
                405                 410                 415

Trp Phe Gln Gln Lys Pro Gly Gln Ser Pro Lys Arg Leu Ile Tyr Ser
            420                 425                 430

Ala Ser Thr Leu Ala Ser Gly Val Pro Ser Arg Phe Ser Gly Ser Gly
        435                 440                 445

Ser Gly Thr Asp Phe Thr Leu Thr Ile Ser Ser Leu Gln Pro Glu Asp
    450                 455                 460
```

```
Phe Ala Thr Tyr Tyr Cys Leu Gly Ser Tyr Ala Cys Ser Ser Ala Asp
465                 470                 475                 480

Cys Tyr Val Phe Gly Thr Gly Thr Lys Val Thr Val Leu Gly
                485                 490


<210> SEQ ID NO 96
<211> LENGTH: 510
<212> TYPE: PRT
<213> ORGANISM: Artificial sequence
<220> FEATURE:
<223> OTHER INFORMATION: artificial antibody-based sequence

<400> SEQUENCE: 96

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Ser Leu Ser Ser Tyr Asp Met Ser Trp Val Arg Gln Ala Pro Gly
    290                 295                 300

Lys Gly Leu Ala Trp Ile Gly Ala Ser Tyr Ala Ser Gly Pro Thr Tyr
305                 310                 315                 320

Tyr Ala Ser Trp Ala Lys Gly Arg Phe Thr Ile Ser Arg Asp Asn Ser
                325                 330                 335
```

```
Lys Asn Thr Val Tyr Leu Gln Met Asn Ser Leu Arg Ala Glu Asp Thr
            340                 345                 350

Ala Thr Tyr Phe Cys Ala Arg Gly Gly Trp Thr Gly Thr Ser His Ser
        355                 360                 365

Asn Ile Trp Gly Gln Gly Thr Leu Val Thr Val Ser Ser Gly Gly Gly
    370                 375                 380

Ser Gly Gly Gly Ser Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Ser Phe Ser Ser Ser Tyr Trp Ile Cys Trp Val Arg Gln Ala Pro Gly
            420                 425                 430

Lys Cys Leu Glu Trp Val Gly Cys Val Phe Thr Gly Asp Gly Thr Thr
        435                 440                 445

Tyr Tyr Ala Ser Trp Ala Lys Gly Arg Phe Thr Ile Ser Arg Asp Asn
    450                 455                 460

Ser Lys Asn Thr Val Tyr Leu Gln Met Asn Ser Leu Arg Ala Glu Asp
465                 470                 475                 480

Thr Ala Thr Tyr Phe Cys Ala Arg Pro Val Ser Val Tyr Tyr Tyr Gly
                485                 490                 495

Met Asp Leu Trp Gly Gln Gly Thr Leu Val Thr Val Ser Ser
            500                 505                 510


<210> SEQ ID NO 97
<211> LENGTH: 599
<212> TYPE: PRT
<213> ORGANISM: Artificial sequence
<220> FEATURE:
<223> OTHER INFORMATION: artificial antibody-based sequence

<400> SEQUENCE: 97

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Asp Val Val Met Thr Gln Ser Pro
        115                 120                 125

Ser Ser Leu Ser Ala Ser Val Gly Asp Arg Val Thr Ile Thr Cys Gln
    130                 135                 140

Ala Ser Gln Ile Ile Ser Ser Arg Ser Ala Trp Tyr Gln Gln Lys Pro
145                 150                 155                 160

Gly Gln Pro Pro Lys Leu Leu Ile Tyr Gln Ala Ser Lys Leu Ala Ser
                165                 170                 175

Gly Val Pro Ser Arg Phe Ser Gly Ser Gly Ser Gly Thr Asp Phe Thr
            180                 185                 190
```

```
Leu Thr Ile Ser Ser Leu Gln Pro Glu Asp Phe Ala Thr Tyr Tyr Cys
        195                 200                 205

Gln Cys Thr Tyr Ile Asp Ser Asn Phe Gly Ala Phe Gly Cys Gly Thr
    210                 215                 220

Lys Leu Thr Val Leu Gly Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

Gly Gly Gly Gly Ser Gly Gly Gly Gly Ser Asp Ile Gln Met Thr Gln
            340                 345                 350

Ser Pro Ser Ser Leu Ser Ala Ser Val Gly Asp Arg Val Thr Ile Thr
        355                 360                 365

Cys Gln Ser Ser Gln Ser Val Phe Ser Asn Asn Tyr Leu Ala Trp Phe
    370                 375                 380

Gln Gln Lys Pro Gly Gln Ser Pro Lys Arg Leu Ile Tyr Ser Ala Ser
385                 390                 395                 400

Thr Leu Ala Ser Gly Val Pro Ser Arg Phe Ser Gly Ser Gly Ser Gly
                405                 410                 415

Thr Asp Phe Thr Leu Thr Ile Ser Ser Leu Gln Pro Glu Asp Phe Ala
            420                 425                 430

Thr Tyr Tyr Cys Leu Gly Ser Tyr Ala Cys Ser Ser Ala Asp Cys Tyr
        435                 440                 445

Val Phe Gly Thr Gly Thr Lys Val Thr Val Leu Gly Gly Gly Gly Gly
    450                 455                 460

Ser Gly Gly Gly Gly Ser Gly Gly Gly Gly Ser Gly Gly Gly Gly Ser
465                 470                 475                 480

Glu Val Gln Leu Val Glu Ser Gly Gly Gly Leu Val Gln Pro Gly Gly
                485                 490                 495

Ser Leu Arg Leu Ser Cys Ala Ala Ser Gly Phe Ser Leu Ser Ser Tyr
            500                 505                 510

Asp Met Ser Trp Val Arg Gln Ala Pro Gly Lys Gly Leu Ala Trp Ile
        515                 520                 525

Gly Ala Ser Tyr Ala Ser Gly Pro Thr Tyr Tyr Ala Ser Trp Ala Lys
    530                 535                 540

Gly Arg Phe Thr Ile Ser Arg Asp Asn Ser Lys Asn Thr Val Tyr Leu
545                 550                 555                 560

Gln Met Asn Ser Leu Arg Ala Glu Asp Thr Ala Thr Tyr Phe Cys Ala
                565                 570                 575

Arg Gly Gly Trp Thr Gly Thr Ser His Ser Asn Ile Trp Gly Gln Gly
            580                 585                 590

Thr Leu Val Thr Val Ser Ser
        595
```

<210> SEQ ID NO 98
<211> LENGTH: 618
<212> TYPE: PRT
<213> ORGANISM: Artificial sequence
<220> FEATURE:
<223> OTHER INFORMATION: artificial antibody-based sequence

<400> SEQUENCE: 98

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Glu Val Gln Leu Val Glu Ser Gly Gly Gly Leu
    130                 135                 140

Val Gln Pro Gly Gly Ser Leu Arg Leu Ser Cys Ala Ala Ser Gly Phe
145                 150                 155                 160

Ser Phe Ser Ser Ser Tyr Trp Ile Cys Trp Val Arg Gln Ala Pro Gly
                165                 170                 175

Lys Cys Leu Glu Trp Val Gly Cys Val Phe Thr Gly Asp Gly Thr Thr
            180                 185                 190

Tyr Tyr Ala Ser Trp Ala Lys Gly Arg Phe Thr Ile Ser Arg Asp Asn
        195                 200                 205

Ser Lys Asn Thr Val Tyr Leu Gln Met Asn Ser Leu Arg Ala Glu Asp
    210                 215                 220

Thr Ala Thr Tyr Phe Cys Ala Arg Pro Val Ser Val Tyr Tyr Tyr Gly
225                 230                 235                 240

Met Asp Leu Trp Gly Gln Gly Thr Leu Val Thr Val Ser Ser Ala Ser
                245                 250                 255

Thr Lys Gly Pro Ser Val Phe Pro Leu Ala Pro Ser Ser Lys Ser Thr
            260                 265                 270

Ser Gly Gly Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Gln Thr Tyr Ile
                325                 330                 335

Cys Asn Val Asn His Lys Pro Ser Asn Thr Lys Val Asp Lys Lys Val
            340                 345                 350

Glu Pro Lys Ser Cys Gly Gly Gly Gly Ser Gly Gly Gly Gly Ser Ile
        355                 360                 365
```

```
Gln Met Thr Gln Ser Pro Ser Ser Leu Ser Ala Ser Val Gly Asp Arg
    370                 375                 380

Val Thr Ile Thr Cys Gln Ala Ser Gln Ser Ile Asn Asp Tyr Leu Ala
385                 390                 395                 400

Trp Tyr Gln Gln Lys Pro Gly Lys Ala Pro Lys Leu Leu Ile Tyr Lys
                405                 410                 415

Ala Ser Thr Leu Ala Ser Gly Val Pro Ser Arg Phe Ser Gly Ser Gly
            420                 425                 430

Ser Gly Thr Asp Phe Thr Leu Thr Ile Ser Ser Leu Gln Pro Glu Asp
        435                 440                 445

Phe Ala Thr Tyr Tyr Cys Gln Ala Ala Tyr Ile Ile Thr Asp Ile Asp
    450                 455                 460

Asn Val Phe Gly Thr Gly Thr Lys Val Thr Val Leu Gly Gly Gly Gly
465                 470                 475                 480

Gly Ser Gly Gly Gly Gly Ser Gly Gly Gly Gly Ser Gly Gly Gly Gly
                485                 490                 495

Ser Gln Val Gln Leu Gln Glu Ser Gly Pro Gly Leu Val Lys Pro Ser
            500                 505                 510

Glu Thr Leu Ser Leu Thr Cys Lys Val Ser Gly Phe Ser Phe Ser Ser
        515                 520                 525

Gly Tyr Asp Met Cys Trp Ile Arg Gln Pro Pro Gly Lys Gly Leu Glu
    530                 535                 540

Trp Ile Gly Cys Val Val Ala Gly Ser Val Asp Ile Thr Tyr Tyr Ala
545                 550                 555                 560

Ser Trp Ala Lys Gly Arg Val Thr Ile Ser Val Asp Ser Ser Lys Asn
                565                 570                 575

Gln Phe Ser Leu Lys Leu Ser Ser Val Thr Ala Ala Asp Thr Ala Val
            580                 585                 590

Tyr Tyr Cys Ala Arg Lys Asp Ala Tyr Ser Asp Ala Phe Asn Leu Trp
        595                 600                 605

Gly Gln Gly Thr Leu Val Thr Val Ser Ser
    610                 615


<210> SEQ ID NO 99
<211> LENGTH: 599
<212> TYPE: PRT
<213> ORGANISM: Artificial sequence
<220> FEATURE:
<223> OTHER INFORMATION: artificial antibody-based sequence

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110
```

-continued

```
Pro Ser Val Phe Ile Phe Pro Pro Asp Val Val Met Thr Gln Ser Pro
        115                 120                 125

Ser Ser Leu Ser Ala Ser Val Gly Asp Arg Val Thr Ile Thr Cys Gln
    130                 135                 140

Ala Ser Gln Ile Ile Ser Ser Arg Ser Ala Trp Tyr Gln Gln Lys Pro
145                 150                 155                 160

Gly Gln Pro Pro Lys Leu Leu Ile Tyr Gln Ala Ser Lys Leu Ala Ser
                165                 170                 175

Gly Val Pro Ser Arg Phe Ser Gly Ser Gly Ser Gly Thr Asp Phe Thr
            180                 185                 190

Leu Thr Ile Ser Ser Leu Gln Pro Glu Asp Phe Ala Thr Tyr Tyr Cys
        195                 200                 205

Gln Cys Thr Tyr Ile Asp Ser Asn Phe Gly Ala Phe Gly Cys Gly Thr
    210                 215                 220

Lys Leu Thr Val Leu Gly Thr Val Ala Ala Pro Ser Val Phe Ile Phe
225                 230                 235                 240

Pro Pro Ser Asp Glu Gln Leu Lys Ser Gly Thr Ala Ser Val Val Cys
                245                 250                 255

Leu Leu Asn Asn Phe Tyr Pro Arg Glu Ala Lys Val Gln Trp Lys Val
            260                 265                 270

Asp Asn Ala Leu Gln Ser Gly Asn Ser Gln Glu Ser Val Thr Glu Gln
        275                 280                 285

Asp Ser Lys Asp Ser Thr Tyr Ser Leu Ser Ser Thr Leu Thr Leu Ser
    290                 295                 300

Lys Ala Asp Tyr Glu Lys His Lys Val Tyr Ala Cys Glu Val Thr His
305                 310                 315                 320

Gln Gly Leu Ser Ser Pro Val Thr Lys Ser Phe Asn Arg Gly Glu Cys
                325                 330                 335

Gly Gly Gly Gly Ser Gly Gly Gly Gly Ser Asp Ile Gln Met Thr Gln
            340                 345                 350

Ser Pro Ser Ser Leu Ser Ala Ser Val Gly Asp Arg Val Thr Ile Thr
        355                 360                 365

Cys Gln Ser Ser Gln Ser Val Phe Ser Asn Asn Tyr Leu Ala Trp Phe
    370                 375                 380

Gln Gln Lys Pro Gly Gln Ser Pro Lys Arg Leu Ile Tyr Ser Ala Ser
385                 390                 395                 400

Thr Leu Ala Ser Gly Val Pro Ser Arg Phe Ser Gly Ser Gly Ser Gly
                405                 410                 415

Thr Asp Phe Thr Leu Thr Ile Ser Ser Leu Gln Pro Glu Asp Phe Ala
            420                 425                 430

Thr Tyr Tyr Cys Leu Gly Ser Tyr Ala Cys Ser Ser Ala Asp Cys Tyr
        435                 440                 445

Val Phe Gly Thr Gly Thr Lys Val Thr Val Leu Gly Gly Gly Gly Gly
    450                 455                 460

Ser Gly Gly Gly Gly Ser Gly Gly Gly Gly Ser Gly Gly Gly Gly Ser
465                 470                 475                 480

Glu Val Gln Leu Val Glu Ser Gly Gly Gly Leu Val Gln Pro Gly Gly
                485                 490                 495

Ser Leu Arg Leu Ser Cys Ala Ala Ser Gly Phe Ser Leu Ser Ser Tyr
            500                 505                 510

Asp Met Ser Trp Val Arg Gln Ala Pro Gly Lys Gly Leu Ala Trp Ile
        515                 520                 525

Gly Ala Ser Tyr Ala Ser Gly Pro Thr Tyr Tyr Ala Ser Trp Ala Lys
```

-continued

```
    530                 535                 540

Gly Arg Phe Thr Ile Ser Arg Asp Asn Ser Lys Asn Thr Val Tyr Leu
545                 550                 555                 560

Gln Met Asn Ser Leu Arg Ala Glu Asp Thr Ala Thr Tyr Phe Cys Ala
                565                 570                 575

Arg Gly Gly Trp Thr Gly Thr Ser His Ser Asn Ile Trp Gly Gln Gly
            580                 585                 590

Thr Leu Val Thr Val Ser Ser
        595


<210> SEQ ID NO 100
<211> LENGTH: 620
<212> TYPE: PRT
<213> ORGANISM: Artificial sequence
<220> FEATURE:
<223> OTHER INFORMATION: artificial antibody-based sequence

<400> SEQUENCE: 100

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Glu Val Gln Leu Val Glu Ser Gly Gly Gly Leu
    130                 135                 140

Val Gln Pro Gly Gly Ser Leu Arg Leu Ser Cys Ala Ala Ser Gly Phe
145                 150                 155                 160

Ser Phe Ser Ser Ser Tyr Trp Ile Cys Trp Val Arg Gln Ala Pro Gly
                165                 170                 175

Lys Cys Leu Glu Trp Val Gly Cys Val Phe Thr Gly Asp Gly Thr Thr
            180                 185                 190

Tyr Tyr Ala Ser Trp Ala Lys Gly Arg Phe Thr Ile Ser Arg Asp Asn
        195                 200                 205

Ser Lys Asn Thr Val Tyr Leu Gln Met Asn Ser Leu Arg Ala Glu Asp
    210                 215                 220

Thr Ala Thr Tyr Phe Cys Ala Arg Pro Val Ser Val Tyr Tyr Tyr Gly
225                 230                 235                 240

Met Asp Leu Trp Gly Gln Gly Thr Leu Val Thr Val Ser Ser Ala Ser
                245                 250                 255

Thr Lys Gly Pro Ser Val Phe Pro Leu Ala Pro Ser Ser Lys Ser Thr
            260                 265                 270

Ser Gly Gly Thr Ala Ala Leu Gly Cys Leu Val Lys Asp Tyr Phe Pro
        275                 280                 285

Glu Pro Val Thr Val Ser Trp Asn Ser Gly Ala Leu Thr Ser Gly Val
```

```
    290                 295                 300

His Thr Phe Pro Ala Val Leu Gln Ser Ser Gly Leu Tyr Ser Leu Ser
305                 310                 315                 320

Ser Val Val Thr Val Pro Ser Ser Ser Leu Gly Thr Gln Thr Tyr Ile
                325                 330                 335

Cys Asn Val Asn His Lys Pro Ser Asn Thr Lys Val Asp Lys Lys Val
            340                 345                 350

Glu Pro Lys Ser Cys Gly Gly Gly Gly Ser Gly Gly Gly Gly Ser Ile
        355                 360                 365

Gln Met Thr Gln Ser Pro Ser Ser Leu Ser Ala Ser Val Gly Asp Arg
    370                 375                 380

Val Thr Ile Thr Cys Gln Ala Ser Glu Asn Ile Tyr Ser Phe Leu Ala
385                 390                 395                 400

Trp Tyr Gln Gln Lys Pro Gly Lys Ala Pro Lys Leu Leu Ile Tyr Ser
                405                 410                 415

Ala Ser Lys Leu Ala Ala Gly Val Pro Ser Arg Phe Ser Gly Ser Gly
            420                 425                 430

Ser Gly Thr Asp Phe Thr Leu Thr Ile Ser Ser Leu Gln Pro Glu Asp
        435                 440                 445

Phe Ala Thr Tyr Tyr Cys Gln Gln Thr Asn Arg Tyr Ser Asn Pro Asp
    450                 455                 460

Ile Tyr Asn Val Phe Gly Thr Gly Thr Lys Val Thr Val Leu Gly Gly
465                 470                 475                 480

Gly Gly Gly Ser Gly Gly Gly Gly Ser Gly Gly Gly Gly Ser Gly Gly
                485                 490                 495

Gly Gly Ser Glu Val Gln Leu Val Glu Ser Gly Gly Gly Leu Val Gln
            500                 505                 510

Pro Gly Gly Ser Leu Arg Leu Ser Cys Ala Ala Ser Gly Ile Asp Phe
        515                 520                 525

Asn Ser Asn Tyr Tyr Met Cys Trp Val Arg Gln Ala Pro Gly Lys Gly
    530                 535                 540

Leu Glu Trp Ile Gly Cys Ile Tyr Val Gly Ser His Val Asn Thr Tyr
545                 550                 555                 560

Tyr Ala Asn Trp Ala Lys Gly Arg Phe Thr Ile Ser Arg Asp Asn Ser
                565                 570                 575

Lys Asn Thr Val Tyr Leu Gln Met Asn Ser Leu Arg Ala Glu Asp Thr
            580                 585                 590

Ala Val Tyr Tyr Cys Ala Thr Ser Gly Ser Ser Val Leu Tyr Phe Lys
        595                 600                 605

Phe Trp Gly Gln Gly Thr Leu Val Thr Val Ser Ser
    610                 615                 620


<210> SEQ ID NO 101
<211> LENGTH: 488
<212> TYPE: PRT
<213> ORGANISM: Artificial sequence
<220> FEATURE:
<223> OTHER INFORMATION: artificial antibody-based sequence

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
```

-continued

```
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Asp Val Val Met Thr Gln Ser Pro Ser Ser Leu Ser Ala Ser
            260                 265                 270

Val Gly Asp Arg Val Thr Ile Thr Cys Gln Ala Ser Gln Ile Ile Ser
        275                 280                 285

Ser Arg Ser Ala Trp Tyr Gln Gln Lys Pro Gly Gln Pro Pro Lys Leu
    290                 295                 300

Leu Ile Tyr Gln Ala Ser Lys Leu Ala Ser Gly Val Pro Ser Arg Phe
305                 310                 315                 320

Ser Gly Ser Gly Ser Gly Thr Asp Phe Thr Leu Thr Ile Ser Ser Leu
                325                 330                 335

Gln Pro Glu Asp Phe Ala Thr Tyr Tyr Cys Gln Cys Thr Tyr Ile Asp
            340                 345                 350

Ser Asn Phe Gly Ala Phe Gly Cys Gly Thr Lys Leu Thr Val Leu Gly
        355                 360                 365

Gly Gly Ser Gly Gly Ser Asp Ile Gln Met Thr Gln Ser Pro Ser Ser
    370                 375                 380

Leu Ser Ala Ser Val Gly Asp Arg Val Thr Ile Thr Cys Gln Ser Ser
385                 390                 395                 400

Gln Ser Val Phe Ser Asn Asn Tyr Leu Ala Trp Phe Gln Gln Lys Pro
                405                 410                 415

Gly Gln Ser Pro Lys Arg Leu Ile Tyr Ser Ala Ser Thr Leu Ala Ser
            420                 425                 430

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460
```

```
Leu Gly Ser Tyr Ala Cys Ser Ser Ala Asp Cys Tyr Val Phe Gly Thr
465                 470                 475                 480

Gly Thr Lys Val Thr Val Leu Gly
                485


<210> SEQ ID NO 102
<211> LENGTH: 512
<212> TYPE: PRT
<213> ORGANISM: Artificial sequence
<220> FEATURE:
<223> OTHER INFORMATION: artificial antibody-based sequence

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
                165                 170                 175

Lys Gly Leu Glu Trp Ile Gly Cys Ile Tyr Val Gly Ser His Val Asn
            180                 185                 190

Thr Tyr Tyr Ala Asn Trp Ala Lys Gly Arg Phe Thr Ile Ser Arg Asp
        195                 200                 205

Asn Ser Lys Asn Thr Val Tyr Leu Gln Met Asn Ser Leu Arg Ala Glu
    210                 215                 220

Asp Thr Ala Val Tyr Tyr Cys Ala Thr Ser Gly Ser Ser Val Leu Tyr
225                 230                 235                 240

Phe Lys Phe Trp Gly Gln Gly Thr Leu Val Thr Val Ser Ser Gly Gly
                245                 250                 255

Gly Gly Ser Gly Gly Gly Gly Ser Glu Val Gln Leu Val Glu Ser Gly
            260                 265                 270

Gly Gly Leu Val Gln Pro Gly Gly Ser Leu Arg Leu Ser Cys Ala Ala
        275                 280                 285

Ser Gly Phe Ser Leu Ser Ser Tyr Asp Met Ser Trp Val Arg Gln Ala
    290                 295                 300

Pro Gly Lys Gly Leu Ala Trp Ile Gly Ala Ser Tyr Ala Ser Gly Pro
305                 310                 315                 320

Thr Tyr Tyr Ala Ser Trp Ala Lys Gly Arg Phe Thr Ile Ser Arg Asp
                325                 330                 335
```

```
Asn Ser Lys Asn Thr Val Tyr Leu Gln Met Asn Ser Leu Arg Ala Glu
            340                 345                 350

Asp Thr Ala Thr Tyr Phe Cys Ala Arg Gly Gly Trp Thr Gly Thr Ser
        355                 360                 365

His Ser Asn Ile Trp Gly Gln Gly Thr Leu Val Thr Val Ser Ser Gly
    370                 375                 380

Gly Gly Ser Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
                405                 410                 415

Gly Phe Ser Phe Ser Ser Ser Tyr Trp Ile Cys Trp Val Arg Gln Ala
            420                 425                 430

Pro Gly Lys Cys Leu Glu Trp Val Gly Cys Val Phe Thr Gly Asp Gly
        435                 440                 445

Thr Thr Tyr Tyr Ala Ser Trp Ala Lys Gly Arg Phe Thr Ile Ser Arg
    450                 455                 460

Asp Asn Ser Lys Asn Thr Val Tyr Leu Gln Met Asn Ser Leu Arg Ala
465                 470                 475                 480

Glu Asp Thr Ala Thr Tyr Phe Cys Ala Arg Pro Val Ser Val Tyr Tyr
                485                 490                 495

Tyr Gly Met Asp Leu Trp Gly Gln Gly Thr Leu Val Thr Val Ser Ser
            500                 505                 510


<210> SEQ ID NO 103
<211> LENGTH: 494
<212> TYPE: PRT
<213> ORGANISM: Artificial sequence
<220> FEATURE:
<223> OTHER INFORMATION: artificial antibody-based sequence

<400> SEQUENCE: 103

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Ala Ala Ser Gly Ile
145                 150                 155                 160

Asp Phe Asn Ser Asn Tyr Tyr Met Cys Trp Val Arg Gln Ala Pro Gly
                165                 170                 175

Lys Gly Leu Glu Trp Ile Gly Cys Ile Tyr Val Gly Ser His Val Asn
            180                 185                 190
```

Thr Tyr Tyr Ala Asn Trp Ala Lys Gly Arg Phe Thr Ile Ser Arg Asp
195 200 205

Asn Ser Lys Asn Thr Val Tyr Leu Gln Met Asn Ser Leu Arg Ala Glu
210 215 220

Asp Thr Ala Val Tyr Tyr Cys Ala Thr Ser Gly Ser Ser Val Leu Tyr
225 230 235 240

Phe Lys Phe Trp Gly Gln Gly Thr Leu Val Thr Val Ser Ser Gly Gly
245 250 255

Gly Gly Ser Gly Gly Gly Gly Ser Asp Val Val Met Thr Gln Ser Pro
260 265 270

Ser Ser Leu Ser Ala Ser Val Gly Asp Arg Val Thr Ile Thr Cys Gln
275 280 285

Ala Ser Gln Ile Ile Ser Ser Arg Ser Ala Trp Tyr Gln Gln Lys Pro
290 295 300

Gly Gln Pro Pro Lys Leu Leu Ile Tyr Gln Ala Ser Lys Leu Ala Ser
305 310 315 320

Gly Val Pro Ser Arg Phe Ser Gly Ser Gly Ser Gly Thr Asp Phe Thr
325 330 335

Leu Thr Ile Ser Ser Leu Gln Pro Glu Asp Phe Ala Thr Tyr Tyr Cys
340 345 350

Gln Cys Thr Tyr Ile Asp Ser Asn Phe Gly Ala Phe Gly Cys Gly Thr
355 360 365

Lys Leu Thr Val Leu Gly Gly Gly Ser Gly Gly Ser Asp Ile Gln Met
370 375 380

Thr Gln Ser Pro Ser Ser Leu Ser Ala Ser Val Gly Asp Arg Val Thr
385 390 395 400

Ile Thr Cys Gln Ser Ser Gln Ser Val Phe Ser Asn Asn Tyr Leu Ala
405 410 415

Trp Phe Gln Gln Lys Pro Gly Gln Ser Pro Lys Arg Leu Ile Tyr Ser
420 425 430

Ala Ser Thr Leu Ala Ser Gly Val Pro Ser Arg Phe Ser Gly Ser Gly
435 440 445

Ser Gly Thr Asp Phe Thr Leu Thr Ile Ser Ser Leu Gln Pro Glu Asp
450 455 460

Phe Ala Thr Tyr Tyr Cys Leu Gly Ser Tyr Ala Cys Ser Ser Ala Asp
465 470 475 480

Cys Tyr Val Phe Gly Thr Gly Thr Lys Val Thr Val Leu Gly
485 490

<210> SEQ ID NO 104
<211> LENGTH: 506
<212> TYPE: PRT
<213> ORGANISM: Artificial sequence
<220> FEATURE:
<223> OTHER INFORMATION: artificial antibody-based sequence

<400> SEQUENCE: 104

Asp Ile Gln Met Thr Gln Ser Pro Ser Ser Leu Ser Ala Ser Val Gly
1 5 10 15

Asp Arg Val Thr Ile Thr Cys Arg Ala Ser Gln Asp Val Asn Thr Ala
20 25 30

Val Ala Trp Tyr Gln Gln Lys Pro Gly Lys Ala Pro Lys Leu Leu Ile
35 40 45

Tyr Ser Ala Ser Phe Leu Tyr Ser Gly Val Pro Ser Arg Phe Ser Gly
50 55 60

-continued

```
Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Glu Val Gln Leu Val Glu Ser Gly Gly Gly Leu Val Gln Pro
            260                 265                 270

Gly Gly Ser Leu Arg Leu Ser Cys Ala Ala Ser Gly Phe Ser Leu Ser
        275                 280                 285

Ser Tyr Asp Met Ser Trp Val Arg Gln Ala Pro Gly Lys Gly Leu Ala
    290                 295                 300

Trp Ile Gly Ala Ser Tyr Ala Ser Gly Pro Thr Tyr Tyr Ala Ser Trp
305                 310                 315                 320

Ala Lys Gly Arg Phe Thr Ile Ser Arg Asp Asn Ser Lys Asn Thr Val
                325                 330                 335

Tyr Leu Gln Met Asn Ser Leu Arg Ala Glu Asp Thr Ala Thr Tyr Phe
            340                 345                 350

Cys Ala Arg Gly Gly Trp Thr Gly Thr Ser His Ser Asn Ile Trp Gly
        355                 360                 365

Gln Gly Thr Leu Val Thr Val Ser Ser Gly Gly Gly Ser Gly Gly Gly
    370                 375                 380

Ser Glu Val Gln Leu Val Glu Ser Gly Gly Gly Leu Val Gln Pro Gly
385                 390                 395                 400

Gly Ser Leu Arg Leu Ser Cys Ala Ala Ser Gly Phe Ser Phe Ser Ser
                405                 410                 415

Ser Tyr Trp Ile Cys Trp Val Arg Gln Ala Pro Gly Lys Cys Leu Glu
            420                 425                 430

Trp Val Gly Cys Val Phe Thr Gly Asp Gly Thr Thr Tyr Tyr Ala Ser
        435                 440                 445

Trp Ala Lys Gly Arg Phe Thr Ile Ser Arg Asp Asn Ser Lys Asn Thr
    450                 455                 460

Val Tyr Leu Gln Met Asn Ser Leu Arg Ala Glu Asp Thr Ala Thr Tyr
465                 470                 475                 480
```

```
Phe Cys Ala Arg Pro Val Ser Val Tyr Tyr Tyr Gly Met Asp Leu Trp
                485                 490                 495

Gly Gln Gly Thr Leu Val Thr Val Ser Ser
            500                 505


<210> SEQ ID NO 105
<211> LENGTH: 485
<212> TYPE: PRT
<213> ORGANISM: Artificial sequence
<220> FEATURE:
<223> OTHER INFORMATION: artificial antibody-based sequence

<400> SEQUENCE: 105

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Asp Ile Gln Met Thr Gln Ser Pro Ser Ser Leu Ser Ala Ser
            260                 265                 270

Val Gly Asp Arg Val Thr Ile Thr Cys Gln Ala Ser Gln Ser Ile Ser
        275                 280                 285

Asn Arg Leu Ala Trp Tyr Gln Gln Lys Pro Gly Lys Ala Pro Lys Leu
    290                 295                 300

Leu Ile Tyr Ser Ala Ser Thr Leu Ala Ser Gly Val Pro Ser Arg Phe
305                 310                 315                 320

Ser Gly Ser Gly Ser Gly Thr Asp Phe Thr Leu Thr Ile Ser Ser Leu
                325                 330                 335
```

-continued

```
Gln Pro Glu Asp Phe Ala Thr Tyr Tyr Cys Gln Ser Thr Tyr Tyr Gly
            340                 345                 350

Asn Asp Gly Asn Ala Phe Gly Cys Gly Thr Lys Val Thr Val Leu Gly
        355                 360                 365

Gly Gly Ser Gly Gly Ser Asp Ile Gln Met Thr Gln Ser Pro Ser Ser
    370                 375                 380

Leu Ser Ala Ser Val Gly Asp Arg Val Thr Ile Thr Cys Gln Ala Ser
385                 390                 395                 400

Gln Ser Ile Asn Asp Tyr Leu Ala Trp Tyr Gln Gln Lys Pro Gly Lys
                405                 410                 415

Ala Pro Lys Leu Leu Ile Tyr Lys Ala Ser Thr Leu Ala Ser Gly Val
            420                 425                 430

Pro Ser Arg Phe Ser Gly Ser Gly Ser Gly Thr Asp Phe Thr Leu Thr
        435                 440                 445

Ile Ser Ser Leu Gln Pro Glu Asp Phe Ala Thr Tyr Tyr Cys Gln Ala
    450                 455                 460

Ala Tyr Ile Ile Thr Asp Ile Asp Asn Val Phe Gly Thr Gly Thr Lys
465                 470                 475                 480

Val Thr Val Leu Gly
                485


<210> SEQ ID NO 106
<211> LENGTH: 512
<212> TYPE: PRT
<213> ORGANISM: Artificial sequence
<220> FEATURE:
<223> OTHER INFORMATION: artificial antibody-based sequence

<400> SEQUENCE: 106

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ile Ile Ser Ser Arg
            20                  25                  30

Ser Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Ile Asp Ser Asn
                85                  90                  95

Phe Gly Ala Phe Gly Gly Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ser Ser Tyr Trp Ile Cys Trp Val Arg Gln Ala Pro Gly Lys Gly Leu
                165                 170                 175

Glu Trp Val Gly Cys Val Phe Thr Gly Asp Gly Thr Thr Tyr Tyr Ala
            180                 185                 190

Ser Trp Ala Lys Gly Arg Phe Thr Ile Ser Arg Asp Asn Ser Lys Asn
        195                 200                 205
```

```
Thr Val Tyr Leu Gln Met Asn Ser Leu Arg Ala Glu Asp Thr Ala Thr
    210                 215                 220

Tyr Phe Cys Ala Arg Pro Val Ser Val Tyr Tyr Tyr Gly Met Asp Leu
225                 230                 235                 240

Trp Gly Gln Gly Thr Leu Val Thr Val Ser Ser Gly Gly Gly Gly Ser
                245                 250                 255

Gly Gly Gly Gly Ser Gln Val Gln Leu Gln Glu Ser Gly Pro Gly Leu
            260                 265                 270

Val Lys Pro Ser Glu Thr Leu Ser Leu Thr Cys Lys Val Ser Gly Phe
        275                 280                 285

Ser Phe Ser Ser Gly Tyr Asp Met Cys Trp Ile Arg Gln Pro Pro Gly
    290                 295                 300

Lys Gly Leu Glu Trp Ile Gly Cys Val Val Ala Gly Ser Val Asp Ile
305                 310                 315                 320

Thr Tyr Tyr Ala Ser Trp Ala Lys Gly Arg Val Thr Ile Ser Val Asp
                325                 330                 335

Ser Ser Lys Asn Gln Phe Ser Leu Lys Leu Ser Ser Val Thr Ala Ala
            340                 345                 350

Asp Thr Ala Val Tyr Tyr Cys Ala Arg Lys Asp Ala Tyr Ser Asp Ala
        355                 360                 365

Phe Asn Leu Trp Gly Gln Gly Thr Leu Val Thr Val Ser Ser Gly Gly
    370                 375                 380

Gly Ser Gly Gly Gly Ser Glu Val Gln Leu Val Glu Ser Gly Gly Gly
385                 390                 395                 400

Leu Val Gln Pro Gly Gly Ser Leu Arg Leu Ser Cys Ala Ala Ser Gly
                405                 410                 415

Phe Ser Phe Ser Ala Asn Tyr Tyr Pro Cys Trp Val Arg Gln Ala Pro
            420                 425                 430

Gly Lys Cys Leu Glu Trp Ile Gly Cys Ile Tyr Gly Gly Ser Ser Asp
        435                 440                 445

Ile Thr Tyr Asp Ala Asn Trp Thr Lys Gly Arg Phe Thr Ile Ser Arg
    450                 455                 460

Asp Asn Ser Lys Asn Thr Val Tyr Leu Gln Met Asn Ser Leu Arg Ala
465                 470                 475                 480

Glu Asp Thr Ala Val Tyr Tyr Cys Ala Arg Ser Ala Trp Tyr Ser Gly
                485                 490                 495

Trp Gly Gly Asp Leu Trp Gly Gln Gly Thr Leu Val Thr Val Ser Ser
            500                 505                 510


<210> SEQ ID NO 107
<211> LENGTH: 485
<212> TYPE: PRT
<213> ORGANISM: Artificial sequence
<220> FEATURE:
<223> OTHER INFORMATION: artificial antibody-based sequence

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60
```

-continued

Ser Arg Ser Gly Thr Asp Phe Thr Leu Thr Ile Ser Ser Leu Gln Pro
65 70 75 80

Glu Asp Phe Ala Thr Tyr Tyr Cys Gln Gln His Tyr Thr Thr Pro Pro
85 90 95

Thr Phe Gly Cys Gly Thr Lys Leu Thr Val Leu Gly Gly Gly Gly Gly
100 105 110

Ser Gly Gly Gly Gly Ser Gly Gly Gly Gly Ser Gly Gly Gly Gly Ser
115 120 125

Glu Val Gln Leu Val Glu Ser Gly Gly Gly Leu Val Gln Pro Gly Gly
130 135 140

Ser Leu Arg Leu Ser Cys Ala Ala Ser Gly Phe Asn Ile Lys Asp Thr
145 150 155 160

Tyr Ile His Trp Val Arg Gln Ala Pro Gly Lys Cys Leu Glu Trp Val
165 170 175

Ala Arg Ile Tyr Pro Thr Asn Gly Tyr Thr Arg Tyr Ala Asp Ser Val
180 185 190

Lys Gly Arg Phe Thr Ile Ser Ala Asp Thr Ser Lys Asn Thr Ala Tyr
195 200 205

Leu Gln Met Asn Ser Leu Arg Ala Glu Asp Thr Ala Val Tyr Tyr Cys
210 215 220

Ser Arg Trp Gly Gly Asp Gly Phe Tyr Ala Met Asp Tyr Trp Gly Gln
225 230 235 240

Gly Thr Leu Val Thr Val Ser Ser Gly Gly Gly Gly Ser Gly Gly Gly
245 250 255

Gly Ser Asp Val Val Met Thr Gln Ser Pro Ser Ser Leu Ser Ala Ser
260 265 270

Val Gly Asp Arg Val Thr Ile Thr Cys Gln Ala Ser Gln Ile Ile Ser
275 280 285

Ser Arg Ser Ala Trp Tyr Gln Gln Lys Pro Gly Gln Pro Pro Lys Leu
290 295 300

Leu Ile Tyr Gln Ala Ser Lys Leu Ala Ser Gly Val Pro Ser Arg Phe
305 310 315 320

Ser Gly Ser Gly Ser Gly Thr Asp Phe Thr Leu Thr Ile Ser Ser Leu
325 330 335

Gln Pro Glu Asp Phe Ala Thr Tyr Tyr Cys Gln Cys Thr Tyr Ile Asp
340 345 350

Ser Asn Phe Gly Ala Phe Gly Cys Gly Thr Lys Leu Thr Val Leu Gly
355 360 365

Gly Gly Ser Gly Gly Ser Asp Ile Gln Met Thr Gln Ser Pro Ser Ser
370 375 380

Leu Ser Ala Ser Val Gly Asp Arg Val Thr Ile Thr Cys Gln Ala Ser
385 390 395 400

Gln Ser Ile Asn Asp Tyr Leu Ala Trp Tyr Gln Gln Lys Pro Gly Lys
405 410 415

Ala Pro Lys Leu Leu Ile Tyr Lys Ala Ser Thr Leu Ala Ser Gly Val
420 425 430

Pro Ser Arg Phe Ser Gly Ser Gly Ser Gly Thr Asp Phe Thr Leu Thr
435 440 445

Ile Ser Ser Leu Gln Pro Glu Asp Phe Ala Thr Tyr Tyr Cys Gln Ala
450 455 460

Ala Tyr Ile Ile Thr Asp Ile Asp Asn Val Phe Gly Thr Gly Thr Lys
465 470 475 480

Val Thr Val Leu Gly

485

<210> SEQ ID NO 108
<211> LENGTH: 512
<212> TYPE: PRT
<213> ORGANISM: Artificial sequence
<220> FEATURE:
<223> OTHER INFORMATION: artificial antibody-based sequence

<400> SEQUENCE: 108

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
                85                  90                  95

Gly Asn Ala Phe Gly Cys Gly Thr Lys Val Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ala Asn Tyr Tyr Pro Cys Trp Val Arg Gln Ala Pro Gly Lys Cys Leu
                165                 170                 175

Glu Trp Ile Gly Cys Ile Tyr Gly Gly Ser Ser Asp Ile Thr Tyr Asp
            180                 185                 190

Ala Asn Trp Thr Lys Gly Arg Phe Thr Ile Ser Arg Asp Asn Ser Lys
        195                 200                 205

Asn Thr Val Tyr Leu Gln Met Asn Ser Leu Arg Ala Glu Asp Thr Ala
    210                 215                 220

Val Tyr Tyr Cys Ala Arg Ser Ala Trp Tyr Ser Gly Trp Gly Gly Asp
225                 230                 235                 240

Leu Trp Gly Gln Gly Thr Leu Val Thr Val Ser Ser Gly Gly Gly Gly
                245                 250                 255

Ser Gly Gly Gly Gly Ser Gln Val Gln Leu Gln Glu Ser Gly Pro Gly
            260                 265                 270

Leu Val Lys Pro Ser Glu Thr Leu Ser Leu Thr Cys Lys Val Ser Gly
        275                 280                 285

Phe Ser Phe Ser Ser Gly Tyr Asp Met Cys Trp Ile Arg Gln Pro Pro
    290                 295                 300

Gly Lys Gly Leu Glu Trp Ile Gly Cys Val Val Ala Gly Ser Val Asp
305                 310                 315                 320

Ile Thr Tyr Tyr Ala Ser Trp Ala Lys Gly Arg Val Thr Ile Ser Val
                325                 330                 335

Asp Ser Ser Lys Asn Gln Phe Ser Leu Lys Leu Ser Ser Val Thr Ala
            340                 345                 350

Ala Asp Thr Ala Val Tyr Tyr Cys Ala Arg Lys Asp Ala Tyr Ser Asp
```

```
        355                 360                 365

Ala Phe Asn Leu Trp Gly Gln Gly Thr Leu Val Thr Val Ser Ser Gly
    370                 375                 380

Gly Gly Ser Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
                405                 410                 415

Gly Phe Ser Phe Ser Ser Ser Tyr Trp Ile Cys Trp Val Arg Gln Ala
            420                 425                 430

Pro Gly Lys Cys Leu Glu Trp Val Gly Cys Val Phe Thr Gly Asp Gly
        435                 440                 445

Thr Thr Tyr Tyr Ala Ser Trp Ala Lys Gly Arg Phe Thr Ile Ser Arg
    450                 455                 460

Asp Asn Ser Lys Asn Thr Val Tyr Leu Gln Met Asn Ser Leu Arg Ala
465                 470                 475                 480

Glu Asp Thr Ala Thr Tyr Phe Cys Ala Arg Pro Val Ser Val Tyr Tyr
                485                 490                 495

Tyr Gly Met Asp Leu Trp Gly Gln Gly Thr Leu Val Thr Val Ser Ser
            500                 505                 510


<210> SEQ ID NO 109
<211> LENGTH: 486
<212> TYPE: PRT
<213> ORGANISM: Artificial sequence
<220> FEATURE:
<223> OTHER INFORMATION: artificial antibody-based sequence

<400> SEQUENCE: 109

Asp Val Val Met Thr Gln Ser Pro Ser Ser Leu Ser Ala Ser Val Gly
1               5                   10                  15

Asp Arg Val Thr Ile Thr Cys Gln Ala Ser Gln Ile Ile Ser Ser Arg
            20                  25                  30

Ser Ala Trp Tyr Gln Gln Lys Pro Gly Gln Pro Pro Lys Leu Leu Ile
        35                  40                  45

Tyr Gln Ala Ser Lys Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Cys Thr Tyr Ile Asp Ser Asn
                85                  90                  95

Phe Gly Ala Phe Gly Thr Gly Thr Lys Leu Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ser Ser Tyr Trp Ile Cys Trp Val Arg Gln Ala Pro Gly Lys Gly Leu
                165                 170                 175

Glu Trp Val Gly Cys Val Phe Thr Gly Asp Gly Thr Thr Tyr Tyr Ala
            180                 185                 190

Ser Trp Ala Lys Gly Arg Phe Thr Ile Ser Arg Asp Asn Ser Lys Asn
        195                 200                 205

Thr Val Tyr Leu Gln Met Asn Ser Leu Arg Ala Glu Asp Thr Ala Thr
```

```
    210                 215                 220

Tyr Phe Cys Ala Arg Pro Val Ser Val Tyr Tyr Tyr Gly Met Asp Leu
225                 230                 235                 240

Trp Gly Gln Gly Thr Leu Val Thr Val Ser Ser Gly Gly Gly Gly Ser
                245                 250                 255

Gly Gly Gly Gly Ser Asp Ile Gln Met Thr Gln Ser Pro Ser Ser Leu
            260                 265                 270

Ser Ala Ser Val Gly Asp Arg Val Thr Ile Thr Cys Lys Ala Ser Gln
        275                 280                 285

Asp Val Ser Ile Gly Val Ala Trp Tyr Gln Gln Lys Pro Gly Lys Ala
    290                 295                 300

Pro Lys Leu Leu Ile Tyr Ser Ala Ser Tyr Arg Tyr Thr Gly Val Pro
305                 310                 315                 320

Ser Arg Phe Ser Gly Ser Gly Ser Gly Thr Asp Phe Thr Leu Thr Ile
                325                 330                 335

Ser Ser Leu Gln Pro Glu Asp Phe Ala Thr Tyr Tyr Cys Gln Gln Tyr
            340                 345                 350

Tyr Ile Tyr Pro Tyr Thr Phe Gly Cys Gly Thr Lys Val Thr Val Leu
        355                 360                 365

Gly Gly Gly Ser Gly Gly Ser Asp Ile Gln Met Thr Gln Ser Pro Ser
    370                 375                 380

Ser Leu Ser Ala Ser Val Gly Asp Arg Val Thr Ile Thr Cys Gln Ala
385                 390                 395                 400

Ser Gln Ser Ile Asn Asp Tyr Leu Ala Trp Tyr Gln Gln Lys Pro Gly
                405                 410                 415

Lys Ala Pro Lys Leu Leu Ile Tyr Lys Ala Ser Thr Leu Ala Ser Gly
            420                 425                 430

Val Pro Ser Arg Phe Ser Gly Ser Gly Ser Gly Thr Asp Phe Thr Leu
        435                 440                 445

Thr Ile Ser Ser Leu Gln Pro Glu Asp Phe Ala Thr Tyr Tyr Cys Gln
    450                 455                 460

Ala Ala Tyr Ile Ile Thr Asp Ile Asp Asn Val Phe Gly Thr Gly Thr
465                 470                 475                 480

Lys Val Thr Val Leu Gly
                485


<210> SEQ ID NO 110
<211> LENGTH: 510
<212> TYPE: PRT
<213> ORGANISM: Artificial sequence
<220> FEATURE:
<223> OTHER INFORMATION: artificial antibody-based sequence

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Ser Asn Arg
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Thr Tyr Tyr Gly Asn Asp
```

-continued

```
                85                  90                  95

Gly Asn Ala Phe Gly Cys Gly Thr Lys Val Thr Val Leu Gly Gly Gly
            100                 105                 110

Gly Gly Ser Gly Gly Gly Gly Ser Gly Gly Gly Gly Ser Gly Gly Gly
        115                 120                 125

Gly Ser Glu Val Gln Leu Val Glu Ser Gly Gly Gly Leu Val Gln Pro
    130                 135                 140

Gly Gly Ser Leu Arg Leu Ser Cys Ala Ala Ser Gly Phe Ser Phe Ser
145                 150                 155                 160

Ala Asn Tyr Tyr Pro Cys Trp Val Arg Gln Ala Pro Gly Lys Cys Leu
                165                 170                 175

Glu Trp Ile Gly Cys Ile Tyr Gly Gly Ser Ser Asp Ile Thr Tyr Asp
            180                 185                 190

Ala Asn Trp Thr Lys Gly Arg Phe Thr Ile Ser Arg Asp Asn Ser Lys
        195                 200                 205

Asn Thr Val Tyr Leu Gln Met Asn Ser Leu Arg Ala Glu Asp Thr Ala
    210                 215                 220

Val Tyr Tyr Cys Ala Arg Ser Ala Trp Tyr Ser Gly Trp Gly Gly Asp
225                 230                 235                 240

Leu Trp Gly Gln Gly Thr Leu Val Thr Val Ser Ser Gly Gly Gly Gly
                245                 250                 255

Ser Gly Gly Gly Gly Ser Gln Val Gln Leu Gln Glu Ser Gly Pro Gly
            260                 265                 270

Leu Val Lys Pro Ser Glu Thr Leu Ser Leu Thr Cys Lys Val Ser Gly
        275                 280                 285

Phe Ser Phe Ser Ser Gly Tyr Asp Met Cys Trp Ile Arg Gln Pro Pro
    290                 295                 300

Gly Lys Gly Leu Glu Trp Ile Gly Cys Val Val Ala Gly Ser Val Asp
305                 310                 315                 320

Ile Thr Tyr Tyr Ala Ser Trp Ala Lys Gly Arg Val Thr Ile Ser Val
                325                 330                 335

Asp Ser Ser Lys Asn Gln Phe Ser Leu Lys Leu Ser Ser Val Thr Ala
            340                 345                 350

Ala Asp Thr Ala Val Tyr Tyr Cys Ala Arg Lys Asp Ala Tyr Ser Asp
        355                 360                 365

Ala Phe Asn Leu Trp Gly Gln Gly Thr Leu Val Thr Val Ser Ser Gly
    370                 375                 380

Gly Gly Ser Gly Gly Gly Ser Glu Val Gln Leu Val Glu Ser Gly Gly
385                 390                 395                 400

Gly Leu Val Gln Pro Gly Gly Ser Leu Arg Leu Ser Cys Ala Ala Ser
                405                 410                 415

Gly Phe Thr Phe Thr Asp Tyr Thr Met Asp Trp Val Arg Gln Ala Pro
            420                 425                 430

Gly Lys Cys Leu Glu Trp Val Ala Asp Val Asn Pro Asn Ser Gly Gly
        435                 440                 445

Ser Ile Tyr Asn Gln Arg Phe Lys Gly Arg Phe Thr Leu Ser Val Asp
    450                 455                 460

Arg Ser Lys Asn Thr Leu Tyr Leu Gln Met Asn Ser Leu Arg Ala Glu
465                 470                 475                 480

Asp Thr Ala Val Tyr Tyr Cys Ala Arg Asn Leu Gly Pro Ser Phe Tyr
                485                 490                 495

Phe Asp Tyr Trp Gly Gln Gly Thr Leu Val Thr Val Ser Ser
            500                 505                 510
```

<210> SEQ ID NO 111
<211> LENGTH: 483
<212> TYPE: PRT
<213> ORGANISM: Artificial sequence
<220> FEATURE:
<223> OTHER INFORMATION: artificial antibody-based sequence

<400> SEQUENCE: 111

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Cys Gly Thr Lys Val Thr Val Leu Gly Gly Gly Gly Gly
100 105 110

Ser Gly Gly Gly Gly Ser Gly Gly Gly Gly Ser Gly Gly Gly Gly Ser
115 120 125

Glu Val Gln Leu Val Glu Ser Gly Gly Gly Leu Val Gln Pro Gly Gly
130 135 140

Ser Leu Arg Leu Ser Cys Ala Ala Ser Gly Phe Thr Phe Thr Asp Tyr
145 150 155 160

Thr Met Asp Trp Val Arg Gln Ala Pro Gly Lys Cys Leu Glu Trp Val
165 170 175

Ala Asp Val Asn Pro Asn Ser Gly Gly Ser Ile Tyr Asn Gln Arg Phe
180 185 190

Lys Gly Arg Phe Thr Leu Ser Val Asp Arg Ser Lys Asn Thr Leu Tyr
195 200 205

Leu Gln Met Asn Ser Leu Arg Ala Glu Asp Thr Ala Val Tyr Tyr Cys
210 215 220

Ala Arg Asn Leu Gly Pro Ser Phe Tyr Phe Asp Tyr Trp Gly Gln Gly
225 230 235 240

Thr Leu Val Thr Val Ser Ser Gly Gly Gly Gly Ser Gly Gly Gly Gly
245 250 255

Ser Asp Val Val Met Thr Gln Ser Pro Ser Ser Leu Ser Ala Ser Val
260 265 270

Gly Asp Arg Val Thr Ile Thr Cys Gln Ala Ser Gln Ile Ile Ser Ser
275 280 285

Arg Ser Ala Trp Tyr Gln Gln Lys Pro Gly Gln Pro Pro Lys Leu Leu
290 295 300

Ile Tyr Gln Ala Ser Lys Leu Ala Ser Gly Val Pro Ser Arg Phe Ser
305 310 315 320

Gly Ser Gly Ser Gly Thr Asp Phe Thr Leu Thr Ile Ser Ser Leu Gln
325 330 335

Pro Glu Asp Phe Ala Thr Tyr Tyr Cys Gln Cys Thr Tyr Ile Asp Ser
340 345 350

Asn Phe Gly Ala Phe Gly Thr Gly Thr Lys Leu Thr Val Leu Gly Gly
355 360 365

```
Gly Ser Gly Gly Ser Asp Ile Gln Met Thr Gln Ser Pro Ser Ser Leu
    370                 375                 380

Ser Ala Ser Val Gly Asp Arg Val Thr Ile Thr Cys Gln Ala Ser Gln
385                 390                 395                 400

Ser Ile Ser Asn Arg Leu Ala Trp Tyr Gln Gln Lys Pro Gly Lys Ala
                405                 410                 415

Pro Lys Leu Leu Ile Tyr Ser Ala Ser Thr Leu Ala Ser Gly Val Pro
            420                 425                 430

Ser Arg Phe Ser Gly Ser Gly Ser Gly Thr Asp Phe Thr Leu Thr Ile
        435                 440                 445

Ser Ser Leu Gln Pro Glu Asp Phe Ala Thr Tyr Tyr Cys Gln Ser Thr
    450                 455                 460

Tyr Tyr Gly Asn Asp Gly Asn Ala Phe Gly Cys Gly Thr Lys Val Thr
465                 470                 475                 480

Val Leu Gly


<210> SEQ ID NO 112
<211> LENGTH: 513
<212> TYPE: PRT
<213> ORGANISM: Artificial sequence
<220> FEATURE:
<223> OTHER INFORMATION: artificial antibody-based sequence

<400> SEQUENCE: 112

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240
```

```
Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Ser Phe Ser Ala Asn Tyr Tyr Pro Cys Trp Val Arg Gln Ala Pro
    290                 295                 300

Gly Lys Cys Leu Glu Trp Ile Gly Cys Ile Tyr Gly Gly Ser Ser Asp
305                 310                 315                 320

Ile Thr Tyr Asp Ala Asn Trp Thr Lys Gly Arg Phe Thr Ile Ser Arg
                325                 330                 335

Asp Asn Ser Lys Asn Thr Val Tyr Leu Gln Met Asn Ser Leu Arg Ala
            340                 345                 350

Glu Asp Thr Ala Val Tyr Tyr Cys Ala Arg Ser Ala Trp Tyr Ser Gly
        355                 360                 365

Trp Gly Gly Asp Leu Trp Gly Gln Gly Thr Leu Val Thr Val Ser Ser
    370                 375                 380

Gly Gly Gly Ser Gly Gly Gly Ser Glu Val Gln Leu Val Glu Ser Gly
385                 390                 395                 400

Gly Gly Leu Val Gln Pro Gly Gly Ser Leu Arg Leu Ser Cys Ala Ala
                405                 410                 415

Ser Gly Phe Ser Phe Ser Ser Ser Tyr Trp Ile Cys Trp Val Arg Gln
            420                 425                 430

Ala Pro Gly Lys Gly Leu Glu Trp Val Gly Cys Val Phe Thr Gly Asp
        435                 440                 445

Gly Thr Thr Tyr Tyr Ala Ser Trp Ala Lys Gly Arg Phe Thr Ile Ser
    450                 455                 460

Arg Asp Asn Ser Lys Asn Thr Val Tyr Leu Gln Met Asn Ser Leu Arg
465                 470                 475                 480

Ala Glu Asp Thr Ala Thr Tyr Phe Cys Ala Arg Pro Val Ser Val Tyr
                485                 490                 495

Tyr Tyr Gly Met Asp Leu Trp Gly Gln Gly Thr Leu Val Thr Val Ser
            500                 505                 510

Ser


<210> SEQ ID NO 113
<211> LENGTH: 485
<212> TYPE: PRT
<213> ORGANISM: Artificial sequence
<220> FEATURE:
<223> OTHER INFORMATION: artificial antibody-based sequence

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
```

```
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Gln Ser Ser Glu Ser Val Tyr Ser
        275                 280                 285

Asn Asn Gln Leu Ser Trp Tyr Gln Gln Lys Pro Gly Gln Pro Pro Lys
    290                 295                 300

Leu Leu Ile Tyr Asp Ala Ser Asp Leu Ala Ser Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Ala Gly Gly Phe Ser
            340                 345                 350

Ser Ser Ser Asp Thr Ala Phe Gly Gly Gly Thr Lys Leu Thr Val Leu
        355                 360                 365

Gly Gly Gly Ser Gly Gly Ser Asp Ile Gln Met Thr Gln Ser Pro Ser
    370                 375                 380

Ser Leu Ser Ala Ser Val Gly Asp Arg Val Thr Ile Thr Cys Gln Ala
385                 390                 395                 400

Ser Gln Ser Ile Ser Asn Arg Leu Ala Trp Tyr Gln Gln Lys Pro Gly
                405                 410                 415

Lys Ala Pro Lys Leu Leu Ile Tyr Ser Ala Ser Thr Leu Ala Ser Gly
            420                 425                 430

Val Pro Ser Arg Phe Ser Gly Ser Gly Ser Gly Thr Asp Phe Thr Leu
        435                 440                 445

Thr Ile Ser Ser Leu Gln Pro Glu Asp Phe Ala Thr Tyr Tyr Cys Gln
    450                 455                 460

Ser Thr Tyr Tyr Gly Asn Asp Gly Asn Ala Phe Gly Cys Gly Thr Lys
465                 470                 475                 480

Val Thr Val Leu Gly
                485
```

<210> SEQ ID NO 114

<211> LENGTH: 513
<212> TYPE: PRT
<213> ORGANISM: Artificial sequence
<220> FEATURE:
<223> OTHER INFORMATION: artificial antibody-based sequence

<400> SEQUENCE: 114

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Ser Phe Ser Ala Asn Tyr Tyr Pro Cys Trp Val Arg Gln Ala Pro
    290                 295                 300

Gly Lys Cys Leu Glu Trp Ile Gly Cys Ile Tyr Gly Gly Ser Ser Asp
305                 310                 315                 320

Ile Thr Tyr Asp Ala Asn Trp Thr Lys Gly Arg Phe Thr Ile Ser Arg
                325                 330                 335

Asp Asn Ser Lys Asn Thr Val Tyr Leu Gln Met Asn Ser Leu Arg Ala
            340                 345                 350

Glu Asp Thr Ala Val Tyr Tyr Cys Ala Arg Ser Ala Trp Tyr Ser Gly
        355                 360                 365

Trp Gly Gly Asp Leu Trp Gly Gln Gly Thr Leu Val Thr Val Ser Ser
    370                 375                 380
```

Gly Gly Gly Ser Gly Gly Gly Ser Glu Val Gln Leu Val Glu Ser Gly
385 390 395 400

Gly Gly Leu Val Gln Pro Gly Gly Ser Leu Arg Leu Ser Cys Ala Ala
405 410 415

Ser Gly Phe Ser Leu Ser Ser Asn Ala Met Gly Trp Val Arg Gln Ala
420 425 430

Pro Gly Lys Gly Leu Glu Tyr Ile Gly Ile Ile Ser Val Gly Gly Phe
435 440 445

Thr Tyr Tyr Ala Ser Trp Ala Lys Gly Arg Phe Thr Ile Ser Arg Asp
450 455 460

Asn Ser Lys Asn Thr Val Tyr Leu Gln Met Asn Ser Leu Arg Ala Glu
465 470 475 480

Asp Thr Ala Thr Tyr Phe Cys Ala Arg Asp Arg His Gly Gly Asp Ser
485 490 495

Ser Gly Ala Phe Tyr Leu Trp Gly Gln Gly Thr Leu Val Thr Val Ser
500 505 510

Ser

<210> SEQ ID NO 115
<211> LENGTH: 749
<212> TYPE: PRT
<213> ORGANISM: Artificial sequence
<220> FEATURE:
<223> OTHER INFORMATION: artificial antibody-based sequence

<400> SEQUENCE: 115

Asp Ile Gln Met Thr Gln Ser Pro Ser Ser Leu Ser Ala Ser Val Gly
1 5 10 15

Asp Arg Val Thr Ile Thr Cys Gln Ala Ser Gln Ser Ile Asn Asp Tyr
20 25 30

Leu Ala Trp Tyr Gln Gln Lys Pro Gly Lys Ala Pro Lys Leu Leu Ile
35 40 45

Tyr Lys Ala Ser Thr Leu Ala Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Ala Ala Tyr Ile Ile Thr Asp
85 90 95

Ile Asp Asn Val Phe Gly Thr Gly Thr Lys Val Thr Val Leu Gly Gly
100 105 110

Gly Gly Gly Ser Glu Val Gln Leu Val Glu Ser Gly Gly Gly Leu Val
115 120 125

Gln Pro Gly Gly Ser Leu Arg Leu Ser Cys Ala Ala Ser Gly Phe Asn
130 135 140

Ile Lys Asp Thr Tyr Ile His Trp Val Arg Gln Ala Pro Gly Lys Cys
145 150 155 160

Leu Glu Trp Val Ala Arg Ile Tyr Pro Thr Asn Gly Tyr Thr Arg Tyr
165 170 175

Ala Asp Ser Val Lys Gly Arg Phe Thr Ile Ser Ala Asp Thr Ser Lys
180 185 190

Asn Thr Ala Tyr Leu Gln Met Asn Ser Leu Arg Ala Glu Asp Thr Ala
195 200 205

Val Tyr Tyr Cys Ser Arg Trp Gly Gly Asp Gly Phe Tyr Ala Met Asp
210 215 220

-continued

```
Tyr Trp Gly Gln Gly Thr Leu Val Thr Val Ser Ser Gly Gly Gly Gly
225                 230                 235                 240

Ser Gly Gly Gly Gly Ser Gly Gly Gly Gly Ser Gly Gly Gly Gly Ser
                245                 250                 255

Ile Gln Met Thr Gln Ser Pro Ser Ser Leu Ser Ala Ser Val Gly Asp
            260                 265                 270

Arg Val Thr Ile Thr Cys Arg Ala Ser Gln Asp Val Asn Thr Ala Val
        275                 280                 285

Ala Trp Tyr Gln Gln Lys Pro Gly Lys Ala Pro Lys Leu Leu Ile Tyr
    290                 295                 300

Ser Ala Ser Phe Leu Tyr Ser Gly Val Pro Ser Arg Phe Ser Gly Ser
305                 310                 315                 320

Arg Ser Gly Thr Asp Phe Thr Leu Thr Ile Ser Ser Leu Gln Pro Glu
                325                 330                 335

Asp Phe Ala Thr Tyr Tyr Cys Gln Gln His Tyr Thr Thr Pro Pro Thr
            340                 345                 350

Phe Gly Cys Gly Thr Lys Leu Thr Val Leu Gly Gly Gly Gly Gly Ser
        355                 360                 365

Gln Val Gln Leu Gln Glu Ser Gly Pro Gly Leu Val Lys Pro Ser Glu
    370                 375                 380

Thr Leu Ser Leu Thr Cys Lys Val Ser Gly Phe Ser Phe Ser Ser Gly
385                 390                 395                 400

Tyr Asp Met Cys Trp Ile Arg Gln Pro Pro Gly Lys Gly Leu Glu Trp
                405                 410                 415

Ile Gly Cys Val Val Ala Gly Ser Val Asp Ile Thr Tyr Tyr Ala Ser
            420                 425                 430

Trp Ala Lys Gly Arg Val Thr Ile Ser Val Asp Ser Ser Lys Asn Gln
        435                 440                 445

Phe Ser Leu Lys Leu Ser Ser Val Thr Ala Ala Asp Thr Ala Val Tyr
    450                 455                 460

Tyr Cys Ala Arg Lys Asp Ala Tyr Ser Asp Ala Phe Asn Leu Trp Gly
465                 470                 475                 480

Gln Gly Thr Leu Val Thr Val Ser Ser Gly Gly Gly Gly Ser Gly Gly
                485                 490                 495

Gly Gly Ser Val Val Met Thr Gln Ser Pro Ser Ser Leu Ser Ala Ser
            500                 505                 510

Val Gly Asp Arg Val Thr Ile Thr Cys Gln Ala Ser Gln Ile Ile Ser
        515                 520                 525

Ser Arg Ser Ala Trp Tyr Gln Gln Lys Pro Gly Gln Pro Pro Lys Leu
    530                 535                 540

Leu Ile Tyr Gln Ala Ser Lys Leu Ala Ser Gly Val Pro Ser Arg Phe
545                 550                 555                 560

Ser Gly Ser Gly Ser Gly Thr Asp Phe Thr Leu Thr Ile Ser Ser Leu
                565                 570                 575

Gln Pro Glu Asp Phe Ala Thr Tyr Tyr Cys Gln Cys Thr Tyr Ile Asp
            580                 585                 590

Ser Asn Phe Gly Ala Phe Gly Gly Gly Thr Lys Leu Thr Val Leu Gly
        595                 600                 605

Gly Gly Gly Gly Ser Gly Gly Gly Gly Ser Gly Gly Gly Gly Ser Gly
    610                 615                 620

Gly Gly Gly Ser Glu Val Gln Leu Val Glu Ser Gly Gly Gly Leu Val
625                 630                 635                 640

Gln Pro Gly Gly Ser Leu Arg Leu Ser Cys Ala Ala Ser Gly Phe Ser
```

```
                645                 650                 655

Phe Ser Ser Ser Tyr Trp Ile Cys Trp Val Arg Gln Ala Pro Gly Lys
            660                 665                 670

Gly Leu Glu Trp Val Gly Cys Val Phe Thr Gly Asp Gly Thr Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Pro Val Ser Val Tyr Tyr Tyr Gly Met
                725                 730                 735

Asp Leu Trp Gly Gln Gly Thr Leu Val Thr Val Ser Ser
            740                 745


<210> SEQ ID NO 116
<211> LENGTH: 749
<212> TYPE: PRT
<213> ORGANISM: Artificial sequence
<220> FEATURE:
<223> OTHER INFORMATION: artificial antibody-based sequence

<400> SEQUENCE: 116

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gln Val Gln Leu Gln Glu Ser Gly Pro Gly Leu Val Lys Pro Ser
        115                 120                 125

Glu Thr Leu Ser Leu Thr Cys Lys Val Ser Gly Phe Ser Phe Ser Ser
    130                 135                 140

Gly Tyr Asp Met Cys Trp Ile Arg Gln Pro Pro Gly Lys Gly Leu Glu
145                 150                 155                 160

Trp Ile Gly Cys Val Val Ala Gly Ser Val Asp Ile Thr Tyr Tyr Ala
                165                 170                 175

Ser Trp Ala Lys Gly Arg Val Thr Ile Ser Val Asp Ser Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Lys Asp Ala Tyr Ser Asp Ala Phe Asn Leu Trp
    210                 215                 220

Gly Gln Gly Thr Leu Val Thr Val Ser Ser Gly Gly Gly Gly Ser Gly
225                 230                 235                 240

Gly Gly Gly Ser Gly Gly Gly Gly Ser Gly Gly Gly Gly Ser Ile Gln
                245                 250                 255

Met Thr Gln Ser Pro Ser Ser Leu Ser Ala Ser Val Gly Asp Arg Val
```

-continued 260 265 270

Thr Ile Thr Cys Gln Ala Ser Gln Ser Ile Asn Asp Tyr Leu Ala Trp
275 280 285

Tyr Gln Gln Lys Pro Gly Lys Ala Pro Lys Leu Leu Ile Tyr Lys Ala
290 295 300

Ser Thr Leu Ala Ser Gly Val Pro Ser Arg Phe Ser Gly Ser Gly Ser
305 310 315 320

Gly Thr Asp Phe Thr Leu Thr Ile Ser Ser Leu Gln Pro Glu Asp Phe
325 330 335

Ala Thr Tyr Tyr Cys Gln Ala Ala Tyr Ile Ile Thr Asp Ile Asp Asn
340 345 350

Val Phe Gly Thr Gly Thr Lys Val Thr Val Leu Gly Gly Gly Gly Gly
355 360 365

Ser Glu Val Gln Leu Val Glu Ser Gly Gly Gly Leu Val Gln Pro Gly
370 375 380

Gly Ser Leu Arg Leu Ser Cys Ala Ala Ser Gly Phe Asn Ile Lys Asp
385 390 395 400

Thr Tyr Ile His Trp Val Arg Gln Ala Pro Gly Lys Cys Leu Glu Trp
405 410 415

Val Ala Arg Ile Tyr Pro Thr Asn Gly Tyr Thr Arg Tyr Ala Asp Ser
420 425 430

Val Lys Gly Arg Phe Thr Ile Ser Ala Asp Thr Ser Lys Asn Thr Ala
435 440 445

Tyr Leu Gln Met Asn Ser Leu Arg Ala Glu Asp Thr Ala Val Tyr Tyr
450 455 460

Cys Ser Arg Trp Gly Gly Asp Gly Phe Tyr Ala Met Asp Tyr Trp Gly
465 470 475 480

Gln Gly Thr Leu Val Thr Val Ser Ser Gly Gly Gly Gly Ser Gly Gly
485 490 495

Gly Gly Ser Val Val Met Thr Gln Ser Pro Ser Ser Leu Ser Ala Ser
500 505 510

Val Gly Asp Arg Val Thr Ile Thr Cys Gln Ala Ser Gln Ile Ile Ser
515 520 525

Ser Arg Ser Ala Trp Tyr Gln Gln Lys Pro Gly Gln Pro Pro Lys Leu
530 535 540

Leu Ile Tyr Gln Ala Ser Lys Leu Ala Ser Gly Val Pro Ser Arg Phe
545 550 555 560

Ser Gly Ser Gly Ser Gly Thr Asp Phe Thr Leu Thr Ile Ser Ser Leu
565 570 575

Gln Pro Glu Asp Phe Ala Thr Tyr Tyr Cys Gln Cys Thr Tyr Ile Asp
580 585 590

Ser Asn Phe Gly Ala Phe Gly Gly Gly Thr Lys Leu Thr Val Leu Gly
595 600 605

Gly Gly Gly Gly Ser Gly Gly Gly Gly Ser Gly Gly Gly Gly Ser Gly
610 615 620

Gly Gly Gly Ser Glu Val Gln Leu Val Glu Ser Gly Gly Gly Leu Val
625 630 635 640

Gln Pro Gly Gly Ser Leu Arg Leu Ser Cys Ala Ala Ser Gly Phe Ser
645 650 655

Phe Ser Ser Ser Tyr Trp Ile Cys Trp Val Arg Gln Ala Pro Gly Lys
660 665 670

Gly Leu Glu Trp Val Gly Cys Val Phe Thr Gly Asp Gly Thr Thr Tyr
675 680 685

```
Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Pro Val Ser Val Tyr Tyr Tyr Gly Met
                725                 730                 735

Asp Leu Trp Gly Gln Gly Thr Leu Val Thr Val Ser Ser
            740                 745


<210> SEQ ID NO 117
<211> LENGTH: 749
<212> TYPE: PRT
<213> ORGANISM: Artificial sequence
<220> FEATURE:
<223> OTHER INFORMATION: artificial antibody-based sequence

<400> SEQUENCE: 117

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Asn
    130                 135                 140

Ile Lys Asp Thr Tyr Ile His Trp Val Arg Gln Ala Pro Gly Lys Cys
145                 150                 155                 160

Leu Glu Trp Val Ala Arg Ile Tyr Pro Thr Asn Gly Tyr Thr Arg Tyr
                165                 170                 175

Ala Asp Ser Val Lys Gly Arg Phe Thr Ile Ser Ala Asp Thr Ser Lys
            180                 185                 190

Asn Thr Ala Tyr Leu Gln Met Asn Ser Leu Arg Ala Glu Asp Thr Ala
        195                 200                 205

Val Tyr Tyr Cys Ser Arg Trp Gly Gly Asp Gly Phe Tyr Ala Met Asp
    210                 215                 220

Tyr Trp Gly Gln Gly Thr Leu Val Thr Val Ser Ser Gly Gly Gly Gly
225                 230                 235                 240

Ser Gly Gly Gly Gly Ser Gly Gly Gly Gly Ser Gly Gly Gly Gly Ser
                245                 250                 255

Ile Gln Met Thr Gln Ser Pro Ser Ser Leu Ser Ala Ser Val Gly Asp
            260                 265                 270

Arg Val Thr Ile Thr Cys Arg Ala Ser Gln Asp Val Asn Thr Ala Val
        275                 280                 285

Ala Trp Tyr Gln Gln Lys Pro Gly Lys Ala Pro Lys Leu Leu Ile Tyr
    290                 295                 300
```

-continued

Ser Ala Ser Phe Leu Tyr Ser Gly Val Pro Ser Arg Phe Ser Gly Ser
305 310 315 320

Arg Ser Gly Thr Asp Phe Thr Leu Thr Ile Ser Ser Leu Gln Pro Glu
325 330 335

Asp Phe Ala Thr Tyr Tyr Cys Gln Gln His Tyr Thr Thr Pro Pro Thr
340 345 350

Phe Gly Cys Gly Thr Lys Leu Thr Val Leu Gly Gly Gly Gly Gly Ser
355 360 365

Gln Val Gln Leu Gln Glu Ser Gly Pro Gly Leu Val Lys Pro Ser Glu
370 375 380

Thr Leu Ser Leu Thr Cys Lys Val Ser Gly Phe Ser Phe Ser Ser Gly
385 390 395 400

Tyr Asp Met Cys Trp Ile Arg Gln Pro Pro Gly Lys Gly Leu Glu Trp
405 410 415

Ile Gly Cys Val Val Ala Gly Ser Val Asp Ile Thr Tyr Tyr Ala Ser
420 425 430

Trp Ala Lys Gly Arg Val Thr Ile Ser Val Asp Ser Ser Lys Asn Gln
435 440 445

Phe Ser Leu Lys Leu Ser Ser Val Thr Ala Ala Asp Thr Ala Val Tyr
450 455 460

Tyr Cys Ala Arg Lys Asp Ala Ala Ser Asp Ala Phe Asn Leu Trp Gly
465 470 475 480

Gln Gly Thr Leu Val Thr Val Ser Ser Gly Gly Gly Gly Ser Gly Gly
485 490 495

Gly Gly Ser Val Val Met Thr Gln Ser Pro Ser Ser Leu Ser Ala Ser
500 505 510

Val Gly Asp Arg Val Thr Ile Thr Cys Gln Ala Ser Gln Ile Ile Ser
515 520 525

Ser Arg Ser Ala Trp Tyr Gln Gln Lys Pro Gly Gln Pro Pro Lys Leu
530 535 540

Leu Ile Tyr Gln Ala Ser Lys Leu Ala Ser Gly Val Pro Ser Arg Phe
545 550 555 560

Ser Gly Ser Gly Ser Gly Thr Asp Phe Thr Leu Thr Ile Ser Ser Leu
565 570 575

Gln Pro Glu Asp Phe Ala Thr Tyr Tyr Cys Gln Cys Thr Tyr Ile Asp
580 585 590

Ser Asn Phe Gly Ala Phe Gly Gly Gly Thr Lys Leu Thr Val Leu Gly
595 600 605

Gly Gly Gly Gly Ser Gly Gly Gly Gly Ser Gly Gly Gly Gly Ser Gly
610 615 620

Gly Gly Gly Ser Glu Val Gln Leu Val Glu Ser Gly Gly Gly Leu Val
625 630 635 640

Gln Pro Gly Gly Ser Leu Arg Leu Ser Cys Ala Ala Ser Gly Phe Ser
645 650 655

Phe Ser Ser Ser Tyr Trp Ile Cys Trp Val Arg Gln Ala Pro Gly Lys
660 665 670

Gly Leu Glu Trp Val Gly Cys Val Phe Thr Gly Asp Gly Thr Thr Tyr
675 680 685

Tyr Ala Ser Trp Ala Lys Gly Arg Phe Thr Ile Ser Arg Asp Asn Ser
690 695 700

Lys Asn Thr Val Tyr Leu Gln Met Asn Ser Leu Arg Ala Glu Asp Thr
705 710 715 720

```
Ala Thr Tyr Phe Cys Ala Arg Pro Val Ser Val Tyr Tyr Tyr Gly Met
                725                 730                 735

Asp Leu Trp Gly Gln Gly Thr Leu Val Thr Val Ser Ser
            740                 745


<210> SEQ ID NO 118
<211> LENGTH: 749
<212> TYPE: PRT
<213> ORGANISM: Artificial sequence
<220> FEATURE:
<223> OTHER INFORMATION: artificial antibody-based sequence

<400> SEQUENCE: 118

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
            100                 105                 110

Ser Gln Val Gln Leu Gln Glu Ser Gly Pro Gly Leu Val Lys Pro Ser
        115                 120                 125

Glu Thr Leu Ser Leu Thr Cys Lys Val Ser Gly Phe Ser Phe Ser Ser
    130                 135                 140

Gly Tyr Asp Met Cys Trp Ile Arg Gln Pro Pro Gly Lys Gly Leu Glu
145                 150                 155                 160

Trp Ile Gly Cys Val Val Ala Gly Ser Val Asp Ile Thr Tyr Tyr Ala
                165                 170                 175

Ser Trp Ala Lys Gly Arg Val Thr Ile Ser Val Asp Ser Ser Lys Asn
            180                 185                 190

Gln Phe Ser Leu Lys Leu Ser Ser Val Thr Ala Ala Asp Thr Ala Val
        195                 200                 205

Tyr Tyr Cys Ala Arg Lys Asp Ala Ala Ser Asp Ala Phe Asn Leu Trp
    210                 215                 220

Gly Gln Gly Thr Leu Val Thr Val Ser Ser Gly Gly Gly Gly Ser Gly
225                 230                 235                 240

Gly Gly Gly Ser Gly Gly Gly Gly Ser Gly Gly Gly Gly Ser Ile Gln
                245                 250                 255

Met Thr Gln Ser Pro Ser Ser Leu Ser Ala Ser Val Gly Asp Arg Val
            260                 265                 270

Thr Ile Thr Cys Gln Ala Ser Gln Ser Ile Asn Asp Tyr Leu Ala Trp
        275                 280                 285

Tyr Gln Gln Lys Pro Gly Lys Ala Pro Lys Leu Leu Ile Tyr Lys Ala
    290                 295                 300

Ser Thr Leu Ala Ser Gly Val Pro Ser Arg Phe Ser Gly Ser Gly Ser
305                 310                 315                 320

Gly Thr Asp Phe Thr Leu Thr Ile Ser Ser Leu Gln Pro Glu Asp Phe
                325                 330                 335
```

-continued

```
Ala Thr Tyr Tyr Cys Gln Ala Gly Tyr Ile Ile Thr Asp Ile Asp Asn
            340                 345                 350

Val Phe Gly Thr Gly Thr Lys Val Thr Val Leu Gly Gly Gly Gly Gly
        355                 360                 365

Ser Glu Val Gln Leu Val Glu Ser Gly Gly Gly Leu Val Gln Pro Gly
    370                 375                 380

Gly Ser Leu Arg Leu Ser Cys Ala Ala Ser Gly Phe Asn Ile Lys Asp
385                 390                 395                 400

Thr Tyr Ile His Trp Val Arg Gln Ala Pro Gly Lys Cys Leu Glu Trp
                405                 410                 415

Val Ala Arg Ile Tyr Pro Thr Asn Gly Tyr Thr Arg Tyr Ala Asp Ser
            420                 425                 430

Val Lys Gly Arg Phe Thr Ile Ser Ala Asp Thr Ser Lys Asn Thr Ala
        435                 440                 445

Tyr Leu Gln Met Asn Ser Leu Arg Ala Glu Asp Thr Ala Val Tyr Tyr
    450                 455                 460

Cys Ser Arg Trp Gly Gly Asp Gly Phe Tyr Ala Met Asp Tyr Trp Gly
465                 470                 475                 480

Gln Gly Thr Leu Val Thr Val Ser Ser Gly Gly Gly Gly Ser Gly Gly
                485                 490                 495

Gly Gly Ser Val Val Met Thr Gln Ser Pro Ser Ser Leu Ser Ala Ser
            500                 505                 510

Val Gly Asp Arg Val Thr Ile Thr Cys Gln Ala Ser Gln Ile Ile Ser
        515                 520                 525

Ser Arg Ser Ala Trp Tyr Gln Gln Lys Pro Gly Gln Pro Pro Lys Leu
    530                 535                 540

Leu Ile Tyr Gln Ala Ser Lys Leu Ala Ser Gly Val Pro Ser Arg Phe
545                 550                 555                 560

Ser Gly Ser Gly Ser Gly Thr Asp Phe Thr Leu Thr Ile Ser Ser Leu
                565                 570                 575

Gln Pro Glu Asp Phe Ala Thr Tyr Tyr Cys Gln Cys Thr Tyr Ile Asp
            580                 585                 590

Ser Asn Phe Gly Ala Phe Gly Gly Gly Thr Lys Leu Thr Val Leu Gly
        595                 600                 605

Gly Gly Gly Gly Ser Gly Gly Gly Gly Ser Gly Gly Gly Gly Ser Gly
    610                 615                 620

Gly Gly Gly Ser Glu Val Gln Leu Val Glu Ser Gly Gly Gly Leu Val
625                 630                 635                 640

Gln Pro Gly Gly Ser Leu Arg Leu Ser Cys Ala Ala Ser Gly Phe Ser
                645                 650                 655

Phe Ser Ser Ser Tyr Trp Ile Cys Trp Val Arg Gln Ala Pro Gly Lys
            660                 665                 670

Gly Leu Glu Trp Val Gly Cys Val Phe Thr Gly Asp Gly Thr Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Pro Val Ser Val Tyr Tyr Tyr Gly Met
                725                 730                 735

Asp Leu Trp Gly Gln Gly Thr Leu Val Thr Val Ser Ser
            740                 745
```

```
<210> SEQ ID NO 119
<211> LENGTH: 751
<212> TYPE: PRT
<213> ORGANISM: Artificial sequence
<220> FEATURE:
<223> OTHER INFORMATION: artificial antibody-based sequence

<400> SEQUENCE: 119

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Thr Asp Tyr Thr Met Asp Trp Val Arg Gln Ala Pro Gly Lys Gly
145                 150                 155                 160

Leu Glu Trp Val Ala Asp Val Asn Pro Asn Ser Gly Gly Ser Ile Tyr
                165                 170                 175

Asn Gln Arg Phe Lys Gly Arg Phe Thr Leu Ser Val Asp Arg Ser Lys
            180                 185                 190

Asn Thr Leu Tyr Leu Gln Met Asn Ser Leu Arg Ala Glu Asp Thr Ala
        195                 200                 205

Val Tyr Tyr Cys Ala Arg Asn Leu Gly Pro Ser Phe Tyr Phe Asp Tyr
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Asp
                245                 250                 255

Ile Gln Met Thr Gln Ser Pro Ser Ser Leu Ser Ala Ser Val Gly Asp
            260                 265                 270

Arg Val Thr Ile Thr Cys Lys Ala Ser Gln Asp Val Ser Ile Gly Val
        275                 280                 285

Ala Trp Tyr Gln Gln Lys Pro Gly Lys Ala Pro Lys Leu Leu Ile Tyr
    290                 295                 300

Ser Ala Ser Tyr Arg Tyr Thr Gly Val Pro Ser Arg Phe Ser Gly Ser
305                 310                 315                 320

Gly Ser Gly Thr Asp Phe Thr Leu Thr Ile Ser Ser Leu Gln Pro Glu
                325                 330                 335

Asp Phe Ala Thr Tyr Tyr Cys Gln Gln Tyr Tyr Ile Tyr Pro Tyr Thr
            340                 345                 350

Phe Gly Thr Gly Thr Lys Val Thr Val Leu Gly Gly Gly Gly Gly Ser
        355                 360                 365

Gln Val Gln Leu Gln Glu Ser Gly Pro Gly Leu Val Lys Pro Ser Glu
```

```
    370                 375                 380

Thr Leu Ser Leu Thr Cys Lys Val Ser Gly Phe Ser Phe Ser Ser Gly
385                 390                 395                 400

Tyr Asp Met Cys Trp Ile Arg Gln Pro Pro Gly Lys Gly Leu Glu Trp
                405                 410                 415

Ile Gly Cys Val Val Ala Gly Ser Val Asp Ile Thr Tyr Tyr Ala Ser
            420                 425                 430

Trp Ala Lys Gly Arg Val Thr Ile Ser Val Asp Ser Ser Lys Asn Gln
        435                 440                 445

Phe Ser Leu Lys Leu Ser Ser Val Thr Ala Ala Asp Thr Ala Val Tyr
    450                 455                 460

Tyr Cys Ala Arg Lys Asp Ala Tyr Ser Asp Ala Phe Asn Leu Trp Gly
465                 470                 475                 480

Gln Gly Thr Leu Val Thr Val Ser Ser Gly Gly Gly Gly Ser Gly Gly
                485                 490                 495

Gly Gly Ser Ile Gln Met Thr Gln Ser Pro Ser Ser Leu Ser Ala Ser
            500                 505                 510

Val Gly Asp Arg Val Thr Ile Thr Cys Gln Ser Ser Glu Ser Val Tyr
        515                 520                 525

Ser Asn Asn Gln Leu Ser Trp Tyr Gln Gln Lys Pro Gly Gln Pro Pro
    530                 535                 540

Lys Leu Leu Ile Tyr Asp Ala Ser Asp Leu Ala Ser Gly Val Pro Ser
545                 550                 555                 560

Arg Phe Ser Gly Ser Gly Ser Gly Thr Asp Phe Thr Leu Thr Ile Ser
                565                 570                 575

Ser Leu Gln Pro Glu Asp Phe Ala Thr Tyr Tyr Cys Ala Gly Gly Phe
            580                 585                 590

Ser Ser Ser Ser Asp Thr Ala Phe Gly Gly Gly Thr Lys Leu Thr Val
        595                 600                 605

Leu Gly Gly Gly Gly Gly Ser Gly Gly Gly Gly Ser Gly Gly Gly Gly
    610                 615                 620

Ser Gly Gly Gly Gly Ser Glu Val Gln Leu Val Glu Ser Gly Gly Gly
625                 630                 635                 640

Leu Val Gln Pro Gly Gly Ser Leu Arg Leu Ser Cys Ala Ala Ser Gly
                645                 650                 655

Phe Ser Leu Ser Ser Asn Ala Met Gly Trp Val Arg Gln Ala Pro Gly
            660                 665                 670

Lys Gly Leu Glu Tyr Ile Gly Ile Ile Ser Val Gly Gly Phe Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Asp Arg His Gly Gly Asp Ser Ser Gly
                725                 730                 735

Ala Phe Tyr Leu Trp Gly Gln Gly Thr Leu Val Thr Val Ser Ser
            740                 745                 750
```

<210> SEQ ID NO 120
<211> LENGTH: 751
<212> TYPE: PRT
<213> ORGANISM: Artificial sequence
<220> FEATURE:
<223> OTHER INFORMATION: artificial antibody-based sequence

<400> SEQUENCE: 120

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Thr Asp Tyr Thr Met Asp Trp Val Arg Gln Ala Pro Gly Lys Cys
145                 150                 155                 160

Leu Glu Trp Val Ala Asp Val Asn Pro Asn Ser Gly Gly Ser Ile Tyr
                165                 170                 175

Asn Gln Arg Phe Lys Gly Arg Phe Thr Leu Ser Val Asp Arg Ser Lys
            180                 185                 190

Asn Thr Leu Tyr Leu Gln Met Asn Ser Leu Arg Ala Glu Asp Thr Ala
        195                 200                 205

Val Tyr Tyr Cys Ala Arg Asn Leu Gly Pro Ser Phe Tyr Phe Asp Tyr
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Asp
                245                 250                 255

Ile Gln Met Thr Gln Ser Pro Ser Ser Leu Ser Ala Ser Val Gly Asp
            260                 265                 270

Arg Val Thr Ile Thr Cys Lys Ala Ser Gln Asp Val Ser Ile Gly Val
        275                 280                 285

Ala Trp Tyr Gln Gln Lys Pro Gly Lys Ala Pro Lys Leu Leu Ile Tyr
    290                 295                 300

Ser Ala Ser Tyr Arg Tyr Thr Gly Val Pro Ser Arg Phe Ser Gly Ser
305                 310                 315                 320

Gly Ser Gly Thr Asp Phe Thr Leu Thr Ile Ser Ser Leu Gln Pro Glu
                325                 330                 335

Asp Phe Ala Thr Tyr Tyr Cys Gln Gln Tyr Tyr Ile Tyr Pro Tyr Thr
            340                 345                 350

Phe Gly Cys Gly Thr Lys Val Thr Val Leu Gly Gly Gly Gly Ser
        355                 360                 365

Gln Val Gln Leu Gln Glu Ser Gly Pro Gly Leu Val Lys Pro Ser Glu
    370                 375                 380

Thr Leu Ser Leu Thr Cys Lys Val Ser Gly Phe Ser Phe Ser Ser Gly
385                 390                 395                 400

Tyr Asp Met Cys Trp Ile Arg Gln Pro Pro Gly Lys Gly Leu Glu Trp
                405                 410                 415
```

```
Ile Gly Cys Val Val Ala Gly Ser Val Asp Ile Thr Tyr Tyr Ala Ser
            420                 425                 430

Trp Ala Lys Gly Arg Val Thr Ile Ser Val Asp Ser Ser Lys Asn Gln
        435                 440                 445

Phe Ser Leu Lys Leu Ser Ser Val Thr Ala Ala Asp Thr Ala Val Tyr
    450                 455                 460

Tyr Cys Ala Arg Lys Asp Ala Tyr Ser Asp Ala Phe Asn Leu Trp Gly
465                 470                 475                 480

Gln Gly Thr Leu Val Thr Val Ser Ser Gly Gly Gly Gly Ser Gly Gly
                485                 490                 495

Gly Gly Ser Ile Gln Met Thr Gln Ser Pro Ser Ser Leu Ser Ala Ser
            500                 505                 510

Val Gly Asp Arg Val Thr Ile Thr Cys Gln Ser Ser Glu Ser Val Tyr
        515                 520                 525

Ser Asn Asn Gln Leu Ser Trp Tyr Gln Gln Lys Pro Gly Gln Pro Pro
    530                 535                 540

Lys Leu Leu Ile Tyr Asp Ala Ser Asp Leu Ala Ser Gly Val Pro Ser
545                 550                 555                 560

Arg Phe Ser Gly Ser Gly Ser Gly Thr Asp Phe Thr Leu Thr Ile Ser
                565                 570                 575

Ser Leu Gln Pro Glu Asp Phe Ala Thr Tyr Tyr Cys Ala Gly Gly Phe
            580                 585                 590

Ser Ser Ser Ser Asp Thr Ala Phe Gly Gly Gly Thr Lys Leu Thr Val
        595                 600                 605

Leu Gly Gly Gly Gly Gly Ser Gly Gly Gly Gly Ser Gly Gly Gly Gly
    610                 615                 620

Ser Gly Gly Gly Gly Ser Glu Val Gln Leu Val Glu Ser Gly Gly Gly
625                 630                 635                 640

Leu Val Gln Pro Gly Gly Ser Leu Arg Leu Ser Cys Ala Ala Ser Gly
                645                 650                 655

Phe Ser Leu Ser Ser Asn Ala Met Gly Trp Val Arg Gln Ala Pro Gly
            660                 665                 670

Lys Gly Leu Glu Tyr Ile Gly Ile Ile Ser Val Gly Gly Phe Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Asp Arg His Gly Gly Asp Ser Ser Gly
                725                 730                 735

Ala Phe Tyr Leu Trp Gly Gln Gly Thr Leu Val Thr Val Ser Ser
            740                 745                 750
```

<210> SEQ ID NO 121
<211> LENGTH: 751
<212> TYPE: PRT
<213> ORGANISM: Artificial sequence
<220> FEATURE:
<223> OTHER INFORMATION: artificial antibody-based sequence

<400> SEQUENCE: 121

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30
```

-continued

```
Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Thr Asp Tyr Thr Met Asp Trp Val Arg Gln Ala Pro Gly Lys Gly
145                 150                 155                 160

Leu Glu Trp Val Ala Asp Val Asn Pro Asn Ser Gly Gly Ser Ile Tyr
                165                 170                 175

Asn Gln Arg Phe Lys Gly Arg Phe Thr Leu Ser Val Asp Arg Ser Lys
            180                 185                 190

Asn Thr Leu Tyr Leu Gln Met Asn Ser Leu Arg Ala Glu Asp Thr Ala
        195                 200                 205

Val Tyr Tyr Cys Ala Arg Asn Leu Gly Pro Ser Phe Tyr Phe Asp Tyr
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Asp
                245                 250                 255

Ile Gln Met Thr Gln Ser Pro Ser Ser Leu Ser Ala Ser Val Gly Asp
            260                 265                 270

Arg Val Thr Ile Thr Cys Lys Ala Ser Gln Asp Val Ser Ile Gly Val
        275                 280                 285

Ala Trp Tyr Gln Gln Lys Pro Gly Lys Ala Pro Lys Leu Leu Ile Tyr
    290                 295                 300

Ser Ala Ser Tyr Arg Tyr Thr Gly Val Pro Ser Arg Phe Ser Gly Ser
305                 310                 315                 320

Gly Ser Gly Thr Asp Phe Thr Leu Thr Ile Ser Ser Leu Gln Pro Glu
                325                 330                 335

Asp Phe Ala Thr Tyr Tyr Cys Gln Gln Tyr Tyr Ile Tyr Pro Tyr Thr
            340                 345                 350

Phe Gly Thr Gly Thr Lys Val Thr Val Leu Gly Gly Gly Gly Gly Ser
        355                 360                 365

Gln Val Gln Leu Gln Glu Ser Gly Pro Gly Leu Val Lys Pro Ser Glu
    370                 375                 380

Thr Leu Ser Leu Thr Cys Lys Val Ser Gly Phe Ser Phe Ser Ser Gly
385                 390                 395                 400

Tyr Asp Met Cys Trp Ile Arg Gln Pro Pro Gly Lys Gly Leu Glu Trp
                405                 410                 415

Ile Gly Cys Val Val Ala Gly Ser Val Asp Ile Thr Tyr Tyr Ala Ser
            420                 425                 430

Trp Ala Lys Gly Arg Val Thr Ile Ser Val Asp Ser Ser Lys Asn Gln
        435                 440                 445
```

-continued

```
Phe Ser Leu Lys Leu Ser Ser Val Thr Ala Ala Asp Thr Ala Val Tyr
    450                 455                 460

Tyr Cys Ala Arg Lys Asp Ala Ala Ser Asp Ala Phe Asn Leu Trp Gly
465                 470                 475                 480

Gln Gly Thr Leu Val Thr Val Ser Ser Gly Gly Gly Gly Ser Gly Gly
                485                 490                 495

Gly Gly Ser Ile Gln Met Thr Gln Ser Pro Ser Ser Leu Ser Ala Ser
            500                 505                 510

Val Gly Asp Arg Val Thr Ile Thr Cys Gln Ser Ser Glu Ser Val Tyr
        515                 520                 525

Ser Asn Asn Gln Leu Ser Trp Tyr Gln Gln Lys Pro Gly Gln Pro Pro
    530                 535                 540

Lys Leu Leu Ile Tyr Asp Ala Ser Asp Leu Ala Ser Gly Val Pro Ser
545                 550                 555                 560

Arg Phe Ser Gly Ser Gly Ser Gly Thr Asp Phe Thr Leu Thr Ile Ser
                565                 570                 575

Ser Leu Gln Pro Glu Asp Phe Ala Thr Tyr Tyr Cys Ala Gly Gly Phe
            580                 585                 590

Ser Ser Ser Ser Asp Thr Ala Phe Gly Gly Gly Thr Lys Leu Thr Val
        595                 600                 605

Leu Gly Gly Gly Gly Gly Ser Gly Gly Gly Gly Ser Gly Gly Gly Gly
    610                 615                 620

Ser Gly Gly Gly Gly Ser Glu Val Gln Leu Val Glu Ser Gly Gly Gly
625                 630                 635                 640

Leu Val Gln Pro Gly Gly Ser Leu Arg Leu Ser Cys Ala Ala Ser Gly
                645                 650                 655

Phe Ser Leu Ser Ser Asn Ala Met Gly Trp Val Arg Gln Ala Pro Gly
            660                 665                 670

Lys Gly Leu Glu Tyr Ile Gly Ile Ile Ser Val Gly Gly Phe Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Asp Arg His Gly Gly Asp Ser Ser Gly
                725                 730                 735

Ala Phe Tyr Leu Trp Gly Gln Gly Thr Leu Val Thr Val Ser Ser
            740                 745                 750
```

<210> SEQ ID NO 122
<211> LENGTH: 751
<212> TYPE: PRT
<213> ORGANISM: Artificial sequence
<220> FEATURE:
<223> OTHER INFORMATION: artificial antibody-based sequence

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60
```

-continued

```
Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Glu Val Gln Leu Val Glu Ser Gly Gly Gly Leu Val
        115                 120                 125

Gln Pro Gly Gly Ser Leu Arg Leu Ser Cys Ala Ala Ser Gly Phe Thr
    130                 135                 140

Phe Thr Asp Tyr Thr Met Asp Trp Val Arg Gln Ala Pro Gly Lys Cys
145                 150                 155                 160

Leu Glu Trp Val Ala Asp Val Asn Pro Asn Ser Gly Gly Ser Ile Tyr
                165                 170                 175

Asn Gln Arg Phe Lys Gly Arg Phe Thr Leu Ser Val Asp Arg Ser Lys
            180                 185                 190

Asn Thr Leu Tyr Leu Gln Met Asn Ser Leu Arg Ala Glu Asp Thr Ala
        195                 200                 205

Val Tyr Tyr Cys Ala Arg Asn Leu Gly Pro Ser Phe Tyr Phe Asp Tyr
    210                 215                 220

Trp Gly Gln Gly Thr Leu Val Thr Val Ser Ser Gly Gly Gly Gly Ser
225                 230                 235                 240

Gly Gly Gly Gly Ser Gly Gly Gly Gly Ser Gly Gly Gly Gly Ser Asp
                245                 250                 255

Ile Gln Met Thr Gln Ser Pro Ser Ser Leu Ser Ala Ser Val Gly Asp
            260                 265                 270

Arg Val Thr Ile Thr Cys Lys Ala Ser Gln Asp Val Ser Ile Gly Val
        275                 280                 285

Ala Trp Tyr Gln Gln Lys Pro Gly Lys Ala Pro Lys Leu Leu Ile Tyr
    290                 295                 300

Ser Ala Ser Tyr Arg Tyr Thr Gly Val Pro Ser Arg Phe Ser Gly Ser
305                 310                 315                 320

Gly Ser Gly Thr Asp Phe Thr Leu Thr Ile Ser Ser Leu Gln Pro Glu
                325                 330                 335

Asp Phe Ala Thr Tyr Tyr Cys Gln Gln Tyr Tyr Ile Tyr Pro Tyr Thr
            340                 345                 350

Phe Gly Cys Gly Thr Lys Val Thr Val Leu Gly Gly Gly Gly Gly Ser
        355                 360                 365

Gln Val Gln Leu Gln Glu Ser Gly Pro Gly Leu Val Lys Pro Ser Glu
    370                 375                 380

Thr Leu Ser Leu Thr Cys Lys Val Ser Gly Phe Ser Phe Ser Ser Gly
385                 390                 395                 400

Tyr Asp Met Cys Trp Ile Arg Gln Pro Pro Gly Lys Gly Leu Glu Trp
                405                 410                 415

Ile Gly Cys Val Val Ala Gly Ser Val Asp Ile Thr Tyr Tyr Ala Ser
            420                 425                 430

Trp Ala Lys Gly Arg Val Thr Ile Ser Val Asp Ser Ser Lys Asn Gln
        435                 440                 445

Phe Ser Leu Lys Leu Ser Ser Val Thr Ala Ala Asp Thr Ala Val Tyr
    450                 455                 460

Tyr Cys Ala Arg Lys Asp Ala Ala Ser Asp Ala Phe Asn Leu Trp Gly
465                 470                 475                 480

Gln Gly Thr Leu Val Thr Val Ser Ser Gly Gly Gly Gly Ser Gly Gly
```

```
                485                 490                 495

Gly Gly Ser Ile Gln Met Thr Gln Ser Pro Ser Ser Leu Ser Ala Ser
            500                 505                 510

Val Gly Asp Arg Val Thr Ile Thr Cys Gln Ser Ser Glu Ser Val Tyr
        515                 520                 525

Ser Asn Asn Gln Leu Ser Trp Tyr Gln Gln Lys Pro Gly Gln Pro Pro
    530                 535                 540

Lys Leu Leu Ile Tyr Asp Ala Ser Asp Leu Ala Ser Gly Val Pro Ser
545                 550                 555                 560

Arg Phe Ser Gly Ser Gly Ser Gly Thr Asp Phe Thr Leu Thr Ile Ser
                565                 570                 575

Ser Leu Gln Pro Glu Asp Phe Ala Thr Tyr Tyr Cys Ala Gly Gly Phe
            580                 585                 590

Ser Ser Ser Ser Asp Thr Ala Phe Gly Gly Gly Thr Lys Leu Thr Val
        595                 600                 605

Leu Gly Gly Gly Gly Gly Ser Gly Gly Gly Gly Ser Gly Gly Gly Gly
    610                 615                 620

Ser Gly Gly Gly Gly Ser Glu Val Gln Leu Val Glu Ser Gly Gly Gly
625                 630                 635                 640

Leu Val Gln Pro Gly Gly Ser Leu Arg Leu Ser Cys Ala Ala Ser Gly
                645                 650                 655

Phe Ser Leu Ser Ser Asn Ala Met Gly Trp Val Arg Gln Ala Pro Gly
            660                 665                 670

Lys Gly Leu Glu Tyr Ile Gly Ile Ile Ser Val Gly Gly Phe Thr Tyr
        675                 680                 685

Tyr Ala Ser Trp Ala Lys Gly Arg Phe Thr Ile Ser Arg Asp Asn Ser
    690                 695                 700

Lys Asn Thr Val Tyr Leu Gln Met Asn Ser Leu Arg Ala Glu Asp Thr
705                 710                 715                 720

Ala Thr Tyr Phe Cys Ala Arg Asp Arg His Gly Gly Asp Ser Ser Gly
                725                 730                 735

Ala Phe Tyr Leu Trp Gly Gln Gly Thr Leu Val Thr Val Ser Ser
            740                 745                 750


<210> SEQ ID NO 123
<211> LENGTH: 490
<212> TYPE: PRT
<213> ORGANISM: Artificial sequence
<220> FEATURE:
<223> OTHER INFORMATION: artificial antibody-based sequence

<400> SEQUENCE: 123

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Cys Gly Thr Lys Leu Thr Val Leu Gly Gly Gly Gly Gly
```

-continued

```
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Asn Ile Lys Asp Thr
145                 150                 155                 160

Tyr Ile His Trp Val Arg Gln Ala Pro Gly Lys Cys Leu Glu Trp Val
                165                 170                 175

Ala Arg Ile Tyr Pro Thr Asn Gly Tyr Thr Arg Tyr Ala Asp Ser Val
            180                 185                 190

Lys Gly Arg Phe Thr Ile Ser Ala Asp Thr Ser Lys Asn Thr Ala Tyr
        195                 200                 205

Leu Gln Met Asn Ser Leu Arg Ala Glu Asp Thr Ala Val Tyr Tyr Cys
    210                 215                 220

Ser Arg Trp Gly Gly Asp Gly Phe Tyr Ala Met Asp Tyr Trp Gly Gln
225                 230                 235                 240

Gly Thr Leu Val Thr Val Ser Ser Gly Gly Gly Gly Ser Gly Gly Gly
                245                 250                 255

Gly Ser Asp Ile Gln Met Thr Gln Ser Pro Ser Ser Leu Ser Ala Ser
            260                 265                 270

Val Gly Asp Arg Val Thr Ile Thr Cys Gln Ser Ser Glu Ser Val Tyr
        275                 280                 285

Ser Asn Asn Gln Leu Ser Trp Tyr Gln Gln Lys Pro Gly Gln Pro Pro
    290                 295                 300

Lys Leu Leu Ile Tyr Asp Ala Ser Asp Leu Ala Ser Gly Val Pro Ser
305                 310                 315                 320

Arg Phe Ser Gly Ser Gly Ser Gly Thr Asp Phe Thr Leu Thr Ile Ser
                325                 330                 335

Ser Leu Gln Pro Glu Asp Phe Ala Thr Tyr Tyr Cys Ala Gly Gly Phe
            340                 345                 350

Ser Ser Ser Ser Asp Thr Ala Phe Gly Cys Gly Thr Lys Leu Thr Val
        355                 360                 365

Leu Gly Gly Gly Ser Gly Gly Ser Asp Ile Gln Met Thr Gln Ser Pro
    370                 375                 380

Ser Ser Leu Ser Ala Ser Val Gly Asp Arg Val Thr Ile Thr Cys Gln
385                 390                 395                 400

Ser Ser Gln Ser Val Phe Ser Asn Asn Tyr Leu Ala Trp Phe Gln Gln
                405                 410                 415

Lys Pro Gly Gln Ser Pro Lys Arg Leu Ile Tyr Ser Ala Ser Thr Leu
            420                 425                 430

Ala Ser Gly Val Pro Ser Arg Phe Ser Gly Ser Gly Ser Gly Thr Asp
        435                 440                 445

Phe Thr Leu Thr Ile Ser Ser Leu Gln Pro Glu Asp Phe Ala Thr Tyr
    450                 455                 460

Tyr Cys Leu Gly Ser Tyr Ala Cys Ser Ser Ala Asp Cys Tyr Val Phe
465                 470                 475                 480

Gly Thr Gly Thr Lys Val Thr Val Leu Gly
                485                 490
```

<210> SEQ ID NO 124
<211> LENGTH: 510
<212> TYPE: PRT
<213> ORGANISM: Artificial sequence
<220> FEATURE:
<223> OTHER INFORMATION: artificial antibody-based sequence

<400> SEQUENCE: 124

```
Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Ser Leu Ser Ser Tyr Asp Met Ser Trp Val Arg Gln Ala Pro Gly
    290                 295                 300

Lys Gly Leu Ala Trp Ile Gly Ala Ser Tyr Ala Ser Gly Pro Thr Tyr
305                 310                 315                 320

Tyr Ala Ser Trp Ala Lys Gly Arg Phe Thr Ile Ser Arg Asp Asn Ser
                325                 330                 335

Lys Asn Thr Val Tyr Leu Gln Met Asn Ser Leu Arg Ala Glu Asp Thr
            340                 345                 350

Ala Thr Tyr Phe Cys Ala Arg Gly Gly Trp Thr Gly Thr Ser His Ser
        355                 360                 365

Asn Ile Trp Gly Gln Gly Thr Leu Val Thr Val Ser Ser Gly Gly Gly
    370                 375                 380

Ser Gly Gly Gly Ser Glu Val Gln Leu Val Glu Ser Gly Gly Gly Leu
385                 390                 395                 400
```

```
Val Gln Pro Gly Gly Ser Leu Arg Leu Ser Cys Ala Ala Ser Gly Phe
                405                 410                 415

Ser Leu Ser Ser Asn Ala Met Gly Trp Val Arg Gln Ala Pro Gly Lys
            420                 425                 430

Cys Leu Glu Tyr Ile Gly Ile Ile Ser Val Gly Gly Phe Thr Tyr Tyr
        435                 440                 445

Ala Ser Trp Ala Lys Gly Arg Phe Thr Ile Ser Arg Asp Asn Ser Lys
    450                 455                 460

Asn Thr Val Tyr Leu Gln Met Asn Ser Leu Arg Ala Glu Asp Thr Ala
465                 470                 475                 480

Thr Tyr Phe Cys Ala Arg Asp Arg His Gly Gly Asp Ser Ser Gly Ala
                485                 490                 495

Phe Tyr Leu Trp Gly Gln Gly Thr Leu Val Thr Val Ser Ser
            500                 505                 510


<210> SEQ ID NO 125
<211> LENGTH: 487
<212> TYPE: PRT
<213> ORGANISM: Artificial sequence
<220> FEATURE:
<223> OTHER INFORMATION: artificial antibody-based sequence

<400> SEQUENCE: 125

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255
```

```
Ser Asp Val Val Met Thr Gln Ser Pro Ser Ser Leu Ser Ala Ser Val
            260                 265                 270

Gly Asp Arg Val Thr Ile Thr Cys Gln Ala Ser Gln Ile Ile Ser Ser
        275                 280                 285

Arg Ser Ala Trp Tyr Gln Gln Lys Pro Gly Gln Pro Pro Lys Leu Leu
    290                 295                 300

Ile Tyr Gln Ala Ser Lys Leu Ala Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Cys Thr Tyr Ile Asp Ser
            340                 345                 350

Asn Phe Gly Ala Phe Gly Cys Gly Thr Lys Leu Thr Val Leu Gly Gly
        355                 360                 365

Gly Ser Gly Gly Ser Asp Ile Gln Met Thr Gln Ser Pro Ser Ser Leu
    370                 375                 380

Ser Ala Ser Val Gly Asp Arg Val Thr Ile Thr Cys Gln Ser Ser Gln
385                 390                 395                 400

Ser Val Phe Ser Asn Asn Tyr Leu Ala Trp Phe Gln Gln Lys Pro Gly
                405                 410                 415

Gln Ser Pro Lys Arg Leu Ile Tyr Ser Ala Ser Thr Leu Ala Ser Gly
            420                 425                 430

Val Pro Ser Arg Phe Ser Gly Ser Gly Ser Gly Thr Asp Phe Thr Leu
        435                 440                 445

Thr Ile Ser Ser Leu Gln Pro Glu Asp Phe Ala Thr Tyr Tyr Cys Leu
    450                 455                 460

Gly Ser Tyr Ala Cys Ser Ser Ala Asp Cys Tyr Val Phe Gly Thr Gly
465                 470                 475                 480

Thr Lys Val Thr Val Leu Gly
                485


<210> SEQ ID NO 126
<211> LENGTH: 510
<212> TYPE: PRT
<213> ORGANISM: Artificial sequence
<220> FEATURE:
<223> OTHER INFORMATION: artificial antibody-based sequence

<400> SEQUENCE: 126

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Ala Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125
```

```
Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Tyr Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270

Leu Val Gln Pro Gly Gly Ser Leu Arg Leu Ser Cys Ala Ala Ser Gly
        275                 280                 285

Phe Ser Leu Ser Ser Tyr Asp Met Ser Trp Val Arg Gln Ala Pro Gly
    290                 295                 300

Lys Gly Leu Ala Trp Ile Gly Ala Ser Tyr Ala Ser Gly Pro Thr Tyr
305                 310                 315                 320

Tyr Ala Ser Trp Ala Lys Gly Arg Phe Thr Ile Ser Arg Asp Asn Ser
                325                 330                 335

Lys Asn Thr Val Tyr Leu Gln Met Asn Ser Leu Arg Ala Glu Asp Thr
            340                 345                 350

Ala Thr Tyr Phe Cys Ala Arg Gly Gly Trp Thr Gly Thr Ser His Ser
        355                 360                 365

Asn Ile Trp Gly Gln Gly Thr Leu Val Thr Val Ser Ser Gly Gly Gly
    370                 375                 380

Ser Gly Gly Gly Ser Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Ser Phe Ser Ser Ser Tyr Trp Ile Cys Trp Val Arg Gln Ala Pro Gly
            420                 425                 430

Lys Cys Leu Glu Trp Val Gly Cys Val Phe Thr Gly Asp Gly Thr Thr
        435                 440                 445

Tyr Tyr Ala Ser Trp Ala Lys Gly Arg Phe Thr Ile Ser Arg Asp Asn
    450                 455                 460

Ser Lys Asn Thr Val Tyr Leu Gln Met Asn Ser Leu Arg Ala Glu Asp
465                 470                 475                 480

Thr Ala Thr Tyr Phe Cys Ala Arg Pro Val Ser Val Tyr Tyr Tyr Gly
                485                 490                 495

Met Asp Leu Trp Gly Gln Gly Thr Leu Val Thr Val Ser Ser
            500                 505                 510
```

<210> SEQ ID NO 127
<211> LENGTH: 486
<212> TYPE: PRT
<213> ORGANISM: Artificial sequence
<220> FEATURE:

<223> OTHER INFORMATION: artificial antibody-based sequence

<400> SEQUENCE: 127

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Ala Phe Glu Leu Thr Gln Ser Pro Ser Ser Leu Ser Ala Ser Val
            260                 265                 270

Gly Asp Arg Val Thr Ile Thr Cys Gln Ala Ser Glu Ser Ile Asn Ser
        275                 280                 285

Arg Leu Ala Trp Tyr Gln Gln Lys Pro Gly Gln Pro Pro Lys Leu Leu
    290                 295                 300

Ile Tyr Asp Ala Ser Asp Leu Thr Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Gly Tyr Gly Gly Ser Ser
            340                 345                 350

Thr Thr Thr Phe Gly Cys Gly Thr Lys Leu Thr Val Leu Gly Gly Gly
        355                 360                 365

Ser Gly Gly Ser Asp Ile Gln Met Thr Gln Ser Pro Ser Ser Leu Ser
    370                 375                 380

Ala Ser Val Gly Asp Arg Val Thr Ile Thr Cys Gln Ser Ser Gln Ser
385                 390                 395                 400

```
Val Phe Ser Asn Asn Tyr Leu Ala Trp Phe Gln Gln Lys Pro Gly Gln
                405                 410                 415

Ser Pro Lys Arg Leu Ile Tyr Ser Ala Ser Thr Leu Ala Ser Gly Val
            420                 425                 430

Pro Ser Arg Phe Ser Gly Ser Gly Ser Gly Thr Asp Phe Thr Leu Thr
        435                 440                 445

Ile Ser Ser Leu Gln Pro Glu Asp Phe Ala Thr Tyr Tyr Cys Leu Gly
    450                 455                 460

Ser Tyr Ala Cys Ser Ser Ala Asp Cys Tyr Val Phe Gly Thr Gly Thr
465                 470                 475                 480

Lys Val Thr Val Leu Gly
                485


<210> SEQ ID NO 128
<211> LENGTH: 509
<212> TYPE: PRT
<213> ORGANISM: Artificial sequence
<220> FEATURE:
<223> OTHER INFORMATION: artificial antibody-based sequence

<400> SEQUENCE: 128

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asp Tyr
            20                  25                  30

Leu Ala Trp Tyr Gln Gln Lys Pro Gly Lys Ala Pro Lys Leu Leu Ile
        35                  40                  45

Tyr Lys Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ala Gly Tyr Ile Ile Thr Asp
                85                  90                  95

Ile Asp Asn Val Phe Gly Thr Gly Thr Lys Val Thr Val Leu Gly Gly
            100                 105                 110

Gly Gly Gly Ser Gly Gly Gly Gly Ser Gly Gly Gly Gly Ser Gly Gly
        115                 120                 125

Gly Gly Ser Gln Val Gln Leu Gln Glu Ser Gly Pro Gly Leu Val Lys
    130                 135                 140

Pro Ser Glu Thr Leu Ser Leu Thr Cys Lys Val Ser Gly Phe Ser Phe
145                 150                 155                 160

Ser Ser Gly Tyr Asp Met Cys Trp Ile Arg Gln Pro Pro Gly Lys Gly
                165                 170                 175

Leu Glu Trp Ile Gly Cys Val Val Ala Gly Ser Val Asp Ile Thr Tyr
            180                 185                 190

Tyr Ala Ser Trp Ala Lys Gly Arg Val Thr Ile Ser Val Asp Ser Ser
        195                 200                 205

Lys Asn Gln Phe Ser Leu Lys Leu Ser Ser Val Thr Ala Ala Asp Thr
    210                 215                 220

Ala Val Tyr Tyr Cys Ala Arg Lys Asp Ala Ala Ser Asp Ala Phe Asn
225                 230                 235                 240

Leu Trp Gly Gln Gly Thr Leu Val Thr Val Ser Ser Gly Gly Gly Gly
                245                 250                 255

Ser Gly Gly Gly Gly Ser Glu Val Gln Leu Val Glu Ser Gly Gly Gly
            260                 265                 270
```

```
Leu Val Gln Pro Gly Gly Ser Leu Arg Leu Ser Cys Ala Ala Ser Gly
        275                 280                 285

Phe Ser Leu Ser Ser Tyr Asp Met Ser Trp Val Arg Gln Ala Pro Gly
    290                 295                 300

Lys Gly Leu Ala Trp Ile Gly Ala Ser Tyr Ala Ser Gly Pro Thr Tyr
305                 310                 315                 320

Tyr Ala Ser Trp Ala Lys Gly Arg Phe Thr Ile Ser Arg Asp Asn Ser
                325                 330                 335

Lys Asn Thr Val Tyr Leu Gln Met Asn Ser Leu Arg Ala Glu Asp Thr
            340                 345                 350

Ala Thr Tyr Phe Cys Ala Arg Gly Gly Trp Thr Gly Thr Ser His Ser
        355                 360                 365

Asn Ile Trp Gly Gln Gly Thr Leu Val Thr Val Ser Ser Gly Gly Gly
    370                 375                 380

Ser Gly Gly Gly Ser Glu Val Gln Leu Val Glu Ser Gly Gly Gly Leu
385                 390                 395                 400

Val Gln Pro Gly Gly Ser Leu Arg Leu Ser Cys Ala Ala Ser Gly Phe
                405                 410                 415

Ser Leu Ser Ser Tyr Ala Met Asn Trp Val Arg Gln Ala Pro Gly Lys
            420                 425                 430

Cys Leu Glu Trp Ile Gly His Ile Asn Ala Gly Asp Ile Ala Tyr Tyr
        435                 440                 445

Ala Thr Trp Ala Lys Gly Arg Phe Thr Ile Ser Arg Asp Asn Ser Lys
    450                 455                 460

Asn Thr Val Tyr Leu Gln Met Asn Ser Leu Arg Ala Glu Asp Thr Ala
465                 470                 475                 480

Val Tyr Phe Cys Ala Arg Gly Ala Gly Gly Phe Ser Thr Gly Pro Phe
                485                 490                 495

Lys Leu Trp Gly Gln Gly Thr Leu Val Thr Val Ser Ser
            500                 505


<210> SEQ ID NO 129
<211> LENGTH: 488
<212> TYPE: PRT
<213> ORGANISM: Artificial sequence
<220> FEATURE:
<223> OTHER INFORMATION: artificial antibody-based sequence

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125
```

```
Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Gln Ala Ser Gln Ser Ile Asn Asp
        275                 280                 285

Tyr Leu Ala Trp Tyr Gln Gln Lys Pro Gly Lys Ala Pro Lys Leu Leu
    290                 295                 300

Ile Tyr Lys Ala Ser Thr Leu Ala Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Ala Gly Tyr Ile Ile Thr
            340                 345                 350

Asp Ile Asp Asn Val Phe Gly Cys Gly Thr Lys Val Thr Val Leu Gly
        355                 360                 365

Gly Gly Ser Gly Gly Ser Asp Ile Gln Met Thr Gln Ser Pro Ser Ser
    370                 375                 380

Leu Ser Ala Ser Val Gly Asp Arg Val Thr Ile Thr Cys Gln Ser Ser
385                 390                 395                 400

Gln Ser Val Phe Ser Asn Asn Tyr Leu Ala Trp Phe Gln Gln Lys Pro
                405                 410                 415

Gly Gln Ser Pro Lys Arg Leu Ile Tyr Ser Ala Ser Thr Leu Ala Ser
            420                 425                 430

Gly Val Pro Ser Arg Phe Ser Gly Ser Gly Ser Gly Thr Asp Phe Thr
        435                 440                 445

Leu Thr Ile Ser Ser Leu Gln Pro Glu Asp Phe Ala Thr Tyr Tyr Cys
    450                 455                 460

Leu Gly Ser Tyr Ala Cys Ser Ser Ala Asp Cys Tyr Val Phe Gly Thr
465                 470                 475                 480

Gly Thr Lys Val Thr Val Leu Gly
                485
```

<210> SEQ ID NO 130
<211> LENGTH: 507
<212> TYPE: PRT
<213> ORGANISM: Artificial sequence
<220> FEATURE:
<223> OTHER INFORMATION: artificial antibody-based sequence

<400> SEQUENCE: 130

-continued

```
Ala Phe Glu Leu Thr Gln Ser Pro Ser Ser Leu Ser Ala Ser Val Gly
1               5                   10                  15

Asp Arg Val Thr Ile Thr Cys Gln Ala Ser Glu Ser Ile Asn Ser Arg
            20                  25                  30

Leu Ala Trp Tyr Gln Gln Lys Pro Gly Gln Pro Pro Lys Leu Leu Ile
        35                  40                  45

Tyr Asp Ala Ser Asp Leu Thr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Gly Gly Ser Ser Thr
                85                  90                  95

Thr Thr Phe Gly Cys Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Phe Ser Leu Ser Ser
145                 150                 155                 160

Tyr Ala Met Asn Trp Val Arg Gln Ala Pro Gly Lys Cys Leu Glu Trp
                165                 170                 175

Ile Gly His Ile Asn Ala Gly Asp Ile Ala Tyr Tyr Ala Thr Trp Ala
            180                 185                 190

Lys Gly Arg Phe Thr Ile Ser Arg Asp Asn Ser Lys Asn Thr Val Tyr
        195                 200                 205

Leu Gln Met Asn Ser Leu Arg Ala Glu Asp Thr Ala Val Tyr Phe Cys
    210                 215                 220

Ala Arg Gly Ala Gly Gly Phe Ser Thr Gly Pro Phe Lys Leu Trp Gly
225                 230                 235                 240

Gln Gly Thr Leu Val Thr Val Ser Ser Gly Gly Gly Gly Ser Gly Gly
                245                 250                 255

Gly Gly Ser Glu Val Gln Leu Val Glu Ser Gly Gly Gly Leu Val Gln
            260                 265                 270

Pro Gly Gly Ser Leu Arg Leu Ser Cys Ala Ala Ser Gly Phe Ser Leu
        275                 280                 285

Ser Ser Tyr Asp Met Ser Trp Val Arg Gln Ala Pro Gly Lys Gly Leu
    290                 295                 300

Ala Trp Ile Gly Ala Ser Tyr Ala Ser Gly Pro Thr Tyr Tyr Ala Ser
305                 310                 315                 320

Trp Ala Lys Gly Arg Phe Thr Ile Ser Arg Asp Asn Ser Lys Asn Thr
                325                 330                 335

Val Tyr Leu Gln Met Asn Ser Leu Arg Ala Glu Asp Thr Ala Thr Tyr
            340                 345                 350

Phe Cys Ala Arg Gly Gly Trp Thr Gly Thr Ser His Ser Asn Ile Trp
        355                 360                 365

Gly Gln Gly Thr Leu Val Thr Val Ser Ser Gly Gly Gly Ser Gly Gly
    370                 375                 380

Gly Ser Gln Val Gln Leu Gln Glu Ser Gly Pro Gly Leu Val Lys Pro
385                 390                 395                 400

Ser Glu Thr Leu Ser Leu Thr Cys Lys Val Ser Gly Phe Ser Phe Ser
                405                 410                 415

Ser Gly Tyr Asp Met Cys Trp Ile Arg Gln Pro Pro Gly Lys Cys Leu
```

```
            420                 425                 430

Glu Trp Ile Gly Cys Val Val Ala Gly Ser Val Asp Ile Thr Tyr Tyr
        435                 440                 445

Ala Ser Trp Ala Lys Gly Arg Val Thr Ile Ser Val Asp Ser Ser Lys
    450                 455                 460

Asn Gln Phe Ser Leu Lys Leu Ser Ser Val Thr Ala Ala Asp Thr Ala
465                 470                 475                 480

Val Tyr Tyr Cys Ala Arg Lys Asp Ala Ala Ser Asp Ala Phe Asn Leu
                485                 490                 495

Trp Gly Gln Gly Thr Leu Val Thr Val Ser Ser
            500                 505


<210> SEQ ID NO 131
<211> LENGTH: 489
<212> TYPE: PRT
<213> ORGANISM: Artificial sequence
<220> FEATURE:
<223> OTHER INFORMATION: artificial antibody-based sequence

<400> SEQUENCE: 131

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Gly Ser Gly Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser Gly Gly Gly
                245                 250                 255

Gly Ser Gly Gly Gly Gly Ser Ala Phe Glu Leu Thr Gln Ser Pro Ser
            260                 265                 270

Ser Leu Ser Ala Ser Val Gly Asp Arg Val Thr Ile Thr Cys Gln Ala
```

```
        275                 280                 285

Ser Glu Ser Ile Asn Ser Arg Leu Ala Trp Tyr Gln Gln Lys Pro Gly
    290                 295                 300

Gln Pro Pro Lys Leu Leu Ile Tyr Asp Ala Ser Asp Leu Thr Ser Gly
305                 310                 315                 320

Val Pro Ser Arg Phe Ser Gly Ser Gly Ser Gly Thr Asp Phe Thr Leu
                325                 330                 335

Thr Ile Ser Ser Leu Gln Pro Glu Asp Phe Ala Thr Tyr Tyr Cys Gln
            340                 345                 350

Gly Tyr Gly Gly Ser Ser Thr Thr Thr Phe Gly Cys Gly Thr Lys Leu
        355                 360                 365

Thr Val Leu Gly Gly Gly Ser Gly Gly Ser Asp Ile Gln Met Thr Gln
    370                 375                 380

Ser Pro Ser Ser Leu Ser Ala Ser Val Gly Asp Arg Val Thr Ile Thr
385                 390                 395                 400

Cys Gln Ala Ser Gln Ser Ile Asn Asp Tyr Leu Ala Trp Tyr Gln Gln
                405                 410                 415

Lys Pro Gly Lys Ala Pro Lys Leu Leu Ile Tyr Lys Ala Ser Thr Leu
            420                 425                 430

Ala Ser Gly Val Pro Ser Arg Phe Ser Gly Ser Gly Ser Gly Thr Asp
        435                 440                 445

Phe Thr Leu Thr Ile Ser Ser Leu Gln Pro Glu Asp Phe Ala Thr Tyr
    450                 455                 460

Tyr Cys Gln Ala Gly Tyr Ile Ile Thr Asp Ile Asp Asn Val Phe Gly
465                 470                 475                 480

Thr Gly Thr Lys Val Thr Val Leu Gly
                485


<210> SEQ ID NO 132
<211> LENGTH: 506
<212> TYPE: PRT
<213> ORGANISM: Artificial sequence
<220> FEATURE:
<223> OTHER INFORMATION: artificial antibody-based sequence

<400> SEQUENCE: 132

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
```

```
145                 150                 155                 160

Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Gln Val Gln Leu Gln Glu Ser Gly Pro Gly Leu Val Lys Pro Ser
            260                 265                 270

Glu Thr Leu Ser Leu Thr Cys Lys Val Ser Gly Phe Ser Phe Ser Ser
        275                 280                 285

Gly Tyr Asp Met Cys Trp Ile Arg Gln Pro Pro Gly Lys Gly Leu Glu
    290                 295                 300

Trp Ile Gly Cys Val Val Ala Gly Ser Val Asp Ile Thr Tyr Tyr Ala
305                 310                 315                 320

Ser Trp Ala Lys Gly Arg Val Thr Ile Ser Val Asp Ser Ser Lys Asn
                325                 330                 335

Gln Phe Ser Leu Lys Leu Ser Ser Val Thr Ala Ala Asp Thr Ala Val
            340                 345                 350

Tyr Tyr Cys Ala Arg Lys Asp Ala Ala Ser Asp Ala Phe Asn Leu Trp
        355                 360                 365

Gly Gln Gly Thr Leu Val Thr Val Ser Ser Gly Gly Gly Ser Gly Gly
    370                 375                 380

Gly Ser Glu Val Gln Leu Val Glu Ser Gly Gly Gly Leu Val Gln Pro
385                 390                 395                 400

Gly Gly Ser Leu Arg Leu Ser Cys Ala Ala Ser Gly Phe Ser Leu Ser
                405                 410                 415

Ser Tyr Ala Met Asn Trp Val Arg Gln Ala Pro Gly Lys Cys Leu Glu
            420                 425                 430

Trp Ile Gly His Ile Asn Ala Gly Asp Ile Ala Tyr Tyr Ala Thr Trp
        435                 440                 445

Ala Lys Gly Arg Phe Thr Ile Ser Arg Asp Asn Ser Lys Asn Thr Val
    450                 455                 460

Tyr Leu Gln Met Asn Ser Leu Arg Ala Glu Asp Thr Ala Val Tyr Phe
465                 470                 475                 480

Cys Ala Arg Gly Ala Gly Gly Phe Ser Thr Gly Pro Phe Lys Leu Trp
                485                 490                 495

Gly Gln Gly Thr Leu Val Thr Val Ser Ser
            500                 505


<210> SEQ ID NO 133
<211> LENGTH: 484
<212> TYPE: PRT
<213> ORGANISM: Artificial sequence
<220> FEATURE:
<223> OTHER INFORMATION: artificial antibody-based sequence

<400> SEQUENCE: 133

Ala Phe Glu Leu Thr Gln Ser Pro Ser Ser Leu Ser Ala Ser Val Gly
```

-continued

```
1               5                   10                  15

Asp Arg Val Thr Ile Thr Cys Gln Ala Ser Glu Ser Ile Asn Ser Arg
            20                  25                  30

Leu Ala Trp Tyr Gln Gln Lys Pro Gly Gln Pro Pro Lys Leu Leu Ile
        35                  40                  45

Tyr Asp Ala Ser Asp Leu Thr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Tyr Gly Gly Ser Ser Thr
                85                  90                  95

Thr Thr Phe Gly Cys Gly Thr Lys Leu Thr Val Leu Gly Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Ala Ala Ser Gly Phe Ser Leu Ser Ser
145                 150                 155                 160

Tyr Ala Met Asn Trp Val Arg Gln Ala Pro Gly Lys Cys Leu Glu Trp
                165                 170                 175

Ile Gly His Ile Asn Ala Gly Asp Ile Ala Tyr Tyr Ala Thr Trp Ala
            180                 185                 190

Lys Gly Arg Phe Thr Ile Ser Arg Asp Asn Ser Lys Asn Thr Val Tyr
        195                 200                 205

Leu Gln Met Asn Ser Leu Arg Ala Glu Asp Thr Ala Val Tyr Phe Cys
    210                 215                 220

Ala Arg Gly Ala Gly Gly Phe Ser Thr Gly Pro Phe Lys Leu Trp Gly
225                 230                 235                 240

Gln Gly Thr Leu Val Thr Val Ser Ser Gly Gly Gly Gly Ser Gly Gly
                245                 250                 255

Gly Gly Ser Asp Ile Gln Met Thr Gln Ser Pro Ser Ser Leu Ser Ala
            260                 265                 270

Ser Val Gly Asp Arg Val Thr Ile Thr Cys Lys Ala Ser Gln Asp Val
        275                 280                 285

Ser Ile Gly Val Ala Trp Tyr Gln Gln Lys Pro Gly Lys Ala Pro Lys
    290                 295                 300

Leu Leu Ile Tyr Ser Ala Ser Tyr Arg Tyr Thr Gly Val Pro Ser Arg
305                 310                 315                 320

Phe Ser Gly Ser Gly Ser Gly Thr Asp Phe Thr Leu Thr Ile Ser Ser
                325                 330                 335

Leu Gln Pro Glu Asp Phe Ala Thr Tyr Tyr Cys Gln Gln Tyr Tyr Ile
            340                 345                 350

Tyr Pro Tyr Thr Phe Gly Cys Gly Thr Lys Val Thr Val Leu Gly Gly
        355                 360                 365

Gly Ser Gly Gly Ser Asp Ile Gln Met Thr Gln Ser Pro Ser Ser Leu
    370                 375                 380

Ser Ala Ser Val Gly Asp Arg Val Thr Ile Thr Cys Gln Ala Ser Gln
385                 390                 395                 400

Ser Ile Asn Asp Tyr Leu Ala Trp Tyr Gln Gln Lys Pro Gly Lys Ala
                405                 410                 415

Pro Lys Leu Leu Ile Tyr Lys Ala Ser Thr Leu Ala Ser Gly Val Pro
            420                 425                 430
```

```
Ser Arg Phe Ser Gly Ser Gly Ser Gly Thr Asp Phe Thr Leu Thr Ile
        435                 440                 445

Ser Ser Leu Gln Pro Glu Asp Phe Ala Thr Tyr Tyr Cys Gln Ala Gly
    450                 455                 460

Tyr Ile Ile Thr Asp Ile Asp Asn Val Phe Gly Thr Gly Thr Lys Val
465                 470                 475                 480

Thr Val Leu Gly


<210> SEQ ID NO 134
<211> LENGTH: 511
<212> TYPE: PRT
<213> ORGANISM: Artificial sequence
<220> FEATURE:
<223> OTHER INFORMATION: artificial antibody-based sequence

<400> SEQUENCE: 134

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Gly Ser Gly Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser Gly Gly Gly
                245                 250                 255

Gly Ser Gly Gly Gly Gly Ser Gln Val Gln Leu Gln Glu Ser Gly Pro
            260                 265                 270

Gly Leu Val Lys Pro Ser Glu Thr Leu Ser Leu Thr Cys Lys Val Ser
        275                 280                 285

Gly Phe Ser Phe Ser Ser Gly Tyr Asp Met Cys Trp Ile Arg Gln Pro
    290                 295                 300
```

```
Pro Gly Lys Gly Leu Glu Trp Ile Gly Cys Val Val Ala Gly Ser Val
305                 310                 315                 320

Asp Ile Thr Tyr Tyr Ala Ser Trp Ala Lys Gly Arg Val Thr Ile Ser
                325                 330                 335

Val Asp Ser Ser Lys Asn Gln Phe Ser Leu Lys Leu Ser Ser Val Thr
            340                 345                 350

Ala Ala Asp Thr Ala Val Tyr Tyr Cys Ala Arg Lys Asp Ala Ala Ser
        355                 360                 365

Asp Ala Phe Asn Leu Trp Gly Gln Gly Thr Leu Val Thr Val Ser Ser
    370                 375                 380

Gly Gly Gly Ser Gly Gly Gly Ser Glu Val Gln Leu Val Glu Ser Gly
385                 390                 395                 400

Gly Gly Leu Val Gln Pro Gly Gly Ser Leu Arg Leu Ser Cys Ala Ala
                405                 410                 415

Ser Gly Phe Thr Phe Thr Asp Tyr Thr Met Asp Trp Val Arg Gln Ala
            420                 425                 430

Pro Gly Lys Cys Leu Glu Trp Val Ala Asp Val Asn Pro Asn Ser Gly
        435                 440                 445

Gly Ser Ile Tyr Asn Gln Arg Phe Lys Gly Arg Phe Thr Leu Ser Val
    450                 455                 460

Asp Arg Ser Lys Asn Thr Leu Tyr Leu Gln Met Asn Ser Leu Arg Ala
465                 470                 475                 480

Glu Asp Thr Ala Val Tyr Tyr Cys Ala Arg Asn Leu Gly Pro Ser Phe
                485                 490                 495

Tyr Phe Asp Tyr Trp Gly Gln Gly Thr Leu Val Thr Val Ser Ser
            500                 505                 510


<210> SEQ ID NO 135
<211> LENGTH: 483
<212> TYPE: PRT
<213> ORGANISM: Artificial sequence
<220> FEATURE:
<223> OTHER INFORMATION: artificial antibody-based sequence

<400> SEQUENCE: 135

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Cys Gly Thr Lys Val Thr Val Leu Gly Gly Gly Gly Gly
            100                 105                 110

Ser Gly Gly Gly Gly Ser Gly Gly Gly Gly Ser Gly Gly Gly Gly Ser
        115                 120                 125

Glu Val Gln Leu Val Glu Ser Gly Gly Gly Leu Val Gln Pro Gly Gly
    130                 135                 140

Ser Leu Arg Leu Ser Cys Ala Ala Ser Gly Phe Thr Phe Thr Asp Tyr
145                 150                 155                 160
```

```
Thr Met Asp Trp Val Arg Gln Ala Pro Gly Lys Cys Leu Glu Trp Val
                165                 170                 175

Ala Asp Val Asn Pro Asn Ser Gly Gly Ser Ile Tyr Asn Gln Arg Phe
            180                 185                 190

Lys Gly Arg Phe Thr Leu Ser Val Asp Arg Ser Lys Asn Thr Leu Tyr
        195                 200                 205

Leu Gln Met Asn Ser Leu Arg Ala Glu Asp Thr Ala Val Tyr Tyr Cys
    210                 215                 220

Ala Arg Asn Leu Gly Pro Ser Phe Tyr Phe Asp Tyr Trp Gly Gln Gly
225                 230                 235                 240

Thr Leu Val Thr Val Ser Ser Gly Gly Gly Gly Ser Gly Gly Gly Gly
                245                 250                 255

Ser Asp Ile Gln Met Thr Gln Ser Pro Ser Ser Leu Ser Ala Ser Val
            260                 265                 270

Gly Asp Arg Val Thr Ile Thr Cys Gln Ala Ser Gln Ser Ile Asn Asp
        275                 280                 285

Tyr Leu Ala Trp Tyr Gln Gln Lys Pro Gly Lys Ala Pro Lys Leu Leu
    290                 295                 300

Ile Tyr Lys Ala Ser Thr Leu Ala Ser Gly Val Pro Ser Arg Phe Ser
305                 310                 315                 320

Gly Ser Gly Ser Gly Thr Asp Phe Thr Leu Thr Ile Ser Ser Leu Gln
                325                 330                 335

Pro Glu Asp Phe Ala Thr Tyr Tyr Cys Gln Ala Gly Tyr Ile Ile Thr
            340                 345                 350

Asp Ile Asp Asn Val Phe Gly Thr Gly Thr Lys Val Thr Val Leu Gly
        355                 360                 365

Gly Gly Ser Gly Gly Ser Ala Phe Glu Leu Thr Gln Ser Pro Ser Ser
    370                 375                 380

Leu Ser Ala Ser Val Gly Asp Arg Val Thr Ile Thr Cys Gln Ala Ser
385                 390                 395                 400

Glu Ser Ile Asn Ser Arg Leu Ala Trp Tyr Gln Gln Lys Pro Gly Gln
                405                 410                 415

Pro Pro Lys Leu Leu Ile Tyr Asp Ala Ser Asp Leu Thr Ser Gly Val
            420                 425                 430

Pro Ser Arg Phe Ser Gly Ser Gly Ser Gly Thr Asp Phe Thr Leu Thr
        435                 440                 445

Ile Ser Ser Leu Gln Pro Glu Asp Phe Ala Thr Tyr Tyr Cys Gln Gly
    450                 455                 460

Tyr Gly Gly Ser Ser Thr Thr Thr Phe Gly Cys Gly Thr Lys Leu Thr
465                 470                 475                 480

Val Leu Gly


<210> SEQ ID NO 136
<211> LENGTH: 512
<212> TYPE: PRT
<213> ORGANISM: Artificial sequence
<220> FEATURE:
<223> OTHER INFORMATION: artificial antibody-based sequence

<400> SEQUENCE: 136

Asp Ile Gln Met Thr Gln Ser Pro Ser Ser Leu Ser Ala Ser Val Gly
1               5                   10                  15

Asp Arg Val Thr Ile Thr Cys Gln Ser Ser Gln Ser Val Phe Ser Asn
            20                  25                  30

Asn Tyr Leu Ala Trp Phe Gln Gln Lys Pro Gly Gln Ser Pro Lys Arg
```

```
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Ser Tyr Ala Cys
                85                  90                  95

Ser Ser Ala Asp Cys Tyr Val Phe Gly Thr Gly Thr Lys Val Thr Val
            100                 105                 110

Leu Gly Gly Gly Gly Gly Ser Gly Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Ala Ala Ser Gly
145                 150                 155                 160

Phe Ser Leu Ser Ser Tyr Asp Met Ser Trp Val Arg Gln Ala Pro Gly
                165                 170                 175

Lys Gly Leu Ala Trp Ile Gly Ala Ser Tyr Ala Ser Gly Pro Thr Tyr
            180                 185                 190

Tyr Ala Ser Trp Ala Lys Gly Arg Phe Thr Ile Ser Arg Asp Asn Ser
        195                 200                 205

Lys Asn Thr Val Tyr Leu Gln Met Asn Ser Leu Arg Ala Glu Asp Thr
    210                 215                 220

Ala Thr Tyr Phe Cys Ala Arg Gly Gly Trp Thr Gly Thr Ser His Ser
225                 230                 235                 240

Asn Ile Trp Gly Gln Gly Thr Leu Val Thr Val Ser Ser Gly Gly Gly
                245                 250                 255

Gly Ser Gly Gly Gly Gly Ser Glu Val Gln Leu Val Glu Ser Gly Gly
            260                 265                 270

Gly Leu Val Gln Pro Gly Gly Ser Leu Arg Leu Ser Cys Ala Ala Ser
        275                 280                 285

Gly Phe Ser Leu Ser Ser Tyr Ala Met Asn Trp Val Arg Gln Ala Pro
    290                 295                 300

Gly Lys Cys Leu Glu Trp Ile Gly His Ile Asn Ala Gly Asp Ile Ala
305                 310                 315                 320

Tyr Tyr Ala Thr Trp Ala Lys Gly Arg Phe Thr Ile Ser Arg Asp Asn
                325                 330                 335

Ser Lys Asn Thr Val Tyr Leu Gln Met Asn Ser Leu Arg Ala Glu Asp
            340                 345                 350

Thr Ala Val Tyr Phe Cys Ala Arg Gly Ala Gly Gly Phe Ser Thr Gly
        355                 360                 365

Pro Phe Lys Leu Trp Gly Gln Gly Thr Leu Val Thr Val Ser Ser Gly
    370                 375                 380

Gly Gly Ser Gly Gly Gly Ser Gln Val Gln Leu Gln Glu Ser Gly Pro
385                 390                 395                 400

Gly Leu Val Lys Pro Ser Glu Thr Leu Ser Leu Thr Cys Lys Val Ser
                405                 410                 415

Gly Phe Ser Phe Ser Ser Gly Tyr Asp Met Cys Trp Ile Arg Gln Pro
            420                 425                 430

Pro Gly Lys Gly Leu Glu Trp Ile Gly Cys Val Val Ala Gly Ser Val
        435                 440                 445

Asp Ile Thr Tyr Tyr Ala Ser Trp Ala Lys Gly Arg Val Thr Ile Ser
    450                 455                 460
```

```
Val Asp Ser Ser Lys Asn Gln Phe Ser Leu Lys Leu Ser Ser Val Thr
465                 470                 475                 480

Ala Ala Asp Thr Ala Val Tyr Tyr Cys Ala Arg Lys Asp Ala Ala Ser
                485                 490                 495

Asp Ala Phe Asn Leu Trp Gly Gln Gly Thr Leu Val Thr Val Ser Ser
            500                 505                 510


<210> SEQ ID NO 137
<211> LENGTH: 121
<212> TYPE: PRT
<213> ORGANISM: Artificial sequence
<220> FEATURE:
<223> OTHER INFORMATION: artificial antibody-based sequence

<400> SEQUENCE: 137

Glu Val Gln Leu Val Glu Ser Gly Gly Gly Leu Val Gln Pro Gly Gly
1               5                   10                  15

Ser Leu Arg Leu Ser Cys Ala Ala Ser Gly Ile Asp Phe Asn Ser Asn
            20                  25                  30

Tyr Tyr Met Cys Trp Val Arg Gln Ala Pro Gly Lys Gly Leu Glu Trp
        35                  40                  45

Ile Gly Cys Ile Tyr Val Gly Ser His Val Asn Thr Tyr Tyr Ala Asn
    50                  55                  60

Trp Ala Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Thr Ser Gly Ser Ser Val Leu Tyr Phe Lys Phe Trp Gly
            100                 105                 110

Gln Gly Thr Leu Val Thr Val Ser Ser
        115                 120


<210> SEQ ID NO 138
<211> LENGTH: 113
<212> TYPE: PRT
<213> ORGANISM: Artificial sequence
<220> FEATURE:
<223> OTHER INFORMATION: artificial antibody-based sequence

<400> SEQUENCE: 138

Asp Ile Gln Met Thr Gln Ser Pro Ser Ser Leu Ser Ala Ser Val Gly
1               5                   10                  15

Asp Arg Val Thr Ile Thr Cys Gln Ala Ser Glu Asn Ile Tyr Ser Phe
            20                  25                  30

Leu Ala Trp Tyr Gln Gln Lys Pro Gly Lys Ala Pro Lys Leu Leu Ile
        35                  40                  45

Tyr Ser Ala Ser Lys Leu Ala Ala Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Arg Tyr Ser Asn
                85                  90                  95

Pro Asp Ile Tyr Asn Val Phe Gly Thr Gly Thr Lys Val Thr Val Leu
            100                 105                 110

Gly


<210> SEQ ID NO 139
```

<211> LENGTH: 20
<212> TYPE: PRT
<213> ORGANISM: Artificial sequence
<220> FEATURE:
<223> OTHER INFORMATION: artificial linker sequence

<400> SEQUENCE: 139

Gly Gly Gly Gly Ser Gly Gly Gly Gly Ser Gly Gly Gly Gly Ser Gly
1               5                   10                  15

Gly Gly Gly Ser
            20

<210> SEQ ID NO 140
<211> LENGTH: 5
<212> TYPE: PRT
<213> ORGANISM: Artificial sequence
<220> FEATURE:
<223> OTHER INFORMATION: artificial linker sequence

<400> SEQUENCE: 140

Gly Gly Gly Gly Ser
1               5

<210> SEQ ID NO 141
<211> LENGTH: 5
<212> TYPE: PRT
<213> ORGANISM: Artificial sequence
<220> FEATURE:
<223> OTHER INFORMATION: artificial linker sequence
<220> FEATURE:
<221> NAME/KEY: REPEAT
<222> LOCATION: (1)..(5)
<223> OTHER INFORMATION: the sequence GGXXS is present 2, 3, 4, 5 or 6
      times in the linker sequence
<220> FEATURE:
<221> NAME/KEY: VARIANT
<222> LOCATION: (3)..(4)
<223> OTHER INFORMATION: X is either G or absent

<400> SEQUENCE: 141

Gly Gly Xaa Xaa Ser
1               5

<210> SEQ ID NO 142
<211> LENGTH: 122
<212> TYPE: PRT
<213> ORGANISM: Artificial sequence
<220> FEATURE:
<223> OTHER INFORMATION: artificial antibody-based sequence

<400> SEQUENCE: 142

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Phe Ser Ala Asn
            20                  25                  30

Tyr Tyr Pro Cys Trp Val Arg Gln Ala Pro Gly Lys Gly Leu Glu Trp
        35                  40                  45

Ile Gly Cys Ile Tyr Gly Gly Ser Ser Asp Ile Thr Tyr Asp Ala Asn
    50                  55                  60

Trp Thr Lys Gly Arg Phe Thr Ile Ser Arg Asp Asn Ser Lys Asn Thr
65                  70                  75                  80

Val Tyr Leu Gln Met Asn Ser Leu Arg Ala Glu Asp Thr Ala Val Tyr
                85                  90                  95

Tyr Cys Ala Arg Ser Ala Trp Tyr Ser Gly Trp Gly Gly Asp Leu Trp
            100                 105                 110

```
Gly Gln Gly Thr Leu Val Thr Val Ser Ser
        115                 120


<210> SEQ ID NO 143
<211> LENGTH: 124
<212> TYPE: PRT
<213> ORGANISM: Artificial sequence
<220> FEATURE:
<223> OTHER INFORMATION: artificial antibody-based sequence

<400> SEQUENCE: 143

Gln Val Gln Leu Gln Glu Ser Gly Pro Gly Leu Val Lys Pro Ser Glu
1               5                   10                  15

Thr Leu Ser Leu Thr Cys Lys Val Ser Gly Phe Ser Phe Ser Asn Ser
            20                  25                  30

Tyr Trp Ile Cys Trp Ile Arg Gln Pro Pro Gly Lys Gly Leu Glu Trp
        35                  40                  45

Ile Gly Cys Thr Phe Val Gly Ser Ser Asp Ser Thr Tyr Tyr Ala Asn
    50                  55                  60

Trp Ala Lys Gly Arg Val Thr Ile Ser Val Asp Ser Ser Lys Asn Gln
65                  70                  75                  80

Phe Ser Leu Lys Leu Ser Ser Val Thr Ala Ala Asp Thr Ala Val Tyr
                85                  90                  95

Tyr Cys Ala Arg His Pro Ser Asp Ala Val Tyr Gly Tyr Ala Asn Asn
            100                 105                 110

Leu Trp Gly Gln Gly Thr Leu Val Thr Val Ser Ser
        115                 120


<210> SEQ ID NO 144
<211> LENGTH: 108
<212> TYPE: PRT
<213> ORGANISM: Artificial sequence
<220> FEATURE:
<223> OTHER INFORMATION: artificial antibody-based sequence

<400> SEQUENCE: 144

Asp Ile Gln Met Thr Gln Ser Pro Ser Ser Leu Ser Ala Ser Val Gly
1               5                   10                  15

Asp Arg Val Thr Ile Thr Cys Gln Ala Ser Gln Ser Ile Asn Asn Val
            20                  25                  30

Leu Ala Trp Tyr Gln Gln Lys Pro Gly Lys Ala Pro Lys Leu Leu Ile
        35                  40                  45

Tyr Arg Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Ser Ser Tyr Gly Asn Tyr Gly
                85                  90                  95

Asp Phe Gly Thr Gly Thr Lys Val Thr Val Leu Gly
            100                 105


<210> SEQ ID NO 145
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 145
```

-continued

Phe Gly Thr Gly Thr Lys Val Thr Val Leu Gly
1 5 10

<210> SEQ ID NO 146
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 146

Phe Gly Gly Gly Thr Lys Leu Thr Val Leu Gly
1 5 10

<210> SEQ ID NO 147
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 147

Phe Gly Gly Gly Thr Gln Leu Ile Ile Leu Gly
1 5 10

<210> SEQ ID NO 148
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 148

Phe Gly Glu Gly Thr Glu Leu Thr Val Leu Gly
1 5 10

<210> SEQ ID NO 149
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 149

Phe Gly Ser Gly Thr Lys Val Thr Val Leu Gly
1 5 10

<210> SEQ ID NO 150
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 150

Phe Gly Gly Gly Thr Gln Leu Thr Val Leu Gly
1 5 10

<210> SEQ ID NO 151
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 151

Phe Gly Gly Gly Thr Gln Leu Thr Ala Leu Gly
1 5 10

<210> SEQ ID NO 152
<211> LENGTH: 11
<212> TYPE: PRT
<213> ORGANISM: Artificial sequence
<220> FEATURE:
<223> OTHER INFORMATION: artificial antibody-based sequence

<400> SEQUENCE: 152

Phe Gly Cys Gly Thr Lys Leu Thr Val Leu Gly
1 5 10

<210> SEQ ID NO 153
<211> LENGTH: 255
<212> TYPE: PRT
<213> ORGANISM: Homo sapiens

<400> SEQUENCE: 153

Met Gly Asn Ser Cys Tyr Asn Ile Val Ala Thr Leu Leu Leu Val Leu
1 5 10 15

Asn Phe Glu Arg Thr Arg Ser Leu Gln Asp Pro Cys Ser Asn Cys Pro
20 25 30

Ala Gly Thr Phe Cys Asp Asn Asn Arg Asn Gln Ile Cys Ser Pro Cys
35 40 45

Pro Pro Asn Ser Phe Ser Ser Ala Gly Gly Gln Arg Thr Cys Asp Ile
50 55 60

Cys Arg Gln Cys Lys Gly Val Phe Arg Thr Arg Lys Glu Cys Ser Ser
65 70 75 80

Thr Ser Asn Ala Glu Cys Asp Cys Thr Pro Gly Phe His Cys Leu Gly
85 90 95

Ala Gly Cys Ser Met Cys Glu Gln Asp Cys Lys Gln Gly Gln Glu Leu
100 105 110

Thr Lys Lys Gly Cys Lys Asp Cys Cys Phe Gly Thr Phe Asn Asp Gln
115 120 125

Lys Arg Gly Ile Cys Arg Pro Trp Thr Asn Cys Ser Leu Asp Gly Lys
130 135 140

Ser Val Leu Val Asn Gly Thr Lys Glu Arg Asp Val Val Cys Gly Pro
145 150 155 160

Ser Pro Ala Asp Leu Ser Pro Gly Ala Ser Ser Val Thr Pro Pro Ala
165 170 175

Pro Ala Arg Glu Pro Gly His Ser Pro Gln Ile Ile Ser Phe Phe Leu
180 185 190

Ala Leu Thr Ser Thr Ala Leu Leu Phe Leu Leu Phe Phe Leu Thr Leu
195 200 205

Arg Phe Ser Val Val Lys Arg Gly Arg Lys Lys Leu Leu Tyr Ile Phe
210 215 220

Lys Gln Pro Phe Met Arg Pro Val Gln Thr Thr Gln Glu Glu Asp Gly
225 230 235 240

Cys Ser Cys Arg Phe Pro Glu Glu Glu Glu Gly Gly Cys Glu Leu
245 250 255